(12) United States Patent
Yang et al.

(10) Patent No.: US 7,294,459 B1
(45) Date of Patent: Nov. 13, 2007

(54) CELL REGULATORY GENES, ENCODED PRODUCTS, AND USES RELATED THERETO

(75) Inventors: Annie Yang, Boston, MA (US); Frank McKeon, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/174,493

(22) Filed: Oct. 15, 1998

Related U.S. Application Data

(60) Provisional application No. 60/087,216, filed on May 29, 1998, provisional application No. 60/062,076, filed on Oct. 15, 1997.

(51) Int. Cl.
*C12Q 1/68* (2006.01)
*C12N 15/63* (2006.01)
*C07H 21/04* (2006.01)
*C07K 14/435* (2006.01)

(52) U.S. Cl. .................... 435/6; 435/320.1; 536/23.5
(58) Field of Classification Search ............ 536/23.1, 536/23.5, 24.31, 24.3, 23.4; 435/320.1, 69.1, 435/70.1, 325, 6; 436/320.1
See application file for complete search history.

(56) References Cited

U.S. PATENT DOCUMENTS 6,476,206 B1 * 11/2002 Sidransky et al. .......... 536/23.1
6,518,256 B1    2/2003  Wang et al.

FOREIGN PATENT DOCUMENTS

| EP | 377295 | 7/1990 |
|----|--------|--------|
| FR | 2 692 594 | 12/1993 |
| WO | WO94/01563 | 1/1994 |
| WO | WO94/08241 | 4/1994 |

OTHER PUBLICATIONS

Accession No. AA798748, Database EST, Marra, M. et al.*
Burgess, W.H. et al. Possible dissociationof the heparin-binding and mitogenic activities of heparin-binding (acidic fibroblast) growth factor-1 from its receptor-binding activities by site-directedmutagenesis of a single lysine residue. Journal of Cell.*
Lazar, E. et al. Transforming growth factor alpha: mutation of aspartic acid 47 and leucine 48 results in different biological activities. Molecular and Cellular Biology, 8(3): 1247-1252.*
Schweizer et al, Journal of Cell Science, vol. 4, pp. 685-694.*
Sakamoto et al, PNAS, 1994, vol. 91, pp. 8974-8978.*
Friedman et al, PNAS, 1993, vol. 90, pp. 3319-3323.*
Abstract of Theis et al (International Journal of Cancer, 1997, vol. 71, pp. 858-866).*
Abstract of Mitchell et al (Genes and Development, 1991, vol. 5, pp. 105-119).*
Schmale et al (Oncogene, 1997, vol. 15, pp. 1363-1367).*
Abstract of Hagiwara (Cancer Research, 1999, vol. 59, pp. 4165-4169).*

Baylin et al., "KILLER/DR5 is a DNA damage-inducible p53-regulated death receptor gene," Nature Genetics, 17:141-142 (1997).
Beaudry et al., "Therapeutic targeting of the p53 tumor suppressor gene," Pharmaceutical Biotechnology, 592-600.
Cviko et al., "Adenoid basal carcinomas of the cervix: a unique morphological evolution with cell cycle correlates," Hum Pathol., 31(6):740-744 (2000).
Damiani et al., "Myoepithelial cells and basal lamina in poorly differentiated in situ duct carcinoma of the breast," Virchows Arch, 434:27-234 (1999).
De Laurenzi et al., "Evolutions of Functions within the p53/p63/p73 Family," Ann N Y Acad Sci., 926:90-100 (2000).
Foschini et al., "Carcinomas of the breast showing myoepithelial cell differentiation," Virchows Arch, 432:303-310 (1998).
Huibregtse et al., "A cellular protein mediates association of p53 with the E6 oncoprotein of human papillomavirus types 16 or 18," The EMBO Journal, 10(13):4129-4135 (1991).
Huibregtse et al., "Cloning and Expression of the cDNA for E6-AP, a Protein that Mediates the Interaction of the Human Papillomavirus E6 Oncoprotein with p53," Molecular and Cellular Biology, 13(2):775-784 (1993).
Ince et al., "p63 Coordinates Anogenital Modeling and Epithelial Cell Differentiation in the Developing Female Urogenital Tract," Am Journal of Pathol., 161(4):1111-1117 (2002).
Lazar et al., "Transforming Growth Factor α: Mutation of Aspartic Acid 47 and Leucine 48 Results in Different Biological Activities," Molecular and Cellular Biology, 8(3):1247-1252 (1988).
Le Bras et al., "Monoclonal antibodies raised against Xenopus p53 interact with human p73," Oncogene, 21:1304-1308 (2002).
Levero et al., "The p53/p63/p73 family of transcription factors: overlapping and distinct functions," J Cell Sci. 113:1661-1670 (2000).
Lohrum et al., "Regulation and function of the p53-related proteins: same family, different rules," Trends Cell Biol., 10(5):197-202 (2000).
Mills et al., "p63 is a p53 homologue required for limb and epidermal morphogenesis," Nature, 398:708-713 (1999).
Nayar et al., "Immunoreactivity of ductal cells with putative myoepithelial markers: a potential pitfall in breast carcinoma," Ann Diagn Pathol., 3:165-173 (1999).
O'Connell et al., "identification of a Basal/Reserve Cell Immunophenotype in Benign and Neoplastic Endometrium: A Study with the p53 Homologue p63," Gynecol Oncol., 80(1):30-36 (2001).
Osada et al., "Cloning and functional analysis of human p51, which structurally and functionally resembles p53," Nat Med., 4(7):839-843 (1998).

(Continued)

*Primary Examiner*—Karen A. Canella
(74) *Attorney, Agent, or Firm*—Fish & Richardson P.C.

(57) ABSTRACT

This application describes the cloning of p63, a gene at chromosome 3q27-29, that bears homology to the tumor suppressor p53. The p63 gene encodes at least six different isotypes. p63 was detected in a variety of human and mouse tissue and demonstrates remarkably divergent activities, such as the ability to transactivate p53 reporter genes and induce apoptosis. Isotopes of p63 lacking a transactivation domain act as dominant negatives towards the transactivation by p53 and p63.

20 Claims, 37 Drawing Sheets

OTHER PUBLICATIONS

Figure 2A:
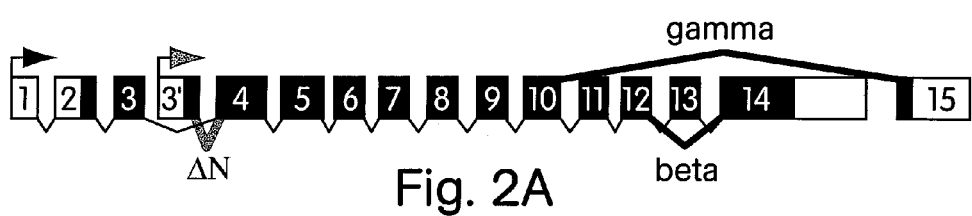

Quade et al., "Expression of the p53 Homologue p63 in Early Cervical Neoplasia," Gynecol Oncol, 80(1):24-29 (2001).

Ramnani et al., "Basal Cell-Specific Anti-Keratin Antibody 34βE12: Optimizing Its Use in Distinguishing Benign Prostate and Cancer," Mod. Pathology, 12:443-444 (1999).

Scheffner et al., "Interaction of the Human Papillomavirus Type 16 E6 Oncoprotein with Wild-Type and Mutant Human p53 Proteins," Journal of Virology, 66(8):5100-5105 (1992).

Scheffner et al., "The HPV-16E6 and E6-AP Complex Functions as a Ubiquitin-Protein Ligase in the Ubiquitination of p53," Cell, 75:495-505 (1993).

Theis et al., "A function in apoptosis other than transactivation inherent in the $NH_2$-terminal domain of p53," International Journal of Cancer, 71:858-866 (1997).

Senoo et al., "A Second p53-Related Protein, p73L, with High Homology to p73," Biochem Biophys Res Commun., 248(3):603-607 (1998).

Signoretti et al., "Basal Cell Specific p63 is Useful in the Differential Diagnosis of benign vs. Malignant Lesions of the Prostate," Presentation at the United States and Canadian Academy of Pathology (USCAP), Mar. 29, 2000.

Signoretti et al., "p63 Is a Prostate Basal Cell Marker and is Required for Prostate Development," Am Journal of Pathol., 157(6):1769-1775 (2000).

Sternlicht et al., "The Human Myoepithelial Cell Is a Natural Tumor Suppressor," Clin Cancer Research, 3:1949-1958 (1997).

Totten et al., "Microscopic Differential Diagnosis of Latent Carcinoma of Prostate," Arch Pathol., 55:131-141 (1953).

Trink et al., "A new human p53 homologue," Nat. Med. 4(7):747-748 (1998).

Urist et al., "Loss of p63 Expression is Associated with Tumor Progression in Bladder Cancer," Am Journal of Pathol., 161(4):1199-1206 (2002).

Varma et al., "Discriminant staining patterns of small glandular and preneoplastic lesions of the prostate using high molecular weight cytokeratin (HMCK)—A study of 301 consecutive needle biopsies," Abstract, Mod Pathol., 1997, 10:93A.

Varma et al., "Effect of Formalin Fixation and Epitope Retrieval Techniques on Antibody 34βE12 Immunostaining of Prostatic Tissues," Mod Pathol., 12:472 (1999).

Wang et al., "Histologic and Immunophenotypic Classification of Cervical Carcinomas by Expression of the p53 Homologue p63: A Study of 250 Cases," Hum Pathol., 32(5):479-486 (2001).

Yang et al., "Lineage-specific expression of the P53 homologue P63 in genital tract neoplasia," Abstract, Mod Pathol., Jan. 1999, 127A.

Yang et al., "P63: a P53 homologue that is a differentiation-specific marker in cervical squamous epithelium," Abstract, Mod Pathol., Jan. 1999, 178A.

Yang et al., "Rare Expression of High-Molecular-Weight Cytokeratin in Adenocarcinoma of the Prostate Gland," Am J Surg Pathol., 23(2):147-152 (1999).

Zeng et al., "NBP is the p53 homolog p63," Carcinogenesis, 22(2):215-219 (2001).

Baylin et al., "KILLER/DR5 is a DNA damage-inducible p53-regulated death receptor gene," Nature Genetics, 17:141-142 (1997).

Beaudry et al., "Therapeutic targeting of the p53 tumor suppressor gene," Pharmaceutical Biotechnology, 592-600.

Cviko et al., "Adenoid basal carcinomas of the cervix: a unique morphological evolution with cell cycle correlates," Hum Pathol., 31(6):740-744 (2000).

Damiani et al., "Myoepithelial cells and basal lamina in poorly differentiated in situ duct carcinoma of the breast," Virchows Arch, 434:27-234 (1999).

De Laurenzi et al., "Evolution of Functions within the p53/p63/p73 Family," Ann N Y Acad Sci., 926:90-100 (2000).

Foschini et al., "Carcinomas of the breast showing myoepithelial cell differentiation," Virchows Arch, 432:303-310 (1998).

Huibregtse et al., "A cellular protein mediates association of p53 with the E6 oncoprotein of human papillomavirus types 16 or 18," The EMBO Journal, 10(13):4129-4135 (1991).

Kraegel et al., "Sequence Analysis of Canine p53 in the Region of Exons 3-8" Cancer Letters 92(2): 181-186 (Jun. 8, 1995).

Kunz, Jeannette et al., "Target of Rapamycin in Yeast, TOR2, Is and Essential Phosphatidylinositol Kinase Homolog Required for G1 Progression", Cell 73: 585-596 (May 7, 1993).

McNaughton et al., "A Cluster of Transposon-Like Repetitive Sequences in Intron 7 of the Human Dystrophin Gene" J. Mol. Biol, 232(1):314-321 (1993).

Neumann et al., "Multifactorial Inheritance of Neural Tube Defects: Localization of the Major Gene and Recognition of Modifiers in ct Mutant Mice," Nature Genetics, 6(4):357-362 (Apr. 1994).

Oren, M. "Relationship of p53 to the Control of Apoptotic Cell Death", Semin Cancer Biol 5(3): 221-227 (Jun. 1994).

Parsa, R. et al., "Association of p63 Proliferative Potential in Normal and Neoplastic Human Keratinocytes"J. Invest Dermatol, 113:1099-1105 (Dec. 1999).

Righi, E. et al., "Does p53 Immunostaining Improve Accuracy in Urine Cytology?"Diagnostic Cytopathology, 17(6):436-439 (Dec. 1997).

Shaw, H. Phillip., "The Role of p53 in Cell Cycle Regulation," Path. Res. Pract. 192: 669-675 (1996).

Strano, Sabrina et al., "From p53 to p53 Across p73", FEBS letters 490: 163-170 (2001).

Sturzbecher, HW et al., "Mutant p53 Proteins Bind hsp 72/73 Cellular Heat Shock-Related Proteins in SV40-Transformed Monkey Cells", Oncogene 1(2): 201-211 (May 1987).

Teoule et al., "Gamma-Irradiation of Homodeoxyoligonucleotides $^{32}$P-Labelled at One End: Computer Smulation of the Chain Length Distribution of the Radioactive Fragments," Int. J. Radiat. Biol. Relat. Stud. Phys., Chem. Med., 51(3):429-439 (1987).

Wang, T. et al., "p53, Apoptosis and Human Cancers," J. Formos. Med. Assoc., 95(7):509-522 (1996).

Wilson et al., "2.2 Mb of Contiguous Nucleotide Sequence from Chromosome III of C. elegans", Nature, 368: 32-38 (1994).

Yang et al., "p63, a p53 Homolog at 3q27-29, Encodes Multiple Products with Transactivating, Death-Induced, and Dominant-Negative Activities," Molecular Cell 2: 305-316 (Sep. 1998).

Yang et al., "P63 and P73: P53 Mimics, Menaces and More", Nat Rev Mol Cell Biol 1(3): 199-207 (Dec. 2000).

Yang et al., "p63 Is Essential for Regenerative Proliferation In Limb, Craniofacial and Epithelial Development," Nature, vol. 398:714-178 (Apr. 1999).

Sequence alignments cited in co-pending application.

Pujol et al (Proc Amer Ass of Cancer Res Ann Meeting 1994; 35(0): 165)- Abstract Only.

Li et al (Zhonghua Zhongliu Zazhi 1994; 16(3):172-176)- Abstract Only.

Arai et al., "Immunologically Distinct p53 Molecules Generated by Alternative Splicing" Mol. Cell. Biol. 6(9): 3232-3239 (Sep. 1986).

Bargonetti, J. et al., "Site-Specific Binding of Wild-Type p53 to Cellular DNA is Inhibited by SV40 T Antigen and Mutant p53", Genes Dev 6(10): 1886-1898 (Oct. 1992).

Bodrug, "Molecular Analysis of a Constitutional X-Autosome Translocation in a Female with Muscular Dystrophy", Science 237: 1620-1624 (Apr. 6, 1993).

De Fromentel et al., "Rainbow Trout p53: cDNA Cloning and Biochemical Characterization", Gene 112: 241-245 (1992).

Desquiedt et al., "Nucleotide Sequence of Bovine p53 Tumor-Suppressor cDNA", DNA Seq. 5(4): 261-264 (1995).

El-Deiry, WS et al., "Definition of a Consensus Binding Site for p53", Nat Genet 1(1): 45-49 (Apr. 1992).

Gryaznov et al., "Selective O-Phosphitilation With Nucleoside Phosphoramidite Reagents," Nucleic Acids Research, 20(8):1879-1882 (1992).

Hall, P. et al., "Expression of the p53 Homologue p63α and ΔNp63α in Normal and Neoplastic Cells"Carcinogenesis, 21(2):153-160 (Feb. 2000).

Iwase et al., "identification of Protein-Tyrosine Kinase Genes Preferentially Expressed in Embryo Stomach and Gastric Cancer," Biochemical & Biophysical Research. Communications., 194(2):698-705 (Jul. 1993).

* cited by examiner

| | | |
|---|---|---|
| 1 | ------------------------------------------MEE | Hu p53 |
| 1 | -------------------------------------------M | Hu p73β |
| 1 | -------------------------------------------M | Hu p63γ |
| 1 | MNFETSRCATLQYCPDPYIQRFIETPAHFSWKESYYRSAM | Mu p63γ |
| 4 | PQSDPSVEPPLSQETFSD-LWKLLPE---NNVLSP----- | Hu p53 |
| 2 | AQSTATS-PDGGTT--FEHLWSSLEPD--STYF------D | Hu p73β |
| 2 | SQSTQTNEF-LSPEV-FQHIWDFLEQPICSVQPIDLNFVD | Hu p63γ |
| 41 | SQSTQTSEF-LSPEV-FQHIWDFLEQPICSVQPIELNFVD | Mu p63γ |
| 35 | LP-----------------SQAMDDLMLSPDDIEQWFTEDPGP | Hu p53 |
| 31 | LPQSSRGNNEVVGGTDSS-MDVFHLEG-MTTSVMAQFNL- | Hu p73β |
| 40 | EPSEDGATNKIEISMDCIRMQDSDLSDPMWPQYT---NLG | Hu p63γ |
| 79 | EPSENGATNKIEISMDCIRMQDSDLSDPMWPQYT---NLG | Mu p63γ |
| 61 | -----DEAPRMP--EAAPPVA---PAPAAPT-PAAPAPAP | Hu p53 |
| 68 | LSSTMDQM----SSRAASASPY-TPEHAA-SVPT-HSPYA | Hu p73β |
| 77 | LLNSMDQQIQNGSS---STSPYNT-DHAQNSV-TAPSPYA | Hu p63γ |
| 116 | LLNSMDQQIQNGSS---STSPYNT-DHAQNSV-TAPSPYA | Mu p63γ |
| 90 | SWPLSSSVP--SQ------KT-YQGSYGFRLGFLHSGTAK | Hu p53 |
| 101 | Q-P-SSTFDTMSPAPVIPSNTDYPGPHHFEVTFQQSSTAK | Hu p73β |
| 112 | Q-P-SSTFDALSPSPAIPSNTDYPGPHSFDVSFQQSSTAK | Hu p63γ |
| 151 | Q-P-SSTFDALSPSPAIPSNTDYPGPHSFDVSFQQSSTAK | Mu p63γ |
| 121 | SVTCTYSPALNKMFCQLAKTCPVQLWVDSTPPPGTRVRAM | Hu p53 |
| 139 | SATWTYSPLLKKLYCQIAKTCPIQIKVSTPPPPGTAIRAM | Hu p73β |
| 150 | SATWTYSTELKKLYCQIAKTCPIQIKVMTPPPQCAVIRAM | Hu p63γ |
| 189 | SATWTYSTELKKLYCQIAKTCPIQIKVMTPPPQCAVIRAM | Mu p63γ |
| 161 | AIYKQSQHMTEVVRRCPHHE--RCSDSDGLAPPQHLIRVE | Hu p53 |
| 179 | PVYKKAEHVTDVVKRCPNHEELGRDFNEGQSAPASHLIRVE | Hu p73β |
| 190 | PVYKKAEHVTEVVKRCPNHELSREFNEGQIAPPSHLIRVE | Hu p63γ |
| 229 | PVVKKAEHVTEVVKRCPNHELSREFNEGQIAPPSHLIRVE | Mu p63γ |
| 199 | GNLRVEYLDDRNTFRHSVVVPYEPPEVGSDCTTIHYNYMC | Hu p53 |
| 219 | GNNLSQYVDDPVTGRQSVVVPYEPPQVGTEFTTILYNFMC | Hu p73β |
| 230 | GNSHAQYVEDPITGRQSVLVPYEPPQVGTEFTTVLYNFMC | Hu p63γ |
| 269 | GNSHAQYVEDPITGRQSVLVPYEPPQVGTEFTTVLYNFMC | Mu p63γ |
| 239 | NSSCMGGMNRRPILTIITTLEDSSGNLLGRNSFEVHVCACP | Hu p53 |
| 259 | NSSCVGGMNRRPILTIITLEMRDCQVLGRRSEEGRICACP | Hu p73β |
| 270 | NSSCVGGMNRRPILIITVTLETRDGQVLGRRCFEARICACP | Hu p63γ |
| 309 | NSSCVGGMNRRPILIILVTLETRDGQVLGRRCFEARICACP | Mu p63γ |
| 279 | GRDRRTEEENLRKKGEPHHELPPGST-------KRALPN | Hu p53 |
| 299 | GRDRKADEDHYREQQALN-E---SSA-KNGAASKRAFKQ | Hu p73β |
| 310 | GRDRKADEDSIRKQQVS--D---ST--KNGDGTKRPFRQ | Hu p63γ |
| 349 | GRDRKADEDSIRKQQVS--D---SA--KNGDA----FRQ | Mu p63γ |
| 311 | N-----TSSSPQPKKKPLDGEYFTLQIRGRERFEMFREL | Hu p53 |
| 333 | -SPPAVPALGAGVKKRRHGDEDTYYLQVRGRENFEILMKL | Hu p73β |
| 342 | NTHGIQMTS---IKKRRSPDDELLYLPVRGRETYEMLLKI | Hu p63γ |
| 377 | NTHGIQMTS---IKKRRSPDDELLYLPVRGRETYEMLLKI | Mu p63γ |
| 345 | NEALELKDAQAGKEPGGSR----------AHSSHLKS-- | Hu p53 |
| 372 | KESLELMELVPQPLVDSYRQQQ----LLQRPSHLQPPS | Hu p73β |
| 379 | KESLELMQYLPQHTIETYRQQQQQQHQHLLQK--HLLSAC | Hu p63γ |
| 414 | KESLELMQYLPQHTIETYRQQQQQQHQHLLQK--HLLSAC | Mu p63γ |
| 372 | --------KKGQSTSRHKKLMFKTEGPDSD | Hu p53 |
| 407 | YGPVLSPMNKVHGG--MNKLPSVNQLVGQPPPHSSAATPN | Hu p73β |
| 417 | FRNELVEPRRETPKQSD--VFFRHSKPPNRSVYP | Hu p63γ |
| 452 | FRNELVEPRGEAPTQSD--VFFRHSNPPNHSVYPZ | Mu p63γ |
| 393 | | Hu p53 |
| 445 | LGPVGPGMLNNHGHAVPANGEMSSSHSAQSMVSGSHCTPP | Hu p73β |
| 448 | | Hu p63γ |
| 484 | | Mu p63γ |
| 393 | | Hu p53 |
| 485 | PPYHADPSLVRTWGP | Hu p73β |
| 448 | | Hu p63γ |
| 484 | | Mu p63γ |

Fig. 1

```
  1 M N F E T S R C A T L Q Y C P D P Y I Q R F I E T P A H F S Mu TA*p63
  1 - - - - - - - - - - - - - - - - - - - - - - - - - - - - - - Hu TAp63
  1 - - - - - - - - - - - - - - - - - - - - - - - - - - - - - - Hu ΔNp63

31 W K E S Y Y R S A M S Q S T Q T S E F L S P E V F Q H I W D Mu TA*p63
  1 - - - - - - - - - M S Q S T Q T N E F L S P E V F Q H I W D Hu TAp63
  1 - - - - - - - - - - - - - - - - - - - - - - - - - - - - - - Hu ΔNp63

61 F L E Q P I C S V Q P I E L N F V D E P S E N G A T N K I E Mu TA*p63
 22 F L E Q P I C S V Q P I D L N F V D E P S E D G A T N K I E Hu TAp63
  1 - - - - - - - - - - - - - - - - - - - - - - - - - - - - - - Hu ΔNp63

91 I S M D C I R M Q D S D L S D P M W P Q Y T N L G L L N S M Mu TA*p63
 52 I S M D C I R M Q D S D L S D P M W P Q Y T N L G L L N S M Hu TAp63
  1 - - - - M L Y L E N N A Q T Q F S E P Q Y T N L G L L N S M Hu ΔNp63
```

```
1/1                                                 31/11
ATG TCC CAG AGC ACA CAG ACA AAT GAA TTC cTC AGT CCA GAG GTT TTC CAG CAT ATC TGG
 M   S   Q   S   T   Q   T   N   E   F   L   S   P   E   V   F   Q   H   I   W
61/21                                               91/31
GAT TTT CTG GAA CAG CcT ATA TGT TCA GTT CAG CCC ATT GAC TTG AAC TTT GTG GAT GAA
 D   F   L   E   Q   P   I   C   S   V   Q   P   I   D   L   N   F   V   D   E
121/41                                              151/51
CCA TCA GAA GAT GGT GCG ACA AAC AAG ATT GAG ATT AGC ATG GAC TGT ATC CGC ATG CAG
 P   S   E   D   G   A   T   N   K   I   E   I   S   M   D   C   I   R   M   Q
181/61                                              211/71
GAC TCG GAC CTG AGT GAC CCC ATG TGG CCA CAG TAC ACG AAC CTG GGG CTC CTG AAC AGC
 D   S   D   L   S   D   P   M   W   P   Q   Y   T   N   L   G   L   L   N   S
241/81                                              271/91
ATG GAC CAG CAG ATT CAG AAC GGC TCC TCG TCC ACC AGT CCC TAT AAC ACA GAC CAC GCG
 M   D   Q   Q   I   Q   N   G   S   S   S   T   S   P   Y   N   T   D   H   A
301/101                                             331/111
CAG AAC AGC GTC ACG GCG CCC TCG CCC TAC GCA CAG CCC AGC TCC ACC TTC GAT GCT CTC
 Q   N   S   V   T   A   P   S   P   Y   A   Q   P   S   S   T   F   D   A   L
361/121                                             391/131
TCT CCA TCA CCC GCC ATC CCC TCC AAC ACC GAC TAC CCA GGC CCG CAC AGT TTC GAC GTG
 S   P   S   P   A   I   P   S   N   T   D   Y   P   G   P   H   S   F   D   V
421/141                                             451/151
TCC TTC CAG CAG TCG AGC ACC GCC AAG TCG GCC ACC TGG ACG TAT TCC ACT GAA CTG AAG
 S   F   Q   Q   S   S   T   A   K   S   A   T   W   T   Y   S   T   E   L   K
481/161                                             511/171
AAA CTC TAC TGC CAA ATT GCA AAG ACA TGC CCC ATC CAG ATC AAG GTG ATG ACC CCA CCT
 K   L   Y   C   Q   I   A   K   T   C   P   I   Q   I   K   V   M   T   P   P
541/181                                             571/191
CCT CAG GGA GCT GTT ATC CGC GCC ATG CCT GTC TAC AAA AAA GCT GAG CAC GTC ACG GAG
 P   Q   G   A   V   I   R   A   M   P   V   Y   K   K   A   E   H   V   T   E
601/201                                             631/211
GTG GTG AAG CGG TGC CCC AAC CAT GAG CTG AGC CGT GAA TTC AAC GAG GGA CAG ATT GCC
 V   V   K   R   C   P   N   H   E   L   S   R   E   F   N   E   G   Q   I   A
661/221                                             691/231
CCT CCT AGT CAT TTG ATT CGA GTA GAG GGG AAC AGC CAT GCC CAG TAT GTA GAA GAT CCC
 P   P   S   H   L   I   R   V   E   G   N   S   H   A   Q   Y   V   E   D   P
721/241                                             751/251
ATC ACA GGA AGA CAG AGT GTG CTG GTA CCT TAT GAG CCA CCC CAG GTT GGC ACT GAA TTC
 I   T   G   R   Q   S   V   L   V   P   Y   E   P   P   Q   V   G   T   E   F
781/261                                             811/271
ACG ACA GTc TTG TAC AAT TTC ATG TGT AAC AGC AGT TGT GTT GGA GGG ATG AAc cgC Cgt
 T   T   V   L   Y   N   F   M   C   N   S   S   C   V   G   G   M   N   R   R
841/281                                             871/291
CCa aTT TTA ATC ATT GTT ACT CTG GAA ACC AGA GAT GGG CAA GTC CTG GGC CGA CGC TGC
 P   I   L   I   I   V   T   L   E   T   R   D   G   Q   V   L   G   R   R   C
901/301                                             931/311
TTT GAG GCC CGG ATC TGT GCT TGC CCA GGA AGA GAC AGG AAG GCG GAT GAA GAT AGC ATC
 F   E   A   R   I   C   A   C   P   G   R   D   R   K   A   D   E   D   S   I
961/321                                             991/331
AGA AAG CAG CAA GTT TCG GAC AGT ACA AAG AAC GGT GAT GGT ACG AAG CGC CCG TTT CGT
 R   K   Q   Q   V   S   D   S   T   K   N   G   D   G   T   K   R   P   F   R
1021/341                                            1051/351
CAG AAC ACA CAT GGT ATC CAG ATG ACA TCC ATC AAG AAA CGA AGA TCC CCA GAT GAT GAA
 Q   N   T   H   G   I   Q   M   T   S   I   K   K   R   R   S   P   D   D   E
1081/361                                            1111/371
CTG TTA TAC TTA CCA GTG AGG GGC CGT GAG ACT TAT GAA ATG CTG TTG AAG ATC AAA GAG
 L   L   Y   L   P   V   R   G   R   E   T   Y   E   M   L   L   K   I   K   E
1141/381                                            1171/391
TCC CTG GAA CTC ATG CAG TAC CTT CCT CAG CAC ACA ATT GAA ACG TAC AGG CAA CAA
 S   L   E   L   M   Q   Y   L   P   Q   H   T   I   E   T   Y   R   Q   Q
```

Figure 9A

```
1201/401                                        1231/411
CAG CAG CAG CAC CAG CAC TTA CTT CAG AAA CAG ACC TCA ATA CAG TCT CCA TCT TCA TAT
 Q   Q   Q   H   Q   H   L   L   Q   K   Q   T   S   I   Q   S   P   S   S   Y
1261/421                                        1291/431
GGT AAC AGC TCC CCA CCT CTG AAC AAA ATG AAC AGC ATG AAC AAG CTG CCT TCT GTG AGC
 G   N   S   S   P   P   L   N   K   M   N   S   M   N   K   L   P   S   V   S
1321/441                                        1351/451
CAG CTT ATC AAC CCT CAG CAG CGC AAC GCC CTC ACT CCT ACA ACC ATT CCT GAT GGC ATG
 Q   L   I   N   P   Q   Q   R   N   A   L   T   P   T   T   I   P   D   G   M
1381/461                                        1411/471
GGA GCC AAC ATT CCC ATG ATG GGC ACC CAC ATG CCA ATG GCT GGA GAC ATG AAT GGA CTC
 G   A   N   I   P   M   M   G   T   H   M   P   M   A   G   D   M   N   G   L
1441/481                                        1471/491
AGC CCC ACC CAG GCA CTC CCT CCC CCA CTC TCC ATG CCA TCC ACC TCC CAC TGC ACA CCC
 S   P   T   Q   A   L   P   P   P   L   S   M   P   S   T   S   H   C   T   P
1501/501                                        1531/511
CCA CCT CCG TAT CCC ACA GAT TGC AGC ATT GTC AGT TTC TTA GCG AGG TTG GGC TGT TCA
 P   P   P   Y   P   T   D   C   S   I   V   S   F   L   A   R   L   G   C   S
1561/521                                        1591/531
TCA TGT CTG GAC TAT TTC ACG ACC CAG GGG CTG ACC ACC ATC TAT CAG ATT GAG CAT TAC
 S   C   L   D   Y   F   T   T   Q   G   L   T   T   I   Y   Q   I   E   H   Y
1621/541                                        1651/551
TCC ATG GAT GAT CTG GCA AGT CTG AAA ATC CCT GAG CAA TTT CGA CAT GCG ATC TGG AAG
 S   M   D   D   L   A   S   L   K   I   P   E   Q   F   R   H   A   I   W   K
1681/561                                        1711/571
GGC ATC CTG GAC CAC CGG CAG CTC CAC GAA TTC TCC TCC CCT TCT CAT CTC CTG CGG ACC
 G   I   L   D   H   R   Q   L   H   E   F   S   S   P   S   H   L   L   R   T
1741/581                                        1771/591
CCA AGC AGT GCC TCT ACA GTC AGT GTG GGC TCC AGT GAG ACC CGG GGT GAG CGT GTT ATT
 P   S   S   A   S   T   V   S   V   G   S   S   E   T   R   G   E   R   V   I
1801/601                                        1831/611
GAT GCT GTG CGA TTC ACC CTC CGC CAG ACC ATC TCT TTC CCA CCC CGA GAT GAG TGG AAT
 D   A   V   R   F   T   L   R   Q   T   I   S   F   P   P   R   D   E   W   N
1861/621                                        1891/631
GAC TTC AAC TTT GAC ATG GAT GCT CGC CGC AAT AAG CAA CAG CGC ATC AAA GAG GAG GGG
 D   F   N   F   D   M   D   A   R   R   N   K   Q   Q   R   I   K   E   E   G
1921/641
GAG TGA
 E   *
```

Figure 10

```
1/1                                          31/11
ATG TCC CAG AGC ACA CAG ACA AAT GAA TTC      CTC AGT CCA GAG GTT TTC CAG CAT ATC TGG
 M   S   Q   S   T   Q   T   N   E   F        L   S   P   E   V   F   Q   H   I   W
61/21                                        91/31
GAT TTT CTG GAA CAG CcT ATA TGT TCA GTT      CAG CCC ATT GAC TTG AAC TTT GTG GAT GAA
 D   F   L   E   Q   P   I   C   S   V        Q   P   I   D   L   N   F   V   D   E
121/41                                       151/51
CCA TCA GAA GAT GGT GCG ACA AAC AAG ATT      GAG ATT AGC ATG GAC TGT ATC CGC ATG CAG
 P   S   E   D   G   A   T   N   K   I        E   I   S   M   D   C   I   R   M   Q
181/61                                       211/71
GAC TCG GAC CTG AGT GAC CCC ATG TGG CCA      CAG TAC ACG AAC CTG GGG CTC CTG AAC AGC
 D   S   D   L   S   D   P   M   W   P        Q   Y   T   N   L   G   L   L   N   S
241/81                                       271/91
ATG GAC CAG CAG ATT CAG AAC GGC TCC TCG      TCC ACC AGT CCC TAT AAC ACA GAC CAC GCG
 M   D   Q   Q   I   Q   N   G   S   S        S   T   S   P   Y   N   T   D   H   A
301/101                                      331/111
CAG AAC AGC GTC ACG GCG CCC TCG CCC TAC      GCA CAG CCC AGC TCC ACC TTC GAT GCT CTC
 Q   N   S   V   T   A   P   S   P   Y        A   Q   P   S   S   T   F   D   A   L
361/121                                      391/131
TCT CCA TCA CCC GCC ATC CCC TCC AAC ACC      GAC TAC CCA GGC CCG CAC AGT TTC GAC GTG
 S   P   S   P   A   I   P   S   N   T        D   Y   P   G   P   H   S   F   D   V
421/141                                      451/151
TCC TTC CAG CAG TCG AGC ACC GCC AAG TCG      GCC ACC TGG ACG TAT TCC ACT GAA CTG AAG
 S   F   Q   Q   S   S   T   A   K   S        A   T   W   T   Y   S   T   E   L   K
481/161                                      511/171
AAA CTC TAC TGC CAA ATT GCA AAG ACA TGC      CCC ATC CAG ATC AAG GTG ATG ACC CCA CCT
 K   L   Y   C   Q   I   A   K   T   C        P   I   Q   I   K   V   M   T   P   P
541/181                                      571/191
CCT CAG GGA GCT GTT ATC CGC GCC ATG CCT      GTC TAC AAA AAA GCT GAG CAC GTC ACG GAG
 P   Q   G   A   V   I   R   A   M   P        V   Y   K   K   A   E   H   V   T   E
601/201                                      631/211
GTG GTG AAG CGG TGC CCC AAC CAT GAG CTG      AGC CGT GAA TTC AAC GAG GGA CAG ATT GCC
 V   V   K   R   C   P   N   H   E   L        S   R   E   F   N   E   G   Q   I   A
661/221                                      691/231
CCT CCT AGT CAT TTG ATT CGA GTA GAG GGG      AAC AGC CAT GCC CAG TAT GTA GAA GAT CCC
 P   P   S   H   L   I   R   V   E   G        N   S   H   A   Q   Y   V   E   D   P
721/241                                      751/251
ATC ACA GGA AGA CAG AGT GTG CTG GTA CCT      TAT GAG CCA CCC CAG GTT GGC ACT GAA TTC
 I   T   G   R   Q   S   V   L   V   P        Y   E   P   P   Q   V   G   T   E   F
781/261                                      811/271
ACG ACA GTc TTG TAC AAT TTC ATG TGT AAC      AGC AGT TGT GTT GGA GGG ATG AAc cgC Cgt
 T   T   V   L   Y   N   F   M   C   N        S   S   C   V   G   G   M   N   R   R
841/281                                      871/291
CCa aTT TTA ATC ATT GTT ACT CTG GAA ACC      AGA GAT GGG CAA GTC CTG GGC CGA CGC TGC
 P   I   L   I   I   V   T   L   E   T        R   D   G   Q   V   L   G   R   R   C
901/301                                      931/311
TTT GAG GCC CGG ATC TGT GCT TGC CCA GGA      AGA GAC AGG AAG GCG GAT GAA GAT AGC ATC
 F   E   A   R   I   C   A   C   P   G        R   D   R   K   A   D   E   D   S   I
961/321                                      991/331
AGA AAG CAG CAA GTT TCG GAC AGT ACA AAG      AAC GGT GAT GGT ACG AAG CGC CCG TTT CGT
 R   K   Q   Q   V   S   D   S   T   K        N   G   D   G   T   K   R   P   F   R
1021/341                                     1051/351
CAG AAC ACA CAT GGT ATC CAG ATG ACA TCC      ATC AAG AAA CGA AGA TCC CCA GAT GAT GAA
 Q   N   T   H   G   I   Q   M   T   S        I   K   K   R   R   S   P   D   D   E
1081/361                                     1111/371
CTG TTA TAC TTA CCA GTG AGG GGC GTG GAG      ACT TAT GAA ATG CTG TTG AAG ATC AAA GAG
 L   L   Y   L   P   V   R   G   R   E        T   Y   E   M   L   L   K   I   K   E
1141/381                                     1171/391
TCC CTG GAA CTC ATG CAG TAC CTT CCT CAG      CAC ACA ATT GAA ACG TAC AGG CAA CAG CAA
 S   L   E   L   M   Q   Y   L   P   Q        H   T   I   E   T   Y   R   Q   Q   Q
```

Figure 10A

```
1201/401                                          1231/411
CAG CAG CAG CAC CAG CAC TTA CTT CAG AAA CAG ACC TCA ATA CAG TCT CCA TCT TCA TAT
 Q   Q   Q   H   Q   H   L   L   Q   K   Q   T   S   I   Q   S   P   S   S   Y
1261/421                                          1291/431
GGT AAC AGC TCC CCA CCT CTG AAC AAA ATG AAC AGC ATG AAC AAG CTG CCT TCT GTG AGC
 G   N   S   S   P   P   L   N   K   M   N   S   M   N   K   L   P   S   V   S
1321/441                                          1351/451
CAG CTT ATC AAC CCT CAG CAG CGC AAC GCC CTC ACT CCT ACA ACC ATT CCT GAT GGC ATG
 Q   L   I   N   P   Q   Q   R   N   A   L   T   P   T   T   I   P   D   G   M
1381/461                                          1411/471
GGA GCC AAC ATT CCC ATG ATG GGC ACC CAC ATG CCA ATG GCT GGA GAC ATG AAT GGA CTC
 G   A   N   I   P   M   M   G   T   H   M   P   M   A   G   D   M   N   G   L
1441/481                                          1471/491
AGC CCC ACC CAG GCA CTC CCT CCC CCA CTC TCC ATG CCA TCC ACC TCC CAC TGC ACA CCC
 S   P   T   Q   A   L   P   P   P   L   S   M   P   S   T   S   H   C   T   P
1501/501                                          1531/511
CCA CCT CCG TAT CCC ACA GAT TGC AGC ATT GTC AGG ATC TGG CAA GTC TGA
 P   P   P   Y   P   T   D   C   S   I   V   R   I   W   Q   V   *
```

Figure 11

```
1/1                                         31/11
ATG TCC CAG AGC ACA CAG ACA AAT GAA TTC    CTC AGT CCA GAG GTT TTC CAG CAT ATC TGG
 M   S   Q   S   T   Q   T   N   E   F      L   S   P   E   V   F   Q   H   I   W
61/21                                       91/31
GAT TTT CTG GAA CAG CCT ATA TGT TCA GTT    CAG CCC ATT GAC TTG AAC TTT GTG GAT GAA
 D   F   L   E   Q   P   I   C   S   V      Q   P   I   D   L   N   F   V   D   E
121/41                                      151/51
CCA TCA GAA GAT GGT GCG ACA AAC AAG ATT    GAG ATT AGC ATG GAC TGT ATC CGC ATG CAG
 P   S   E   D   G   A   T   N   K   I      E   I   S   M   D   C   I   R   M   Q
181/61                                      211/71
GAC TCG GAC CTG AGT GAC CCC ATG TGG CCA    CAG TAC ACG AAC CTG GGC TCC TGA AAC AGC
 D   S   D   L   S   D   P   M   W   P      Q   Y   T   N   L   G   L   L   N   S
241/81                                      271/91
ATG GAC CAG CAG ATT CAG AAC GGC TCC TCG    TCC ACC AGT CCC TAT AAC ACA GAC CAC GCG
 M   D   Q   Q   I   Q   N   G   S   S      S   T   S   P   Y   N   T   D   H   A
301/101                                     331/111
CAG AAC AGC GTC ACG GCG CCC TCG CCC TAC    GCA CAG CCC AGC TCC ACC TTC GAT GCT CTC
 Q   N   S   V   T   A   P   S   P   Y      A   Q   P   S   S   T   F   D   A   L
361/121                                     391/131
TCT CCA TCA CCC GCC ATC CCC TCC AAC ACC    GAC TAC CCA GGC CCG CAC AGT TTC GAC GTG
 S   P   S   P   A   I   P   S   N   T      D   Y   P   G   P   H   S   F   D   V
421/141                                     451/151
TCC TTC CAG CAG TCG AGC ACC GCC AAG TCG    GCC ACC TGG ACG TAT TCC ACT GAA CTG AAG
 S   F   Q   Q   S   S   T   A   K   S      A   T   W   T   Y   S   T   E   L   K
481/161                                     511/171
AAA CTC TAC TGC CAA ATT GCA AAG ACA TGC    CCC ATC CAG ATC AAG GTG ATG ACC CCA CCT
 K   L   Y   C   Q   I   A   K   T   C      P   I   Q   I   K   V   M   T   P   P
541/181                                     571/191
CCT CAG GGA GCT GTT ATC CGC GCC ATG CCT    GTC TAC AAA AAA GCT GAG CAC GTC ACG GAG
 P   Q   G   A   V   I   R   A   M   P      V   Y   K   K   A   E   H   V   T   E
601/201                                     631/211
GTG GTG AAG CGG TGC CCC AAC CAT GAG CTG    AGC CGT GAA TTC AAC GAG GGA CAG ATT GCC
 V   V   K   R   C   P   N   H   E   L      S   R   E   F   N   E   G   Q   I   A
661/221                                     691/231
CCT CCT AGT CAT TTG ATT CGA GTA GAG GGG    AAC AGC CAT GCC CAG TAT GTA GAA GAT CCC
 P   P   S   H   L   I   R   V   E   G      N   S   H   A   Q   Y   V   E   D   P
721/241                                     751/251
ATC ACA GGA AGA CAG AGT GTG CTG GTA CCT    TAT GAG CCA CCC CAG GTT GGC ACT GAA TTC
 I   T   G   R   Q   S   V   L   V   P      Y   E   P   P   Q   V   G   T   E   F
781/261                                     811/271
ACG ACA GTc TTG TAC AAT TTC ATG TGT AAC    AGC AGT TGT GTT GGA GGG ATG AAc cgC cgt
 T   T   V   L   Y   N   F   M   C   N      S   S   C   V   G   G   M   N   R   R
841/281                                     871/291
CCa aTT TTA ATC ATT GTT ACT CTG GAA ACC    AGA GAT GGG CAA GTC CTG GGC CGA CGC TGC
 P   I   L   I   I   V   T   L   E   T      R   D   G   Q   V   L   G   R   R   C
901/301                                     931/311
TTT GAG GCC CGG ATC TGT GCT TGC CCA GGA    AGA GAC AGG AAG GCG GAT GAA GAT AGC ATC
 F   E   A   R   I   C   A   C   P   G      R   D   R   K   A   D   E   D   S   I
961/321                                     991/331
AGA AAG CAG CAA GTT TCG GAC AGT ACA AAG    AAC GGT GAT GGT ACG AAG CGC CCG TTT CGT
 R   K   Q   Q   V   S   D   S   T   K      N   G   D   G   T   K   R   P   F   R
1021/341                                    1051/351
CAG AAC ACA CAT GGT ATC CAG ATG ACA TCC    ATC AAG AAA CGA AGA TCC CCA GAT GAT GAA
 Q   N   T   H   G   I   Q   M   T   S      I   K   K   R   R   S   P   D   D   E
1081/361                                    1111/371
CTG TTA TAC TTA CCA GTG AGG GGC CGT GAG    ACT TAT GAA ATG CTG TTG AAG ATC AAA GAG
 L   L   Y   L   P   V   R   G   R   E      T   Y   E   M   L   L   K   I   K   E
1141/381                                    1171/391
TCC CTG GAA CTC ATG CAG TAC CTT CCT CAG    CAC ACA ATT GAA ACG TAG AGG CAA CAG CAA
 S   L   E   L   M   Q   Y   L   P   Q      H   T   I   E   T   *   R   Q   Q   Q
```

Figure 11A

```
1201/401                                           1231/411
CAG CAG CAG CAC CAG CAC TTA CTT CAG AAA  CAT CTC CTT TCA GCC TGC TTC AGG AAT GAG
 Q   Q   Q   H   Q   H   L   L   Q   K    H   L   L   S   A   C   F   R   N   E
1261/421                                           1291/431
CTT GTG GAG CCC CGG AGA GAA ACT CCA AAA  CAA TCT GAC GTC TTC TTT AGA CAT TCC AAG
 L   V   E   P   R   R   E   T   P   K    Q   S   D   V   F   F   R   H   S   K
1321/441
CCC CCA AAC CGA TCA GTG TAC CCA TAG
 P   P   N   R   S   V   Y   P   *
```

Figure 12

```
1/1                                         31/11
ATG TTG TAC CTG GAA AAC AAT GCC CAG ACT CAA TTT AGT GAG CCA CAG TAC ACG AAC CTG
 M   L   Y   L   E   N   N   A   Q   T   Q   F   S   E   P   Q   Y   T   N   L
61/21                                       91/31
GGG CTC CTG AAC AGC ATG GAC CAG CAG ATT CAG AAC GGC TCC TCG TCC ACC AGT CCC TAT
 G   L   L   N   S   M   D   Q   Q   I   Q   N   G   S   S   S   T   S   P   Y
121/41                                      151/51
AAC ACA GAC CAC GCG CAG AAC AGC GTC ACG GCG CCC TCG CCC TAC GCA CAG CCC AGC TCC
 N   T   D   H   A   Q   N   S   V   T   A   P   S   P   Y   A   Q   P   S   S
181/61                                      211/71
ACC TTC GAT GCT CTC TCT CCA TCA CCC GCC ATC CCC TCC AAC ACC GAC TAC CCA GGC CCG
 T   F   D   A   L   S   P   S   P   A   I   P   S   N   T   D   Y   P   G   P
241/81                                      271/91
CAC AGT TTC GAC GTG TCC TTC CAG CAG TCG AGC ACC GCC AAG TCG GCC ACC TGG ACG TAT
 H   S   F   D   V   S   F   Q   Q   S   S   T   A   K   S   A   T   W   T   Y
301/101                                     331/111
TCC ACT GAA CTG AAG AAA CTC TAC TGC CAA ATT GCA AAG ACA TGC CCC ATC CAG ATC AAG
 S   T   E   L   K   K   L   Y   C   Q   I   A   K   T   C   P   I   Q   I   K
361/121                                     391/131
GTG ATG ACC CCA CCT CCT CAG GGA GCT GTT ATC CGC GCC ATG CCT GTC TAC AAA AAA GCT
 V   M   T   P   P   P   Q   G   A   V   I   R   A   M   P   V   Y   K   K   A
421/141                                     451/151
GAG CAC GTC ACG GAG GTG GTG AAG CGG TGC CCC AAC CAT GAG CTG AGC CGT GAA TTC AAC
 E   H   V   T   E   V   V   K   R   C   P   N   H   E   L   S   R   E   F   N
481/161                                     511/171
GAG GGA CAG ATT GCC CCT CCT AGT CAT TTG ATT CGA GTA GAG GGA AAC AGC CAT GCC CAG
 E   G   Q   I   A   P   P   S   H   L   I   R   V   E   G   N   S   H   A   Q
541/181                                     571/191
TAT GTA GAA GAT CCC ATC ACA GGA AGA CAG AGT GTG CTG GTA CCT TAT GAG CCA CCC CAG
 Y   V   E   D   P   I   T   G   R   Q   S   V   L   V   P   Y   E   P   P   Q
601/201                                     631/211
GTT GGC ACT GAA TTC ACG ACA GTc TTG TAC AAT TTC ATG TGT AAC AGC AGT TGT GTT GGA
 V   G   T   E   F   T   T   V   L   Y   N   F   M   C   N   S   S   C   V   G
661/221                                     691/231
GGG ATG AAc cgC Cgt CCa aTT TTA ATC ATT GTT ACT CTG GAA ACC AGA GAT GGG CAA GTC
 G   M   N   R   R   P   I   L   I   I   V   T   L   E   T   R   D   G   Q   V
721/241                                     751/251
CTG GGC CGA CGC TGC TTT GAG GCC CGG ATC TGT GCT TGC CCA GGA AGA GAC AGG AAG GCG
 L   G   R   R   C   F   E   A   R   I   C   A   C   P   G   R   D   R   K   A
781/261                                     811/271
GAT GAA GAT AGC ATC AGA AAG CAG CAA GTT TCG GAC AGT ACA AAG AAC GGT GAT GGT ACG
 D   E   D   S   I   R   K   Q   Q   V   S   D   S   T   K   N   G   D   G   T
841/281                                     871/291
AAG CGC CCG TTT CGT CAG AAC ACA CAT GGT ATC CAG ATG ACA TCC ATC AAG AAA CGA AGA
 K   R   P   F   R   Q   N   T   H   G   I   Q   M   T   S   I   K   K   R   R
901/301                                     931/311
TCC CCA GAT GAT GAA CTG TTA TAC TTA CCA GTG AGG GGC CGT GAG ACT TAT GAA ATG CTG
 S   P   D   D   E   L   L   Y   L   P   V   R   G   R   E   T   Y   E   M   L
961/321                                     991/331
TTG AAG ATC AAA GAG TCC CTG GAA CTC ATG CAG TAC CTT CCT CAG CAC ACA ATT GAA ACG
 L   K   I   K   E   S   L   E   L   M   Q   Y   L   P   Q   H   T   I   E   T
1021/341                                    1051/351
TAC AGG CAA CAG CAA CAG CAG CAG CAC CAG CAC TTA CTT CAG AAA CAG ACC TCA ATA CAG
 Y   R   Q   Q   Q   Q   Q   Q   H   Q   H   L   L   Q   K   Q   T   S   I   Q
1081/361                                    1111/371
TCT CCA TCT TCA TAT GGT AAC AGC TCC CCA CCT CTG AAC AAA ATG AAC AGC ATG AAC AAG
 S   P   S   S   Y   G   N   S   S   P   P   L   N   K   M   N   S   M   N   K
1141/381                                    1171/391
CTG CCT TCT GTG AGC CAG CTT ATC AAC CCT CAG CAG CGC AAC GCC CTC ACT CCT ACA ACC
 L   P   S   V   S   Q   L   I   N   P   Q   Q   R   N   A   L   T   P   T   T
```

Figure 12A

```
1201/401                                    1231/411
ATT CCT GAT GGC ATG GGA GCC AAC ATT CCC ATG ATG GGC ACC CAC ATG CCA ATG GCT GGA
 I   P   D   G   M   G   A   N   I   P   M   M   G   T   H   M   P   M   A   G
1261/421                                    1291/431
GAC ATG AAT GGA CTC AGC CCC ACC CAG GCA CTC CCT CCC CCA CTC TCC ATG CCA TCC ACC
 D   M   N   G   L   S   P   T   Q   A   L   P   P   P   L   S   M   P   S   T
1321/441                                    1351/451
TCC CAC TGC ACA CCC CCA CCT CCG TAT CCC ACA GAT TGC AGC ATT GTC AGT TTC TTA GCG
 S   H   C   T   P   P   P   P   Y   P   T   D   C   S   I   V   S   F   L   A
1381/461                                    1411/471
AGG TTG GGC TGT TCA TCA TGT CTG GAC TAT TTC ACG ACC CAG GGG CTG ACC ACC ATC TAT
 R   L   G   C   S   S   C   L   D   Y   F   T   T   Q   G   L   T   T   I   Y
1441/481                                    1471/491
CAG ATT GAG CAT TAC TCC ATG GAT GAT CTG GCA AGT CTG AAA ATC CCT GAG CAA TTT CGA
 Q   I   E   H   Y   S   M   D   D   L   A   S   L   K   I   P   E   Q   F   R
1501/501                                    1531/511
CAT GCG ATC TGG AAG GGC ATC CTG GAC CAC CGG CAG CTC CAC GAA TTC TCC TCC CCT TCT
 H   A   I   W   K   G   I   L   D   H   R   Q   L   H   E   F   S   S   P   S
1561/521                                    1591/531
CAT CTC CTG CGG ACC CCA AGC AGT GCC TCT ACA GTC AGT GTG GGC TCC AGT GAG ACC CGG
 H   L   L   R   T   P   S   S   A   S   T   V   S   V   G   S   S   E   T   R
1621/541                                    1651/551
GGT GAG CGT GTT ATT GAT GCT GTG CGA TTC ACC CTC CGC CAG ACC ATC TCT TTC CCA CCC
 G   E   R   V   I   D   A   V   R   F   T   L   R   Q   T   I   S   F   P   P
1681/561                                    1711/571
CGA GAT GAG TGG AAT GAC TTC AAC TTT GAC ATG GAT GCT CGC CGC AAT AAG CAA CAG CGC
 R   D   E   W   N   D   F   N   F   D   M   D   A   R   R   N   K   Q   Q   R
1741/581
ATC AAA GAG GAG GGG GAG TGA
 I   K   E   E   G   E   *
```

Figure 13

```
1/1                                      31/11
ATG TTG TAC CTG GAA AAC AAT GCC CAG ACT CAA TTT AGT GAG CCA CAG TAC ACG AAC CTG
 M   L   Y   L   E   N   N   A   Q   T   Q   F   S   E   P   Q   Y   T   N   L
61/21                                    91/31
GGG CTC CTG AAC AGC ATG GAC CAG CAG ATT CAG AAC GGC TCC TCG TCC ACC AGT CCC TAT
 G   L   L   N   S   M   D   Q   Q   I   Q   N   G   S   S   S   T   S   P   Y
121/41                                   151/51
AAC ACA GAC CAC GCG CAG AAC AGC GTC ACG GCG CCC TCG CCC TAC GCA CAG CCC AGC TCC
 N   T   D   H   A   Q   N   S   V   T   A   P   S   P   Y   A   Q   P   S   S
181/61                                   211/71
ACC TTC GAT GCT CTC TCT CCA TCA CCC GCC ATC CCC TCC AAC ACC GAC TAC CCA GGC CCG
 T   F   D   A   L   S   P   S   P   A   I   P   S   N   T   D   Y   P   G   P
241/81                                   271/91
CAC AGT TTC GAC GTG TCC TTC CAG CAG TCG AGC ACC GCC AAG TCG GCC ACC TGG ACG TAT
 H   S   F   D   V   S   F   Q   Q   S   S   T   A   K   S   A   T   W   T   Y
301/101                                  331/111
TCC ACT GAA CTG AAG AAA CTC TAC TGC CAA ATT GCA AAG ACA TGC CCC ATC CAG ATC AAG
 S   T   E   L   K   K   L   Y   C   Q   I   A   K   T   C   P   I   Q   I   K
361/121                                  391/131
GTG ATG ACC CCA CCT CCT CAG GGA GCT GTT ATC CGC GCC ATG CCT GTC TAC AAA AAA GCT
 V   M   T   P   P   P   Q   G   A   V   I   R   A   M   P   V   Y   K   K   A
421/141                                  451/151
GAG CAC GTC ACG GAG GTG GTG AAG CGG TGC CCC AAC CAT GAG CTG AGC CGT GAA TTC AAC
 E   H   V   T   E   V   V   K   R   C   P   N   H   E   L   S   R   E   F   N
481/161                                  511/171
GAG GGA CAG ATT GCC CCT CCT AGT CAT TTG ATT CGA GTA GAG GGG AAC AGC CAT GCC CAG
 E   G   Q   I   A   P   P   S   H   L   I   R   V   E   G   N   S   H   A   Q
541/181                                  571/191
TAT GTA GAA GAT CCC ATC ACA GGA AGA CAG AGT GTG CTG GTA CCT TAT GAG CCA CCC CAG
 Y   V   E   D   P   I   T   G   R   Q   S   V   L   V   P   Y   E   P   P   Q
601/201                                  631/211
GTT GGC ACT GAA TTC ACG ACA GTc TTG TAC AAT TTC ATG TGT AAC AGC AGT TGT GTT GGA
 V   G   T   E   F   T   T   V   L   Y   N   F   M   C   N   S   S   C   V   G
661/221                                  691/231
·GGG ATG AAc cgC Cgt CCa aTT TTA ATC ATT GTT ACT CTG GAA ACC AGA GAT GGG CAA GTC
 G   M   N   R   R   P   I   L   I   I   V   T   L   E   T   R   D   G   Q   V
721/241                                  751/251
CTG GGC CGA CGC TGC TTT GAG GCC CGG ATC TGT GCT TGC CCA GGA AGA GAC AGG AAG GCG
 L   G   R   R   C   F   E   A   R   I   C   A   C   P   G   R   D   R   K   A
781/261                                  811/271
GAT GAA GAT AGC ATC AGA AAG CAG CAA GTT TCG GAC AGT ACA AAG AAC GGT GAT GGT ACG
 D   E   D   S   I   R   K   Q   Q   V   S   D   S   T   K   N   G   D   G   T
841/281                                  871/291
AAG CGC CCG TTT CGT CAG AAC ACA CAT GGT ATC CAG ATG ACA TCC ATC AAG AAA CGA AGA
 K   R   P   F   R   Q   N   T   H   G   I   Q   M   T   S   I   K   K   R   R
901/301                                  931/311
TCC CCA GAT GAT GAA CTG TTA TAC TTA CCA GTG AGG GGC CGT GAG ACT TAT GAA ATG CTG
 S   P   D   D   E   L   L   Y   L   P   V   R   G   R   E   T   Y   E   M   L
961/321                                  991/331
TTG AAG ATC AAA GAG TCC CTG GAA CTC ATG CAG TAC CTT CCT CAG CAC ACA ATT GAA ACG
 L   K   I   K   E   S   L   E   L   M   Q   Y   L   P   Q   H   T   I   E   T
1021/341                                 1051/351
TAC AGG CAA CAG CAA CAG CAG CAG CAC CAG CAC TTA CTT CAG AAA CAG ACC TCA ATA cAG
 Y   R   Q   Q   Q   Q   Q   Q   H   Q   H   L   L   Q   K   Q   T   S   I   Q
1081/361                                 1111/371
TCT CCA TCT TCA TAT GGT AAC AGC TCC CCA CCT CTG AAC AAA ATG AAC AGC ATG AAC AAG
 S   P   S   S   Y   G   N   S   S   P   P   L   N   K   M   N   S   M   N   K
1141/381                                 1171/391
CTG CCT TCT GTG AGC CAG CTT ATC AAC CCT CAG CAG CGC AAC GCC CTC ACT CCT ACA ACC
 L   P   S   V   S   Q   L   I   N   P   Q   Q   R   N   A   L   T   P   T   T
```

Figure 13A

```
1201/401                                    1231/411
ATT CCT GAT GGC ATG GGA GCC AAC ATT CCC ATG ATG GGC ACC CAC ATG CCA ATG GCT GGA
 I   P   D   G   M   G   A   N   I   P   M   M   G   T   H   M   P   M   A   G
1261/421                                    1291/431
GAC ATG AAT GGA CTC AGC CCC ACC CAG GCA CTC CCT CCC CCA CTC TCC ATG CCA TCC ACC
 D   M   N   G   L   S   P   T   Q   A   L   P   P   P   L   S   M   P   S   T
1321/441                                    1351/451
TCC CAC TGC ACA CCC CCA CCT CCG TAT CCC ACA GAT TGC AGC ATT GTC AGG ATC TGG CAA
 S   H   C   T   P   P   P   P   Y   P   T   D   C   S   I   V   R   I   W   Q
1381/461
GTC TGA
 V   *
```

Figure 14

```
1/1                                             31/11
ATG TTG TAC CTG GAA AAC AAT GCC CAG ACT CAA TTT AGT GAG CCA CAG TAC ACG AAC CTG
 M   L   Y   L   E   N   N   A   Q   T   Q   F   S   E   P   Q   Y   T   N   L
61/21                                           91/31
GGG CTC CTG AAC AGC ATG GAC CAG CAG ATT CAG AAC GGC TCC TCG TCC ACC AGT CCC TAT
 G   L   L   N   S   M   D   Q   Q   I   Q   N   G   S   S   S   T   S   P   Y
121/41                                          151/51
AAC ACA GAC CAC GCG CAG AAC AGC GTC ACG GCG CCC TCG CCC TAC GCA CAG CCC AGC TCC
 N   T   D   H   A   Q   N   S   V   T   A   P   S   P   Y   A   Q   P   S   S
181/61                                          211/71
ACC TTC GAT GCT CTC TCT CCA TCA CCC GCC ATC CCC TCC AAC ACC GAC TAC CCA GGC CCG
 T   F   D   A   L   S   P   S   P   A   I   P   S   N   T   D   Y   P   G   P
241/81                                          271/91
CAC AGT TTC GAC GTG TCC TTC CAG CAG TCG AGC ACC GCC AAG TCG GCC ACC TGG ACG TAT
 H   S   F   D   V   S   F   Q   Q   S   S   T   A   K   S   A   T   W   T   Y
301/101                                         331/111
TCC ACT GAA CTG AAG AAA CTC TAC TGC CAA ATT GCA AAG ACA TGC CCC ATC CAG ATC AAG
 S   T   E   L   K   K   L   Y   C   Q   I   A   K   T   C   P   I   Q   I   K
361/121                                         391/131
GTG ATG ACC CCA CCT CCT CAG GGA GCT GTT ATC CGC GCC ATG CCT GTC TAC AAA AAA GCT
 V   M   T   P   P   P   Q   G   A   V   I   R   A   M   P   V   Y   K   K   A
421/141                                         451/151
GAG CAC GTC ACG GAG GTG GTG AAG CGG TGC CCC AAC CAT GAG CTG AGC CGT GAA TTC AAC
 E   H   V   T   E   V   V   K   R   C   P   N   H   E   L   S   R   E   F   N
481/161                                         511/171
GAG GGA CAG ATT GCC CCT CCT AGT CAT TTG ATT CGA GTA GAG GGG AAC AGC CAT GCC CAG
 E   G   Q   I   A   P   P   S   H   L   I   R   V   E   G   N   S   H   A   Q
541/181                                         571/191
TAT GTA GAA GAT CCC ATC ACA GGA AGA CAG AGT GTG CTG GTA CCT TAT GAG CCA CCC CAG
 Y   V   E   D   P   I   T   G   R   Q   S   V   L   V   P   Y   E   P   P   Q
601/201                                         631/211
GTT GGC ACT GAA TTC ACG ACA GTC TTG TAC AAT TTC ATG TGT AAC AGC AGT TGT GTT GGA
 V   G   T   E   F   T   T   V   L   Y   N   F   M   C   N   S   S   C   V   G
661/221                                         691/231
GGG ATG AAC cgC Cgt CCa aTT TTA ATC ATT GTT ACT CTG GAA ACC AGA GAT GGG CAA GTC
 G   M   N   R   R   P   I   L   I   I   V   T   L   E   T   R   D   G   Q   V
721/241                                         751/251
CTG GGC CGA CGC TGC TTT GAG GCC CGG ATC TGT GCT TGC CCA GGA AGA GAC AGG AAG GCG
 L   G   R   R   C   F   E   A   R   I   C   A   C   P   G   R   D   R   K   A
781/261                                         811/271
GAT GAA GAT AGC ATC AGA AAG CAG CAA GTT TCG GAC AGT ACA AAG AAC GGT GAT GGT ACG
 D   E   D   S   I   R   K   Q   Q   V   S   D   S   T   K   N   G   D   G   T
841/281                                         871/291
AAG CGC CCG TTT CGT CAG AAC ACA CAT GGT ATC CAG ATG ACA TCC ATC AAG AAA CGA AGA
 K   R   P   F   R   Q   N   T   H   G   I   Q   M   T   S   I   K   K   R   R
901/301                                         931/311
TCC CCA GAT GAT GAA CTG TTA TAC TTA CCA GTG AGG GGC CGT GAG ACT TAT GAA ATG CTG
 S   P   D   D   E   L   L   Y   L   P   V   R   G   R   E   T   Y   E   M   L
961/321                                         991/331
TTG AAG ATC AAA GAG TCC CTG GAA CTC ATG CAG TAC CTT CCT CAG CAC ACA ATT GAA ACG
 L   K   I   K   E   S   L   E   L   M   Q   Y   L   P   Q   H   T   I   E   T
1021/341                                        1051/351
TAC AGG CAA CAG CAA CAG CAG CAG CAC CAG CAC TTA CTT CAG AAA CAT CTC CTT TCA GCC
 Y   R   Q   Q   Q   Q   Q   Q   H   Q   H   L   L   Q   K   H   L   L   S   A
1081/361                                        1111/371
TGC TTC AGG AAT GAG CTT GTG GAG CCC CGG AGA GAA ACT CCA AAA CAA TCT GAC GTC TTC
 C   F   R   N   E   L   V   E   P   R   R   E   T   P   K   Q   S   D   V   F
1141/381                                        1171/391
TTT AGA CAT TCC AAG CCC CCA AAC CGA TCA GTG TAC CCA TAG
 F   R   H   S   K   P   P   N   R   S   V   Y   P   *
```

Figure 15

```
1/1                                              31/11
ATG AAT TTT GAA ACT TCA CGG TGT GCC ACC CTA CAG TAC TGC CCC GAC CCT TAC ATC CAG
 M   N   F   E   T   S   R   C   A   T   L   Q   Y   C   P   D   P   Y   I   Q
61/21                                            91/31
CGT TTC ATA GAA ACC CCA GCT CAT TTC TCG TGG AAA GAA AGT TAT TAC AGA TCT GCC ATG
 R   F   I   E   T   P   A   H   F   S   W   K   E   S   Y   Y   R   S   A   M
121/41                                           151/51
TCG CAG AGC ACC CAG ACA AGC GAG TTC CTC AGC CCA GAG GTC TTC CAG CAT ATC TGG GAT
 S   Q   S   T   Q   T   S   E   F   L   S   P   E   V   F   Q   H   I   W   D
181/61                                           211/71
TTT CTG GAA CAG CCT ATA TGC TCA GTA CAG ccc ATC GAG TTG AAC TTT GTG GAT GAA CCT
 F   L   E   Q   P   I   C   S   V   Q   P   I   E   L   N   F   V   D   E   P
241/81                                           271/91
TCC GAA AAT GGT GCa aCa aaC aaG ATT GAG ATT AGC ATG GAT TGT ATc cGC ATG Caa GAC
 S   E   N   G   A   T   N   K   I   E   I   S   M   D   C   I   R   M   Q   D
301/101                                          331/111
TCA GAc cTC AGT GAc ccc ATG Tgg CCA CAG TAC ACG AAC CTG GGG CTC CTG AAC AGC ATG
 S   D   L   S   D   P   M   W   P   Q   Y   T   N   L   G   L   L   N   S   M
361/121                                          391/131
GAC CAG CAG ATT CAG AAC GGC TCC TCG TCC ACC AGC CCC TAC AaC ACA GAC CAC GCA CAG
 D   Q   Q   I   Q   N   G   S   S   S   T   S   P   Y   N   T   D   H   A   Q
421/141                                          451/151
AAT AGC GTG ACG GCG CCC TCG CCC TAT GCA CAG CCC AGC TCC ACC TTT GAT GCC CTC TCT
 N   S   V   T   A   P   S   P   Y   A   Q   P   S   S   T   F   D   A   L   S
481/161                                          511/171
CCA TCC CCT GCC ATT CCC TCC AAC ACA GAT TAC CCG GGC CCA CAC AGC TTC GAT GTG TCC
 P   S   P   A   I   P   S   N   T   D   Y   P   G   P   H   S   F   D   V   S
541/181                                          571/191
TTC CAG CAG TCA AGC ACT GCC AAG TCA GCC ACC TGG ACG TAT TCC ACC GAA CTG AAG AAG
 F   Q   Q   S   S   T   A   K   S   A   T   W   T   Y   S   T   E   L   K   K
601/201                                          631/211
CTG TAC TGC CAG ATT GCG AAG ACA TGC CCC ATC CAG ATC AAG GTG ATG ACC CCA CCC CCA
 L   Y   C   Q   I   A   K   T   C   P   I   Q   I   K   V   M   T   P   P   P
661/221                                          691/231
CAG GGC GCT GTt ATC CGT GCC ATG CCT GTC TAC AAG AAA GCT GAG CAT GTC ACC GAG GTT
 Q   G   A   V   I   R   A   M   P   V   Y   K   K   A   E   H   V   T   E   V
721/241                                          751/251
GTG AAA CGA TGC CCT AAC CAT GAG CTG AGC CGT GAG TTC AAT GAG GGA CAG ATT GCC CCT
 V   K   R   C   P   N   H   E   L   S   R   E   F   N   E   G   Q   I   A   P
781/261                                          811/271
CCC AGT CAT CTG ATT CGA GTA gAA GGG AAC AGC CAT GCC CAG TAT GTA GAA GAT CCT ATC
 P   S   H   L   I   R   V   E   G   N   S   H   A   Q   Y   V   E   D   P   I
841/281                                          871/291
ACG GGA AGG CAG AGC GTG CTG GTC CCT TAT GAG CCA CCA CaG GTT GGC ACT GAA TTC ACA
 T   G   R   Q   S   V   L   V   P   Y   E   P   P   Q   V   G   T   E   F   T
901/301                                          931/311
ACA GTC CTG TAC aAT TTC ATG TGT AAC AGC AGC TGC GTC GGA GGA ATG AAC AGA CgT CCA
 T   V   L   Y   N   F   M   C   N   S   S   C   V   G   G   M   N   R   R   P
961/321                                          991/331
ATT TTA ATC ATC GTT ACT CTG GAA ACC AGA GAT GGG CAA gTC CTG GGC CGA CGG TGC TTT
 I   L   I   I   V   T   L   E   T   R   D   G   Q   V   L   G   R   R   C   F
1021/341                                         1051/351
GAG GCC CGG ATC TGT GCt TGC CCA GGA AGA GAC CGG AAG GCA GAT GAA GAC AGC ATC AGA
 E   A   R   I   C   A   C   P   G   R   D   R   K   A   D   E   D   S   I   R
1081/361                                         1111/371
AAG CAG CAA GTA TCG GAC AGC GCA AAG AAC GGC GAT GGT ACG AAG CGC CCT TTC CGT CAG
 K   Q   Q   V   S   D   S   A   K   N   G   D   G   T   K   R   P   F   R   Q
1141/381                                         1171/391
AAT ACA CAC GGA ATC CAG ATG ACT TCC ATC AAG AAA CGG AGA TCC CCA GAT GAT GAG CTG
 N   T   H   G   I   Q   M   T   S   I   K   K   R   R   S   P   D   D   E   L
```

Figure 15A

```
1201/401                                           1231/411
CTG TAC CTA CCA GTG AGA GGT CGT GAG ACG TAC GAG ATG TTG CTG AAG ATC AAA GAG TCA
 L   Y   L   P   V   R   G   R   E   T   Y   E   M   L   L   K   I   K   E   S
1261/421                                           1291/431
CTG GAG CTC ATG CAG TAC CTC CCT CAG CAC ACG ATC GAA ACG TAC AGG CAG CAG CAG CAG
 L   E   L   M   Q   Y   L   P   Q   H   T   I   E   T   Y   R   Q   Q   Q   Q
1321/441                                           1351/451
CAG CAG CAC CAG CAC CTA CTT CAG AAA CAG ACC TCG ATG CAG TCT CAG TCT TCA TAT GGC
 Q   Q   H   Q   H   L   L   Q   K   Q   T   S   M   Q   S   Q   S   S   Y   G
1381/461                                           1411/471
AAC AGT TCC CCA CCT CTG AAC AAA ATG AAC AGC ATG AAC AAG CTG CCT TCC GTG AGC CAG
 N   S   S   P   P   L   N   K   M   N   S   M   N   K   L   P   S   V   S   Q
1441/481                                           1471/491
CTT ATC AAC CCA CAG CAG CGC AAT GCC CTC ACT CCC ACC ACC ATG CCT GAG GGC ATG GGA
 L   I   N   P   Q   Q   R   N   A   L   T   P   T   T   M   P   E   G   M   G
1501/501                                           1531/511
GCC AAC ATT CCT ATG ATG GGC ACT CAC ATG CCA ATG GCT GGA GAC ATG AAT GGA CTC AGC
 A   N   I   P   M   M   G   T   H   M   P   M   A   G   D   M   N   G   L   S
1561/521                                           1591/531
CCT ACC CAA GCT CTC CCT CCT CCA CTC TCC ATG CCC TCC ACC TCC CAC TGC ACC CCA CCA
 P   T   Q   A   L   P   P   P   L   S   M   P   S   T   S   H   C   T   P   P
1621/541                                           1651/551
CCG CCC TAC CCC ACA GAC TGC AGC ATT GTC AGT TTC TTA GCA Agg Ttg ggC TGC TCA TCA
 P   P   Y   P   T   D   C   S   I   V   S   F   L   A   R   L   G   C   S   S
1661/561                                           1711/571
TGC CTG GAC TAT TTC ACG ACC CAg ggg CTG AcC ACC ATC TaT CAG ATT GAG CAT TAC TCC
 C   L   D   Y   F   T   T   Q   G   L   T   T   I   Y   Q   I   E   H   Y   S
1741/581                                           1771/591
ATG GAT GAT TtG GCa aGT CTG AAG ATc ccT GAA CAG TTC CGA CAT GCC ATC TGG AAg GGC
 M   D   D   L   A   S   L   K   I   P   E   Q   F   R   H   A   I   W   K   G
1801/601                                           1831/611
aTC CTG GAC CAC AGG cAG cTG CAC GAC TTC TCC TCA CCT CCT CaT CTC CTG AGG ACC CCA
 I   L   D   H   R   Q   L   H   D   F   S   S   P   P   H   L   L   R   T   P
1861/621                                           1891/631
AGT GGT GCC TCT ACC GTC AGT GTG GGC TCC AGT GAG ACC CGT GGT GAA CGT GTG ATC GAT
 S   G   A   S   T   V   S   V   G   S   S   E   T   R   G   E   R   V   I   D
1921/641                                           1951/651
GCC GTG CGC TTT ACC CTC CGC CAG ACC ATC TCT TTT CCA CCC CGT GAC GAG TGG AAT GAT
 A   V   R   F   T   L   R   Q   T   I   S   F   P   P   R   D   E   W   N   D
1981/661                                           2011/671
TTC AAC TTT GAC ATG GAT TCT CGT CGC AAC AAG CAG CAG CGT aTC AAA GAG GAA GGA GAA
 F   N   F   D   M   D   S   R   R   N   K   Q   Q   R   I   K   E   E   G   E
2041/681
TGA
 *
```

Figure 16

```
1/1                                             31/11
ATG AAT TTT GAA ACT TCA CGG TGT GCC ACC CTA CAG TAC TGC CCC GAC CCT TAC ATC CAG
 M   N   F   E   T   S   R   C   A   T   L   Q   Y   C   P   D   P   Y   I   Q
61/21                                           91/31
CGT TTC ATA GAA ACC CCA GCT CAT TTC TCG TGG AAA GAA AGT TAT TAC AGA TCT GCC ATG
 R   F   I   E   T   P   A   H   F   S   W   K   E   S   Y   Y   R   S   A   M
121/41                                          151/51
TCG CAG AGC ACC CAG ACA AGC GAG TTC CTC AGC CCA GAG GTC TTC CAG CAT ATC TGG GAT
 S   Q   S   T   Q   T   S   E   F   L   S   P   E   V   F   Q   H   I   W   D
181/61                                          211/71
TTT CTG GAA CAG CCT ATA TGC TCA GTA CAG ccc ATC GAG TTG AAC TTT GTG GAT GAA CCT
 F   L   E   Q   P   I   C   S   V   Q   P   I   E   L   N   F   V   D   E   P
241/81                                          271/91
TCC GAA AAT GGT GCa aCa aaC aaG ATT GAG ATT AGC ATG GAT TGT ATc cGC ATG Caa GAc
 S   E   N   G   A   T   N   K   I   E   I   S   M   D   C   I   R   M   Q   D
301/101                                         331/111
TCA GAc CTC AGT GAc ccc ATG Tgg CCA CAG TAC ACG AAC CTG GGG CTC CTG AAC AGC ATG
 S   D   L   S   D   P   M   W   P   Q   Y   T   N   L   G   L   L   N   S   M
361/121                                         391/131
GAC CAG CAG ATT CAG AAC GGC TCC TCG TCC ACC AGC CCC TAC AaC ACA GAC CAC GCA CAG
 D   Q   Q   I   Q   N   G   S   S   S   T   S   P   Y   N   T   D   H   A   Q
421/141                                         451/151
AAT AGC GTG ACG GCG CCC TCG CCC TAT GCA CAG CCC AGC TCC ACC TTT GAT GCC CTC TCT
 N   S   V   T   A   P   S   P   Y   A   Q   P   S   S   T   F   D   A   L   S
481/161                                         511/171
CCA TCC CCT GCC ATT CCC TCC AAC ACA GAT TAC CCG GGC CCA CAC AGC TTC GAT GTG TCC
 P   S   P   A   I   P   S   N   T   D   Y   P   G   P   H   S   F   D   V   S
541/181                                         571/191
TTC CAG CAG TCA AGC ACT GCC AAG TCA GCC ACC TGG ACG TAT TCC ACC GAA CTG AAG AAG
 F   Q   Q   S   S   T   A   K   S   A   T   W   T   Y   S   T   E   L   K   K
601/201                                         631/211
CTG TAC TGC CAG ATT GCG AAG ACA TGC CCC ATC CAG ATC AAG GTG ATG ACC CCA CCC CCA
 L   Y   C   Q   I   A   K   T   C   P   I   Q   I   K   V   M   T   P   P   P
661/221                                         691/231
CAG GGC GCT GTt ATC CGT GCC ATG CCT GTC TAC AAG AAA GCT GAG CAT GTC ACC GAG GTT
 Q   G   A   V   I   R   A   M   P   V   Y   K   K   A   E   H   V   T   E   V
721/241                                         751/251
GTG AAA CGA TGC CCT AAC CAT GAG CTG AGC CGT GAG TTC AAT GAG GGA CAG ATT GCC CCT
 V   K   R   C   P   N   H   E   L   S   R   E   F   N   E   G   Q   I   A   P
781/261                                         811/271
CCC AGT CAT CTG ATT CGA GTA gAA GGG AAC AGC CAT GCC CAG TAT GTA GAA GAT CCT ATC
 P   S   H   L   I   R   V   E   G   N   S   H   A   Q   Y   V   E   D   P   I
841/281                                         871/291
ACG GGA AGG CAG AGC GTG CTG GTC CCT TAT GAG CCA CCA CaG GTT GGC ACT GAA TTC ACA
 T   G   R   Q   S   V   L   V   P   Y   E   P   P   Q   V   G   T   E   F   T
901/301                                         931/311
ACA GTC CTG TAC aAT TTC ATG TGT AAC AGC AGC TGC GTC GGA GGA ATG AAC AGA CgT CCA
 T   V   L   Y   N   F   M   C   N   S   S   C   V   G   G   M   N   R   R   P
961/321                                         991/331
ATT TTA ATC ATC GTT ACT CTG GAA ACC AGA GAT GGG CAA gTC CTG GGC CGA CGG TGC TTT
 I   L   I   I   V   T   L   E   T   R   D   G   Q   V   L   G   R   R   C   F
1021/341                                        1051/351
GAG GCC CGG ATC TGT GCt TGC CCA GGA AGA GAC CGG AAG GCA GAT GAA GAC AGC ATC AGA
 E   A   R   I   C   A   C   P   G   R   D   R   K   A   D   E   D   S   I   R
1081/361                                        1111/371
AAG CAG CAA GTA TCG GAC AGC GCA AAG AAC GGC GAT GGT ACG AAG CGC CCT TTC CGT CAG
 K   Q   Q   V   S   D   S   A   K   N   G   D   G   T   K   R   P   F   R   Q
1141/381                                        1171/391
AAT ACA CAC GGA ATC CAG ATG ACT TCC ATC AAG AAA CGG AGA TCC CCA GAT GAT GAG CTG
 N   T   H   G   I   Q   M   T   S   I   K   K   R   R   S   P   D   D   E   L
```

Figure 16A

```
1201/401                                    1231/411
CTG TAC CTA CCA GTG AGA GGT CGT GAG ACG TAC GAG ATG TTG CTG AAG ATC AAA GAG TCA
 L   Y   L   P   V   R   G   R   E   T   Y   E   M   L   L   K   I   K   E   S
1261/421                                    1291/431
CTG GAG CTC ATG CAG TAC CTC CCT CAG CAC ACG ATC GAA ACG TAC AGG CAG CAG CAG CAG
 L   E   L   M   Q   Y   L   P   Q   H   T   I   E   T   Y   R   Q   Q   Q   Q
1321/441                                    1351/451
CAG CAG CAC CAG CAC CTA CTT CAG AAA CAG ACC TCG ATG CAG TCT CAG TCT TCA TAT GGC
 Q   Q   H   Q   H   L   L   Q   K   Q   T   S   M   Q   S   Q   S   S   Y   G
1381/461                                    1411/471
AAC AGT TCC CCA CCT CTG AAC AAA ATG AAC AGC ATG AAC AAG CTG CCT TCC GTG AGC CAG
 N   S   S   P   P   L   N   K   M   N   S   M   N   K   L   P   S   V   S   Q
1441/481                                    1471/491
CTT ATC AAC CCA CAG CAG CGC AAT GCC CTC ACT CCC ACC ACC ATG CCT GAG GGC ATG GGA
 L   I   N   P   Q   Q   R   N   A   L   T   P   T   T   M   P   E   G   M   G
1501/501                                    1531/511
GCC AAC ATT CCT ATG ATG GGC ACT CAC ATG CCA ATG GCT GGA GAC ATG AAT GGA CTC AGC
 A   N   I   P   M   M   G   T   H   M   P   M   A   G   D   M   N   G   L   S
1561/521                                    1591/531
CCT ACC CAA GCT CTC CCT CCT CCA CTC TCC ATG CCC TCC ACC TCC CAC TGC ACC CCA CCA
 P   T   Q   A   L   P   P   P   L   S   M   P   S   T   S   H   C   T   P   P
1621/541                                    1651/551
CCG CCC TAC CCC ACA GAC TGC AGC ATT GTC AGG ATT tGG Caa GTC TGA
 P   P   Y   P   T   D   C   S   I   V   R   I   W   Q   V   *
```

Figure 17

```
1/1                                       31/11
ATG AAT TTT GAA ACT TCA CGG TGT GCC ACC   CTA CAG TAC TGC CCC GAC CCT TAC ATC CAG
 M   N   F   E   T   S   R   C   A   T    L   Q   Y   C   P   D   P   Y   I   Q
61/21                                     91/31
CGT TTC ATA GAA ACC CCA GCT CAT TTC TCG   TGG AAA GAA AGT TAT TAC AGA TCT GCC ATG
 R   F   I   E   T   P   A   H   F   S    W   K   E   S   Y   Y   R   S   A   M
121/41                                    151/51
TCG CAG AGC ACC CAG ACA AGC GAG TTC CTC   AGC CCA GAG GTC TTC CAG CAT ATC TGG GAT
 S   Q   S   T   Q   T   S   E   F   L    S   P   E   V   F   Q   H   I   W   D
181/61                                    211/71
TTT CTG GAA CAG CCT ATA TGC TCA GTA CAG   ccc ATC GAG TTG AAC TTT GTG GAT GAA CCT
 F   L   E   Q   P   I   C   S   V   Q    P   I   E   L   N   F   V   D   E   P
241/81                                    271/91
TCC GAA AAT GGT GCa aCa aaC aaG ATT GAG   ATT AGC ATG GAT TGT ATc cGC ATG Caa GAc
 S   E   N   G   A   T   N   K   I   E    I   S   M   D   C   I   R   M   Q   D
301/101                                   331/111
TCA GAc CTC AGT GAc ccc ATG Tgg CCA CAG   TAC ACG aAC cTg ggg CTC CTG aAC AGC ATg
 S   D   L   S   D   P   M   W   P   Q    Y   T   N   L   G   L   L   N   S   M
361/121                                   391/131
GAc cAG CAG ATT CAG AAC GGc TCc TcG TCC   ACC AGC CCc TAC aaC ACA GAC CAC GCA CAG
 D   Q   Q   I   Q   N   G   S   S   S    T   S   P   Y   N   T   D   H   A   Q
421/141                                   451/151
AAT AGC GTG ACG GCG CCc TCG CCc TAT GCA   CAG CCC AGC TCC ACc TTt GAT GCC cTC TCT
 N   S   V   T   A   P   S   P   Y   A    Q   P   S   S   T   F   D   A   L   S
481/161                                   511/171
CCA Tcc ccT GCC ATT CCc TCC aAC ACA GAT   TAC CCG GGC CCA CAC AGc TTC GAT GTG TCC
 P   S   P   A   I   P   S   N   T   D    Y   P   G   P   H   S   F   D   V   S
541/181                                   571/191
TTC CAG CAG TCA AGC AcT GCC AAG TCA GCC   Acc TGG ACG TAT TCC ACC GAA CTG AAG AAG
 F   Q   Q   S   S   T   A   K   S   A    T   W   T   Y   S   T   E   L   K   K
601/201                                   631/211
CTG TAC TGC CAG ATT GCG AAG ACA TGC CCC   ATC CAG ATC AAG GTG ATG ACC CCA CCC CCA
 L   Y   C   Q   I   A   K   T   C   P    I   Q   I   K   V   M   T   P   P   P
661/221                                   691/231
CAG GGC GCT GTT ATC CGT GCC ATG CCT GTC   TAC AAG AAA GCT GAG CAT GTC ACC GAG GTT
 Q   G   A   V   I   R   A   M   P   V    Y   K   K   A   E   H   V   T   E   V
721/241                                   751/251
GTG AAA CGA TGC CCT AAC CAT GAG CTG AGC   CGT GAG TTC AAT GAG GGA CAG ATT GCC CCT
 V   K   R   C   P   N   H   E   L   S    R   E   F   N   E   G   Q   I   A   P
781/261                                   811/271
CCC AGT CAT CTG ATT CGA GTA GAA GGG AAC   AGC CAT GCC CAG TAT GTA GAA GAT CCT ATC
 P   S   H   L   I   R   V   E   G   N    S   H   A   Q   Y   V   E   D   P   I
841/281                                   871/291
ACG GGA AGG CAG AGC GTG CTG GTC CCT TAT   GAG CCA CCA CAG GTT GGC ACT GAA TTC ACA
 T   G   R   Q   S   V   L   V   P   Y    E   P   P   Q   V   G   T   E   F   T
901/301                                   931/311
ACA GTC CTG TAC AAT TTC ATG TGT AAC AGC   AGC TGC GTC GGA GGA ATG AAC AGA CGT CCA
 T   V   L   Y   N   F   M   C   N   S    S   C   V   G   G   M   N   R   R   P
961/321                                   991/331
ATT TTA ATC ATC GTT ACT CTG GAA ACC AGA   GAT GGG CAA GTC CTG GGC CGA CGG TGC TTT
 I   L   I   I   V   T   L   E   T   R    D   G   Q   V   L   G   R   R   C   F
1021/341                                  1051/351
GAG GCC CCG ATC TGT GCT TGC CCA GGA AGA   GAC CGG AAG GCA GAT GAA GAC AGC ATC AGA
 E   A   P   I   C   A   C   P   G   R    D   R   K   A   D   E   D   S   I   R
1081/361                                  1111/371
AAG CAG CAA GTA TCG GAC AGC GCA AAG AAC   GGC GAT GCT TTC CGT CAG AAT ACA CAC GGA
 K   Q   Q   V   S   D   S   A   K   N    G   D   A   F   R   Q   N   T   H   G
1141/381                                  1171/391
ATC CAG ATG ACT TCC ATC AAG AAA CGG AGA   TCC CCA GAT GAT GAG CTG CTG TAC CTA CCA
 I   Q   M   T   S   I   K   K   R   R    S   P   D   D   E   L   L   Y   L   P
```

Figure 17A

```
1201/401                                          1231/411
GTG AGA GGT CGT GAG ACG TAC GAG ATG TTG CTG AAG ATC AAA GAG TCA CTG GAG CTC ATG
 V   R   G   R   E   T   Y   E   M   L   L   K   I   K   E   S   L   E   L   M
1261/421                                          1291/431
CAG TAC CTC CCT CAG CAC ACG ATC GAA ACG TAC AGG CAG CAG CAG CAG CAG CAC CAG
 Q   Y   L   P   Q   H   T   I   E   T   Y   R   Q   Q   Q   Q   Q   H   Q
1321/441                                          1351/451
CAC CTA CTT CAG AAA CAT CTC CTT TCA GCC TGC TTC AGG AAT GAG CTT GTG GAG CCC CGG
 H   L   L   Q   K   H   L   L   S   A   C   F   R   N   E   L   V   E   P   R
1381/461                                          1411/471
GGA GAA GCT CCG ACA CAG TCT GAC GTC TTC TTT AGA CAT TCC AAC CCC CCA AAC CAC TCC
 G   E   A   P   T   Q   S   D   V   F   F   R   H   S   N   P   P   N   H   S
1441/481
GTG TAC CCA TAG
 V   Y   P   *
```

Figure 18

```
1/1                                             31/11
ATG TTG TAC CTG gAA AAC AAT GCC CAG ACT CAA TTT AGT GAG CCA CAG TAC ACG AAC CTG
 M   L   Y   L   E   N   N   A   Q   T   Q   F   S   E   P   Q   Y   T   N   L
61/21                                           91/31
GGG CTC CTG AAC AGC ATG GAC CAG CAG ATT CAG AAC GGC TCC TCG TCC ACC AGC CCC TAC
 G   L   L   N   S   M   D   Q   Q   I   Q   N   G   S   S   S   T   S   P   Y
121/41                                          151/51
AAC ACA GAC CAC GCA CAG AAT AGC GTG ACG GCG CCC TCG CCC TAT GCA CAG CCC AGC TCC
 N   T   D   H   A   Q   N   S   V   T   A   P   S   P   Y   A   Q   P   S   S
181/61                                          211/71
ACC TTT GAT GCC CTC TCT CCA TCC CCT GCC ATT CCC TCC AAC ACA GAT TAC CCG GGC CCA
 T   F   D   A   L   S   P   S   P   A   I   P   S   N   T   D   Y   P   G   P
241/81                                          271/91
CAC AGC TTC GAT GTG TCC TTC CAG CAG TCA AGC ACT GCC AAG TCA GCC ACC TGG ACG TAT
 H   S   F   D   V   S   F   Q   Q   S   S   T   A   K   S   A   T   W   T   Y
301/101                                         331/111
TCC ACC GAA CTG AAG AAG CTG TAC TGC CAG ATT GCG AAG ACA TGC CCC ATC CAG ATC AAG
 S   T   E   L   K   K   L   Y   C   Q   I   A   K   T   C   P   I   Q   I   K
361/121                                         391/131
GTG ATG ACC CCA CCC CCA CAG GGC GCT GTt ATC CGT GCC ATG CCT GTC TAC AAG AAA GCT
 V   M   T   P   P   P   Q   G   A   V   I   R   A   M   P   V   Y   K   K   A
421/141                                         451/151
GAG CAT GTC ACC GAG GTT GTG AAA CGA TGC CCT AAC CAT GAG CTG AGC CGT GAG TTC AAT
 E   H   V   T   E   V   V   K   R   C   P   N   H   E   L   S   R   E   F   N
481/161                                         511/171
GAG GGA CAG ATT GCC CCT CCC AGT CAT CTG ATT CGA GTA gAA GGG AAC AGC CAT GCC CAG
 E   G   Q   I   A   P   P   S   H   L   I   R   V   E   G   N   S   H   A   Q
541/181                                         571/191
TAT GTA GAA GAT CCT ATC ACG GGA AGG CAG AGC GTG CTG GTC CCT TAT GAG CCA CCA CaG
 Y   V   E   D   P   I   T   G   R   Q   S   V   L   V   P   Y   E   P   P   Q
601/201                                         631/211
GTT GGC ACT GAA TTC ACA ACA GTC CTG TAC aAT TTC ATG TGT AAC AGC AGC TGC GTC GGA
 V   G   T   E   F   T   T   V   L   Y   N   F   M   C   N   S   S   C   V   G
661/221                                         691/231
GGA ATG AAC AGA CgT CCA ATT TTA ATC ATC GTT ACT CTG GAA ACC AGA GAT GGG CAA gTC
 G   M   N   R   R   P   I   L   I   I   V   T   L   E   T   R   D   G   Q   V
721/241                                         751/251
CTG GGC CGA CGG TGC TTT GAG GCC CGG ATC TGT GCt TGC CCA GGA AGA GAC CGG AAG GCA
 L   G   R   R   C   F   E   A   R   I   C   A   C   P   G   R   D   R   K   A
781/261                                         811/271
GAT GAA GAC AGC ATC AGA AAG CAG CAA GTA TCG GAC AGC GCA AAG AAC GGC GAT GGT ACG
 D   E   D   S   I   R   K   Q   Q   V   S   D   S   A   K   N   G   D   G   T
841/281                                         871/291
AAG CGC CCT TTC CGT CAG AAT ACA CAC GGA ATC CAG ATG ACT TCC ATC AAG AAA CGG AGA
 K   R   P   F   R   Q   N   T   H   G   I   Q   M   T   S   I   K   K   R   R
901/301                                         931/311
TCC CCA GAT GAT GAG CTG CTG TAC CTA CCA GTG AGA GGT CGT GAG ACG TAC GAG ATG TTG
 S   P   D   D   E   L   L   Y   L   P   V   R   G   R   E   T   Y   E   M   L
961/321                                         991/331
CTG AAG ATC AAA GAG TCA CTG GAG CTC ATG CAG TAC CTC CCT CAG CAC ACG ATC GAA ACG
 L   K   I   K   E   S   L   E   L   M   Q   Y   L   P   Q   H   T   I   E   T
1021/341                                        1051/351
TAC AGG CAG CAG CAG CAG CAG CAG CAC CAG CAC CTA CTT CAG AAA CAG ACC TCG ATG CAG
 Y   R   Q   Q   Q   Q   Q   Q   H   Q   H   L   L   Q   K   Q   T   S   M   Q
1081/361                                        1111/371
TCT CAG TCT TCA TAT GGC AAC AGT TCC CCA CCT CTG AAC AAA ATG AAC AGC ATG AAC AAG
 S   Q   S   S   Y   G   N   S   S   P   P   L   N   K   M   N   S   M   N   K
1141/381                                        1171/391
CTG CCT TCC GTG AGC CAG CTT ATC AAC CCA CAG CAG CGC AAT GCC CTC ACT CCC ACC ACC
 L   P   S   V   S   Q   L   I   N   P   Q   Q   R   N   A   L   T   P   T   T
```

Figure 18A

```
1201/401                                        1231/411
ATG CCT GAG GGC ATG GGA GCC AAC ATT CCT ATG ATG GGC ACT CAC ATG CCA ATG GCT GGA
 M   P   E   G   M   G   A   N   I   P   M   M   G   T   H   M   P   M   A   G
1261/421                                        1291/431
GAC ATG AAT GGA CTC AGC CCT ACC CAA GCT CTC CCT CCT CCA CTC TCC ATG CCC TCC ACC
 D   M   N   G   L   S   P   T   Q   A   L   P   P   P   L   S   M   P   S   T
1321/441                                        1351/451
TCC CAC TGC ACC CCA CCA CCG CCC TAC CCC ACA GAC TGC AGC ATT GTC AGT TTC TTA GCA
 S   H   C   T   P   P   P   P   Y   P   T   D   C   S   I   V   S   F   L   A
1381/461                                        1411/471
Agg Ttg ggC TGC TCA TCA TGC CTG GAC TAT TTC ACG ACC CAg ggg CTG AcC ACC ATC TaT
 R   L   G   C   S   S   C   L   D   Y   F   T   T   Q   G   L   T   T   I   Y
1441/481                                        1471/491
CAG ATT GAG CAT TAC TCC ATG GAT GAT TtG GCa aGT CTG AAG ATc ccT GAA CAG TTC CGA
 Q   I   E   H   Y   S   M   D   D   L   A   S   L   K   I   P   E   Q   F   R
1501/501                                        1531/511
CAT GCC ATC TGG AAg GGC aTC CTG GAc CAC AGG cAG cTG CAC GAC TTC TCC TCA CCT CCT
 H   A   I   W   K   G   I   L   D   H   R   Q   L   H   D   F   S   S   P   P
1561/521                                        1591/531
CaT CTC CTG AGG ACC CCA AGT GGT GCC TCT ACC GTC AGT GTG GGC TCC AGT GAG ACC CGT
 H   L   L   R   T   P   S   G   A   S   T   V   S   V   G   S   S   E   T   R
1621/541                                        1651/551
GGT GAA CGT GTG ATC GAT GCC GTG CGC TTT ACC CTC CGC CAG ACC ATC TCT TTT CCA CCC
 G   E   R   V   I   D   A   V   R   F   T   L   R   Q   T   I   S   F   P   P
1681/561                                        1711/571
CGT GAC GAG TGG AAT GAT TTC AAC TTT GAC ATG GAT TCT CGT CGC AAC AAG CAG CAG CGT
 R   D   E   W   N   D   F   N   F   D   M   D   S   R   R   N   K   Q   Q   R
1741/581
aTC AAA GAG GAA GGA GAA TGA
 I   K   E   E   G   E   *
```

Figure 19

```
1/1                                              31/11
ATG TTG TAC CTG gAA AAC AAT GCC CAG ACT          CAA TTT AGT GAG CCA CAG TAC ACG AAC CTG
 M   L   Y   L   E   N   N   A   Q   T            Q   F   S   E   P   Q   Y   T   N   L
61/21                                            91/31
GGG CTC CTG AAC AGC ATG GAC CAG CAG ATT          CAG AAC GGC TCC TCG TCC ACC AGC CCC TAC
 G   L   L   N   S   M   D   Q   Q   I            Q   N   G   S   S   S   T   S   P   Y
121/41                                           151/51
AaC ACA GAC CAC GCA CAG AAT AGC GTG ACG          GCG CCC TCG CCC TAT GCA CAG CCC AGC TCC
 N   T   D   H   A   Q   N   S   V   T            A   P   S   P   Y   A   Q   P   S   S
181/61                                           211/71
ACC TTT GAT GCC CTC TCT CCA TCC CCT GCC          ATT CCC TCC AAC ACA GAT TAC CCG GGC CCA
 T   F   D   A   L   S   P   S   P   A            I   P   S   N   T   D   Y   P   G   P
241/81                                           271/91
CAC AGC TTC GAT GTG TCC TTC CAG CAG TCA          AGC ACT GCC AAG TCA GCC ACC TGG ACG TAT
 H   S   F   D   V   S   F   Q   Q   S            S   T   A   K   S   A   T   W   T   Y
301/101                                          331/111
TCC ACC GAA CTG AAG AAG CTG TAC TGC CAG          ATT GCG AAG ACA TGC CCC ATC CAG ATC AAG
 S   T   E   L   K   K   L   Y   C   Q            I   A   K   T   C   P   I   Q   I   K
361/121                                          391/131
GTG ATG ACC CCA CCC CCA CAG GGC GCT GTt          ATC CGT GCC ATG CCT GTC TAC AAG AAA GCT
 V   M   T   P   P   P   Q   G   A   V            I   R   A   M   P   V   Y   K   K   A
421/141                                          451/151
GAG CAT GTC ACC GAG GTT GTG AAA CGA TGC          CCT AAC CAT GAG CTG AGC CGT GAG TTC AAT
 E   H   V   T   E   V   V   K   R   C            P   N   H   E   L   S   R   E   F   N
481/161                                          511/171
GAG GGA CAG ATT GCC CCT CCC AGT CAT CTG          ATT CGA GTA gAA GGG AAC AGC CAT GCC CAG
 E   G   Q   I   A   P   P   S   H   L            I   R   V   E   G   N   S   H   A   Q
541/181                                          571/191
TAT GTA GAA GAT CCT ATC ACG GGA AGG CAG          AGC GTG CTG GTC CCT TAT GAG CCA CCA CaG
 Y   V   E   D   P   I   T   G   R   Q            S   V   L   V   P   Y   E   P   P   Q
601/201                                          631/211
GTT GGC ACT GAA TTC ACA ACA GTC CTG TAC          aAT TTC ATG TGT AAC AGC AGC TGC GTC GGA
 V   G   T   E   F   T   T   V   L   Y            N   F   M   C   N   S   S   C   V   G
661/221                                          691/231
GGA ATG AAC AGA CgT CCA ATT TTA ATC ATC          GTT ACT CTG GAA ACC AGA GAT GGG CAA gTC
 G   M   N   R   R   P   I   L   I   I            V   T   L   E   T   R   D   G   Q   V
721/241                                          751/251
CTG GGC CGA CGG TGC TTT GAG GCC CGG ATC          TGT GCt TGC CCA GGA AGA GAC CGG AAG GCA
 L   G   R   R   C   F   E   A   R   I            C   A   C   P   G   R   D   R   K   A
781/261                                          811/271
GAT GAA GAC AGC ATC AGA AAG CAG CAA GTA          TCG GAC AGC GCA AAG AAC GGC GAT GGT ACG
 D   E   D   S   I   R   K   Q   Q   V            S   D   S   A   K   N   G   D   G   T
841/281                                          871/291
AAG CGC CCT TTC CGT CAG AAT ACA CAC GGA          ATC CAG ATG ACT TCC ATC AAG AAA CGG AGA
 K   R   P   F   R   Q   N   T   H   G            I   Q   M   T   S   I   K   K   R   R
901/301                                          931/311
TCC CCA GAT GAT GAG CTG CTG TAC CTA CCA          GTG AGA GGT CGT GAG ACG TAC GAG ATG TTG
 S   P   D   D   E   L   L   Y   L   P            V   R   G   R   E   T   Y   E   M   L
961/321                                          991/331
CTG AAG ATC AAA GAG TCA CTG GAG CTC ATG          CAG TAC CTC CCT CAG CAC ACG ATC GAA ACG
 L   K   I   K   E   S   L   E   L   M            Q   Y   L   P   Q   H   T   I   E   T
1021/341                                         1051/351
TAC AGG CAG CAG CAG CAG CAG CAG CAC CAG          CAC CTA CTT CAG AAA CAG ACC TCG ATG CAG
 Y   R   Q   Q   Q   Q   Q   Q   H   Q            H   L   L   Q   K   Q   T   S   M   Q
1081/361                                         1111/371
TCT CAG TCT TCA TAT GGC AAC AGT CCC CCA          CCT CTG AAC AAA ATG AAC AGC ATG AAC AAG
 S   Q   S   S   Y   G   N   S   P   P            P   L   N   K   M   N   S   M   N   K
1141/381                                         1171/391
CTG CCT TCC GTG AGC CAG CTT ATC AAC CCA          CAG CAG CGC AAT GCC CTC ACT CCC ACC ACC
 L   P   S   V   S   Q   L   I   N   P            Q   Q   R   N   A   L   T   P   T   T
```

Figure 19A

```
1201/401                                1231/411
ATG CCT GAG GGC ATG GGA GCC AAC ATT CCT ATG ATG GGC ACT CAC ATG CCA ATG GCT GGA
 M   P   E   G   M   G   A   N   I   P   M   M   G   T   H   M   P   M   A   G
1261/421                                1291/431
GAC ATG AAT GGA CTC AGC CCT ACC CAA GCT CTC CCT CCT CCA CTC TCC ATG CCC TCC ACC
 D   M   N   G   L   S   P   T   Q   A   L   P   P   P   L   S   M   P   S   T
1321/441                                1351/451
TCC CAC TGC ACC CCA CCA CCG CCC TAC CCC ACA GAC TGC AGC ATT GTC AGG ATT tGG Caa
 S   H   C   T   P   P   P   P   Y   P   T   D   C   S   I   V   R   I   W   Q
1381/461
GTC TGA
 V   *
```

Figure 20

```
1/1                                           31/11
ATG TTG TAC CTG gAA AAC AAT GCC CAG ACT       CAA TTT AGT GAG CCA CAG TAC ACG AAC CTG
 M   L   Y   L   E   N   N   A   Q   T         Q   F   S   E   P   Q   Y   T   N   L
61/21                                         91/31
GGG CTC CTG AAC AGC ATG GAC CAG CAG ATT       CAG AAC GGC TCC TCG TCC ACC AGC CCC TAC
 G   L   L   N   S   M   D   Q   Q   I         Q   N   G   S   S   S   T   S   P   Y
121/41                                        151/51
AAC ACA GAC CAC GCA CAG AAT AGC GTG ACG       GCG CCC TCG CCC TAT GCA CAG CCC AGC TCC
 N   T   D   H   A   Q   N   S   V   T         A   P   S   P   Y   A   Q   P   S   S
181/61                                        211/71
ACC TTT GAT GCC CTC TCT CCA TCC CCT GCC       ATT CCC TCC AAC ACA GAT TAC CCG GGC CCA
 T   F   D   A   L   S   P   S   P   A         I   P   S   N   T   D   Y   P   G   P
241/81                                        271/91
CAC AGC TTC GAT GTG TCC TTC CAG CAG TCA       AGC ACT GCC AAG TCA GCC ACC TGg ACG TAT
 H   S   F   D   V   S   F   Q   Q   S         S   T   A   K   S   A   T   W   T   Y
301/101                                       331/111
TCC ACC GAA CTG AAG AAG CTG TAC TGC CAG       ATT GCG AAG ACA TGC CCC ATC CAG ATC AAG
 S   T   E   L   K   K   L   Y   C   Q         I   A   K   T   C   P   I   Q   I   K
361/121                                       391/131
GTG ATG ACC CCA CCC CCA CAG GGC GCT GTT       ATC CGT GCC ATG CCT GTC TAC AAG AAA GCT
 V   M   T   P   P   P   Q   G   A   V         I   R   A   M   P   V   Y   K   K   A
421/141                                       451/151
GAG CAT GTC AcC GAG GTT GTG AAA CGA tGC       CCT AAC CAT GAG CTG AGC CGT GAG TTC AAT
 E   H   V   T   E   V   V   K   R   C         P   N   H   E   L   S   R   E   F   N
481/161                                       511/171
GAG GGA CAG ATT GCC CCT CCC AGT CAT CTG       ATT CGA GTA GAA GGG AAC AGC CAT GCC CAG
 E   G   Q   I   A   P   P   S   H   L         I   R   V   E   G   N   S   H   A   Q
541/181                                       571/191
TaT GTA GAA gAT CCT ATC aCG GGA AGG CAG       AGC GTG CTG GTC CCT tAT GAG CCA CCA CAG
 Y   V   E   D   P   I   T   G   R   Q         S   V   L   V   P   Y   E   P   P   Q
601/201                                       631/211
GTT GGC ACT GAA TTC ACA ACA gTC CTG TAC       AAT TTC ATG TGT aAC AGC AGC TGC GTC GGA
 V   G   T   E   F   T   T   V   L   Y         N   F   M   C   N   S   S   C   V   G
661/221                                       691/231
GGA ATG AAC AGA CGT CCA aTT TTA ATC ATC       GTT ACT CTG GAA ACC AgA GAT GGG CAa GTC
 G   M   N   R   R   P   I   L   I   I         V   T   L   E   T   R   D   G   Q   V
721/241                                       751/251
CTG gGC CGA CGG TGC TTT GAG GCC CGG ATC       TGT GCT TGC CCA GGA AGA GAC CGG AAG GCA
 L   G   R   R   C   F   E   A   R   I         C   A   C   P   G   R   D   R   K   A
781/261                                       811/271
GAT GAA GAC AGC ATC AGA AAG CAG CAA GTA       TCG GAC AGC GCA AAG AAC GGC GAT GCT TTC
 D   E   D   S   I   R   K   Q   Q   V         S   D   S   A   K   N   G   D   A   F
841/281                                       871/291
CGT CAG AAT ACA CAC GGA ATC CAG ATG ACT       TCC ATC AAG AAA CGG AGA TCC CCA GAT GAT
 R   Q   N   T   H   G   I   Q   M   T         S   I   K   K   R   R   S   P   D   D
901/301                                       931/311
GAG CTG CTG TAC CTA CCA GTG AGA GGT CGT       GAG ACG TAC GAG ATG TTG CTG AAG ATC AAA
 E   L   L   Y   L   P   V   R   G   R         E   T   Y   E   M   L   L   K   I   K
961/321                                       991/331
GAG TCA CTG GAG CTC ATG CAG TAC CTC CCT       CAG CAC ACG ATC GAA ACG TAC AGG CAG CAG
 E   S   L   E   L   M   Q   Y   L   P         Q   H   T   I   E   T   Y   R   Q   Q
1021/341                                      1051/351
CAG CAG CAG CAG CAC CAG CAC CTA CTT CAG       AAA CAT CTC CTT TCA GCC TGC TTC AGG AAT
 Q   Q   Q   Q   H   Q   H   L   L   Q         K   H   L   L   S   A   C   F   R   N
1081/361                                      1111/371
GAG CTT GTG GAG CCC CGG GGA GAA GCT CCG       ACA CAG TCT GAC GTC TTC TTT AGA CAT TCC
 E   L   V   E   P   R   G   E   A   P         T   Q   S   D   V   F   F   R   H   S
1141/381
AAC CCC CCA AAC CAC TCC GTG TAC CCA TAG
 N   P   P   N   H   S   V   Y   P   *
```

United States Patent US 7,294,459 B1

SEQUENCE LISTING

```
<160> NUMBER OF SEQ ID NOS: 56

<210> SEQ ID NO 1
<211> LENGTH: 1926
<212> TYPE: DNA
<213> ORGANISM: Homo sapiens
```

<220> FEATURE:
<221> NAME/KEY: CDS
<222> LOCATION: (1)..(1923)

<400> SEQUENCE: 1

```
atg tcc cag agc aca cag aca aat gaa ttc ctc agt cca gag gtt ttc      48
Met Ser Gln Ser Thr Gln Thr Asn Glu Phe Leu Ser Pro Glu Val Phe
 1               5                  10                  15 cag cat atc tgg gat ttt ctg gaa cag cct ata tgt tca gtt cag ccc      96
Gln His Ile Trp Asp Phe Leu Glu Gln Pro Ile Cys Ser Val Gln Pro
             20                  25                  30 att gac ttg aac ttt gtg gat gaa cca tca gaa gat ggt gcg aca aac     144
Ile Asp Leu Asn Phe Val Asp Glu Pro Ser Glu Asp Gly Ala Thr Asn
         35                  40                  45 aag att gag att agc atg gac tgt atc cgc atg cag gac tcg gac ctg     192
Lys Ile Glu Ile Ser Met Asp Cys Ile Arg Met Gln Asp Ser Asp Leu
     50                  55                  60 agt gac ccc atg tgg cca cag tac acg aac ctg ggg ctc ctg aac agc     240
Ser Asp Pro Met Trp Pro Gln Tyr Thr Asn Leu Gly Leu Leu Asn Ser
 65                  70                  75                  80 atg gac cag cag att cag aac ggc tcc tcg tcc acc agt ccc tat aac     288
Met Asp Gln Gln Ile Gln Asn Gly Ser Ser Ser Thr Ser Pro Tyr Asn
                 85                  90                  95 aca gac cac gcg cag aac agc gtc acg gcg ccc tcg ccc tac gca cag     336
Thr Asp His Ala Gln Asn Ser Val Thr Ala Pro Ser Pro Tyr Ala Gln
            100                 105                 110 ccc agc tcc acc ttc gat gct ctc tct cca tca ccc gcc atc ccc tcc     384
Pro Ser Ser Thr Phe Asp Ala Leu Ser Pro Ser Pro Ala Ile Pro Ser
        115                 120                 125 aac acc gac tac cca ggc ccg cac agt ttc gac gtg tcc ttc cag cag     432
Asn Thr Asp Tyr Pro Gly Pro His Ser Phe Asp Val Ser Phe Gln Gln
    130                 135                 140 tcg agc acc gcc aag tcg gcc acc tgg acg tat tcc act gaa ctg aag     480
Ser Ser Thr Ala Lys Ser Ala Thr Trp Thr Tyr Ser Thr Glu Leu Lys
145                 150                 155                 160 aaa ctc tac tgc caa att gca aag aca tgc ccc atc cag atc aag gtg     528
Lys Leu Tyr Cys Gln Ile Ala Lys Thr Cys Pro Ile Gln Ile Lys Val
                165                 170                 175 atg acc cca cct cct cag gga gct gtt atc cgc gcc atg cct gtc tac     576
Met Thr Pro Pro Pro Gln Gly Ala Val Ile Arg Ala Met Pro Val Tyr
            180                 185                 190 aaa aaa gct gag cac gtc acg gag gtg gtg aag cgg tgc ccc aac cat     624
Lys Lys Ala Glu His Val Thr Glu Val Val Lys Arg Cys Pro Asn His
        195                 200                 205 gag ctg agc cgt gaa ttc aac gag gga cag att gcc cct cct agt cat     672
Glu Leu Ser Arg Glu Phe Asn Glu Gly Gln Ile Ala Pro Pro Ser His
    210                 215                 220 ttg att cga gta gag ggg aac agc cat gcc cag tat gta gaa gat ccc     720
Leu Ile Arg Val Glu Gly Asn Ser His Ala Gln Tyr Val Glu Asp Pro
225                 230                 235                 240 atc aca gga aga cag agt gtg ctg gta cct tat gag cca ccc cag gtt     768
Ile Thr Gly Arg Gln Ser Val Leu Val Pro Tyr Glu Pro Pro Gln Val
                245                 250                 255 ggc act gaa ttc acg aca gtc ttg tac aat ttc atg tgt aac agc agt     816
Gly Thr Glu Phe Thr Thr Val Leu Tyr Asn Phe Met Cys Asn Ser Ser
            260                 265                 270 tgt gtt gga ggg atg aac cgc cgt cca att tta atc att gtt act ctg     864
Cys Val Gly Gly Met Asn Arg Arg Pro Ile Leu Ile Ile Val Thr Leu
        275                 280                 285 gaa acc aga gat ggg caa gtc ctg ggc cga cgc tgc ttt gag gcc cgg     912
Glu Thr Arg Asp Gly Gln Val Leu Gly Arg Arg Cys Phe Glu Ala Arg
```

|  |  |
|---|---|
| Glu Thr Arg Asp Gly Gln Val Leu Gly Arg Arg Cys Phe Glu Ala Arg<br>    290                        295                  300 | |
| atc tgt gct tgc cca gga aga gac agg aag gcg gat gaa gat agc atc<br>Ile Cys Ala Cys Pro Gly Arg Asp Arg Lys Ala Asp Glu Asp Ser Ile<br>305                    310                  315                  320 | 960 |
| aga aag cag caa gtt tcg gac agt aca aag aac ggt gat ggt acg aag<br>Arg Lys Gln Gln Val Ser Asp Ser Thr Lys Asn Gly Asp Gly Thr Lys<br>                325                  330                  335 | 1008 |
| cgc ccg ttt cgt cag aac aca cat ggt atc cag atg aca tcc atc aag<br>Arg Pro Phe Arg Gln Asn Thr His Gly Ile Gln Met Thr Ser Ile Lys<br>                340                  345                  350 | 1056 |
| aaa cga aga tcc cca gat gat gaa ctg tta tac tta cca gtg agg ggc<br>Lys Arg Arg Ser Pro Asp Asp Glu Leu Leu Tyr Leu Pro Val Arg Gly<br>              355                  360                  365 | 1104 |
| cgt gag act tat gaa atg ctg ttg aag atc aaa gag tcc ctg gaa ctc<br>Arg Glu Thr Tyr Glu Met Leu Leu Lys Ile Lys Glu Ser Leu Glu Leu<br>370                    375                  380 | 1152 |
| atg cag tac ctt cct cag cac aca att gaa acg tac agg caa cag caa<br>Met Gln Tyr Leu Pro Gln His Thr Ile Glu Thr Tyr Arg Gln Gln Gln<br>385                    390                  395                  400 | 1200 |
| cag cag cag cac cag cac tta ctt cag aaa cag acc tca ata cag tct<br>Gln Gln Gln His Gln His Leu Leu Gln Lys Gln Thr Ser Ile Gln Ser<br>                405                  410                  415 | 1248 |
| cca tct tca tat ggt aac agc tcc cca cct ctg aac aaa atg aac agc<br>Pro Ser Ser Tyr Gly Asn Ser Ser Pro Pro Leu Asn Lys Met Asn Ser<br>                  420                  425                  430 | 1296 |
| atg aac aag ctg cct tct gtg agc cag ctt atc aac cct cag cag cgc<br>Met Asn Lys Leu Pro Ser Val Ser Gln Leu Ile Asn Pro Gln Gln Arg<br>              435                  440                  445 | 1344 |
| aac gcc ctc act cct aca acc att cct gat ggc atg gga gcc aac att<br>Asn Ala Leu Thr Pro Thr Thr Ile Pro Asp Gly Met Gly Ala Asn Ile<br>450                    455                  460 | 1392 |
| ccc atg atg ggc acc cac atg cca atg gct gga gac atg aat gga ctc<br>Pro Met Met Gly Thr His Met Pro Met Ala Gly Asp Met Asn Gly Leu<br>465                    470                  475                  480 | 1440 |
| agc ccc acc cag gca ctc cct ccc cca ctc tcc atg cca tcc acc tcc<br>Ser Pro Thr Gln Ala Leu Pro Pro Pro Leu Ser Met Pro Ser Thr Ser<br>                  485                  490                  495 | 1488 |
| cac tgc aca ccc cca cct ccg tat ccc aca gat tgc agc att gtc agt<br>His Cys Thr Pro Pro Pro Pro Tyr Pro Thr Asp Cys Ser Ile Val Ser<br>                  500                  505                  510 | 1536 |
| ttc tta gcg agg ttg ggc tgt tca tca tgt ctg gac tat ttc acg acc<br>Phe Leu Ala Arg Leu Gly Cys Ser Ser Cys Leu Asp Tyr Phe Thr Thr<br>              515                  520                  525 | 1584 |
| cag ggg ctg acc acc atc tat cag att gag cat tac tcc atg gat gat<br>Gln Gly Leu Thr Thr Ile Tyr Gln Ile Glu His Tyr Ser Met Asp Asp<br>530                    535                  540 | 1632 |
| ctg gca agt ctg aaa atc cct gag caa ttt cga cat gcg atc tgg aag<br>Leu Ala Ser Leu Lys Ile Pro Glu Gln Phe Arg His Ala Ile Trp Lys<br>545                    550                  555                  560 | 1680 |
| ggc atc ctg gac cac cgg cag ctc cac gaa ttc tcc tcc cct tct cat<br>Gly Ile Leu Asp His Arg Gln Leu His Glu Phe Ser Ser Pro Ser His<br>                565                  570                  575 | 1728 |
| ctc ctg cgg acc cca agc agt gcc tct aca gtc agt gtg ggc tcc agt<br>Leu Leu Arg Thr Pro Ser Ser Ala Ser Thr Val Ser Val Gly Ser Ser<br>                  580                  585                  590 | 1776 |
| gag acc cgg ggt gag cgt gtt att gat gct gtg cga ttc acc ctc cgc<br>Glu Thr Arg Gly Glu Arg Val Ile Asp Ala Val Arg Phe Thr Leu Arg<br>              595                  600                  605 | 1824 |

```
cag acc atc tct ttc cca ccc cga gat gag tgg aat gac ttc aac ttt      1872
Gln Thr Ile Ser Phe Pro Pro Arg Asp Glu Trp Asn Asp Phe Asn Phe
        610                 615                 620 gac atg gat gct cgc cgc aat aag caa cag cgc atc aaa gag gag ggg      1920
Asp Met Asp Ala Arg Arg Asn Lys Gln Gln Arg Ile Lys Glu Glu Gly
625                 630                 635                 640 gag tga                                                               1926
Glu

<210> SEQ ID NO 2
<211> LENGTH: 1551
<212> TYPE: DNA
<213> ORGANISM: Homo sapiens
<220> FEATURE:
<221> NAME/KEY: CDS
<222> LOCATION: (1)..(1548)

<400> SEQUENCE: 2 atg tcc cag agc aca cag aca aat gaa ttc ctc agt cca gag gtt ttc        48
Met Ser Gln Ser Thr Gln Thr Asn Glu Phe Leu Ser Pro Glu Val Phe
1               5                  10                  15 cag cat atc tgg gat ttt ctg gaa cag cct ata tgt tca gtt cag ccc        96
Gln His Ile Trp Asp Phe Leu Glu Gln Pro Ile Cys Ser Val Gln Pro
                20                  25                  30 att gac ttg aac ttt gtg gat gaa cca tca gaa gat ggt gcg aca aac       144
Ile Asp Leu Asn Phe Val Asp Glu Pro Ser Glu Asp Gly Ala Thr Asn
            35                  40                  45 aag att gag att agc atg gac tgt atc cgc atg cag gac tcg gac ctg       192
Lys Ile Glu Ile Ser Met Asp Cys Ile Arg Met Gln Asp Ser Asp Leu
        50                  55                  60 agt gac ccc atg tgg cca cag tac acg aac ctg ggg ctc ctg aac agc       240
Ser Asp Pro Met Trp Pro Gln Tyr Thr Asn Leu Gly Leu Leu Asn Ser
65                  70                  75                  80 atg gac cag cag att cag aac ggc tcc tcg tcc acc agt ccc tat aac       288
Met Asp Gln Gln Ile Gln Asn Gly Ser Ser Ser Thr Ser Pro Tyr Asn
                85                  90                  95 aca gac cac gcg cag aac agc gtc acg gcg ccc tcg ccc tac gca cag       336
Thr Asp His Ala Gln Asn Ser Val Thr Ala Pro Ser Pro Tyr Ala Gln
            100                 105                 110 ccc agc tcc acc ttc gat gct ctc tct cca tca ccc gcc atc ccc tcc       384
Pro Ser Ser Thr Phe Asp Ala Leu Ser Pro Ser Pro Ala Ile Pro Ser
        115                 120                 125 aac acc gac tac cca ggc ccg cac agt ttc gac gtg tcc ttc cag cag       432
Asn Thr Asp Tyr Pro Gly Pro His Ser Phe Asp Val Ser Phe Gln Gln
130                 135                 140 tcg agc acc gcc aag tcg gcc acc tgg acg tat tcc act gaa ctg aag       480
Ser Ser Thr Ala Lys Ser Ala Thr Trp Thr Tyr Ser Thr Glu Leu Lys
145                 150                 155                 160 aaa ctc tac tgc caa att gca aag aca tgc ccc atc cag atc aag gtg       528
Lys Leu Tyr Cys Gln Ile Ala Lys Thr Cys Pro Ile Gln Ile Lys Val
                165                 170                 175 atg acc cca cct cct cag gga gct gtt atc cgc gcc atg cct gtc tac       576
Met Thr Pro Pro Pro Gln Gly Ala Val Ile Arg Ala Met Pro Val Tyr
            180                 185                 190 aaa aaa gct gag cac gtc acg gag gtg gtg aag cgg tgc ccc aac cat       624
Lys Lys Ala Glu His Val Thr Glu Val Val Lys Arg Cys Pro Asn His
        195                 200                 205 gag ctg agc cgt gaa ttc aac gag gga cag att gcc cct cct agt cat       672
Glu Leu Ser Arg Glu Phe Asn Glu Gly Gln Ile Ala Pro Pro Ser His
210                 215                 220 ttg att cga gta gag ggg aac agc cat gcc cag tat gta gaa gat ccc       720
```

```
Leu Ile Arg Val Glu Gly Asn Ser His Ala Gln Tyr Val Glu Asp Pro
225                 230                 235                 240 atc aca gga aga cag agt gtg ctg gta cct tat gag cca ccc cag gtt      768
Ile Thr Gly Arg Gln Ser Val Leu Val Pro Tyr Glu Pro Pro Gln Val
                245                 250                 255 ggc act gaa ttc acg aca gtc ttg tac aat ttc atg tgt aac agc agt      816
Gly Thr Glu Phe Thr Thr Val Leu Tyr Asn Phe Met Cys Asn Ser Ser
            260                 265                 270 tgt gtt gga ggg atg aac cgc cgt cca att tta atc att gtt act ctg      864
Cys Val Gly Gly Met Asn Arg Arg Pro Ile Leu Ile Ile Val Thr Leu
        275                 280                 285 gaa acc aga gat ggg caa gtc ctg ggc cga cgc tgc ttt gag gcc cgg      912
Glu Thr Arg Asp Gly Gln Val Leu Gly Arg Arg Cys Phe Glu Ala Arg
    290                 295                 300 atc tgt gct tgc cca gga aga gac agg aag gcg gat gaa gat agc atc      960
Ile Cys Ala Cys Pro Gly Arg Asp Arg Lys Ala Asp Glu Asp Ser Ile
305                 310                 315                 320 aga aag cag caa gtt tcg gac agt aca aag aac ggt gat ggt acg aag     1008
Arg Lys Gln Gln Val Ser Asp Ser Thr Lys Asn Gly Asp Gly Thr Lys
                325                 330                 335 cgc ccg ttt cgt cag aac aca cat ggt atc cag atg aca tcc atc aag     1056
Arg Pro Phe Arg Gln Asn Thr His Gly Ile Gln Met Thr Ser Ile Lys
            340                 345                 350 aaa cga aga tcc cca gat gat gaa ctg tta tac tta cca gtg agg ggc     1104
Lys Arg Arg Ser Pro Asp Asp Glu Leu Leu Tyr Leu Pro Val Arg Gly
        355                 360                 365 cgt gag act tat gaa atg ctg ttg aag atc aaa gag tcc ctg gaa ctc     1152
Arg Glu Thr Tyr Glu Met Leu Leu Lys Ile Lys Glu Ser Leu Glu Leu
    370                 375                 380 atg cag tac ctt cct cag cac aca att gaa acg tac agg caa cag caa     1200
Met Gln Tyr Leu Pro Gln His Thr Ile Glu Thr Tyr Arg Gln Gln Gln
385                 390                 395                 400 cag cag cag cac cag cac tta ctt cag aaa cag acc tca ata cag tct     1248
Gln Gln Gln His Gln His Leu Leu Gln Lys Gln Thr Ser Ile Gln Ser
                405                 410                 415 cca tct tca tat ggt aac agc tcc cca cct ctg aac aaa atg aac agc     1296
Pro Ser Ser Tyr Gly Asn Ser Ser Pro Pro Leu Asn Lys Met Asn Ser
            420                 425                 430 atg aac aag ctg cct tct gtg agc cag ctt atc aac cct cag cag cgc     1344
Met Asn Lys Leu Pro Ser Val Ser Gln Leu Ile Asn Pro Gln Gln Arg
        435                 440                 445 aac gcc ctc act cct aca acc att cct gat ggc atg gga gcc aac att     1392
Asn Ala Leu Thr Pro Thr Thr Ile Pro Asp Gly Met Gly Ala Asn Ile
    450                 455                 460 ccc atg atg ggc acc cac atg cca atg gct gga gac atg aat gga ctc     1440
Pro Met Met Gly Thr His Met Pro Met Ala Gly Asp Met Asn Gly Leu
465                 470                 475                 480 agc ccc acc cag gca ctc cct ccc cca ctc tcc atg cca tcc acc tcc     1488
Ser Pro Thr Gln Ala Leu Pro Pro Pro Leu Ser Met Pro Ser Thr Ser
                485                 490                 495 cac tgc aca ccc cca cct ccg tat ccc aca gat tgc agc att gtc agg     1536
His Cys Thr Pro Pro Pro Pro Tyr Pro Thr Asp Cys Ser Ile Val Arg
            500                 505                 510 atc tgg caa gtc tga                                                 1551
Ile Trp Gln Val
        515

<210> SEQ ID NO 3
<211> LENGTH: 1347
<212> TYPE: DNA
```

<213> ORGANISM: Homo sapiens
<220> FEATURE:
<221> NAME/KEY: CDS
<222> LOCATION: (1)..(1344)

<400> SEQUENCE: 3

| | | | | | | | | | | | | | | | | |
|---|---|---|---|---|---|---|---|---|---|---|---|---|---|---|---|---|
| atg | tcc | cag | agc | aca | cag | aca | aat | gaa | ttc | ctc | agt | cca | gag | gtt | ttc | 48 |
| Met | Ser | Gln | Ser | Thr | Gln | Thr | Asn | Glu | Phe | Leu | Ser | Pro | Glu | Val | Phe | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cag | cat | atc | tgg | gat | ttt | ctg | gaa | cag | cct | ata | tgt | tca | gtt | cag | ccc | 96 |
| Gln | His | Ile | Trp | Asp | Phe | Leu | Glu | Gln | Pro | Ile | Cys | Ser | Val | Gln | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| att | gac | ttg | aac | ttt | gtg | gat | gaa | cca | tca | gaa | gat | ggt | gcg | aca | aac | 144 |
| Ile | Asp | Leu | Asn | Phe | Val | Asp | Glu | Pro | Ser | Glu | Asp | Gly | Ala | Thr | Asn | |
| | | | 35 | | | | | 40 | | | | | 45 | | | |

| | | | | | | | | | | | | | | | | |
|---|---|---|---|---|---|---|---|---|---|---|---|---|---|---|---|---|
| aag | att | gag | att | agc | atg | gac | tgt | atc | cgc | atg | cag | gac | tcg | gac | ctg | 192 |
| Lys | Ile | Glu | Ile | Ser | Met | Asp | Cys | Ile | Arg | Met | Gln | Asp | Ser | Asp | Leu | |
| | | | | 50 | | | | | 55 | | | | | 60 | | |

| | | | | | | | | | | | | | | | | |
|---|---|---|---|---|---|---|---|---|---|---|---|---|---|---|---|---|
| agt | gac | ccc | atg | tgg | cca | cag | tac | acg | aac | ctg | ggg | ctc | ctg | aac | agc | 240 |
| Ser | Asp | Pro | Met | Trp | Pro | Gln | Tyr | Thr | Asn | Leu | Gly | Leu | Leu | Asn | Ser | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| atg | gac | cag | cag | att | cag | aac | ggc | tcc | tcg | tcc | acc | agt | ccc | tat | aac | 288 |
| Met | Asp | Gln | Gln | Ile | Gln | Asn | Gly | Ser | Ser | Ser | Thr | Ser | Pro | Tyr | Asn | |
| | | | | 85 | | | | | 90 | | | | | 95 | | |

| | | | | | | | | | | | | | | | | |
|---|---|---|---|---|---|---|---|---|---|---|---|---|---|---|---|---|
| aca | gac | cac | gcg | cag | aac | agc | gtc | acg | gcg | ccc | tcg | ccc | tac | gca | cag | 336 |
| Thr | Asp | His | Ala | Gln | Asn | Ser | Val | Thr | Ala | Pro | Ser | Pro | Tyr | Ala | Gln | |
| | | | 100 | | | | | 105 | | | | | 110 | | | |

| | | | | | | | | | | | | | | | | |
|---|---|---|---|---|---|---|---|---|---|---|---|---|---|---|---|---|
| ccc | agc | tcc | acc | ttc | gat | gct | ctc | tct | cca | tca | ccc | gcc | atc | ccc | tcc | 384 |
| Pro | Ser | Ser | Thr | Phe | Asp | Ala | Leu | Ser | Pro | Ser | Pro | Ala | Ile | Pro | Ser | |
| | | | 115 | | | | | 120 | | | | | 125 | | | |

| | | | | | | | | | | | | | | | | |
|---|---|---|---|---|---|---|---|---|---|---|---|---|---|---|---|---|
| aac | acc | gac | tac | cca | ggc | ccg | cac | agt | ttc | gac | gtg | tcc | ttc | cag | cag | 432 |
| Asn | Thr | Asp | Tyr | Pro | Gly | Pro | His | Ser | Phe | Asp | Val | Ser | Phe | Gln | Gln | |
| | | 130 | | | | | 135 | | | | | 140 | | | | |

| | | | | | | | | | | | | | | | | |
|---|---|---|---|---|---|---|---|---|---|---|---|---|---|---|---|---|
| tcg | agc | acc | gcc | aag | tcg | gcc | acc | tgg | acg | tat | tcc | act | gaa | ctg | aag | 480 |
| Ser | Ser | Thr | Ala | Lys | Ser | Ala | Thr | Trp | Thr | Tyr | Ser | Thr | Glu | Leu | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| aaa | ctc | tac | tgc | caa | att | gca | aag | aca | tgc | ccc | atc | cag | atc | aag | gtg | 528 |
| Lys | Leu | Tyr | Cys | Gln | Ile | Ala | Lys | Thr | Cys | Pro | Ile | Gln | Ile | Lys | Val | |
| | | | | 165 | | | | | 170 | | | | | 175 | | |

| | | | | | | | | | | | | | | | | |
|---|---|---|---|---|---|---|---|---|---|---|---|---|---|---|---|---|
| atg | acc | cca | cct | cct | cag | gga | gct | gtt | atc | cgc | gcc | atg | cct | gtc | tac | 576 |
| Met | Thr | Pro | Pro | Pro | Gln | Gly | Ala | Val | Ile | Arg | Ala | Met | Pro | Val | Tyr | |
| | | | 180 | | | | | 185 | | | | | 190 | | | |

| | | | | | | | | | | | | | | | | |
|---|---|---|---|---|---|---|---|---|---|---|---|---|---|---|---|---|
| aaa | aaa | gct | gag | cac | gtc | acg | gag | gtg | gtg | aag | cgg | tgc | ccc | aac | cat | 624 |
| Lys | Lys | Ala | Glu | His | Val | Thr | Glu | Val | Val | Lys | Arg | Cys | Pro | Asn | His | |
| | | | 195 | | | | | 200 | | | | | 205 | | | |

| | | | | | | | | | | | | | | | | |
|---|---|---|---|---|---|---|---|---|---|---|---|---|---|---|---|---|
| gag | ctg | agc | cgt | gaa | ttc | aac | gag | gga | cag | att | gcc | cct | cct | agt | cat | 672 |
| Glu | Leu | Ser | Arg | Glu | Phe | Asn | Glu | Gly | Gln | Ile | Ala | Pro | Pro | Ser | His | |
| | | 210 | | | | | 215 | | | | | 220 | | | | |

| | | | | | | | | | | | | | | | | |
|---|---|---|---|---|---|---|---|---|---|---|---|---|---|---|---|---|
| ttg | att | cga | gta | gag | ggg | aac | agc | cat | gcc | cag | tat | gta | gaa | gat | ccc | 720 |
| Leu | Ile | Arg | Val | Glu | Gly | Asn | Ser | His | Ala | Gln | Tyr | Val | Glu | Asp | Pro | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| atc | aca | gga | aga | cag | agt | gtg | ctg | gta | cct | tat | gag | cca | ccc | cag | gtt | 768 |
| Ile | Thr | Gly | Arg | Gln | Ser | Val | Leu | Val | Pro | Tyr | Glu | Pro | Pro | Gln | Val | |
| | | | | 245 | | | | | 250 | | | | | 255 | | |

| | | | | | | | | | | | | | | | | |
|---|---|---|---|---|---|---|---|---|---|---|---|---|---|---|---|---|
| ggc | act | gaa | ttc | acg | aca | gtc | ttg | tac | aat | ttc | atg | tgt | aac | agc | agt | 816 |
| Gly | Thr | Glu | Phe | Thr | Thr | Val | Leu | Tyr | Asn | Phe | Met | Cys | Asn | Ser | Ser | |
| | | | 260 | | | | | 265 | | | | | 270 | | | |

| | | | | | | | | | | | | | | | | |
|---|---|---|---|---|---|---|---|---|---|---|---|---|---|---|---|---|
| tgt | gtt | gga | ggg | atg | aac | cgc | cgt | cca | att | tta | atc | att | gtt | act | ctg | 864 |
| Cys | Val | Gly | Gly | Met | Asn | Arg | Arg | Pro | Ile | Leu | Ile | Ile | Val | Thr | Leu | |
| | | | 275 | | | | | 280 | | | | | 285 | | | |

-continued

| | | |
|---|---|---|
| gaa acc aga gat ggg caa gtc ctg ggc cga cgc tgc ttt gag gcc cgg<br>Glu Thr Arg Asp Gly Gln Val Leu Gly Arg Arg Cys Phe Glu Ala Arg<br>290                            295                      300 | 912 |
| atc tgt gct tgc cca gga aga gac agg aag gcg gat gaa gat agc atc<br>Ile Cys Ala Cys Pro Gly Arg Asp Arg Lys Ala Asp Glu Asp Ser Ile<br>305                           310                      315                320 | 960 |
| aga aag cag caa gtt tcg gac agt aca aag aac ggt gat ggt acg aag<br>Arg Lys Gln Gln Val Ser Asp Ser Thr Lys Asn Gly Asp Gly Thr Lys<br>                    325                      330                      335 | 1008 |
| cgc ccg ttt cgt cag aac aca cat ggt atc cag atg aca tcc atc aag<br>Arg Pro Phe Arg Gln Asn Thr His Gly Ile Gln Met Thr Ser Ile Lys<br>              340                      345                      350 | 1056 |
| aaa cga aga tcc cca gat gat gaa ctg tta tac tta cca gtg agg ggc<br>Lys Arg Arg Ser Pro Asp Asp Glu Leu Leu Tyr Leu Pro Val Arg Gly<br>                    355                      360                      365 | 1104 |
| cgt gag act tat gaa atg ctg ttg aag atc aaa gag tcc ctg gaa ctc<br>Arg Glu Thr Tyr Glu Met Leu Leu Lys Ile Lys Glu Ser Leu Glu Leu<br>370                            375                      380 | 1152 |
| atg cag tac ctt cct cag cac aca att gaa acg tac agg caa cag caa<br>Met Gln Tyr Leu Pro Gln His Thr Ile Glu Thr Tyr Arg Gln Gln Gln<br>385                            390                      395                400 | 1200 |
| cag cag cag cac cag cac tta ctt cag aaa cat ctc ctt tca gcc tgc<br>Gln Gln Gln His Gln His Leu Leu Gln Lys His Leu Leu Ser Ala Cys<br>                    405                      410                      415 | 1248 |
| ttc agg aat gag ctt gtg gag ccc cgg aga gaa act cca aaa caa tct<br>Phe Arg Asn Glu Leu Val Glu Pro Arg Arg Glu Thr Pro Lys Gln Ser<br>              420                      425                      430 | 1296 |
| gac gtc ttc ttt aga cat tcc aag ccc cca aac cga tca gtg tac cca<br>Asp Val Phe Phe Arg His Ser Lys Pro Pro Asn Arg Ser Val Tyr Pro<br>                  435                      440                      445 | 1344 |
| tag | 1347 |

<210> SEQ ID NO 4
<211> LENGTH: 1761
<212> TYPE: DNA
<213> ORGANISM: Homo sapiens
<220> FEATURE:
<221> NAME/KEY: CDS
<222> LOCATION: (1)..(1758)

<400> SEQUENCE: 4

| | |
|---|---|
| atg ttg tac ctg gaa aac aat gcc cag act caa ttt agt gag cca cag<br>Met Leu Tyr Leu Glu Asn Asn Ala Gln Thr Gln Phe Ser Glu Pro Gln<br>1                    5                    10                  15 | 48 |
| tac acg aac ctg ggg ctc ctg aac agc atg gac cag cag att cag aac<br>Tyr Thr Asn Leu Gly Leu Leu Asn Ser Met Asp Gln Gln Ile Gln Asn<br>                  20                    25                    30 | 96 |
| ggc tcc tcg tcc acc agt ccc tat aac aca gac cac gcg cag aac agc<br>Gly Ser Ser Ser Thr Ser Pro Tyr Asn Thr Asp His Ala Gln Asn Ser<br>              35                      40                      45 | 144 |
| gtc acg gcg ccc tcg ccc tac gca cag ccc agc tcc acc ttc gat gct<br>Val Thr Ala Pro Ser Pro Tyr Ala Gln Pro Ser Ser Thr Phe Asp Ala<br>50                            55                      60 | 192 |
| ctc tct cca tca ccc gcc atc ccc tcc aac acc gac tac cca ggc ccg<br>Leu Ser Pro Ser Pro Ala Ile Pro Ser Asn Thr Asp Tyr Pro Gly Pro<br>65                      70                    75                80 | 240 |
| cac agt ttc gac gtg tcc ttc cag cag tcg agc acc gcc aag tcg gcc<br>His Ser Phe Asp Val Ser Phe Gln Gln Ser Ser Thr Ala Lys Ser Ala<br>                  85                    90                    95 | 288 |
| acc tgg acg tat tcc act gaa ctg aag aaa ctc tac tgc caa att gca<br>Thr Trp Thr Tyr Ser Thr Glu Leu Lys Lys Leu Tyr Cys Gln Ile Ala | 336 |

-continued

|  | 100 |  |  |  | 105 |  |  |  | 110 |  |  |  |  |
|---|---|---|---|---|---|---|---|---|---|---|---|---|---|
| aag | aca | tgc | ccc | atc | cag | atc | aag | gtg | atg | acc | cca | cct cct cag gga | 384 |
| Lys | Thr | Cys | Pro | Ile | Gln | Ile | Lys | Val | Met | Thr | Pro | Pro Pro Gln Gly |  |
|  |  | 115 |  |  |  | 120 |  |  |  | 125 |  |  |  |
| gct | gtt | atc | cgc | gcc | atg | cct | gtc | tac | aaa | aaa | gct | gag cac gtc acg | 432 |
| Ala | Val | Ile | Arg | Ala | Met | Pro | Val | Tyr | Lys | Lys | Ala | Glu His Val Thr |  |
|  | 130 |  |  |  | 135 |  |  |  | 140 |  |  |  |  |
| gag | gtg | gtg | aag | cgg | tgc | ccc | aac | cat | gag | ctg | agc | cgt gaa ttc aac | 480 |
| Glu | Val | Val | Lys | Arg | Cys | Pro | Asn | His | Glu | Leu | Ser | Arg Glu Phe Asn |  |
| 145 |  |  |  | 150 |  |  |  | 155 |  |  |  | 160 |  |
| gag | gga | cag | att | gcc | cct | cct | agt | cat | ttg | att | cga | gta gag ggg aac | 528 |
| Glu | Gly | Gln | Ile | Ala | Pro | Pro | Ser | His | Leu | Ile | Arg | Val Glu Gly Asn |  |
|  |  |  | 165 |  |  |  | 170 |  |  |  | 175 |  |  |
| agc | cat | gcc | cag | tat | gta | gaa | gat | ccc | atc | aca | gga | aga cag agt gtg | 576 |
| Ser | His | Ala | Gln | Tyr | Val | Glu | Asp | Pro | Ile | Thr | Gly | Arg Gln Ser Val |  |
|  |  | 180 |  |  |  | 185 |  |  |  | 190 |  |  |  |
| ctg | gta | cct | tat | gag | cca | ccc | cag | gtt | ggc | act | gaa | ttc acg aca gtc | 624 |
| Leu | Val | Pro | Tyr | Glu | Pro | Pro | Gln | Val | Gly | Thr | Glu | Phe Thr Thr Val |  |
|  | 195 |  |  |  | 200 |  |  |  | 205 |  |  |  |  |
| ttg | tac | aat | ttc | atg | tgt | aac | agc | agt | tgt | gtt | gga | ggg atg aac cgc | 672 |
| Leu | Tyr | Asn | Phe | Met | Cys | Asn | Ser | Ser | Cys | Val | Gly | Gly Met Asn Arg |  |
|  | 210 |  |  |  | 215 |  |  |  | 220 |  |  |  |  |
| cgt | cca | att | tta | atc | att | gtt | act | ctg | gaa | acc | aga | gat ggg caa gtc | 720 |
| Arg | Pro | Ile | Leu | Ile | Ile | Val | Thr | Leu | Glu | Thr | Arg | Asp Gly Gln Val |  |
| 225 |  |  |  | 230 |  |  |  | 235 |  |  |  | 240 |  |
| ctg | ggc | cga | cgc | tgc | ttt | gag | gcc | cgg | atc | tgt | gct | tgc cca gga aga | 768 |
| Leu | Gly | Arg | Arg | Cys | Phe | Glu | Ala | Arg | Ile | Cys | Ala | Cys Pro Gly Arg |  |
|  |  |  | 245 |  |  |  | 250 |  |  |  | 255 |  |  |
| gac | agg | aag | gcg | gat | gaa | gat | agc | atc | aga | aag | cag | caa gtt tcg gac | 816 |
| Asp | Arg | Lys | Ala | Asp | Glu | Asp | Ser | Ile | Arg | Lys | Gln | Gln Val Ser Asp |  |
|  |  | 260 |  |  |  | 265 |  |  |  | 270 |  |  |  |
| agt | aca | aag | aac | ggt | gat | ggt | acg | aag | cgc | ccg | ttt | cgt cag aac aca | 864 |
| Ser | Thr | Lys | Asn | Gly | Asp | Gly | Thr | Lys | Arg | Pro | Phe | Arg Gln Asn Thr |  |
|  | 275 |  |  |  | 280 |  |  |  | 285 |  |  |  |  |
| cat | ggt | atc | cag | atg | aca | tcc | atc | aag | aaa | cga | aga | tcc cca gat gat | 912 |
| His | Gly | Ile | Gln | Met | Thr | Ser | Ile | Lys | Lys | Arg | Arg | Ser Pro Asp Asp |  |
|  | 290 |  |  |  | 295 |  |  |  | 300 |  |  |  |  |
| gaa | ctg | tta | tac | tta | cca | gtg | agg | ggc | cgt | gag | act | tat gaa atg ctg | 960 |
| Glu | Leu | Leu | Tyr | Leu | Pro | Val | Arg | Gly | Arg | Glu | Thr | Tyr Glu Met Leu |  |
| 305 |  |  |  | 310 |  |  |  | 315 |  |  |  | 320 |  |
| ttg | aag | atc | aaa | gag | tcc | ctg | gaa | ctc | atg | cag | tac | ctt cct cag cac | 1008 |
| Leu | Lys | Ile | Lys | Glu | Ser | Leu | Glu | Leu | Met | Gln | Tyr | Leu Pro Gln His |  |
|  |  |  | 325 |  |  |  | 330 |  |  |  | 335 |  |  |
| aca | att | gaa | acg | tac | agg | caa | cag | caa | cag | cag | cac | cag cac tta | 1056 |
| Thr | Ile | Glu | Thr | Tyr | Arg | Gln | Gln | Gln | Gln | Gln | His | Gln His Leu |  |
|  |  | 340 |  |  |  | 345 |  |  |  | 350 |  |  |  |
| ctt | cag | aaa | cag | acc | tca | ata | cag | tct | cca | tct | tca | tat ggt aac agc | 1104 |
| Leu | Gln | Lys | Gln | Thr | Ser | Ile | Gln | Ser | Pro | Ser | Ser | Tyr Gly Asn Ser |  |
|  | 355 |  |  |  | 360 |  |  |  | 365 |  |  |  |  |
| tcc | cca | cct | ctg | aac | aaa | atg | aac | agc | atg | aac | aag | ctg cct tct gtg | 1152 |
| Ser | Pro | Pro | Leu | Asn | Lys | Met | Asn | Ser | Met | Asn | Lys | Leu Pro Ser Val |  |
| 370 |  |  |  | 375 |  |  |  | 380 |  |  |  |  |  |
| agc | cag | ctt | atc | aac | cct | cag | cag | cgc | aac | gcc | ctc | act cct aca acc | 1200 |
| Ser | Gln | Leu | Ile | Asn | Pro | Gln | Gln | Arg | Asn | Ala | Leu | Thr Pro Thr Thr |  |
| 385 |  |  |  | 390 |  |  |  | 395 |  |  |  | 400 |  |
| att | cct | gat | ggc | atg | gga | gcc | aac | att | ccc | atg | atg | ggc acc cac atg | 1248 |
| Ile | Pro | Asp | Gly | Met | Gly | Ala | Asn | Ile | Pro | Met | Met | Gly Thr His Met |  |
|  |  |  | 405 |  |  |  | 410 |  |  |  | 415 |  |  |
| cca | atg | gct | gga | gac | atg | aat | gga | ctc | agc | ccc | acc | cag gca ctc cct | 1296 |

-continued

```
                Pro Met Ala Gly Asp Met Asn Gly Leu Ser Pro Thr Gln Ala Leu Pro
                                420                 425                 430 ccc cca ctc tcc atg cca tcc acc tcc cac tgc aca ccc cca cct ccg        1344
Pro Pro Leu Ser Met Pro Ser Thr Ser His Cys Thr Pro Pro Pro Pro
            435                 440                 445 tat ccc aca gat tgc agc att gtc agt ttc tta gcg agg ttg ggc tgt        1392
Tyr Pro Thr Asp Cys Ser Ile Val Ser Phe Leu Ala Arg Leu Gly Cys
450                 455                 460 tca tca tgt ctg gac tat ttc acg acc cag ggg ctg acc acc atc tat        1440
Ser Ser Cys Leu Asp Tyr Phe Thr Thr Gln Gly Leu Thr Thr Ile Tyr
465                 470                 475                 480 cag att gag cat tac tcc atg gat gat ctg gca agt ctg aaa atc cct        1488
Gln Ile Glu His Tyr Ser Met Asp Asp Leu Ala Ser Leu Lys Ile Pro
                485                 490                 495 gag caa ttt cga cat gcg atc tgg aag ggc atc ctg gac cac cgg cag        1536
Glu Gln Phe Arg His Ala Ile Trp Lys Gly Ile Leu Asp His Arg Gln
            500                 505                 510 ctc cac gaa ttc tcc tcc cct tct cat ctc ctg cgg acc cca agc agt        1584
Leu His Glu Phe Ser Ser Pro Ser His Leu Leu Arg Thr Pro Ser Ser
        515                 520                 525 gcc tct aca gtc agt gtg ggc tcc agt gag acc cgg ggt gag cgt gtt        1632
Ala Ser Thr Val Ser Val Gly Ser Ser Glu Thr Arg Gly Glu Arg Val
    530                 535                 540 att gat gct gtg cga ttc acc ctc cgc cag acc atc tct ttc cca ccc        1680
Ile Asp Ala Val Arg Phe Thr Leu Arg Gln Thr Ile Ser Phe Pro Pro
545                 550                 555                 560 cga gat gag tgg aat gac ttc aac ttt gac atg gat gct cgc cgc aat        1728
Arg Asp Glu Trp Asn Asp Phe Asn Phe Asp Met Asp Ala Arg Arg Asn
                565                 570                 575 aag caa cag cgc atc aaa gag gag ggg gag tga                            1761
Lys Gln Gln Arg Ile Lys Glu Glu Gly Glu
            580                 585

<210> SEQ ID NO 5
<211> LENGTH: 1386
<212> TYPE: DNA
<213> ORGANISM: Homo sapiens
<220> FEATURE:
<221> NAME/KEY: CDS
<222> LOCATION: (1)..(1383)

<400> SEQUENCE: 5 atg ttg tac ctg gaa aac aat gcc cag act caa ttt agt gag cca cag         48
Met Leu Tyr Leu Glu Asn Asn Ala Gln Thr Gln Phe Ser Glu Pro Gln
1               5                   10                  15 tac acg aac ctg ggg ctc ctg aac agc atg gac cag cag att cag aac         96
Tyr Thr Asn Leu Gly Leu Leu Asn Ser Met Asp Gln Gln Ile Gln Asn
            20                  25                  30 ggc tcc tcg tcc acc agt ccc tat aac aca gac cac gcg cag aac agc        144
Gly Ser Ser Ser Thr Ser Pro Tyr Asn Thr Asp His Ala Gln Asn Ser
        35                  40                  45 gtc acg gcg ccc tcg ccc tac gca cag ccc agc tcc acc ttc gat gct        192
Val Thr Ala Pro Ser Pro Tyr Ala Gln Pro Ser Ser Thr Phe Asp Ala
    50                  55                  60 ctc tct cca tca ccc gcc atc ccc tcc aac acc gac tac cca ggc ccg        240
Leu Ser Pro Ser Pro Ala Ile Pro Ser Asn Thr Asp Tyr Pro Gly Pro
65                  70                  75                  80 cac agt ttc gac gtg tcc ttc cag cag tcg agc acc gcc aag tcg gcc        288
His Ser Phe Asp Val Ser Phe Gln Gln Ser Ser Thr Ala Lys Ser Ala
                85                  90                  95 acc tgg acg tat tcc act gaa ctg aag aaa ctc tac tgc caa att gca        336
```

```
Thr Trp Thr Tyr Ser Thr Glu Leu Lys Lys Leu Tyr Cys Gln Ile Ala
            100                 105                 110 aag aca tgc ccc atc cag atc aag gtg atg acc cca cct cct cag gga        384
Lys Thr Cys Pro Ile Gln Ile Lys Val Met Thr Pro Pro Gln Gly
        115                 120                 125 gct gtt atc cgc gcc atg cct gtc tac aaa aaa gct gag cac gtc acg        432
Ala Val Ile Arg Ala Met Pro Val Tyr Lys Lys Ala Glu His Val Thr
130                 135                 140 gag gtg gtg aag cgg tgc ccc aac cat gag ctg agc cgt gaa ttc aac        480
Glu Val Val Lys Arg Cys Pro Asn His Glu Leu Ser Arg Glu Phe Asn
145                 150                 155                 160 gag gga cag att gcc cct cct agt cat ttg att cga gta gag ggg aac        528
Glu Gly Gln Ile Ala Pro Pro Ser His Leu Ile Arg Val Glu Gly Asn
                165                 170                 175 agc cat gcc cag tat gta gaa gat ccc atc aca gga aga cag agt gtg        576
Ser His Ala Gln Tyr Val Glu Asp Pro Ile Thr Gly Arg Gln Ser Val
                180                 185                 190 ctg gta cct tat gag cca ccc cag gtt ggc act gaa ttc acg aca gtc        624
Leu Val Pro Tyr Glu Pro Pro Gln Val Gly Thr Glu Phe Thr Thr Val
        195                 200                 205 ttg tac aat ttc atg tgt aac agc agt tgt gtt gga ggg atg aac cgc        672
Leu Tyr Asn Phe Met Cys Asn Ser Ser Cys Val Gly Gly Met Asn Arg
    210                 215                 220 cgt cca att tta atc att gtt act ctg gaa acc aga gat ggg caa gtc        720
Arg Pro Ile Leu Ile Ile Val Thr Leu Glu Thr Arg Asp Gly Gln Val
225                 230                 235                 240 ctg ggc cga cgc tgc ttt gag gcc cgg atc tgt gct tgc cca gga aga        768
Leu Gly Arg Arg Cys Phe Glu Ala Arg Ile Cys Ala Cys Pro Gly Arg
                245                 250                 255 gac agg aag gcg gat gaa gat agc atc aga aag cag caa gtt tcg gac        816
Asp Arg Lys Ala Asp Glu Asp Ser Ile Arg Lys Gln Gln Val Ser Asp
                260                 265                 270 agt aca aag aac ggt gat ggt acg aag cgc ccg ttt cgt cag aac aca        864
Ser Thr Lys Asn Gly Asp Gly Thr Lys Arg Pro Phe Arg Gln Asn Thr
        275                 280                 285 cat ggt atc cag atg aca tcc atc aag aaa cga aga tcc cca gat gat        912
His Gly Ile Gln Met Thr Ser Ile Lys Lys Arg Arg Ser Pro Asp Asp
290                 295                 300 gaa ctg tta tac tta cca gtg agg ggc cgt gag act tat gaa atg ctg        960
Glu Leu Leu Tyr Leu Pro Val Arg Gly Arg Glu Thr Tyr Glu Met Leu
305                 310                 315                 320 ttg aag atc aaa gag tcc ctg gaa ctc atg cag tac ctt cct cag cac       1008
Leu Lys Ile Lys Glu Ser Leu Glu Leu Met Gln Tyr Leu Pro Gln His
                325                 330                 335 aca att gaa acg tac agg caa cag caa cag cag cag cac cag cac tta       1056
Thr Ile Glu Thr Tyr Arg Gln Gln Gln Gln Gln Gln His Gln His Leu
                340                 345                 350 ctt cag aaa cag acc tca ata cag tct cca tct tca tat ggt aac agc       1104
Leu Gln Lys Gln Thr Ser Ile Gln Ser Pro Ser Ser Tyr Gly Asn Ser
        355                 360                 365 tcc cca cct ctg aac aaa atg aac agc atg aac aag ctg cct tct gtg       1152
Ser Pro Pro Leu Asn Lys Met Asn Ser Met Asn Lys Leu Pro Ser Val
    370                 375                 380 agc cag ctt atc aac cct cag cag cgc aac gcc ctc act cct aca acc       1200
Ser Gln Leu Ile Asn Pro Gln Gln Arg Asn Ala Leu Thr Pro Thr Thr
385                 390                 395                 400 att cct gat ggc atg gga gcc aac att ccc atg atg ggc acc cac atg       1248
Ile Pro Asp Gly Met Gly Ala Asn Ile Pro Met Met Gly Thr His Met
                405                 410                 415
```

-continued

| | |
|---|---|
| cca atg gct gga gac atg aat gga ctc agc ccc acc cag gca ctc cct<br>Pro Met Ala Gly Asp Met Asn Gly Leu Ser Pro Thr Gln Ala Leu Pro<br>420                         425                    430 | 1296 |
| ccc cca ctc tcc atg cca tcc acc tcc cac tgc aca ccc cca cct ccg<br>Pro Pro Leu Ser Met Pro Ser Thr Ser His Cys Thr Pro Pro Pro Pro<br>435                         440                    445 | 1344 |
| tat ccc aca gat tgc agc att gtc agg atc tgg caa gtc tga<br>Tyr Pro Thr Asp Cys Ser Ile Val Arg Ile Trp Gln Val<br>450                         455                    460 | 1386 |

<210> SEQ ID NO 6
<211> LENGTH: 1182
<212> TYPE: DNA
<213> ORGANISM: Homo sapiens
<220> FEATURE:
<221> NAME/KEY: CDS
<222> LOCATION: (1)..(1179)

<400> SEQUENCE: 6

| | |
|---|---|
| atg ttg tac ctg gaa aac aat gcc cag act caa ttt agt gag cca cag<br>Met Leu Tyr Leu Glu Asn Asn Ala Gln Thr Gln Phe Ser Glu Pro Gln<br>1                  5                    10                    15 | 48 |
| tac acg aac ctg ggg ctc ctg aac agc atg gac cag cag att cag aac<br>Tyr Thr Asn Leu Gly Leu Leu Asn Ser Met Asp Gln Gln Ile Gln Asn<br>20                         25                    30 | 96 |
| ggc tcc tcg tcc acc agt ccc tat aac aca gac cac gcg cag aac agc<br>Gly Ser Ser Ser Thr Ser Pro Tyr Asn Thr Asp His Ala Gln Asn Ser<br>35                       40                    45 | 144 |
| gtc acg gcg ccc tcg ccc tac gca cag ccc agc tcc acc ttc gat gct<br>Val Thr Ala Pro Ser Pro Tyr Ala Gln Pro Ser Ser Thr Phe Asp Ala<br>50                         55                    60 | 192 |
| ctc tct cca tca ccc gcc atc ccc tcc aac acc gac tac cca ggc ccg<br>Leu Ser Pro Ser Pro Ala Ile Pro Ser Asn Thr Asp Tyr Pro Gly Pro<br>65                       70                    75                    80 | 240 |
| cac agt ttc gac gtg tcc ttc cag cag tcg agc acc gcc aag tcg gcc<br>His Ser Phe Asp Val Ser Phe Gln Gln Ser Ser Thr Ala Lys Ser Ala<br>85                       90                    95 | 288 |
| acc tgg acg tat tcc act gaa ctg aag aaa ctc tac tgc caa att gca<br>Thr Trp Thr Tyr Ser Thr Glu Leu Lys Lys Leu Tyr Cys Gln Ile Ala<br>100                      105                  110 | 336 |
| aag aca tgc ccc atc cag atc aag gtg atg acc cca cct cct cag gga<br>Lys Thr Cys Pro Ile Gln Ile Lys Val Met Thr Pro Pro Pro Gln Gly<br>115                      120                  125 | 384 |
| gct gtt atc cgc gcc atg cct gtc tac aaa aaa gct gag cac gtc acg<br>Ala Val Ile Arg Ala Met Pro Val Tyr Lys Lys Ala Glu His Val Thr<br>130                      135                  140 | 432 |
| gag gtg gtg aag cgg tgc ccc aac cat gag ctg agc cgt gaa ttc aac<br>Glu Val Val Lys Arg Cys Pro Asn His Glu Leu Ser Arg Glu Phe Asn<br>145                      150                  155                  160 | 480 |
| gag gga cag att gcc cct cct agt cat ttg att cga gta gag ggg aac<br>Glu Gly Gln Ile Ala Pro Pro Ser His Leu Ile Arg Val Glu Gly Asn<br>165                      170                  175 | 528 |
| agc cat gcc cag tat gta gaa gat ccc atc aca gga aga cag agt gtg<br>Ser His Ala Gln Tyr Val Glu Asp Pro Ile Thr Gly Arg Gln Ser Val<br>180                      185                  190 | 576 |
| ctg gta cct tat gag cca ccc cag gtt ggc act gaa ttc acg aca gtc<br>Leu Val Pro Tyr Glu Pro Pro Gln Val Gly Thr Glu Phe Thr Thr Val<br>195                      200                  205 | 624 |
| ttg tac aat ttc atg tgt aac agc agt tgt gtt gga ggg atg aac cgc<br>Leu Tyr Asn Phe Met Cys Asn Ser Ser Cys Val Gly Gly Met Asn Arg<br>210                      215                  220 | 672 |

| | | |
|---|---|---|
| cgt cca att tta atc att gtt act ctg gaa acc aga gat ggg caa gtc<br>Arg Pro Ile Leu Ile Ile Val Thr Leu Glu Thr Arg Asp Gly Gln Val<br>225                   230                      235                   240 | 720 |
| ctg ggc cga cgc tgc ttt gag gcc cgg atc tgt gct tgc cca gga aga<br>Leu Gly Arg Arg Cys Phe Glu Ala Arg Ile Cys Ala Cys Pro Gly Arg<br>                   245                   250                   255 | 768 |
| gac agg aag gcg gat gaa gat agc atc aga aag cag caa gtt tcg gac<br>Asp Arg Lys Ala Asp Glu Asp Ser Ile Arg Lys Gln Gln Val Ser Asp<br>        260                   265                   270 | 816 |
| agt aca aag aac ggt gat ggt acg aag cgc ccg ttt cgt cag aac aca<br>Ser Thr Lys Asn Gly Asp Gly Thr Lys Arg Pro Phe Arg Gln Asn Thr<br>275                   280                   285 | 864 |
| cat ggt atc cag atg aca tcc atc aag aaa cga aga tcc cca gat gat<br>His Gly Ile Gln Met Thr Ser Ile Lys Lys Arg Arg Ser Pro Asp Asp<br>         290                   295                   300 | 912 |
| gaa ctg tta tac tta cca gtg agg ggc cgt gag act tat gaa atg ctg<br>Glu Leu Leu Tyr Leu Pro Val Arg Gly Arg Glu Thr Tyr Glu Met Leu<br>305                   310                   315                   320 | 960 |
| ttg aag atc aaa gag tcc ctg gaa ctc atg cag tac ctt cct cag cac<br>Leu Lys Ile Lys Glu Ser Leu Glu Leu Met Gln Tyr Leu Pro Gln His<br>                   325                   330                   335 | 1008 |
| aca att gaa acg tac agg caa cag caa cag cag cac cag cac tta<br>Thr Ile Glu Thr Tyr Arg Gln Gln Gln Gln Gln His Gln His Leu<br>        340                   345                   350 | 1056 |
| ctt cag aaa cat ctc ctt tca gcc tgc ttc agg aat gag ctt gtg gag<br>Leu Gln Lys His Leu Leu Ser Ala Cys Phe Arg Asn Glu Leu Val Glu<br>355                   360                   365 | 1104 |
| ccc cgg aga gaa act cca aaa caa tct gac gtc ttt ttt aga cat tcc<br>Pro Arg Arg Glu Thr Pro Lys Gln Ser Asp Val Phe Phe Arg His Ser<br>        370                   375                   380 | 1152 |
| aag ccc cca aac cga tca gtg tac cca tag<br>Lys Pro Pro Asn Arg Ser Val Tyr Pro<br>385                   390 | 1182 |

```
<210> SEQ ID NO 7
<211> LENGTH: 2043
<212> TYPE: DNA
<213> ORGANISM: Mus musculus
<220> FEATURE:
<221> NAME/KEY: CDS
<222> LOCATION: (1)..(2040)

<400> SEQUENCE: 7
```

| | | |
|---|---|---|
| atg aat ttt gaa act tca cgg tgt gcc acc cta cag tac tgc ccc gac<br>Met Asn Phe Glu Thr Ser Arg Cys Ala Thr Leu Gln Tyr Cys Pro Asp<br>1                   5                     10                    15 | 48 |
| cct tac atc cag cgt ttc ata gaa acc cca gct cat ttc tcg tgg aaa<br>Pro Tyr Ile Gln Arg Phe Ile Glu Thr Pro Ala His Phe Ser Trp Lys<br>                    20                    25                    30 | 96 |
| gaa agt tat tac aga tct gcc atg tcg cag agc acc cag aca agc gag<br>Glu Ser Tyr Tyr Arg Ser Ala Met Ser Gln Ser Thr Gln Thr Ser Glu<br>        35                   40                   45 | 144 |
| ttc ctc agc cca gag gtc ttc cag cat atc tgg gat ttt ctg gaa cag<br>Phe Leu Ser Pro Glu Val Phe Gln His Ile Trp Asp Phe Leu Glu Gln<br>50                   55                   60 | 192 |
| cct ata tgc tca gta cag ccc atc gag ttg aac ttt gtg gat gaa cct<br>Pro Ile Cys Ser Val Gln Pro Ile Glu Leu Asn Phe Val Asp Glu Pro<br>65                   70                   75                   80 | 240 |
| tcc gaa aat ggt gca aca aac aag att gag att agc atg gat tgt atc<br>Ser Glu Asn Gly Ala Thr Asn Lys Ile Glu Ile Ser Met Asp Cys Ile<br>                   85                   90                   95 | 288 |

```
cgc atg caa gac tca gac ctc agt gac ccc atg tgg cca cag tac acg      336
Arg Met Gln Asp Ser Asp Leu Ser Asp Pro Met Trp Pro Gln Tyr Thr
            100                 105                 110 aac ctg ggg ctc ctg aac agc atg gac cag cag att cag aac ggc tcc      384
Asn Leu Gly Leu Leu Asn Ser Met Asp Gln Gln Ile Gln Asn Gly Ser
        115                 120                 125 tcg tcc acc agc ccc tac aac aca gac cac gca cag aat agc gtg acg      432
Ser Ser Thr Ser Pro Tyr Asn Thr Asp His Ala Gln Asn Ser Val Thr
130                 135                 140 gcg ccc tcg ccc tat gca cag ccc agc tcc acc ttt gat gcc ctc tct      480
Ala Pro Ser Pro Tyr Ala Gln Pro Ser Ser Thr Phe Asp Ala Leu Ser
145                 150                 155                 160 cca tcc cct gcc att ccc tcc aac aca gat tac ccg ggc cca cac agc      528
Pro Ser Pro Ala Ile Pro Ser Asn Thr Asp Tyr Pro Gly Pro His Ser
                165                 170                 175 ttc gat gtg tcc ttc cag cag tca agc act gcc aag tca gcc acc tgg      576
Phe Asp Val Ser Phe Gln Gln Ser Ser Thr Ala Lys Ser Ala Thr Trp
            180                 185                 190 acg tat tcc acc gaa ctg aag aag ctg tac tgc cag att gcg aag aca      624
Thr Tyr Ser Thr Glu Leu Lys Lys Leu Tyr Cys Gln Ile Ala Lys Thr
        195                 200                 205 tgc ccc atc cag atc aag gtg atg acc cca ccc cag ggc gct gtt          672
Cys Pro Ile Gln Ile Lys Val Met Thr Pro Pro Gln Gly Ala Val
210                 215                 220 atc cgt gcc atg cct gtc tac aag aaa gct gag cat gtc acc gag gtt      720
Ile Arg Ala Met Pro Val Tyr Lys Lys Ala Glu His Val Thr Glu Val
225                 230                 235                 240 gtg aaa cga tgc cct aac cat gag ctg agc cgt gag ttc aat gag gga      768
Val Lys Arg Cys Pro Asn His Glu Leu Ser Arg Glu Phe Asn Glu Gly
                245                 250                 255 cag att gcc cct ccc agt cat ctg att cga gta gaa ggg aac agc cat      816
Gln Ile Ala Pro Pro Ser His Leu Ile Arg Val Glu Gly Asn Ser His
            260                 265                 270 gcc cag tat gta gaa gat cct atc acg gga agg cag agc gtg ctg gtc      864
Ala Gln Tyr Val Glu Asp Pro Ile Thr Gly Arg Gln Ser Val Leu Val
        275                 280                 285 cct tat gag cca cca cag gtt ggc act gaa ttc aca aca gtc ctg tac      912
Pro Tyr Glu Pro Pro Gln Val Gly Thr Glu Phe Thr Thr Val Leu Tyr
290                 295                 300 aat ttc atg tgt aac agc agc tgc gtc gga gga atg aac aga cgt cca      960
Asn Phe Met Cys Asn Ser Ser Cys Val Gly Gly Met Asn Arg Arg Pro
305                 310                 315                 320 att tta atc atc gtt act ctg gaa acc aga gat ggg caa gtc ctg ggc     1008
Ile Leu Ile Ile Val Thr Leu Glu Thr Arg Asp Gly Gln Val Leu Gly
                325                 330                 335 cga cgg tgc ttt gag gcc cgg atc tgt gct tgc cca gga aga gac cgg     1056
Arg Arg Cys Phe Glu Ala Arg Ile Cys Ala Cys Pro Gly Arg Asp Arg
            340                 345                 350 aag gca gat gaa gac agc atc aga aag cag caa gta tcg gac agc gca     1104
Lys Ala Asp Glu Asp Ser Ile Arg Lys Gln Gln Val Ser Asp Ser Ala
        355                 360                 365 aag aac ggc gat ggt acg aag cgc cct ttc cgt cag aat aca cac gga     1152
Lys Asn Gly Asp Gly Thr Lys Arg Pro Phe Arg Gln Asn Thr His Gly
370                 375                 380 atc cag atg act tcc atc aag aaa cgg aga tcc cca gat gat gag ctg     1200
Ile Gln Met Thr Ser Ile Lys Lys Arg Arg Ser Pro Asp Asp Glu Leu
385                 390                 395                 400 ctg tac cta cca gtg aga ggt cgt gag acg tac gag atg ttg ctg aag     1248
Leu Tyr Leu Pro Val Arg Gly Arg Glu Thr Tyr Glu Met Leu Leu Lys
                405                 410                 415
```

| | | |
|---|---|---|
| atc aaa gag tca ctg gag ctc atg cag tac ctc cct cag cac acg atc<br>Ile Lys Glu Ser Leu Glu Leu Met Gln Tyr Leu Pro Gln His Thr Ile<br>420                   425                   430 | | 1296 |
| gaa acg tac agg cag cag cag cag cag cac cag cac cta ctt cag<br>Glu Thr Tyr Arg Gln Gln Gln Gln Gln His Gln His Leu Leu Gln<br>                435                   440                   445 | | 1344 |
| aaa cag acc tcg atg cag tct cag tct tca tat ggc aac agt tcc cca<br>Lys Gln Thr Ser Met Gln Ser Gln Ser Ser Tyr Gly Asn Ser Ser Pro<br>450                   455                   460 | | 1392 |
| cct ctg aac aaa atg aac agc atg aac aag ctg cct tcc gtg agc cag<br>Pro Leu Asn Lys Met Asn Ser Met Asn Lys Leu Pro Ser Val Ser Gln<br>465                   470                   475                   480 | | 1440 |
| ctt atc aac cca cag cag cgc aat gcc ctc act ccc acc acc atg cct<br>Leu Ile Asn Pro Gln Gln Arg Asn Ala Leu Thr Pro Thr Thr Met Pro<br>                  485                   490                   495 | | 1488 |
| gag ggc atg gga gcc aac att cct atg atg ggc act cac atg cca atg<br>Glu Gly Met Gly Ala Asn Ile Pro Met Met Gly Thr His Met Pro Met<br>                500                   505                   510 | | 1536 |
| gct gga gac atg aat gga ctc agc cct acc caa gct ctc cct cct cca<br>Ala Gly Asp Met Asn Gly Leu Ser Pro Thr Gln Ala Leu Pro Pro Pro<br>515                   520                   525 | | 1584 |
| ctc tcc atg ccc tcc acc tcc cac tgc acc cca cca ccg ccc tac ccc<br>Leu Ser Met Pro Ser Thr Ser His Cys Thr Pro Pro Pro Pro Tyr Pro<br>530                   535                   540 | | 1632 |
| aca gac tgc agc att gtc agt ttc tta gca agg ttg ggc tgc tca tca<br>Thr Asp Cys Ser Ile Val Ser Phe Leu Ala Arg Leu Gly Cys Ser Ser<br>545                   550                   555                   560 | | 1680 |
| tgc ctg gac tat ttc acg acc cag ggg ctg acc acc atc tat cag att<br>Cys Leu Asp Tyr Phe Thr Thr Gln Gly Leu Thr Thr Ile Tyr Gln Ile<br>                  565                   570                   575 | | 1728 |
| gag cat tac tcc atg gat gat ttg gca agt ctg aag atc cct gaa cag<br>Glu His Tyr Ser Met Asp Asp Leu Ala Ser Leu Lys Ile Pro Glu Gln<br>                580                   585                   590 | | 1776 |
| ttc cga cat gcc atc tgg aag ggc atc ctg gac cac agg cag ctg cac<br>Phe Arg His Ala Ile Trp Lys Gly Ile Leu Asp His Arg Gln Leu His<br>                595                   600                   605 | | 1824 |
| gac ttc tcc tca cct cct cat ctc ctg agg acc cca agt ggt gcc tct<br>Asp Phe Ser Ser Pro Pro His Leu Leu Arg Thr Pro Ser Gly Ala Ser<br>610                   615                   620 | | 1872 |
| acc gtc agt gtg ggc tcc agt gag acc cgt ggt gaa cgt gtg atc gat<br>Thr Val Ser Val Gly Ser Ser Glu Thr Arg Gly Glu Arg Val Ile Asp<br>625                   630                   635                   640 | | 1920 |
| gcc gtg cgc ttt acc ctc cgc cag acc atc tct ttt cca ccc cgt gac<br>Ala Val Arg Phe Thr Leu Arg Gln Thr Ile Ser Phe Pro Pro Arg Asp<br>                  645                   650                   655 | | 1968 |
| gag tgg aat gat ttc aac ttt gac atg gat tct cgt cgc aac aag cag<br>Glu Trp Asn Asp Phe Asn Phe Asp Met Asp Ser Arg Arg Asn Lys Gln<br>                660                   665                   670 | | 2016 |
| cag cgt atc aaa gag gaa gga gaa tga<br>Gln Arg Ile Lys Glu Glu Gly Glu<br>675                   680 | | 2043 |

<210> SEQ ID NO 8
<211> LENGTH: 1668
<212> TYPE: DNA
<213> ORGANISM: Mus musculus
<220> FEATURE:
<221> NAME/KEY: CDS
<222> LOCATION: (1)..(1665)

<400> SEQUENCE: 8

```
atg aat ttt gaa act tca cgg tgt gcc acc cta cag tac tgc ccc gac      48
Met Asn Phe Glu Thr Ser Arg Cys Ala Thr Leu Gln Tyr Cys Pro Asp
  1               5                  10                  15 cct tac atc cag cgt ttc ata gaa acc cca gct cat ttc tcg tgg aaa      96
Pro Tyr Ile Gln Arg Phe Ile Glu Thr Pro Ala His Phe Ser Trp Lys
             20                  25                  30 gaa agt tat tac aga tct gcc atg tcg cag agc acc cag aca agc gag     144
Glu Ser Tyr Tyr Arg Ser Ala Met Ser Gln Ser Thr Gln Thr Ser Glu
                 35                  40                  45 ttc ctc agc cca gag gtc ttc cag cat atc tgg gat ttt ctg gaa cag     192
Phe Leu Ser Pro Glu Val Phe Gln His Ile Trp Asp Phe Leu Glu Gln
 50                  55                  60 cct ata tgc tca gta cag ccc atc gag ttg aac ttt gtg gat gaa cct     240
Pro Ile Cys Ser Val Gln Pro Ile Glu Leu Asn Phe Val Asp Glu Pro
 65                  70                  75                  80 tcc gaa aat ggt gca aca aac aag att gag att agc atg gat tgt atc     288
Ser Glu Asn Gly Ala Thr Asn Lys Ile Glu Ile Ser Met Asp Cys Ile
                 85                  90                  95 cgc atg caa gac tca gac ctc agt gac ccc atg tgg cca cag tac acg     336
Arg Met Gln Asp Ser Asp Leu Ser Asp Pro Met Trp Pro Gln Tyr Thr
                100                 105                 110 aac ctg ggg ctc ctg aac agc atg gac cag cag att cag aac ggc tcc     384
Asn Leu Gly Leu Leu Asn Ser Met Asp Gln Gln Ile Gln Asn Gly Ser
            115                 120                 125 tcg tcc acc agc ccc tac aac aca gac cac gca cag aat agc gtg acg     432
Ser Ser Thr Ser Pro Tyr Asn Thr Asp His Ala Gln Asn Ser Val Thr
130                 135                 140 gcg ccc tcg ccc tat gca cag ccc agc tcc acc ttt gat gcc ctc tct     480
Ala Pro Ser Pro Tyr Ala Gln Pro Ser Ser Thr Phe Asp Ala Leu Ser
145                 150                 155                 160 cca tcc cct gcc att ccc tcc aac aca gat tac ccg ggc cca cac agc     528
Pro Ser Pro Ala Ile Pro Ser Asn Thr Asp Tyr Pro Gly Pro His Ser
                165                 170                 175 ttc gat gtg tcc ttc cag cag tca agc act gcc aag tca gcc acc tgg     576
Phe Asp Val Ser Phe Gln Gln Ser Ser Thr Ala Lys Ser Ala Thr Trp
            180                 185                 190 acg tat tcc acc gaa ctg aag aag ctg tac tgc cag att gcg aag aca     624
Thr Tyr Ser Thr Glu Leu Lys Lys Leu Tyr Cys Gln Ile Ala Lys Thr
            195                 200                 205 tgc ccc atc cag atc aag gtg atg acc cca ccc cag ggc gct gtt         672
Cys Pro Ile Gln Ile Lys Val Met Thr Pro Pro Gln Gly Ala Val
210                 215                 220 atc cgt gcc atg cct gtc tac aag aaa gct gag cat gtc acc gag gtt     720
Ile Arg Ala Met Pro Val Tyr Lys Lys Ala Glu His Val Thr Glu Val
225                 230                 235                 240 gtg aaa cga tgc cct aac cat gag ctg agc cgt gag ttc aat gag gga     768
Val Lys Arg Cys Pro Asn His Glu Leu Ser Arg Glu Phe Asn Glu Gly
                245                 250                 255 cag att gcc cct ccc agt cat ctg att cga gta gaa ggg aac agc cat     816
Gln Ile Ala Pro Pro Ser His Leu Ile Arg Val Glu Gly Asn Ser His
            260                 265                 270 gcc cag tat gta gaa gat cct atc acg gga agg cag agc gtg ctg gtc     864
Ala Gln Tyr Val Glu Asp Pro Ile Thr Gly Arg Gln Ser Val Leu Val
            275                 280                 285 cct tat gag cca cca cag gtt ggc act gaa ttc aca aca gtc ctg tac     912
Pro Tyr Glu Pro Pro Gln Val Gly Thr Glu Phe Thr Thr Val Leu Tyr
290                 295                 300 aat ttc atg tgt aac agc agc tgc gtc gga gga atg aac aga cgt cca     960
Asn Phe Met Cys Asn Ser Ser Cys Val Gly Gly Met Asn Arg Arg Pro
```

-continued

```
att tta atc atc gtt act ctg gaa acc aga gat ggg caa gtc ctg ggc      1008
Ile Leu Ile Ile Val Thr Leu Glu Thr Arg Asp Gly Gln Val Leu Gly
                325                 330                 335 cga cgg tgc ttt gag gcc cgg atc tgt gct tgc cca gga aga gac cgg      1056
Arg Arg Cys Phe Glu Ala Arg Ile Cys Ala Cys Pro Gly Arg Asp Arg
            340                 345                 350 aag gca gat gaa gac agc atc aga aag cag caa gta tcg gac agc gca      1104
Lys Ala Asp Glu Asp Ser Ile Arg Lys Gln Gln Val Ser Asp Ser Ala
        355                 360                 365 aag aac ggc gat ggt acg aag cgc cct ttc cgt cag aat aca cac gga      1152
Lys Asn Gly Asp Gly Thr Lys Arg Pro Phe Arg Gln Asn Thr His Gly
    370                 375                 380 atc cag atg act tcc atc aag aaa cgg aga tcc cca gat gat gag ctg      1200
Ile Gln Met Thr Ser Ile Lys Lys Arg Arg Ser Pro Asp Asp Glu Leu
385                 390                 395                 400 ctg tac cta cca gtg aga ggt cgt gag acg tac gag atg ttg ctg aag      1248
Leu Tyr Leu Pro Val Arg Gly Arg Glu Thr Tyr Glu Met Leu Leu Lys
                405                 410                 415 atc aaa gag tca ctg gag ctc atg cag tac ctc cct cag cac acg atc      1296
Ile Lys Glu Ser Leu Glu Leu Met Gln Tyr Leu Pro Gln His Thr Ile
            420                 425                 430 gaa acg tac agg cag cag cag cag cag cac cag cac cta ctt cag           1344
Glu Thr Tyr Arg Gln Gln Gln Gln Gln His Gln His Leu Leu Gln
        435                 440                 445 aaa cag acc tcg atg cag tct cag tct tca tat ggc aac agt tcc cca      1392
Lys Gln Thr Ser Met Gln Ser Gln Ser Ser Tyr Gly Asn Ser Ser Pro
    450                 455                 460 cct ctg aac aaa atg aac agc atg aac aag ctg cct tcc gtg agc cag      1440
Pro Leu Asn Lys Met Asn Ser Met Asn Lys Leu Pro Ser Val Ser Gln
465                 470                 475                 480 ctt atc aac cca cag cag cgc aat gcc ctc act ccc acc acc atg cct      1488
Leu Ile Asn Pro Gln Gln Arg Asn Ala Leu Thr Pro Thr Thr Met Pro
                485                 490                 495 gag ggc atg gga gcc aac att cct atg atg ggc act cac atg cca atg      1536
Glu Gly Met Gly Ala Asn Ile Pro Met Met Gly Thr His Met Pro Met
            500                 505                 510 gct gga gac atg aat gga ctc agc cct acc caa gct ctc cct cct cca      1584
Ala Gly Asp Met Asn Gly Leu Ser Pro Thr Gln Ala Leu Pro Pro Pro
        515                 520                 525 ctc tcc atg ccc tcc acc tcc cac tgc acc cca cca ccg ccc tac ccc      1632
Leu Ser Met Pro Ser Thr Ser His Cys Thr Pro Pro Pro Pro Tyr Pro
    530                 535                 540 aca gac tgc agc att gtc agg att tgg caa gtc tga                      1668
Thr Asp Cys Ser Ile Val Arg Ile Trp Gln Val
545                 550                 555

<210> SEQ ID NO 9
<211> LENGTH: 1452
<212> TYPE: DNA
<213> ORGANISM: Mus musculus
<220> FEATURE:
<221> NAME/KEY: CDS
<222> LOCATION: (1)..(1449)

<400> SEQUENCE: 9 atg aat ttt gaa act tca cgg tgt gcc acc cta cag tac tgc ccc gac      48
Met Asn Phe Glu Thr Ser Arg Cys Ala Thr Leu Gln Tyr Cys Pro Asp
1               5                   10                  15 cct tac atc cag cgt ttc ata gaa acc cca gct cat ttc tcg tgg aaa      96
Pro Tyr Ile Gln Arg Phe Ile Glu Thr Pro Ala His Phe Ser Trp Lys
```

-continued

```
                         20                      25                      30
gaa agt tat tac aga tct gcc atg tcg cag agc acc cag aca agc gag          144
Glu Ser Tyr Tyr Arg Ser Ala Met Ser Gln Ser Thr Gln Thr Ser Glu
             35                      40                      45 ttc ctc agc cca gag gtc ttc cag cat atc tgg gat ttt ctg gaa cag          192
Phe Leu Ser Pro Glu Val Phe Gln His Ile Trp Asp Phe Leu Glu Gln
 50                      55                      60 cct ata tgc tca gta cag ccc atc gag ttg aac ttt gtg gat gaa cct          240
Pro Ile Cys Ser Val Gln Pro Ile Glu Leu Asn Phe Val Asp Glu Pro
 65                      70                      75                  80 tcc gaa aat ggt gca aca aac aag att gag att agc atg gat tgt atc          288
Ser Glu Asn Gly Ala Thr Asn Lys Ile Glu Ile Ser Met Asp Cys Ile
                 85                      90                      95 cgc atg caa gac tca gac ctc agt gac ccc atg tgg cca cag tac acg          336
Arg Met Gln Asp Ser Asp Leu Ser Asp Pro Met Trp Pro Gln Tyr Thr
                100                     105                     110 aac ctg ggg ctc ctg aac agc atg gac cag cag att cag aac ggc tcc          384
Asn Leu Gly Leu Leu Asn Ser Met Asp Gln Gln Ile Gln Asn Gly Ser
            115                     120                     125 tcg tcc acc agc ccc tac aac aca gac cac gca cag aat agc gtg acg          432
Ser Ser Thr Ser Pro Tyr Asn Thr Asp His Ala Gln Asn Ser Val Thr
        130                     135                     140 gcg ccc tcg ccc tat gca cag ccc agc tcc acc ttt gat gcc ctc tct          480
Ala Pro Ser Pro Tyr Ala Gln Pro Ser Ser Thr Phe Asp Ala Leu Ser
145                     150                     155                     160 cca tcc cct gcc att ccc tcc aac aca gat tac ccg ggc cca cac agc          528
Pro Ser Pro Ala Ile Pro Ser Asn Thr Asp Tyr Pro Gly Pro His Ser
                165                     170                     175 ttc gat gtg tcc ttc cag cag tca agc act gcc aag tca gcc acc tgg          576
Phe Asp Val Ser Phe Gln Gln Ser Ser Thr Ala Lys Ser Ala Thr Trp
            180                     185                     190 acg tat tcc acc gaa ctg aag aag ctg tac tgc cag att gcg aag aca          624
Thr Tyr Ser Thr Glu Leu Lys Lys Leu Tyr Cys Gln Ile Ala Lys Thr
        195                     200                     205 tgc ccc atc cag atc aag gtg atg acc cca ccc cag ggc gct gtt              672
Cys Pro Ile Gln Ile Lys Val Met Thr Pro Pro Gln Gly Ala Val
210                     215                     220 atc cgt gcc atg cct gtc tac aag aaa gct gag cat gtc acc gag gtt          720
Ile Arg Ala Met Pro Val Tyr Lys Lys Ala Glu His Val Thr Glu Val
225                     230                     235                     240 gtg aaa cga tgc cct aac cat gag ctg agc cgt gag ttc aat gag gga          768
Val Lys Arg Cys Pro Asn His Glu Leu Ser Arg Glu Phe Asn Glu Gly
                245                     250                     255 cag att gcc cct ccc agt cat ctg att cga gta gaa ggg aac agc cat          816
Gln Ile Ala Pro Pro Ser His Leu Ile Arg Val Glu Gly Asn Ser His
            260                     265                     270 gcc cag tat gta gaa gat cct atc acg gga agg cag agc gtg ctg gtc          864
Ala Gln Tyr Val Glu Asp Pro Ile Thr Gly Arg Gln Ser Val Leu Val
        275                     280                     285 cct tat gag cca cca cag gtt ggc act gaa ttc aca aca gtc ctg tac          912
Pro Tyr Glu Pro Pro Gln Val Gly Thr Glu Phe Thr Thr Val Leu Tyr
290                     295                     300 aat ttc atg tgt aac agc agc tgc gtc gga gga atg aac aga cgt cca          960
Asn Phe Met Cys Asn Ser Ser Cys Val Gly Gly Met Asn Arg Arg Pro
305                     310                     315                     320 att tta atc atc gtt act ctg gaa acc aga gat ggg caa gtc ctg ggc         1008
Ile Leu Ile Ile Val Thr Leu Glu Thr Arg Asp Gly Gln Val Leu Gly
                325                     330                     335 cga cgg tgc ttt gag gcc cgg atc tgt gct tgc cca gga aga gac cgg         1056
```

```
Arg Arg Cys Phe Glu Ala Arg Ile Cys Ala Cys Pro Gly Arg Asp Arg
        340                 345                 350 aag gca gat gaa gac agc atc aga aag cag caa gta tcg gac agc gca    1104
Lys Ala Asp Glu Asp Ser Ile Arg Lys Gln Gln Val Ser Asp Ser Ala
            355                 360                 365 aag aac ggc gat gct ttc cgt cag aat aca cac gga atc cag atg act    1152
Lys Asn Gly Asp Ala Phe Arg Gln Asn Thr His Gly Ile Gln Met Thr
    370                 375                 380 tcc atc aag aaa cgg aga tcc cca gat gat gag ctg ctg tac cta cca    1200
Ser Ile Lys Lys Arg Arg Ser Pro Asp Asp Glu Leu Leu Tyr Leu Pro
385                 390                 395                 400 gtg aga ggt cgt gag acg tac gag atg ttg ctg aag atc aaa gag tca    1248
Val Arg Gly Arg Glu Thr Tyr Glu Met Leu Leu Lys Ile Lys Glu Ser
                405                 410                 415 ctg gag ctc atg cag tac ctc cct cag cac acg atc gaa acg tac agg    1296
Leu Glu Leu Met Gln Tyr Leu Pro Gln His Thr Ile Glu Thr Tyr Arg
            420                 425                 430 cag cag cag cag cag cag cac cag cac cta ctt cag aaa cat ctc ctt    1344
Gln Gln Gln Gln Gln Gln His Gln His Leu Leu Gln Lys His Leu Leu
        435                 440                 445 tca gcc tgc ttc agg aat gag ctt gtg gag ccc cgg gga gaa gct ccg    1392
Ser Ala Cys Phe Arg Asn Glu Leu Val Glu Pro Arg Gly Glu Ala Pro
    450                 455                 460 aca cag tct gac gtc ttc ttt aga cat tcc aac ccc cca aac cac tcc    1440
Thr Gln Ser Asp Val Phe Phe Arg His Ser Asn Pro Pro Asn His Ser
465                 470                 475                 480 gtg tac cca tag                                                    1452
Val Tyr Pro <210> SEQ ID NO 10
<211> LENGTH: 1761
<212> TYPE: DNA
<213> ORGANISM: Mus musculus
<220> FEATURE:
<221> NAME/KEY: CDS
<222> LOCATION: (1)..(1758)

<400> SEQUENCE: 10 atg ttg tac ctg gaa aac aat gcc cag act caa ttt agt gag cca cag     48
Met Leu Tyr Leu Glu Asn Asn Ala Gln Thr Gln Phe Ser Glu Pro Gln
1               5                   10                  15 tac acg aac ctg ggg ctc ctg aac agc atg gac cag cag att cag aac     96
Tyr Thr Asn Leu Gly Leu Leu Asn Ser Met Asp Gln Gln Ile Gln Asn
            20                  25                  30 ggc tcc tcg tcc acc agc ccc tac aac aca gac cac gca cag aat agc    144
Gly Ser Ser Ser Thr Ser Pro Tyr Asn Thr Asp His Ala Gln Asn Ser
        35                  40                  45 gtg acg gcg ccc tcg ccc tat gca cag ccc agc tcc acc ttt gat gcc    192
Val Thr Ala Pro Ser Pro Tyr Ala Gln Pro Ser Ser Thr Phe Asp Ala
    50                  55                  60 ctc tct cca tcc cct gcc att ccc tcc aac aca gat tac ccg ggc cca    240
Leu Ser Pro Ser Pro Ala Ile Pro Ser Asn Thr Asp Tyr Pro Gly Pro
65                  70                  75                  80 cac agc ttc gat gtg tcc ttc cag cag tca agc act gcc aag tca gcc    288
His Ser Phe Asp Val Ser Phe Gln Gln Ser Ser Thr Ala Lys Ser Ala
                85                  90                  95 acc tgg acg tat tcc acc gaa ctg aag aag ctg tac tgc cag att gcg    336
Thr Trp Thr Tyr Ser Thr Glu Leu Lys Lys Leu Tyr Cys Gln Ile Ala
            100                 105                 110 aag aca tgc ccc atc cag atc aag gtg atg acc cca ccc cca cag ggc    384
Lys Thr Cys Pro Ile Gln Ile Lys Val Met Thr Pro Pro Pro Gln Gly
```

-continued

```
                115                 120                 125
gct gtt atc cgt gcc atg cct gtc tac aag aaa gct gag cat gtc acc    432
Ala Val Ile Arg Ala Met Pro Val Tyr Lys Lys Ala Glu His Val Thr
130                 135                 140 gag gtt gtg aaa cga tgc cct aac cat gag ctg agc cgt gag ttc aat    480
Glu Val Val Lys Arg Cys Pro Asn His Glu Leu Ser Arg Glu Phe Asn
145                 150                 155                 160 gag gga cag att gcc cct ccc agt cat ctg att cga gta gaa ggg aac    528
Glu Gly Gln Ile Ala Pro Pro Ser His Leu Ile Arg Val Glu Gly Asn
                165                 170                 175 agc cat gcc cag tat gta gaa gat cct atc acg gga agg cag agc gtg    576
Ser His Ala Gln Tyr Val Glu Asp Pro Ile Thr Gly Arg Gln Ser Val
            180                 185                 190 ctg gtc cct tat gag cca cca cag gtt ggc act gaa ttc aca aca gtc    624
Leu Val Pro Tyr Glu Pro Pro Gln Val Gly Thr Glu Phe Thr Thr Val
        195                 200                 205 ctg tac aat ttc atg tgt aac agc agc tgc gtc gga gga atg aac aga    672
Leu Tyr Asn Phe Met Cys Asn Ser Ser Cys Val Gly Gly Met Asn Arg
    210                 215                 220 cgt cca att tta atc atc gtt act ctg gaa acc aga gat ggg caa gtc    720
Arg Pro Ile Leu Ile Ile Val Thr Leu Glu Thr Arg Asp Gly Gln Val
225                 230                 235                 240 ctg ggc cga cgg tgc ttt gag gcc cgg atc tgt gct tgc cca gga aga    768
Leu Gly Arg Arg Cys Phe Glu Ala Arg Ile Cys Ala Cys Pro Gly Arg
                245                 250                 255 gac cgg aag gca gat gaa gac agc atc aga aag cag caa gta tcg gac    816
Asp Arg Lys Ala Asp Glu Asp Ser Ile Arg Lys Gln Gln Val Ser Asp
            260                 265                 270 agc gca aag aac ggc gat ggt acg aag cgc cct ttc cgt cag aat aca    864
Ser Ala Lys Asn Gly Asp Gly Thr Lys Arg Pro Phe Arg Gln Asn Thr
        275                 280                 285 cac gga atc cag atg act tcc atc aag aaa cgg aga tcc cca gat gat    912
His Gly Ile Gln Met Thr Ser Ile Lys Lys Arg Arg Ser Pro Asp Asp
    290                 295                 300 gag ctg ctg tac cta cca gtg aga ggt cgt gag acg tac gag atg ttg    960
Glu Leu Leu Tyr Leu Pro Val Arg Gly Arg Glu Thr Tyr Glu Met Leu
305                 310                 315                 320 ctg aag atc aaa gag tca ctg gag ctc atg cag tac ctc cct cag cac    1008
Leu Lys Ile Lys Glu Ser Leu Glu Leu Met Gln Tyr Leu Pro Gln His
                325                 330                 335 acg atc gaa acg tac agg cag cag cag cag cag cag cac cag cac cta    1056
Thr Ile Glu Thr Tyr Arg Gln Gln Gln Gln Gln Gln His Gln His Leu
            340                 345                 350 ctt cag aaa cag acc tcg atg cag tct cag tct tca tat ggc aac agt    1104
Leu Gln Lys Gln Thr Ser Met Gln Ser Gln Ser Ser Tyr Gly Asn Ser
        355                 360                 365 tcc cca cct ctg aac aaa atg aac agc atg aac aag ctg cct tcc gtg    1152
Ser Pro Pro Leu Asn Lys Met Asn Ser Met Asn Lys Leu Pro Ser Val
    370                 375                 380 agc cag ctt atc aac cca cag cag cgc aat gcc ctc act ccc acc acc    1200
Ser Gln Leu Ile Asn Pro Gln Gln Arg Asn Ala Leu Thr Pro Thr Thr
385                 390                 395                 400 atg cct gag ggc atg gga gcc aac att cct atg atg ggc act cac atg    1248
Met Pro Glu Gly Met Gly Ala Asn Ile Pro Met Met Gly Thr His Met
                405                 410                 415 cca atg gct gga gac atg aat gga ctc agc cct acc caa gct ctc cct    1296
Pro Met Ala Gly Asp Met Asn Gly Leu Ser Pro Thr Gln Ala Leu Pro
            420                 425                 430 cct cca ctc tcc atg ccc tcc acc tcc cac tgc acc cca cca ccg ccc    1344
```

```
Pro Pro Leu Ser Met Pro Ser Thr Ser His Cys Thr Pro Pro Pro
        435                 440                 445 tac ccc aca gac tgc agc att gtc agt ttc tta gca agg ttg ggc tgc    1392
Tyr Pro Thr Asp Cys Ser Ile Val Ser Phe Leu Ala Arg Leu Gly Cys
450                 455                 460 tca tca tgc ctg gac tat ttc acg acc cag ggg ctg acc acc atc tat    1440
Ser Ser Cys Leu Asp Tyr Phe Thr Thr Gln Gly Leu Thr Thr Ile Tyr
465                 470                 475                 480 cag att gag cat tac tcc atg gat gat ttg gca agt ctg aag atc cct    1488
Gln Ile Glu His Tyr Ser Met Asp Asp Leu Ala Ser Leu Lys Ile Pro
                485                 490                 495 gaa cag ttc cga cat gcc atc tgg aag ggc atc ctg gac cac agg cag    1536
Glu Gln Phe Arg His Ala Ile Trp Lys Gly Ile Leu Asp His Arg Gln
            500                 505                 510 ctg cac gac ttc tcc tca cct cct cat ctc ctg agg acc cca agt ggt    1584
Leu His Asp Phe Ser Ser Pro Pro His Leu Leu Arg Thr Pro Ser Gly
        515                 520                 525 gcc tct acc gtc agt gtg ggc tcc agt gag acc cgt ggt gaa cgt gtg    1632
Ala Ser Thr Val Ser Val Gly Ser Ser Glu Thr Arg Gly Glu Arg Val
    530                 535                 540 atc gat gcc gtg cgc ttt acc ctc cgc cag acc atc tct ttt cca ccc    1680
Ile Asp Ala Val Arg Phe Thr Leu Arg Gln Thr Ile Ser Phe Pro Pro
545                 550                 555                 560 cgt gac gag tgg aat gat ttc aac ttt gac atg gat tct cgt cgc aac    1728
Arg Asp Glu Trp Asn Asp Phe Asn Phe Asp Met Asp Ser Arg Arg Asn
                565                 570                 575 aag cag cag cgt atc aaa gag gaa gga gaa tga                        1761
Lys Gln Gln Arg Ile Lys Glu Glu Gly Glu
            580                 585

<210> SEQ ID NO 11
<211> LENGTH: 1386
<212> TYPE: DNA
<213> ORGANISM: Mus musculus
<220> FEATURE:
<221> NAME/KEY: CDS
<222> LOCATION: (1)..(1383)

<400> SEQUENCE: 11 atg ttg tac ctg gaa aac aat gcc cag act caa ttt agt gag cca cag     48
Met Leu Tyr Leu Glu Asn Asn Ala Gln Thr Gln Phe Ser Glu Pro Gln
1               5                   10                  15 tac acg aac ctg ggg ctc ctg aac agc atg gac cag cag att cag aac     96
Tyr Thr Asn Leu Gly Leu Leu Asn Ser Met Asp Gln Gln Ile Gln Asn
                20                  25                  30 ggc tcc tcg tcc acc agc ccc tac aac aca gac cac gca cag aat agc    144
Gly Ser Ser Ser Thr Ser Pro Tyr Asn Thr Asp His Ala Gln Asn Ser
            35                  40                  45 gtg acg gcg ccc tcg ccc tat gca cag ccc agc tcc acc ttt gat gcc    192
Val Thr Ala Pro Ser Pro Tyr Ala Gln Pro Ser Ser Thr Phe Asp Ala
        50                  55                  60 ctc tct cca tcc cct gcc att ccc tcc aac aca gat tac ccg ggc cca    240
Leu Ser Pro Ser Pro Ala Ile Pro Ser Asn Thr Asp Tyr Pro Gly Pro
65                  70                  75                  80 cac agc ttc gat gtg tcc ttc cag cag tca agc act gcc aag tca gcc    288
His Ser Phe Asp Val Ser Phe Gln Gln Ser Ser Thr Ala Lys Ser Ala
                85                  90                  95 acc tgg acg tat tcc acc gaa ctg aag aag ctg tac tgc cag att gcg    336
Thr Trp Thr Tyr Ser Thr Glu Leu Lys Lys Leu Tyr Cys Gln Ile Ala
                100                 105                 110 aag aca tgc ccc atc cag atc aag gtg atg acc cca ccc cca cag ggc    384
```

-continued

```
           Lys Thr Cys Pro Ile Gln Ile Lys Val Met Thr Pro Pro Gln Gly
                   115                 120                 125 gct gtt atc cgt gcc atg cct gtc tac aag aaa gct gag cat gtc acc        432
Ala Val Ile Arg Ala Met Pro Val Tyr Lys Lys Ala Glu His Val Thr
        130                 135                 140 gag gtt gtg aaa cga tgc cct aac cat gag ctg agc cgt gag ttc aat        480
Glu Val Val Lys Arg Cys Pro Asn His Glu Leu Ser Arg Glu Phe Asn
145                 150                 155                 160 gag gga cag att gcc cct ccc agt cat ctg att cga gta gaa ggg aac        528
Glu Gly Gln Ile Ala Pro Pro Ser His Leu Ile Arg Val Glu Gly Asn
                165                 170                 175 agc cat gcc cag tat gta gaa gat cct atc acg gga agg cag agc gtg        576
Ser His Ala Gln Tyr Val Glu Asp Pro Ile Thr Gly Arg Gln Ser Val
            180                 185                 190 ctg gtc cct tat gag cca cca cag gtt ggc act gaa ttc aca aca gtc        624
Leu Val Pro Tyr Glu Pro Pro Gln Val Gly Thr Glu Phe Thr Thr Val
        195                 200                 205 ctg tac aat ttc atg tgt aac agc agc tgc gtc gga gga atg aac aga        672
Leu Tyr Asn Phe Met Cys Asn Ser Ser Cys Val Gly Gly Met Asn Arg
    210                 215                 220 cgt cca att tta atc atc gtt act ctg gaa acc aga gat ggg caa gtc        720
Arg Pro Ile Leu Ile Ile Val Thr Leu Glu Thr Arg Asp Gly Gln Val
225                 230                 235                 240 ctg ggc cga cgg tgc ttt gag gcc cgg atc tgt gct tgc cca gga aga        768
Leu Gly Arg Arg Cys Phe Glu Ala Arg Ile Cys Ala Cys Pro Gly Arg
                245                 250                 255 gac cgg aag gca gat gaa gac agc atc aga aag cag caa gta tcg gac        816
Asp Arg Lys Ala Asp Glu Asp Ser Ile Arg Lys Gln Gln Val Ser Asp
                260                 265                 270 agc gca aag aac ggc gat ggt acg aag cgc cct ttc cgt cag aat aca        864
Ser Ala Lys Asn Gly Asp Gly Thr Lys Arg Pro Phe Arg Gln Asn Thr
            275                 280                 285 cac gga atc cag atg act tcc atc aag aaa cgg aga tcc cca gat gat        912
His Gly Ile Gln Met Thr Ser Ile Lys Lys Arg Arg Ser Pro Asp Asp
        290                 295                 300 gag ctg ctg tac cta cca gtg aga ggt cgt gag acg tac gag atg ttg        960
Glu Leu Leu Tyr Leu Pro Val Arg Gly Arg Glu Thr Tyr Glu Met Leu
305                 310                 315                 320 ctg aag atc aaa gag tca ctg gag ctc atg cag tac ctc cct cag cac       1008
Leu Lys Ile Lys Glu Ser Leu Glu Leu Met Gln Tyr Leu Pro Gln His
                325                 330                 335 acg atc gaa acg tac agg cag cag cag cag cag cac cag cac cta            1056
Thr Ile Glu Thr Tyr Arg Gln Gln Gln Gln Gln His Gln His Leu
                340                 345                 350 ctt cag aaa cag acc tcg atg cag tct cag tct tca tat ggc aac agt       1104
Leu Gln Lys Gln Thr Ser Met Gln Ser Gln Ser Ser Tyr Gly Asn Ser
            355                 360                 365 tcc cca cct ctg aac aaa atg aac agc atg aac aag ctg cct tcc gtg       1152
Ser Pro Pro Leu Asn Lys Met Asn Ser Met Asn Lys Leu Pro Ser Val
        370                 375                 380 agc cag ctt atc aac cca cag cag cgc aat gcc ctc act ccc acc acc       1200
Ser Gln Leu Ile Asn Pro Gln Gln Arg Asn Ala Leu Thr Pro Thr Thr
385                 390                 395                 400 atg cct gag ggc atg gga gcc aac att cct atg atg ggc act cac atg       1248
Met Pro Glu Gly Met Gly Ala Asn Ile Pro Met Met Gly Thr His Met
                405                 410                 415 cca atg gct gga gac atg aat gga ctc agc cct acc caa gct ctc cct       1296
Pro Met Ala Gly Asp Met Asn Gly Leu Ser Pro Thr Gln Ala Leu Pro
            420                 425                 430
```

```
cct cca ctc tcc atg ccc tcc acc tcc cac tgc acc cca cca ccg ccc      1344
Pro Pro Leu Ser Met Pro Ser Thr Ser His Cys Thr Pro Pro Pro Pro
            435                 440                 445 tac ccc aca gac tgc agc att gtc agg att tgg caa gtc tga              1386
Tyr Pro Thr Asp Cys Ser Ile Val Arg Ile Trp Gln Val
450                 455                 460

<210> SEQ ID NO 12
<211> LENGTH: 1170
<212> TYPE: DNA
<213> ORGANISM: Mus musculus
<220> FEATURE:
<221> NAME/KEY: CDS
<222> LOCATION: (1)..(1167)

<400> SEQUENCE: 12 atg ttg tac ctg gaa aac aat gcc cag act caa ttt agt gag cca cag       48
Met Leu Tyr Leu Glu Asn Asn Ala Gln Thr Gln Phe Ser Glu Pro Gln
 1               5                  10                  15 tac acg aac ctg ggg ctc ctg aac agc atg gac cag cag att cag aac       96
Tyr Thr Asn Leu Gly Leu Leu Asn Ser Met Asp Gln Gln Ile Gln Asn
             20                  25                  30 ggc tcc tcg tcc acc agc ccc tac aac aca gac cac gca cag aat agc      144
Gly Ser Ser Ser Thr Ser Pro Tyr Asn Thr Asp His Ala Gln Asn Ser
         35                  40                  45 gtg acg gcg ccc tcg ccc tat gca cag ccc agc tcc acc ttt gat gcc      192
Val Thr Ala Pro Ser Pro Tyr Ala Gln Pro Ser Ser Thr Phe Asp Ala
     50                  55                  60 ctc tct cca tcc cct gcc att ccc tcc aac aca gat tac ccg ggc cca      240
Leu Ser Pro Ser Pro Ala Ile Pro Ser Asn Thr Asp Tyr Pro Gly Pro
 65                  70                  75                  80 cac agc ttc gat gtg tcc ttc cag cag tca agc act gcc aag tca gcc      288
His Ser Phe Asp Val Ser Phe Gln Gln Ser Ser Thr Ala Lys Ser Ala
                 85                  90                  95 acc tgg acg tat tcc acc gaa ctg aag aag ctg tac tgc cag att gcg      336
Thr Trp Thr Tyr Ser Thr Glu Leu Lys Lys Leu Tyr Cys Gln Ile Ala
            100                 105                 110 aag aca tgc ccc atc cag atc aag gtg atg acc cca ccc cca cag ggc      384
Lys Thr Cys Pro Ile Gln Ile Lys Val Met Thr Pro Pro Pro Gln Gly
        115                 120                 125 gct gtt atc cgt gcc atg cct gtc tac aag aaa gct gag cat gtc acc      432
Ala Val Ile Arg Ala Met Pro Val Tyr Lys Lys Ala Glu His Val Thr
    130                 135                 140 gag gtt gtg aaa cga tgc cct aac cat gag ctg agc cgt gag ttc aat      480
Glu Val Val Lys Arg Cys Pro Asn His Glu Leu Ser Arg Glu Phe Asn
145                 150                 155                 160 gag gga cag att gcc cct ccc agt cat ctg att cga gta gaa ggg aac      528
Glu Gly Gln Ile Ala Pro Pro Ser His Leu Ile Arg Val Glu Gly Asn
                165                 170                 175 agc cat gcc cag tat gta gaa gat cct atc acg gga agg cag agc gtg      576
Ser His Ala Gln Tyr Val Glu Asp Pro Ile Thr Gly Arg Gln Ser Val
            180                 185                 190 ctg gtc cct tat gag cca cca cag gtt ggc act gaa ttc aca aca gtc      624
Leu Val Pro Tyr Glu Pro Pro Gln Val Gly Thr Glu Phe Thr Thr Val
        195                 200                 205 ctg tac aat ttc atg tgt aac agc agc tgc gtc gga gga atg aac aga      672
Leu Tyr Asn Phe Met Cys Asn Ser Ser Cys Val Gly Gly Met Asn Arg
    210                 215                 220 cgt cca att tta atc atc gtt act ctg gaa acc aga gat ggg caa gtc      720
Arg Pro Ile Leu Ile Ile Val Thr Leu Glu Thr Arg Asp Gly Gln Val
225                 230                 235                 240
```

```
ctg ggc cga cgg tgc ttt gag gcc cgg atc tgt gct tgc cca gga aga        768
Leu Gly Arg Arg Cys Phe Glu Ala Arg Ile Cys Ala Cys Pro Gly Arg
            245                 250                 255 gac cgg aag gca gat gaa gac agc atc aga aag cag caa gta tcg gac        816
Asp Arg Lys Ala Asp Glu Asp Ser Ile Arg Lys Gln Gln Val Ser Asp
        260                 265                 270 agc gca aag aac ggc gat gct ttc cgt cag aat aca cac gga atc cag        864
Ser Ala Lys Asn Gly Asp Ala Phe Arg Gln Asn Thr His Gly Ile Gln
    275                 280                 285 atg act tcc atc aag aaa cgg aga tcc cca gat gat gag ctg ctg tac        912
Met Thr Ser Ile Lys Lys Arg Arg Ser Pro Asp Asp Glu Leu Leu Tyr
290                 295                 300 cta cca gtg aga ggt cgt gag acg tac gag atg ttg ctg aag atc aaa        960
Leu Pro Val Arg Gly Arg Glu Thr Tyr Glu Met Leu Leu Lys Ile Lys
305                 310                 315                 320 gag tca ctg gag ctc atg cag tac ctc cct cag cac acg atc gaa acg       1008
Glu Ser Leu Glu Leu Met Gln Tyr Leu Pro Gln His Thr Ile Glu Thr
            325                 330                 335 tac agg cag cag cag cag cag cag cac cag cac cta ctt cag aaa cat       1056
Tyr Arg Gln Gln Gln Gln Gln Gln His Gln His Leu Leu Gln Lys His
        340                 345                 350 ctc ctt tca gcc tgc ttc agg aat gag ctt gtg gag ccc cgg gga gaa       1104
Leu Leu Ser Ala Cys Phe Arg Asn Glu Leu Val Glu Pro Arg Gly Glu
    355                 360                 365 gct ccg aca cag tct gac gtc ttc ttt aga cat tcc aac ccc cca aac       1152
Ala Pro Thr Gln Ser Asp Val Phe Phe Arg His Ser Asn Pro Pro Asn
370                 375                 380 cac tcc gtg tac cca tag                                               1170
His Ser Val Tyr Pro
385
```

<210> SEQ ID NO 13
<211> LENGTH: 641
<212> TYPE: PRT
<213> ORGANISM: Homo sapiens

<400> SEQUENCE: 13

```
Met Ser Gln Ser Thr Gln Thr Asn Glu Phe Leu Ser Pro Glu Val Phe
1               5                   10                  15

Gln His Ile Trp Asp Phe Leu Glu Gln Pro Ile Cys Ser Val Gln Pro
            20                  25                  30

Ile Asp Leu Asn Phe Val Asp Glu Pro Ser Glu Asp Gly Ala Thr Asn
        35                  40                  45

Lys Ile Glu Ile Ser Met Asp Cys Ile Arg Met Gln Asp Ser Asp Leu
    50                  55                  60

Ser Asp Pro Met Trp Pro Gln Tyr Thr Asn Leu Gly Leu Leu Asn Ser
65                  70                  75                  80

Met Asp Gln Gln Ile Gln Asn Gly Ser Ser Ser Thr Ser Pro Tyr Asn
                85                  90                  95

Thr Asp His Ala Gln Asn Ser Val Thr Ala Pro Ser Pro Tyr Ala Gln
            100                 105                 110

Pro Ser Ser Thr Phe Asp Ala Leu Ser Pro Ser Pro Ala Ile Pro Ser
        115                 120                 125

Asn Thr Asp Tyr Pro Gly Pro His Ser Phe Asp Val Ser Phe Gln Gln
    130                 135                 140

Ser Ser Thr Ala Lys Ser Ala Thr Trp Thr Tyr Ser Thr Glu Leu Lys
145                 150                 155                 160

Lys Leu Tyr Cys Gln Ile Ala Lys Thr Cys Pro Ile Gln Ile Lys Val
```

-continued

```
                165                 170                 175
Met Thr Pro Pro Gln Gly Ala Val Ile Arg Ala Met Pro Val Tyr
                180                 185                 190
Lys Lys Ala Glu His Val Thr Glu Val Val Lys Arg Cys Pro Asn His
                195                 200                 205
Glu Leu Ser Arg Glu Phe Asn Glu Gly Gln Ile Ala Pro Pro Ser His
                210                 215                 220
Leu Ile Arg Val Glu Gly Asn Ser His Ala Gln Tyr Val Glu Asp Pro
225                 230                 235                 240
Ile Thr Gly Arg Gln Ser Val Leu Val Pro Tyr Glu Pro Pro Gln Val
                245                 250                 255
Gly Thr Glu Phe Thr Thr Val Leu Tyr Asn Phe Met Cys Asn Ser Ser
                260                 265                 270
Cys Val Gly Gly Met Asn Arg Arg Pro Ile Leu Ile Ile Val Thr Leu
                275                 280                 285
Glu Thr Arg Asp Gly Gln Val Leu Gly Arg Arg Cys Phe Glu Ala Arg
                290                 295                 300
Ile Cys Ala Cys Pro Gly Arg Asp Arg Lys Ala Asp Glu Asp Ser Ile
305                 310                 315                 320
Arg Lys Gln Gln Val Ser Asp Ser Thr Lys Asn Gly Asp Gly Thr Lys
                325                 330                 335
Arg Pro Phe Arg Gln Asn Thr His Gly Ile Gln Met Thr Ser Ile Lys
                340                 345                 350
Lys Arg Arg Ser Pro Asp Asp Glu Leu Leu Tyr Leu Pro Val Arg Gly
                355                 360                 365
Arg Glu Thr Tyr Glu Met Leu Leu Lys Ile Lys Glu Ser Leu Glu Leu
                370                 375                 380
Met Gln Tyr Leu Pro Gln His Thr Ile Glu Thr Tyr Arg Gln Gln Gln
385                 390                 395                 400
Gln Gln Gln His Gln His Leu Leu Gln Lys Gln Thr Ser Ile Gln Ser
                405                 410                 415
Pro Ser Ser Tyr Gly Asn Ser Ser Pro Pro Leu Asn Lys Met Asn Ser
                420                 425                 430
Met Asn Lys Leu Pro Ser Val Ser Gln Leu Ile Asn Pro Gln Gln Arg
                435                 440                 445
Asn Ala Leu Thr Pro Thr Thr Ile Pro Asp Gly Met Gly Ala Asn Ile
                450                 455                 460
Pro Met Met Gly Thr His Met Pro Met Ala Gly Asp Met Asn Gly Leu
465                 470                 475                 480
Ser Pro Thr Gln Ala Leu Pro Pro Leu Ser Met Pro Ser Thr Ser
                485                 490                 495
His Cys Thr Pro Pro Pro Tyr Pro Thr Asp Cys Ser Ile Val Ser
                500                 505                 510
Phe Leu Ala Arg Leu Gly Cys Ser Ser Cys Leu Asp Tyr Phe Thr Thr
                515                 520                 525
Gln Gly Leu Thr Thr Ile Tyr Gln Ile Glu His Tyr Ser Met Asp Asp
                530                 535                 540
Leu Ala Ser Leu Lys Ile Pro Glu Gln Phe Arg His Ala Ile Trp Lys
545                 550                 555                 560
Gly Ile Leu Asp His Arg Gln Leu His Glu Phe Ser Ser Pro Ser His
                565                 570                 575
Leu Leu Arg Thr Pro Ser Ser Ala Ser Thr Val Ser Val Gly Ser Ser
                580                 585                 590
```

```
Glu Thr Arg Gly Glu Arg Val Ile Asp Ala Val Arg Phe Thr Leu Arg
            595                 600                 605

Gln Thr Ile Ser Phe Pro Pro Arg Asp Glu Trp Asn Asp Phe Asn Phe
        610                 615                 620

Asp Met Asp Ala Arg Arg Asn Lys Gln Gln Arg Ile Lys Glu Glu Gly
625                 630                 635                 640

Glu
```

<210> SEQ ID NO 14
<211> LENGTH: 516
<212> TYPE: PRT
<213> ORGANISM: Homo sapiens

<400> SEQUENCE: 14

```
Met Ser Gln Ser Thr Gln Thr Asn Glu Phe Leu Ser Pro Glu Val Phe
  1               5                  10                  15

Gln His Ile Trp Asp Phe Leu Glu Gln Pro Ile Cys Ser Val Gln Pro
             20                  25                  30

Ile Asp Leu Asn Phe Val Asp Glu Pro Ser Glu Asp Gly Ala Thr Asn
         35                  40                  45

Lys Ile Glu Ile Ser Met Asp Cys Ile Arg Met Gln Asp Ser Asp Leu
     50                  55                  60

Ser Asp Pro Met Trp Pro Gln Tyr Thr Asn Leu Gly Leu Leu Asn Ser
 65                  70                  75                  80

Met Asp Gln Gln Ile Gln Asn Gly Ser Ser Thr Ser Pro Tyr Asn
                 85                  90                  95

Thr Asp His Ala Gln Asn Ser Val Thr Ala Pro Ser Pro Tyr Ala Gln
                100                 105                 110

Pro Ser Ser Thr Phe Asp Ala Leu Ser Pro Ser Pro Ala Ile Pro Ser
            115                 120                 125

Asn Thr Asp Tyr Pro Gly Pro His Ser Phe Asp Val Ser Phe Gln Gln
        130                 135                 140

Ser Ser Thr Ala Lys Ser Ala Thr Trp Thr Tyr Ser Thr Glu Leu Lys
145                 150                 155                 160

Lys Leu Tyr Cys Gln Ile Ala Lys Thr Cys Pro Ile Gln Ile Lys Val
                165                 170                 175

Met Thr Pro Pro Pro Gln Gly Ala Val Ile Arg Ala Met Pro Val Tyr
            180                 185                 190

Lys Lys Ala Glu His Val Thr Glu Val Val Lys Arg Cys Pro Asn His
        195                 200                 205

Glu Leu Ser Arg Glu Phe Asn Glu Gly Gln Ile Ala Pro Pro Ser His
    210                 215                 220

Leu Ile Arg Val Glu Gly Asn Ser His Ala Gln Tyr Val Glu Asp Pro
225                 230                 235                 240

Ile Thr Gly Arg Gln Ser Val Leu Val Pro Tyr Glu Pro Pro Gln Val
                245                 250                 255

Gly Thr Glu Phe Thr Thr Val Leu Tyr Asn Phe Met Cys Asn Ser Ser
            260                 265                 270

Cys Val Gly Gly Met Asn Arg Arg Pro Ile Leu Ile Ile Val Thr Leu
        275                 280                 285

Glu Thr Arg Asp Gly Gln Val Leu Gly Arg Arg Cys Phe Glu Ala Arg
    290                 295                 300

Ile Cys Ala Cys Pro Gly Arg Asp Arg Lys Ala Asp Glu Asp Ser Ile
305                 310                 315                 320
```

-continued

```
Arg Lys Gln Gln Val Ser Asp Ser Thr Lys Asn Gly Asp Gly Thr Lys
                325                 330                 335

Arg Pro Phe Arg Gln Asn Thr His Gly Ile Gln Met Thr Ser Ile Lys
            340                 345                 350

Lys Arg Arg Ser Pro Asp Asp Glu Leu Leu Tyr Leu Pro Val Arg Gly
        355                 360                 365

Arg Glu Thr Tyr Glu Met Leu Leu Lys Ile Lys Glu Ser Leu Glu Leu
    370                 375                 380

Met Gln Tyr Leu Pro Gln His Thr Ile Glu Thr Tyr Arg Gln Gln Gln
385                 390                 395                 400

Gln Gln Gln His Gln His Leu Leu Gln Lys Gln Thr Ser Ile Gln Ser
                405                 410                 415

Pro Ser Ser Tyr Gly Asn Ser Ser Pro Leu Asn Lys Met Asn Ser
                420                 425                 430

Met Asn Lys Leu Pro Ser Val Ser Gln Leu Ile Asn Pro Gln Gln Arg
            435                 440                 445

Asn Ala Leu Thr Pro Thr Thr Ile Pro Asp Gly Met Gly Ala Asn Ile
        450                 455                 460

Pro Met Met Gly Thr His Met Pro Met Ala Gly Asp Met Asn Gly Leu
465                 470                 475                 480

Ser Pro Thr Gln Ala Leu Pro Pro Leu Ser Met Pro Ser Thr Ser
                485                 490                 495

His Cys Thr Pro Pro Pro Tyr Pro Thr Asp Cys Ser Ile Val Arg
            500                 505                 510

Ile Trp Gln Val
        515

<210> SEQ ID NO 15
<211> LENGTH: 448
<212> TYPE: PRT
<213> ORGANISM: Homo sapiens

<400> SEQUENCE: 15

Met Ser Gln Ser Thr Gln Thr Asn Glu Phe Leu Ser Pro Glu Val Phe
1               5                   10                  15

Gln His Ile Trp Asp Phe Leu Glu Gln Pro Ile Cys Ser Val Gln Pro
            20                  25                  30

Ile Asp Leu Asn Phe Val Asp Glu Pro Ser Glu Asp Gly Ala Thr Asn
        35                  40                  45

Lys Ile Glu Ile Ser Met Asp Cys Ile Arg Met Gln Asp Ser Asp Leu
    50                  55                  60

Ser Asp Pro Met Trp Pro Gln Tyr Thr Asn Leu Gly Leu Leu Asn Ser
65                  70                  75                  80

Met Asp Gln Gln Ile Gln Asn Gly Ser Ser Ser Thr Ser Pro Tyr Asn
                85                  90                  95

Thr Asp His Ala Gln Asn Ser Val Thr Ala Pro Ser Pro Tyr Ala Gln
            100                 105                 110

Pro Ser Ser Thr Phe Asp Ala Leu Ser Pro Ser Pro Ala Ile Pro Ser
        115                 120                 125

Asn Thr Asp Tyr Pro Gly Pro His Ser Phe Asp Val Ser Phe Gln Gln
    130                 135                 140

Ser Ser Thr Ala Lys Ser Ala Thr Trp Thr Tyr Ser Thr Glu Leu Lys
145                 150                 155                 160

Lys Leu Tyr Cys Gln Ile Ala Lys Thr Cys Pro Ile Gln Ile Lys Val
```

```
                         165                 170                 175
Met Thr Pro Pro Gln Gly Ala Val Ile Arg Ala Met Pro Val Tyr
            180                 185                 190
Lys Lys Ala Glu His Val Thr Glu Val Val Lys Arg Cys Pro Asn His
            195                 200                 205
Glu Leu Ser Arg Glu Phe Asn Glu Gly Gln Ile Ala Pro Pro Ser His
            210                 215                 220
Leu Ile Arg Val Glu Gly Asn Ser His Ala Gln Tyr Val Glu Asp Pro
225                 230                 235                 240
Ile Thr Gly Arg Gln Ser Val Leu Val Pro Tyr Glu Pro Pro Gln Val
            245                 250                 255
Gly Thr Glu Phe Thr Thr Val Leu Tyr Asn Phe Met Cys Asn Ser Ser
            260                 265                 270
Cys Val Gly Gly Met Asn Arg Arg Pro Ile Leu Ile Ile Val Thr Leu
            275                 280                 285
Glu Thr Arg Asp Gly Gln Val Leu Gly Arg Arg Cys Phe Glu Ala Arg
            290                 295                 300
Ile Cys Ala Cys Pro Gly Arg Asp Arg Lys Ala Asp Glu Asp Ser Ile
305                 310                 315                 320
Arg Lys Gln Gln Val Ser Asp Ser Thr Lys Asn Gly Asp Gly Thr Lys
            325                 330                 335
Arg Pro Phe Arg Gln Asn Thr His Gly Ile Gln Met Thr Ser Ile Lys
            340                 345                 350
Lys Arg Arg Ser Pro Asp Asp Glu Leu Leu Tyr Leu Pro Val Arg Gly
            355                 360                 365
Arg Glu Thr Tyr Glu Met Leu Leu Lys Ile Lys Glu Ser Leu Glu Leu
            370                 375                 380
Met Gln Tyr Leu Pro Gln His Thr Ile Glu Thr Tyr Arg Gln Gln Gln
385                 390                 395                 400
Gln Gln Gln His Gln His Leu Leu Gln Lys His Leu Leu Ser Ala Cys
            405                 410                 415
Phe Arg Asn Glu Leu Val Glu Pro Arg Arg Glu Thr Pro Lys Gln Ser
            420                 425                 430
Asp Val Phe Phe Arg His Ser Lys Pro Pro Asn Arg Ser Val Tyr Pro
            435                 440                 445

<210> SEQ ID NO 16
<211> LENGTH: 586
<212> TYPE: PRT
<213> ORGANISM: Homo sapiens

<400> SEQUENCE: 16

Met Leu Tyr Leu Glu Asn Asn Ala Gln Thr Gln Phe Ser Glu Pro Gln
1               5                   10                  15
Tyr Thr Asn Leu Gly Leu Leu Asn Ser Met Asp Gln Gln Ile Gln Asn
            20                  25                  30
Gly Ser Ser Ser Thr Ser Pro Tyr Asn Thr Asp His Ala Gln Asn Ser
            35                  40                  45
Val Thr Ala Pro Ser Pro Tyr Ala Gln Pro Ser Ser Thr Phe Asp Ala
            50                  55                  60
Leu Ser Pro Ser Pro Ala Ile Pro Ser Asn Thr Asp Tyr Pro Gly Pro
65                  70                  75                  80
His Ser Phe Asp Val Ser Phe Gln Gln Ser Ser Thr Ala Lys Ser Ala
            85                  90                  95
```

```
Thr Trp Thr Tyr Ser Thr Glu Leu Lys Lys Leu Tyr Cys Gln Ile Ala
            100                 105                 110
Lys Thr Cys Pro Ile Gln Ile Lys Val Met Thr Pro Pro Gln Gly
        115                 120                 125
Ala Val Ile Arg Ala Met Pro Val Tyr Lys Lys Ala Glu His Val Thr
        130                 135                 140
Glu Val Val Lys Arg Cys Pro Asn His Glu Leu Ser Arg Glu Phe Asn
145                 150                 155                 160
Glu Gly Gln Ile Ala Pro Pro Ser His Leu Ile Arg Val Glu Gly Asn
                165                 170                 175
Ser His Ala Gln Tyr Val Glu Asp Pro Ile Thr Gly Arg Gln Ser Val
            180                 185                 190
Leu Val Pro Tyr Glu Pro Pro Gln Val Gly Thr Glu Phe Thr Thr Val
            195                 200                 205
Leu Tyr Asn Phe Met Cys Asn Ser Ser Cys Val Gly Gly Met Asn Arg
            210                 215                 220
Arg Pro Ile Leu Ile Ile Val Thr Leu Glu Thr Arg Asp Gly Gln Val
225                 230                 235                 240
Leu Gly Arg Arg Cys Phe Glu Ala Arg Ile Cys Ala Cys Pro Gly Arg
                245                 250                 255
Asp Arg Lys Ala Asp Glu Asp Ser Ile Arg Lys Gln Gln Val Ser Asp
            260                 265                 270
Ser Thr Lys Asn Gly Asp Gly Thr Lys Arg Pro Phe Arg Gln Asn Thr
            275                 280                 285
His Gly Ile Gln Met Thr Ser Ile Lys Lys Arg Arg Ser Pro Asp Asp
            290                 295                 300
Glu Leu Leu Tyr Leu Pro Val Arg Gly Arg Glu Thr Tyr Glu Met Leu
305                 310                 315                 320
Leu Lys Ile Lys Glu Ser Leu Glu Leu Met Gln Tyr Leu Pro Gln His
                325                 330                 335
Thr Ile Glu Thr Tyr Arg Gln Gln Gln Gln Gln His Gln His Leu
            340                 345                 350
Leu Gln Lys Gln Thr Ser Ile Gln Ser Pro Ser Ser Tyr Gly Asn Ser
            355                 360                 365
Ser Pro Pro Leu Asn Lys Met Asn Ser Met Asn Lys Leu Pro Ser Val
            370                 375                 380
Ser Gln Leu Ile Asn Pro Gln Gln Arg Asn Ala Leu Thr Pro Thr Thr
385                 390                 395                 400
Ile Pro Asp Gly Met Gly Ala Asn Ile Pro Met Met Gly Thr His Met
                405                 410                 415
Pro Met Ala Gly Asp Met Asn Gly Leu Ser Pro Thr Gln Ala Leu Pro
            420                 425                 430
Pro Pro Leu Ser Met Pro Ser Thr Ser His Cys Thr Pro Pro Pro
            435                 440                 445
Tyr Pro Thr Asp Cys Ser Ile Val Ser Phe Leu Ala Arg Leu Gly Cys
            450                 455                 460
Ser Ser Cys Leu Asp Tyr Phe Thr Thr Gln Gly Leu Thr Thr Ile Tyr
465                 470                 475                 480
Gln Ile Glu His Tyr Ser Met Asp Asp Leu Ala Ser Leu Lys Ile Pro
                485                 490                 495
Glu Gln Phe Arg His Ala Ile Trp Lys Gly Ile Leu Asp His Arg Gln
            500                 505                 510
Leu His Glu Phe Ser Ser Pro Ser His Leu Leu Arg Thr Pro Ser Ser
```

```
                515                 520                 525
Ala Ser Thr Val Ser Val Gly Ser Ser Glu Thr Arg Gly Glu Arg Val
        530                 535                 540
Ile Asp Ala Val Arg Phe Thr Leu Arg Gln Thr Ile Ser Phe Pro Pro
545                 550                 555                 560
Arg Asp Glu Trp Asn Asp Phe Asn Phe Asp Met Asp Ala Arg Arg Asn
                565                 570                 575
Lys Gln Gln Arg Ile Lys Glu Glu Gly Glu
        580                 585

<210> SEQ ID NO 17
<211> LENGTH: 461
<212> TYPE: PRT
<213> ORGANISM: Homo sapiens

<400> SEQUENCE: 17

Met Leu Tyr Leu Glu Asn Asn Ala Gln Thr Gln Phe Ser Glu Pro Gln
1               5                   10                  15
Tyr Thr Asn Leu Gly Leu Leu Asn Ser Met Asp Gln Gln Ile Gln Asn
                20                  25                  30
Gly Ser Ser Ser Thr Ser Pro Tyr Asn Thr Asp His Ala Gln Asn Ser
            35                  40                  45
Val Thr Ala Pro Ser Pro Tyr Ala Gln Pro Ser Ser Thr Phe Asp Ala
    50                  55                  60
Leu Ser Pro Ser Pro Ala Ile Pro Ser Asn Thr Asp Tyr Pro Gly Pro
65                  70                  75                  80
His Ser Phe Asp Val Ser Phe Gln Gln Ser Ser Thr Ala Lys Ser Ala
                85                  90                  95
Thr Trp Thr Tyr Ser Thr Glu Leu Lys Lys Leu Tyr Cys Gln Ile Ala
                100                 105                 110
Lys Thr Cys Pro Ile Gln Ile Lys Val Met Thr Pro Pro Gln Gly
            115                 120                 125
Ala Val Ile Arg Ala Met Pro Val Tyr Lys Lys Ala Glu His Val Thr
    130                 135                 140
Glu Val Val Lys Arg Cys Pro Asn His Glu Leu Ser Arg Glu Phe Asn
145                 150                 155                 160
Glu Gly Gln Ile Ala Pro Pro Ser His Leu Ile Arg Val Glu Gly Asn
                165                 170                 175
Ser His Ala Gln Tyr Val Glu Asp Pro Ile Thr Gly Arg Gln Ser Val
            180                 185                 190
Leu Val Pro Tyr Glu Pro Pro Gln Val Gly Thr Glu Phe Thr Thr Val
        195                 200                 205
Leu Tyr Asn Phe Met Cys Asn Ser Ser Cys Val Gly Gly Met Asn Arg
    210                 215                 220
Arg Pro Ile Leu Ile Ile Val Thr Leu Glu Thr Arg Asp Gly Gln Val
225                 230                 235                 240
Leu Gly Arg Arg Cys Phe Glu Ala Arg Ile Cys Ala Cys Pro Gly Arg
                245                 250                 255
Asp Arg Lys Ala Asp Glu Asp Ser Ile Arg Lys Gln Gln Val Ser Asp
            260                 265                 270
Ser Thr Lys Asn Gly Asp Gly Thr Lys Arg Pro Phe Arg Gln Asn Thr
        275                 280                 285
His Gly Ile Gln Met Thr Ser Ile Lys Lys Arg Arg Ser Pro Asp Asp
    290                 295                 300
```

```
Glu Leu Leu Tyr Leu Pro Val Arg Gly Arg Glu Thr Tyr Glu Met Leu
305                 310                 315                 320

Leu Lys Ile Lys Glu Ser Leu Glu Leu Met Gln Tyr Leu Pro Gln His
            325                 330                 335

Thr Ile Glu Thr Tyr Arg Gln Gln Gln Gln Gln His Gln His Leu
        340                 345                 350

Leu Gln Lys Gln Thr Ser Ile Gln Ser Pro Ser Ser Tyr Gly Asn Ser
            355                 360                 365

Ser Pro Pro Leu Asn Lys Met Asn Ser Met Asn Lys Leu Pro Ser Val
    370                 375                 380

Ser Gln Leu Ile Asn Pro Gln Gln Arg Asn Ala Leu Thr Pro Thr Thr
385                 390                 395                 400

Ile Pro Asp Gly Met Gly Ala Asn Ile Pro Met Met Gly Thr His Met
                405                 410                 415

Pro Met Ala Gly Asp Met Asn Gly Leu Ser Pro Thr Gln Ala Leu Pro
            420                 425                 430

Pro Pro Leu Ser Met Pro Ser Thr Ser His Cys Thr Pro Pro Pro Pro
            435                 440                 445

Tyr Pro Thr Asp Cys Ser Ile Val Arg Ile Trp Gln Val
    450                 455                 460

<210> SEQ ID NO 18
<211> LENGTH: 393
<212> TYPE: PRT
<213> ORGANISM: Homo sapiens

<400> SEQUENCE: 18

Met Leu Tyr Leu Glu Asn Asn Ala Gln Thr Gln Phe Ser Glu Pro Gln
1               5                   10                  15

Tyr Thr Asn Leu Gly Leu Leu Asn Ser Met Asp Gln Gln Ile Gln Asn
            20                  25                  30

Gly Ser Ser Ser Thr Ser Pro Tyr Asn Thr Asp His Ala Gln Asn Ser
        35                  40                  45

Val Thr Ala Pro Ser Pro Tyr Ala Gln Pro Ser Ser Thr Phe Asp Ala
    50                  55                  60

Leu Ser Pro Ser Pro Ala Ile Pro Ser Asn Thr Asp Tyr Pro Gly Pro
65                  70                  75                  80

His Ser Phe Asp Val Ser Phe Gln Gln Ser Ser Thr Ala Lys Ser Ala
                85                  90                  95

Thr Trp Thr Tyr Ser Thr Glu Leu Lys Lys Leu Tyr Cys Gln Ile Ala
            100                 105                 110

Lys Thr Cys Pro Ile Gln Ile Lys Val Met Thr Pro Pro Pro Gln Gly
        115                 120                 125

Ala Val Ile Arg Ala Met Pro Val Tyr Lys Lys Ala Glu His Val Thr
    130                 135                 140

Glu Val Val Lys Arg Cys Pro Asn His Glu Leu Ser Arg Glu Phe Asn
145                 150                 155                 160

Glu Gly Gln Ile Ala Pro Pro Ser His Leu Ile Arg Val Glu Gly Asn
                165                 170                 175

Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
        195                 200                 205

Leu Tyr Asn Phe Met Cys Asn Ser Ser Cys Val Gly Gly Met Asn Arg
    210                 215                 220
```

```
Arg Pro Ile Leu Ile Ile Val Thr Leu Glu Thr Arg Asp Gly Gln Val
225                 230                 235                 240

Leu Gly Arg Arg Cys Phe Glu Ala Arg Ile Cys Ala Cys Pro Gly Arg
            245                 250                 255

Asp Arg Lys Ala Asp Glu Asp Ser Ile Arg Lys Gln Gln Val Ser Asp
            260                 265                 270

Ser Thr Lys Asn Gly Asp Gly Thr Lys Arg Pro Phe Arg Gln Asn Thr
        275                 280                 285

His Gly Ile Gln Met Thr Ser Ile Lys Lys Arg Arg Ser Pro Asp Asp
    290                 295                 300

Glu Leu Leu Tyr Leu Pro Val Arg Gly Arg Glu Thr Tyr Glu Met Leu
305                 310                 315                 320

Leu Lys Ile Lys Glu Ser Leu Glu Leu Met Gln Tyr Leu Pro Gln His
                325                 330                 335

Thr Ile Glu Thr Tyr Arg Gln Gln Gln Gln Gln His Gln His Leu
            340                 345                 350

Leu Gln Lys His Leu Leu Ser Ala Cys Phe Arg Asn Glu Leu Val Glu
        355                 360                 365

Pro Arg Arg Glu Thr Pro Lys Gln Ser Asp Val Phe Phe Arg His Ser
370                 375                 380

Lys Pro Pro Asn Arg Ser Val Tyr Pro
385                 390

<210> SEQ ID NO 19
<211> LENGTH: 680
<212> TYPE: PRT
<213> ORGANISM: Mus musculus

<400> SEQUENCE: 19

Met Asn Phe Glu Thr Ser Arg Cys Ala Thr Leu Gln Tyr Cys Pro Asp
1               5                   10                  15

Pro Tyr Ile Gln Arg Phe Ile Glu Thr Pro Ala His Phe Ser Trp Lys
            20                  25                  30

Glu Ser Tyr Tyr Arg Ser Ala Met Ser Gln Ser Thr Gln Thr Ser Glu
        35                  40                  45

Phe Leu Ser Pro Glu Val Phe Gln His Ile Trp Asp Phe Leu Glu Gln
    50                  55                  60

Pro Ile Cys Ser Val Gln Pro Ile Glu Leu Asn Phe Val Asp Glu Pro
65                  70                  75                  80

Ser Glu Asn Gly Ala Thr Asn Lys Ile Glu Ile Ser Met Asp Cys Ile
                85                  90                  95

Arg Met Gln Asp Ser Asp Leu Ser Asp Pro Met Trp Pro Gln Tyr Thr
            100                 105                 110

Asn Leu Gly Leu Leu Asn Ser Met Asp Gln Gln Ile Gln Asn Gly Ser
        115                 120                 125

Ser Ser Thr Ser Pro Tyr Asn Thr Asp His Ala Gln Asn Ser Val Thr
    130                 135                 140

Ala Pro Ser Pro Tyr Ala Gln Pro Ser Ser Thr Phe Asp Ala Leu Ser
145                 150                 155                 160

Pro Ser Pro Ala Ile Pro Ser Asn Thr Asp Tyr Pro Gly Pro His Ser
                165                 170                 175

Phe Asp Val Ser Phe Gln Gln Ser Ser Thr Ala Lys Ser Ala Thr Trp
            180                 185                 190

Thr Tyr Ser Thr Glu Leu Lys Lys Leu Tyr Cys Gln Ile Ala Lys Thr
```

-continued

```
                195                 200                 205
Cys Pro Ile Gln Ile Lys Val Met Thr Pro Pro Gln Gly Ala Val
210                 215                 220
Ile Arg Ala Met Pro Val Tyr Lys Lys Ala Glu His Val Thr Glu Val
225                 230                 235                 240
Val Lys Arg Cys Pro Asn His Glu Leu Ser Arg Glu Phe Asn Glu Gly
                245                 250                 255
Gln Ile Ala Pro Pro Ser His Leu Ile Arg Val Glu Gly Asn Ser His
                260                 265                 270
Ala Gln Tyr Val Glu Asp Pro Ile Thr Gly Arg Gln Ser Val Leu Val
            275                 280                 285
Pro Tyr Glu Pro Pro Gln Val Gly Thr Glu Phe Thr Thr Val Leu Tyr
        290                 295                 300
Asn Phe Met Cys Asn Ser Ser Cys Val Gly Gly Met Asn Arg Arg Pro
305                 310                 315                 320
Ile Leu Ile Ile Val Thr Leu Glu Thr Arg Asp Gly Gln Val Leu Gly
                325                 330                 335
Arg Arg Cys Phe Glu Ala Arg Ile Cys Ala Cys Pro Gly Arg Asp Arg
            340                 345                 350
Lys Ala Asp Glu Asp Ser Ile Arg Lys Gln Val Ser Asp Ser Ala
            355                 360                 365
Lys Asn Gly Asp Gly Thr Lys Arg Pro Phe Arg Gln Asn Thr His Gly
        370                 375                 380
Ile Gln Met Thr Ser Ile Lys Lys Arg Ser Pro Asp Asp Glu Leu
385                 390                 395                 400
Leu Tyr Leu Pro Val Arg Gly Arg Glu Thr Tyr Glu Met Leu Leu Lys
                405                 410                 415
Ile Lys Glu Ser Leu Glu Leu Met Gln Tyr Leu Pro Gln His Thr Ile
                420                 425                 430
Glu Thr Tyr Arg Gln Gln Gln Gln Gln His Gln His Leu Leu Gln
            435                 440                 445
Lys Gln Thr Ser Met Gln Ser Gln Ser Ser Tyr Gly Asn Ser Ser Pro
450                 455                 460
Pro Leu Asn Lys Met Asn Ser Met Asn Lys Leu Pro Ser Val Ser Gln
465                 470                 475                 480
Leu Ile Asn Pro Gln Gln Arg Asn Ala Leu Thr Pro Thr Thr Met Pro
                485                 490                 495
Glu Gly Met Gly Ala Asn Ile Pro Met Met Gly Thr His Met Pro Met
            500                 505                 510
Ala Gly Asp Met Asn Gly Leu Ser Pro Thr Gln Ala Leu Pro Pro Pro
            515                 520                 525
Leu Ser Met Pro Ser Thr Ser His Cys Thr Pro Pro Pro Tyr Pro
        530                 535                 540
Thr Asp Cys Ser Ile Val Ser Phe Leu Ala Arg Leu Gly Cys Ser Ser
545                 550                 555                 560
Cys Leu Asp Tyr Phe Thr Thr Gln Gly Leu Thr Thr Ile Tyr Gln Ile
                565                 570                 575
Glu His Tyr Ser Met Asp Asp Leu Ala Ser Leu Lys Ile Pro Glu Gln
                580                 585                 590
Phe Arg His Ala Ile Trp Lys Gly Ile Leu Asp His Arg Gln Leu His
            595                 600                 605
Asp Phe Ser Ser Pro Pro His Leu Leu Arg Thr Pro Ser Gly Ala Ser
610                 615                 620
```

-continued

```
Thr Val Ser Val Gly Ser Ser Glu Thr Arg Gly Glu Arg Val Ile Asp
625                 630                 635                 640

Ala Val Arg Phe Thr Leu Arg Gln Thr Ile Ser Phe Pro Pro Arg Asp
            645                 650                 655

Glu Trp Asn Asp Phe Asn Phe Asp Met Asp Ser Arg Arg Asn Lys Gln
            660                 665                 670

Gln Arg Ile Lys Glu Glu Gly Glu
        675                 680
```

<210> SEQ ID NO 20
<211> LENGTH: 555
<212> TYPE: PRT
<213> ORGANISM: Mus musculus

<400> SEQUENCE: 20

```
Met Asn Phe Glu Thr Ser Arg Cys Ala Thr Leu Gln Tyr Cys Pro Asp
1               5                   10                  15

Pro Tyr Ile Gln Arg Phe Ile Glu Thr Pro Ala His Phe Ser Trp Lys
            20                  25                  30

Glu Ser Tyr Tyr Arg Ser Ala Met Ser Gln Ser Thr Gln Thr Ser Glu
        35                  40                  45

Phe Leu Ser Pro Glu Val Phe Gln His Ile Trp Asp Phe Leu Glu Gln
    50                  55                  60

Pro Ile Cys Ser Val Gln Pro Ile Glu Leu Asn Phe Val Asp Glu Pro
65                  70                  75                  80

Ser Glu Asn Gly Ala Thr Asn Lys Ile Glu Ile Ser Met Asp Cys Ile
                85                  90                  95

Arg Met Gln Asp Ser Asp Leu Ser Asp Pro Met Trp Pro Gln Tyr Thr
            100                 105                 110

Asn Leu Gly Leu Leu Asn Ser Met Asp Gln Gln Ile Gln Asn Gly Ser
        115                 120                 125

Ser Ser Thr Ser Pro Tyr Asn Thr Asp His Ala Gln Asn Ser Val Thr
    130                 135                 140

Ala Pro Ser Pro Tyr Ala Gln Pro Ser Ser Thr Phe Asp Ala Leu Ser
145                 150                 155                 160

Pro Ser Pro Ala Ile Pro Ser Asn Thr Asp Tyr Pro Gly Pro His Ser
                165                 170                 175

Phe Asp Val Ser Phe Gln Gln Ser Ser Thr Ala Lys Ser Ala Thr Trp
            180                 185                 190

Thr Tyr Ser Thr Glu Leu Lys Lys Leu Tyr Cys Gln Ile Ala Lys Thr
        195                 200                 205

Cys Pro Ile Gln Ile Lys Val Met Thr Pro Pro Gln Gly Ala Val
    210                 215                 220

Ile Arg Ala Met Pro Val Tyr Lys Lys Ala Glu His Val Thr Glu Val
225                 230                 235                 240

Val Lys Arg Cys Pro Asn His Glu Leu Ser Arg Glu Phe Asn Glu Gly
                245                 250                 255

Gln Ile Ala Pro Pro Ser His Leu Ile Arg Val Glu Gly Asn Ser His
            260                 265                 270

Ala Gln Tyr Val Glu Asp Pro Ile Thr Gly Arg Gln Ser Val Leu Val
        275                 280                 285

Pro Tyr Glu Pro Pro Gln Val Gly Thr Glu Phe Thr Thr Val Leu Tyr
    290                 295                 300

Asn Phe Met Cys Asn Ser Ser Cys Val Gly Gly Met Asn Arg Arg Pro
```

```
            305                 310                 315                 320
Ile Leu Ile Ile Val Thr Leu Glu Thr Arg Asp Gln Val Leu Gly
                325                 330                 335

Arg Arg Cys Phe Glu Ala Arg Ile Cys Ala Cys Pro Gly Arg Asp Arg
            340                 345                 350

Lys Ala Asp Glu Asp Ser Ile Arg Lys Gln Val Ser Asp Ser Ala
                355                 360                 365

Lys Asn Gly Asp Gly Thr Lys Arg Pro Phe Arg Gln Asn Thr His Gly
            370                 375                 380

Ile Gln Met Thr Ser Ile Lys Lys Arg Ser Pro Asp Asp Glu Leu
385                 390                 395                 400

Leu Tyr Leu Pro Val Arg Gly Arg Glu Thr Tyr Glu Met Leu Leu Lys
                405                 410                 415

Ile Lys Glu Ser Leu Glu Leu Met Gln Tyr Leu Pro Gln His Thr Ile
            420                 425                 430

Glu Thr Tyr Arg Gln Gln Gln Gln Gln His Gln His Leu Leu Gln
                435                 440                 445

Lys Gln Thr Ser Met Gln Ser Gln Ser Ser Tyr Gly Asn Ser Ser Pro
            450                 455                 460

Pro Leu Asn Lys Met Asn Ser Met Asn Lys Leu Pro Ser Val Ser Gln
465                 470                 475                 480

Leu Ile Asn Pro Gln Gln Arg Asn Ala Leu Thr Pro Thr Thr Met Pro
                485                 490                 495

Glu Gly Met Gly Ala Asn Ile Pro Met Met Gly Thr His Met Pro Met
            500                 505                 510

Ala Gly Asp Met Asn Gly Leu Ser Pro Thr Gln Ala Leu Pro Pro Pro
                515                 520                 525

Leu Ser Met Pro Ser Thr Ser His Cys Thr Pro Pro Pro Tyr Pro
            530                 535                 540

Thr Asp Cys Ser Ile Val Arg Ile Trp Gln Val
545                 550                 555

<210> SEQ ID NO 21
<211> LENGTH: 483
<212> TYPE: PRT
<213> ORGANISM: Mus musculus

<400> SEQUENCE: 21

Met Asn Phe Glu Thr Ser Arg Cys Ala Thr Leu Gln Tyr Cys Pro Asp
1               5                   10                  15

Pro Tyr Ile Gln Arg Phe Ile Glu Thr Pro Ala His Phe Ser Trp Lys
            20                  25                  30

Glu Ser Tyr Tyr Arg Ser Ala Met Ser Gln Ser Thr Gln Thr Ser Glu
        35                  40                  45

Phe Leu Ser Pro Glu Val Phe Gln His Ile Trp Asp Phe Leu Glu Gln
    50                  55                  60

Pro Ile Cys Ser Val Gln Pro Ile Glu Leu Asn Phe Val Asp Glu Pro
65                  70                  75                  80

Ser Glu Asn Gly Ala Thr Asn Lys Ile Glu Ile Ser Met Asp Cys Ile
                85                  90                  95

Arg Met Gln Asp Ser Asp Leu Ser Asp Pro Met Trp Pro Gln Tyr Thr
            100                 105                 110

Asn Leu Gly Leu Leu Asn Ser Met Asp Gln Gln Ile Gln Asn Gly Ser
        115                 120                 125
```

```
Ser Ser Thr Ser Pro Tyr Asn Thr Asp His Ala Gln Asn Ser Val Thr
    130                 135                 140

Ala Pro Ser Pro Tyr Ala Gln Pro Ser Ser Thr Phe Asp Ala Leu Ser
145                 150                 155                 160

Pro Ser Pro Ala Ile Pro Ser Asn Thr Asp Tyr Pro Gly Pro His Ser
                165                 170                 175

Phe Asp Val Ser Phe Gln Gln Ser Ser Thr Ala Lys Ser Ala Thr Trp
            180                 185                 190

Thr Tyr Ser Thr Glu Leu Lys Lys Leu Tyr Cys Gln Ile Ala Lys Thr
        195                 200                 205

Cys Pro Ile Gln Ile Lys Val Met Thr Pro Pro Gln Gly Ala Val
    210                 215                 220

Ile Arg Ala Met Pro Val Tyr Lys Lys Ala Glu His Val Thr Glu Val
225                 230                 235                 240

Val Lys Arg Cys Pro Asn His Glu Leu Ser Arg Glu Phe Asn Glu Gly
                245                 250                 255

Gln Ile Ala Pro Pro Ser His Leu Ile Arg Val Glu Gly Asn Ser His
                260                 265                 270

Ala Gln Tyr Val Glu Asp Pro Ile Thr Gly Arg Gln Ser Val Leu Val
        275                 280                 285

Pro Tyr Glu Pro Pro Gln Val Gly Thr Glu Phe Thr Thr Val Leu Tyr
290                 295                 300

Asn Phe Met Cys Asn Ser Ser Cys Val Gly Gly Met Asn Arg Arg Pro
305                 310                 315                 320

Ile Leu Ile Ile Val Thr Leu Glu Thr Arg Asp Gly Gln Val Leu Gly
                325                 330                 335

Arg Arg Cys Phe Glu Ala Arg Ile Cys Ala Cys Pro Gly Arg Asp Arg
            340                 345                 350

Lys Ala Asp Glu Asp Ser Ile Arg Lys Gln Gln Val Ser Asp Ser Ala
        355                 360                 365

Lys Asn Gly Asp Ala Phe Arg Gln Asn Thr His Gly Ile Gln Met Thr
    370                 375                 380

Ser Ile Lys Lys Arg Arg Ser Pro Asp Asp Glu Leu Leu Tyr Leu Pro
385                 390                 395                 400

Val Arg Gly Arg Glu Thr Tyr Glu Met Leu Leu Lys Ile Lys Glu Ser
                405                 410                 415

Leu Glu Leu Met Gln Tyr Leu Pro Gln His Thr Ile Glu Thr Tyr Arg
            420                 425                 430

Gln Gln Gln Gln Gln His Gln His Leu Leu Gln Lys His Leu Leu
        435                 440                 445

Ser Ala Cys Phe Arg Asn Glu Leu Val Glu Pro Arg Gly Glu Ala Pro
    450                 455                 460

Thr Gln Ser Asp Val Phe Phe Arg His Ser Asn Pro Asn His Ser
465                 470                 475                 480

Val Tyr Pro

<210> SEQ ID NO 22
<211> LENGTH: 586
<212> TYPE: PRT
<213> ORGANISM: Mus musculus

<400> SEQUENCE: 22

Met Leu Tyr Leu Glu Asn Asn Ala Gln Thr Gln Phe Ser Glu Pro Gln
  1               5                  10                  15
```

```
Tyr Thr Asn Leu Gly Leu Leu Asn Ser Met Asp Gln Gln Ile Gln Asn
            20                  25                  30

Gly Ser Ser Ser Thr Ser Pro Tyr Asn Thr Asp His Ala Gln Asn Ser
            35                  40                  45

Val Thr Ala Pro Ser Pro Tyr Ala Gln Pro Ser Ser Thr Phe Asp Ala
            50                  55                  60

Leu Ser Pro Ser Pro Ala Ile Pro Ser Asn Thr Asp Tyr Pro Gly Pro
 65                  70                  75                  80

His Ser Phe Asp Val Ser Phe Gln Gln Ser Ser Thr Ala Lys Ser Ala
            85                  90                  95

Thr Trp Thr Tyr Ser Thr Glu Leu Lys Lys Leu Tyr Cys Gln Ile Ala
            100                 105                 110

Lys Thr Cys Pro Ile Gln Ile Lys Val Met Thr Pro Pro Gln Gly
            115                 120                 125

Ala Val Ile Arg Ala Met Pro Val Tyr Lys Lys Ala Glu His Val Thr
 130                 135                 140

Glu Val Val Lys Arg Cys Pro Asn His Glu Leu Ser Arg Glu Phe Asn
145                 150                 155                 160

Glu Gly Gln Ile Ala Pro Pro Ser His Leu Ile Arg Val Glu Gly Asn
            165                 170                 175

Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
            195                 200                 205

Leu Tyr Asn Phe Met Cys Asn Ser Ser Cys Val Gly Gly Met Asn Arg
            210                 215                 220

Arg Pro Ile Leu Ile Ile Val Thr Leu Glu Thr Arg Asp Gly Gln Val
225                 230                 235                 240

Leu Gly Arg Arg Cys Phe Glu Ala Arg Ile Cys Ala Cys Pro Gly Arg
            245                 250                 255

Asp Arg Lys Ala Asp Glu Asp Ser Ile Arg Lys Gln Gln Val Ser Asp
            260                 265                 270

Ser Ala Lys Asn Gly Asp Gly Thr Lys Arg Pro Phe Arg Gln Asn Thr
            275                 280                 285

His Gly Ile Gln Met Thr Ser Ile Lys Lys Arg Arg Ser Pro Asp Asp
            290                 295                 300

Glu Leu Leu Tyr Leu Pro Val Arg Gly Arg Glu Thr Tyr Glu Met Leu
305                 310                 315                 320

Leu Lys Ile Lys Glu Ser Leu Glu Leu Met Gln Tyr Leu Pro Gln His
            325                 330                 335

Thr Ile Glu Thr Tyr Arg Gln Gln Gln Gln Gln His Gln His Leu
            340                 345                 350

Leu Gln Lys Gln Thr Ser Met Gln Ser Gln Ser Ser Tyr Gly Asn Ser
            355                 360                 365

Ser Pro Pro Leu Asn Lys Met Asn Ser Met Asn Lys Leu Pro Ser Val
            370                 375                 380

Ser Gln Leu Ile Asn Pro Gln Gln Arg Asn Ala Leu Thr Pro Thr Thr
385                 390                 395                 400

Met Pro Glu Gly Met Gly Ala Asn Ile Pro Met Met Gly Thr His Met
            405                 410                 415

Pro Met Ala Gly Asp Met Asn Gly Leu Ser Pro Thr Gln Ala Leu Pro
            420                 425                 430

Pro Pro Leu Ser Met Pro Ser Thr Ser His Cys Thr Pro Pro Pro Pro
```

```
                    435                 440                 445
Tyr Pro Thr Asp Cys Ser Ile Val Ser Phe Leu Ala Arg Leu Gly Cys
    450                 455                 460

Ser Ser Cys Leu Asp Tyr Phe Thr Thr Gln Gly Leu Thr Thr Ile Tyr
465                 470                 475                 480

Gln Ile Glu His Tyr Ser Met Asp Asp Leu Ala Ser Leu Lys Ile Pro
                485                 490                 495

Glu Gln Phe Arg His Ala Ile Trp Lys Gly Ile Leu Asp His Arg Gln
            500                 505                 510

Leu His Asp Phe Ser Ser Pro Pro His Leu Leu Arg Thr Pro Ser Gly
        515                 520                 525

Ala Ser Thr Val Ser Val Gly Ser Ser Glu Thr Arg Gly Glu Arg Val
    530                 535                 540

Ile Asp Ala Val Arg Phe Thr Leu Arg Gln Thr Ile Ser Phe Pro Pro
545                 550                 555                 560

Arg Asp Glu Trp Asn Asp Phe Asn Phe Asp Met Asp Ser Arg Arg Asn
                565                 570                 575

Lys Gln Gln Arg Ile Lys Glu Glu Gly Glu
            580                 585

<210> SEQ ID NO 23
<211> LENGTH: 461
<212> TYPE: PRT
<213> ORGANISM: Mus musculus

<400> SEQUENCE: 23

Met Leu Tyr Leu Glu Asn Asn Ala Gln Thr Gln Phe Ser Glu Pro Gln
1               5                   10                  15

Tyr Thr Asn Leu Gly Leu Leu Asn Ser Met Asp Gln Gln Ile Gln Asn
            20                  25                  30

Gly Ser Ser Ser Thr Ser Pro Tyr Asn Thr Asp His Ala Gln Asn Ser
        35                  40                  45

Val Thr Ala Pro Ser Pro Tyr Ala Gln Pro Ser Ser Thr Phe Asp Ala
    50                  55                  60

Leu Ser Pro Ser Pro Ala Ile Pro Ser Asn Thr Asp Tyr Pro Gly Pro
65                  70                  75                  80

His Ser Phe Asp Val Ser Phe Gln Gln Ser Ser Thr Ala Lys Ser Ala
                85                  90                  95

Thr Trp Thr Tyr Ser Thr Glu Leu Lys Lys Leu Tyr Cys Gln Ile Ala
            100                 105                 110

Lys Thr Cys Pro Ile Gln Ile Lys Val Met Thr Pro Pro Gln Gly
        115                 120                 125

Ala Val Ile Arg Ala Met Pro Val Tyr Lys Lys Ala Glu His Val Thr
    130                 135                 140

Glu Val Val Lys Arg Cys Pro Asn His Glu Leu Ser Arg Glu Phe Asn
145                 150                 155                 160

Glu Gly Gln Ile Ala Pro Pro Ser His Leu Ile Arg Val Glu Gly Asn
                165                 170                 175

Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
        195                 200                 205

Leu Tyr Asn Phe Met Cys Asn Ser Ser Cys Val Gly Gly Met Asn Arg
    210                 215                 220
```

```
Arg Pro Ile Leu Ile Val Thr Leu Glu Thr Arg Asp Gly Gln Val
225                 230                 235                 240

Leu Gly Arg Arg Cys Phe Glu Ala Arg Ile Cys Ala Cys Pro Gly Arg
            245                 250                 255

Asp Arg Lys Ala Asp Glu Asp Ser Ile Arg Lys Gln Gln Val Ser Asp
            260                 265                 270

Ser Ala Lys Asn Gly Asp Gly Thr Lys Arg Pro Phe Arg Gln Asn Thr
            275                 280                 285

His Gly Ile Gln Met Thr Ser Ile Lys Lys Arg Arg Ser Pro Asp Asp
290                 295                 300

Glu Leu Leu Tyr Leu Pro Val Arg Gly Arg Glu Thr Tyr Glu Met Leu
305                 310                 315                 320

Leu Lys Ile Lys Glu Ser Leu Glu Leu Met Gln Tyr Leu Pro Gln His
            325                 330                 335

Thr Ile Glu Thr Tyr Arg Gln Gln Gln Gln Gln His Gln His Leu
            340                 345                 350

Leu Gln Lys Gln Thr Ser Met Gln Ser Gln Ser Ser Tyr Gly Asn Ser
            355                 360                 365

Ser Pro Pro Leu Asn Lys Met Asn Ser Met Asn Lys Leu Pro Ser Val
370                 375                 380

Ser Gln Leu Ile Asn Pro Gln Gln Arg Asn Ala Leu Thr Pro Thr Thr
385                 390                 395                 400

Met Pro Glu Gly Met Gly Ala Asn Ile Pro Met Met Gly Thr His Met
                405                 410                 415

Pro Met Ala Gly Asp Met Asn Gly Leu Ser Pro Thr Gln Ala Leu Pro
                420                 425                 430

Pro Pro Leu Ser Met Pro Ser Thr Ser His Cys Thr Pro Pro Pro
            435                 440                 445

Tyr Pro Thr Asp Cys Ser Ile Val Arg Ile Trp Gln Val
    450                 455                 460

<210> SEQ ID NO 24
<211> LENGTH: 389
<212> TYPE: PRT
<213> ORGANISM: Mus musculus

<400> SEQUENCE: 24

Met Leu Tyr Leu Glu Asn Asn Ala Gln Thr Gln Phe Ser Glu Pro Gln
1               5                   10                  15

Tyr Thr Asn Leu Gly Leu Leu Asn Ser Met Asp Gln Gln Ile Gln Asn
                20                  25                  30

Gly Ser Ser Ser Thr Ser Pro Tyr Asn Thr Asp His Ala Gln Asn Ser
            35                  40                  45

Val Thr Ala Pro Ser Pro Tyr Ala Gln Pro Ser Ser Thr Phe Asp Ala
        50                  55                  60

Leu Ser Pro Ser Pro Ala Ile Pro Ser Asn Thr Asp Tyr Pro Gly Pro
65                  70                  75                  80

His Ser Phe Asp Val Ser Phe Gln Gln Ser Ser Thr Ala Lys Ser Ala
                85                  90                  95

Thr Trp Thr Tyr Ser Thr Glu Leu Lys Lys Leu Tyr Cys Gln Ile Ala
                100                 105                 110

Lys Thr Cys Pro Ile Gln Ile Lys Val Met Thr Pro Pro Gln Gly
            115                 120                 125

Ala Val Ile Arg Ala Met Pro Val Tyr Lys Lys Ala Glu His Val Thr
        130                 135                 140
```

-continued

```
Glu Val Val Lys Arg Cys Pro Asn His Glu Leu Ser Arg Glu Phe Asn
145                 150                 155                 160

Glu Gly Gln Ile Ala Pro Pro Ser His Leu Ile Arg Val Glu Gly Asn
                165                 170                 175

Ser His Ala Gln Tyr Val Glu Asp Pro Ile Thr Gly Arg Gln Ser Val
            180                 185                 190

Leu Val Pro Tyr Glu Pro Pro Gln Val Gly Thr Glu Phe Thr Thr Val
        195                 200                 205

Leu Tyr Asn Phe Met Cys Asn Ser Ser Cys Val Gly Met Asn Arg
210                 215                 220

Arg Pro Ile Leu Ile Val Thr Leu Glu Thr Arg Asp Gly Gln Val
225                 230                 235                 240

Leu Gly Arg Arg Cys Phe Glu Ala Arg Ile Cys Ala Cys Pro Gly Arg
                245                 250                 255

Asp Arg Lys Ala Asp Glu Asp Ser Ile Arg Lys Gln Val Ser Asp
            260                 265                 270

Ser Ala Lys Asn Gly Asp Ala Phe Arg Gln Asn Thr His Gly Ile Gln
        275                 280                 285

Met Thr Ser Ile Lys Lys Arg Ser Pro Asp Asp Glu Leu Leu Tyr
290                 295                 300

Leu Pro Val Arg Gly Arg Glu Thr Tyr Glu Met Leu Leu Lys Ile Lys
305                 310                 315                 320

Glu Ser Leu Glu Leu Met Gln Tyr Leu Pro Gln His Thr Ile Glu Thr
                325                 330                 335

Tyr Arg Gln Gln Gln Gln Gln His Gln His Leu Leu Gln Lys His
            340                 345                 350

Leu Leu Ser Ala Cys Phe Arg Asn Glu Leu Val Glu Pro Arg Gly Glu
        355                 360                 365

Ala Pro Thr Gln Ser Asp Val Phe Phe Arg His Ser Asn Pro Pro Asn
370                 375                 380

His Ser Val Tyr Pro
385

<210> SEQ ID NO 25
<211> LENGTH: 393
<212> TYPE: PRT
<213> ORGANISM: Homo sapiens

<400> SEQUENCE: 25

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
```

```
                 115                 120                     125
Ala Leu Asn Lys Met Phe Cys Gln Leu Ala Lys Thr Cys Pro Val Gln
            130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
            195                 200                 205

Arg Asn Thr Phe Arg His Ser Val Val Pro Tyr Glu Pro Pro Glu
        210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

His Val Cys Ala Cys Pro Gly Arg Asp Arg Arg Thr Glu Glu Glu Asn
            275                 280                 285

Leu Arg Lys Lys Gly Glu Pro His His Glu Leu Pro Pro Gly Ser Thr
        290                 295                 300

Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
        370                 375                 380

Phe Lys Thr Glu Gly Pro Asp Ser Asp
385                 390

<210> SEQ ID NO 26
<211> LENGTH: 499
<212> TYPE: PRT
<213> ORGANISM: Homo sapiens

<400> SEQUENCE: 26

Met Ala Gln Ser Thr Ala Thr Ser Pro Asp Gly Gly Thr Thr Phe Glu
 1               5                  10                  15

His Leu Trp Ser Ser Leu Glu Pro Asp Ser Thr Tyr Phe Asp Leu Pro
                20                  25                  30

Gln Ser Ser Arg Gly Asn Asn Glu Val Val Gly Gly Thr Asp Ser Ser
            35                  40                  45

Met Asp Val Phe His Leu Glu Gly Met Thr Thr Ser Val Met Ala Gln
    50                  55                  60

Phe Asn Leu Leu Ser Ser Thr Met Asp Gln Met Ser Ser Arg Ala Ala
65                  70                  75                  80

Ser Ala Ser Pro Tyr Thr Pro Glu His Ala Ala Ser Val Pro Thr His
                85                  90                  95
```

```
Ser Pro Tyr Ala Gln Pro Ser Ser Thr Phe Asp Thr Met Ser Pro Ala
            100                 105                 110
Pro Val Ile Pro Ser Asn Thr Asp Tyr Pro Gly Pro His His Phe Glu
        115                 120                 125
Val Thr Phe Gln Gln Ser Ser Thr Ala Lys Ser Ala Thr Trp Thr Tyr
    130                 135                 140
Ser Pro Leu Leu Lys Lys Leu Tyr Cys Gln Ile Ala Lys Thr Cys Pro
145                 150                 155                 160
Ile Gln Ile Lys Val Ser Thr Pro Pro Pro Gly Thr Ala Ile Arg
                165                 170                 175
Ala Met Pro Val Tyr Lys Lys Ala Glu His Val Thr Asp Val Val Lys
            180                 185                 190
Arg Cys Pro Asn His Glu Leu Gly Arg Asp Phe Asn Glu Gly Gln Ser
        195                 200                 205
Ala Pro Ala Ser His Leu Ile Arg Val Glu Gly Asn Asn Leu Ser Gln
    210                 215                 220
Tyr Val Asp Asp Pro Val Thr Gly Arg Gln Ser Val Val Pro Tyr
225                 230                 235                 240
Glu Pro Pro Gln Val Gly Thr Glu Phe Thr Thr Ile Leu Tyr Asn Phe
                245                 250                 255
Met Cys Asn Ser Ser Cys Val Gly Gly Met Asn Arg Arg Pro Ile Leu
            260                 265                 270
Ile Ile Ile Thr Leu Glu Met Arg Asp Gly Gln Val Leu Gly Arg Arg
        275                 280                 285
Ser Phe Glu Gly Arg Ile Cys Ala Cys Pro Gly Arg Asp Arg Lys Ala
    290                 295                 300
Asp Glu Asp His Tyr Arg Glu Gln Gln Ala Leu Asn Glu Ser Ser Ala
305                 310                 315                 320
Lys Asn Gly Ala Ala Ser Lys Arg Ala Phe Lys Gln Ser Pro Pro Ala
                325                 330                 335
Val Pro Ala Leu Gly Ala Gly Val Lys Lys Arg Arg His Gly Asp Glu
            340                 345                 350
Asp Thr Tyr Tyr Leu Gln Val Arg Gly Arg Glu Asn Phe Glu Ile Leu
        355                 360                 365
Met Lys Leu Lys Glu Ser Leu Glu Leu Met Glu Leu Val Pro Gln Pro
    370                 375                 380
Leu Val Asp Ser Tyr Arg Gln Gln Gln Leu Leu Gln Arg Pro Ser
385                 390                 395                 400
His Leu Gln Pro Pro Ser Tyr Gly Pro Val Leu Ser Pro Met Asn Lys
                405                 410                 415
Val His Gly Gly Met Asn Lys Leu Pro Ser Val Asn Gln Leu Val Gly
            420                 425                 430
Gln Pro Pro Pro His Ser Ser Ala Ala Thr Pro Asn Leu Gly Pro Val
        435                 440                 445
Gly Pro Gly Met Leu Asn Asn His Gly His Ala Val Pro Ala Asn Gly
    450                 455                 460
Glu Met Ser Ser Ser His Ser Ala Gln Ser Met Val Ser Gly Ser His
465                 470                 475                 480
Cys Thr Pro Pro Pro Pro Tyr His Ala Asp Pro Ser Leu Val Arg Thr
                485                 490                 495
Trp Gly Pro
```

<210> SEQ ID NO 27

```
<211> LENGTH: 29
<212> TYPE: DNA
<213> ORGANISM: Artificial Sequence
<220> FEATURE:
<223> OTHER INFORMATION: Description of Artificial Sequence: synthetic
      primer
<220> FEATURE:
<221> NAME/KEY: modified_base
<222> LOCATION: (15)
<223> OTHER INFORMATION: inosine

<400> SEQUENCE: 27
ggcctcgagt acaantwcat gtgtaayag                              29

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: synthetic
      primer

<400> SEQUENCE: 28
ggcatcgatt ctcttccagg gcaagcaca                              29

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: synthetic
      primer

<400> SEQUENCE: 29
ggcatcgatg aactcacggc tcagctc                                27

<210> SEQ ID NO 30
<211> LENGTH: 43
<212> TYPE: DNA
<213> ORGANISM: Artificial Sequence
<220> FEATURE:
<223> OTHER INFORMATION: Description of Artificial Sequence: synthetic
      primer

<400> SEQUENCE: 30
tttagtgagg gttaataagc ggccgcgtcg tgactgggag cgc              43

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: synthetic
      primer

<400> SEQUENCE: 31
gccctggagg cggccgctta ttaaccctca c                           31

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: synthetic
      primer

<400> SEQUENCE: 32
ggcatcgatg tagacaggca tggcacg                                27
```

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: synthetic
     primer

<400> SEQUENCE: 33
gggctcgagc tgaagaagct gtactgc                                        27

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: synthetic
     primer

<400> SEQUENCE: 34
gggatcgatc tccgtttctt gatggaa                                        27

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: synthetic
     primer

<400> SEQUENCE: 35
cctgcctgga cttgcctgg                                                 19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: synthetic
     primer

<400> SEQUENCE: 36
ccaggcaagt ccaggcagg                                                 19

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: synthetic
     primer

<400> SEQUENCE: 37
gaacatgtcc caacatgttg                                                20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: synthetic
     primer

<400> SEQUENCE: 38
caacatgttg ggacatgttc                                                20

```
<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: synthetic
      primer

<400> SEQUENCE: 39
ccttaatgga ctttaatgg                                                    19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: synthetic
      primer

<400> SEQUENCE: 40
ccattaaagt ccattaagg                                                    19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: synthetic
      primer

<400> SEQUENCE: 41
atgtcccaga gccacacag                                                    19

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: synthetic
      primer

<400> SEQUENCE: 42
agctcatggt tggggcac                                                     18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: synthetic
      primer

<400> SEQUENCE: 43
cagactcaat ttagtgag                                                     18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: synthetic
      primer

<400> SEQUENCE: 44
agctcatggt tggggcac                                                     18
```

-continued

<210> SEQ ID NO 45
<211> LENGTH: 120
<212> TYPE: PRT
<213> ORGANISM: Mus musculus

<400> SEQUENCE: 45

Met Asn Phe Glu Thr Ser Arg Cys Ala Thr Leu Gln Tyr Cys Pro Asp
1               5                   10                  15

Pro Tyr Ile Gln Arg Phe Ile Glu Thr Pro Ala His Phe Ser Trp Lys
            20                  25                  30

Glu Ser Tyr Tyr Arg Ser Ala Met Ser Gln Ser Thr Gln Thr Ser Glu
        35                  40                  45

Phe Leu Ser Pro Glu Val Phe Gln His Ile Trp Asp Phe Leu Glu Gln
    50                  55                  60

Pro Ile Cys Ser Val Gln Pro Ile Glu Leu Asn Phe Val Asp Glu Pro
65                  70                  75                  80

Ser Glu Asn Gly Ala Thr Asn Lys Ile Glu Ile Ser Met Asp Cys Ile
                85                  90                  95

Arg Met Gln Asp Ser Asp Leu Ser Asp Pro Met Trp Pro Gln Tyr Thr
            100                 105                 110

Asn Leu Gly Leu Leu Asn Ser Met
        115                 120

<210> SEQ ID NO 46
<211> LENGTH: 81
<212> TYPE: PRT
<213> ORGANISM: Homo sapiens

<400> SEQUENCE: 46

Met Ser Gln Ser Thr Gln Thr Asn Glu Phe Leu Ser Pro Glu Val Phe
1               5                   10                  15

Gln His Ile Trp Asp Phe Leu Glu Gln Pro Ile Cys Ser Val Gln Pro
            20                  25                  30

Ile Asp Leu Asn Phe Val Asp Glu Pro Ser Glu Asp Gly Ala Thr Asn
        35                  40                  45

Lys Ile Glu Ile Ser Met Asp Cys Ile Arg Met Gln Asp Ser Asp Leu
    50                  55                  60

Ser Asp Pro Met Trp Pro Gln Tyr Thr Asn Leu Gly Leu Leu Asn Ser
65                  70                  75                  80

Met

<210> SEQ ID NO 47
<211> LENGTH: 26
<212> TYPE: PRT
<213> ORGANISM: Homo sapiens

<400> SEQUENCE: 47

Met Leu Tyr Leu Glu Asn Asn Ala Gln Thr Gln Phe Ser Glu Pro Gln
1               5                   10                  15

Tyr Thr Asn Leu Gly Leu Leu Asn Ser Met
            20                  25

<210> SEQ ID NO 48
<211> LENGTH: 245
<212> TYPE: PRT
<213> ORGANISM: Homo sapiens

<400> SEQUENCE: 48

Arg Gln Gln Gln Gln Gln Gln His Gln His Leu Leu Gln Lys Gln Thr

```
                1               5                    10                    15
Ser Ile Gln Ser Pro Ser Ser Tyr Gly Asn Ser Ser Pro Pro Leu Asn
                20                        25                        30

Lys Met Asn Ser Met Asn Lys Leu Pro Ser Val Ser Gln Leu Ile Asn
                35                        40                        45

Pro Gln Gln Arg Asn Ala Leu Thr Pro Thr Thr Ile Pro Asp Gly Met
            50                        55                        60

Gly Ala Asn Ile Pro Met Met Gly Thr His Met Pro Met Ala Gly Asp
65                          70                        75                        80

Met Asn Gly Leu Ser Pro Thr Gln Ala Leu Pro Pro Leu Ser Met
                        85                        90                        95

Pro Ser Thr Ser His Cys Thr Pro Pro Pro Tyr Pro Thr Asp Cys
                    100                        105                        110

Ser Ile Val Ser Phe Leu Ala Arg Leu Gly Cys Ser Ser Cys Leu Asp
                    115                        120                        125

Tyr Phe Thr Thr Gln Gly Leu Thr Thr Ile Tyr Gln Ile Glu His Tyr
            130                        135                        140

Ser Met Asp Asp Leu Ala Ser Leu Lys Ile Pro Glu Gln Phe Arg His
145                        150                        155                        160

Ala Ile Trp Lys Gly Ile Leu Asp His Arg Gln Leu His Glu Phe Ser
                    165                        170                        175

Ser Pro Ser His Leu Leu Arg Thr Pro Ser Ser Ala Ser Thr Val Ser
                    180                        185                        190

Val Gly Ser Ser Glu Thr Arg Gly Glu Arg Val Ile Asp Ala Val Arg
            195                        200                        205

Phe Thr Leu Arg Gln Thr Ile Ser Phe Pro Pro Arg Asp Glu Trp Asn
210                        215                        220

Asp Phe Asn Phe Asp Met Asp Ala Arg Arg Asn Lys Gln Gln Arg Ile
225                        230                        235                        240

Lys Glu Glu Gly Glu
            245
```

<210> SEQ ID NO 49
<211> LENGTH: 120
<212> TYPE: PRT
<213> ORGANISM: Homo sapiens

<400> SEQUENCE: 49

```
Arg Gln Gln Gln Gln Gln His Gln His Leu Leu Gln Lys Gln Thr
1               5                    10                    15

Ser Ile Gln Ser Pro Ser Ser Tyr Gly Asn Ser Ser Pro Pro Leu Asn
                20                        25                        30

Lys Met Asn Ser Met Asn Lys Leu Pro Ser Val Ser Gln Leu Ile Asn
                35                        40                        45

Pro Gln Gln Arg Asn Ala Leu Thr Pro Thr Thr Ile Pro Asp Gly Met
            50                        55                        60

Gly Ala Asn Ile Pro Met Met Gly Thr His Met Pro Met Ala Gly Asp
65                          70                        75                        80

Met Asn Gly Leu Ser Pro Thr Gln Ala Leu Pro Pro Leu Ser Met
                        85                        90                        95

Pro Ser Thr Ser His Cys Thr Pro Pro Pro Tyr Pro Thr Asp Cys
                    100                        105                        110

Ser Ile Val Arg Ile Trp Gln Val
            115                        120
```

```
<210> SEQ ID NO 50
<211> LENGTH: 52
<212> TYPE: PRT
<213> ORGANISM: Homo sapiens

<400> SEQUENCE: 50

Arg Gln Gln Gln Gln Gln His Gln His Leu Leu Gln Lys His Leu
 1               5                  10                  15

Leu Ser Ala Cys Phe Arg Asn Glu Leu Val Glu Pro Arg Arg Glu Thr
            20                  25                  30

Pro Lys Gln Ser Asp Val Phe Phe Arg His Ser Lys Pro Pro Asn Arg
        35                  40                  45

Ser Val Tyr Pro
     50

<210> SEQ ID NO 51
<211> LENGTH: 1020
<212> TYPE: DNA
<213> ORGANISM: Mus musculus
<220> FEATURE:
<221> NAME/KEY: CDS
<222> LOCATION: (1)..(1020)

<400> SEQUENCE: 51 cca cag tac acg aac ctg ggg ctc ctg aac agc atg gac cag cag att      48
Pro Gln Tyr Thr Asn Leu Gly Leu Leu Asn Ser Met Asp Gln Gln Ile
 1               5                  10                  15 cag aac ggc tcc tcg tcc acc agc ccc tac aac aca gac cac gca cag      96
Gln Asn Gly Ser Ser Ser Thr Ser Pro Tyr Asn Thr Asp His Ala Gln
            20                  25                  30 aat agc gtg acg gcg ccc tcg ccc tat gca cag ccc agc tcc acc ttt     144
Asn Ser Val Thr Ala Pro Ser Pro Tyr Ala Gln Pro Ser Ser Thr Phe
        35                  40                  45 gat gcc ctc tct cca tcc cct gcc att ccc tcc aac aca gat tac ccg     192
Asp Ala Leu Ser Pro Ser Pro Ala Ile Pro Ser Asn Thr Asp Tyr Pro
    50                  55                  60 ggc cca cac agc ttc gat gtg tcc ttc cag cag tca agc act gcc aag     240
Gly Pro His Ser Phe Asp Val Ser Phe Gln Gln Ser Ser Thr Ala Lys
65                  70                  75                  80 tca gcc acc tgg acg tat tcc acc gaa ctg aag aag ctg tac tgc cag     288
Ser Ala Thr Trp Thr Tyr Ser Thr Glu Leu Lys Lys Leu Tyr Cys Gln
                85                  90                  95 att gcg aag aca tgc ccc atc cag atc aag gtg atg acc cca ccc cca     336
Ile Ala Lys Thr Cys Pro Ile Gln Ile Lys Val Met Thr Pro Pro Pro
            100                 105                 110 cag ggc gct gtt atc cgt gcc atg cct gtc tac aag aaa gct gag cat     384
Gln Gly Ala Val Ile Arg Ala Met Pro Val Tyr Lys Lys Ala Glu His
        115                 120                 125 gtc acc gag gtt gtg aaa cga tgc cct aac cat gag ctg agc cgt gag     432
Val Thr Glu Val Val Lys Arg Cys Pro Asn His Glu Leu Ser Arg Glu
    130                 135                 140 ttc aat gag gga cag att gcc cct ccc agt cat ctg att cga gta gaa     480
Phe Asn Glu Gly Gln Ile Ala Pro Pro Ser His Leu Ile Arg Val Glu
145                 150                 155                 160 ggg aac agc cat gcc cag tat gta gaa gat cct atc acg gga agg cag     528
Gly Asn Ser His Ala Gln Tyr Val Glu Asp Pro Ile Thr Gly Arg Gln
                165                 170                 175 agc gtg ctg gtc cct tat gag cca cca cag gtt ggc act gaa ttc aca     576
Ser Val Leu Val Pro Tyr Glu Pro Pro Gln Val Gly Thr Glu Phe Thr
            180                 185                 190
```

-continued

```
aca gtc ctg tac aat ttc atg tgt aac agc agc tgc gtc gga gga atg      624
Thr Val Leu Tyr Asn Phe Met Cys Asn Ser Ser Cys Val Gly Gly Met
        195                 200                 205 aac aga cgt cca att tta atc atc gtt act ctg gaa acc aga gat ggg      672
Asn Arg Arg Pro Ile Leu Ile Ile Val Thr Leu Glu Thr Arg Asp Gly
    210                 215                 220 caa gtc ctg ggc cga cgg tgc ttt gag gcc cgg atc tgt gct tgc cca      720
Gln Val Leu Gly Arg Arg Cys Phe Glu Ala Arg Ile Cys Ala Cys Pro
225                 230                 235                 240 gga aga gac cgg aag gca gat gaa gac agc atc aga aag cag caa gta      768
Gly Arg Asp Arg Lys Ala Asp Glu Asp Ser Ile Arg Lys Gln Gln Val
                245                 250                 255 tcg gac agc gca aag aac ggc gat ggt acg aag cgc cct ttc cgt cag      816
Ser Asp Ser Ala Lys Asn Gly Asp Gly Thr Lys Arg Pro Phe Arg Gln
            260                 265                 270 aat aca cac gga atc cag atg act tcc atc aag aaa cgg aga tcc cca      864
Asn Thr His Gly Ile Gln Met Thr Ser Ile Lys Lys Arg Arg Ser Pro
        275                 280                 285 gat gat gag ctg ctg tac cta cca gtg aga ggt cgt gag acg tac gag      912
Asp Asp Glu Leu Leu Tyr Leu Pro Val Arg Gly Arg Glu Thr Tyr Glu
    290                 295                 300 atg ttg ctg aag atc aaa gag tca ctg gag ctc atg cag tac ctc cct      960
Met Leu Leu Lys Ile Lys Glu Ser Leu Glu Leu Met Gln Tyr Leu Pro
305                 310                 315                 320 cag cac acg atc gaa acg tac agg cag cag cag cag cag cac cag         1008
Gln His Thr Ile Glu Thr Tyr Arg Gln Gln Gln Gln Gln His Gln
                325                 330                 335 cac cta ctt cag                                                     1020
His Leu Leu Gln
        340
```

<210> SEQ ID NO 52
<211> LENGTH: 340
<212> TYPE: PRT
<213> ORGANISM: Mus musculus

<400> SEQUENCE: 52

```
Pro Gln Tyr Thr Asn Leu Gly Leu Leu Asn Ser Met Asp Gln Gln Ile
1               5                   10                  15

Gln Asn Gly Ser Ser Ser Thr Ser Pro Tyr Asn Thr Asp His Ala Gln
            20                  25                  30

Asn Ser Val Thr Ala Pro Ser Pro Tyr Ala Gln Pro Ser Ser Thr Phe
        35                  40                  45

Asp Ala Leu Ser Pro Ser Pro Ala Ile Pro Ser Asn Thr Asp Tyr Pro
    50                  55                  60

Gly Pro His Ser Phe Asp Val Ser Phe Gln Gln Ser Ser Thr Ala Lys
65                  70                  75                  80

Ser Ala Thr Trp Thr Tyr Ser Thr Glu Leu Lys Lys Leu Tyr Cys Gln
                85                  90                  95

Ile Ala Lys Thr Cys Pro Ile Gln Ile Lys Val Met Thr Pro Pro Pro
            100                 105                 110

Gln Gly Ala Val Ile Arg Ala Met Pro Val Tyr Lys Lys Ala Glu His
        115                 120                 125

Val Thr Glu Val Val Lys Arg Cys Pro Asn His Glu Leu Ser Arg Glu
    130                 135                 140

Phe Asn Glu Gly Gln Ile Ala Pro Pro Ser His Leu Ile Arg Val Glu
145                 150                 155                 160

Gly Asn Ser His Ala Gln Tyr Val Glu Asp Pro Ile Thr Gly Arg Gln
```

-continued

```
                        165                 170                 175
Ser Val Leu Val Pro Tyr Glu Pro Gln Val Gly Thr Glu Phe Thr
                180                 185                 190

Thr Val Leu Tyr Asn Phe Met Cys Asn Ser Ser Cys Val Gly Gly Met
                195                 200                 205

Asn Arg Arg Pro Ile Leu Ile Ile Val Thr Leu Glu Thr Arg Asp Gly
            210                 215                 220

Gln Val Leu Gly Arg Arg Cys Phe Glu Ala Arg Ile Cys Ala Cys Pro
225                 230                 235                 240

Gly Arg Asp Arg Lys Ala Asp Glu Asp Ser Ile Arg Lys Gln Gln Val
                245                 250                 255

Ser Asp Ser Ala Lys Asn Gly Asp Gly Thr Lys Arg Pro Phe Arg Gln
            260                 265                 270

Asn Thr His Gly Ile Gln Met Thr Ser Ile Lys Lys Arg Arg Ser Pro
        275                 280                 285

Asp Asp Glu Leu Leu Tyr Leu Pro Val Arg Gly Arg Glu Thr Tyr Glu
    290                 295                 300

Met Leu Leu Lys Ile Lys Glu Ser Leu Glu Leu Met Gln Tyr Leu Pro
305                 310                 315                 320

Gln His Thr Ile Glu Thr Tyr Arg Gln Gln Gln Gln Gln His Gln
                325                 330                 335

His Leu Leu Gln
            340

<210> SEQ ID NO 53
<211> LENGTH: 1008
<212> TYPE: DNA
<213> ORGANISM: Mus musculus
<220> FEATURE:
<221> NAME/KEY: CDS
<222> LOCATION: (1)..(1008)

<400> SEQUENCE: 53 cca cag tac acg aac ctg ggg ctc ctg aac agc atg gac cag cag att      48
Pro Gln Tyr Thr Asn Leu Gly Leu Leu Asn Ser Met Asp Gln Gln Ile
1               5                   10                  15 cag aac ggc tcc tcg tcc acc agc ccc tac aac aca gac cac gca cag      96
Gln Asn Gly Ser Ser Ser Thr Ser Pro Tyr Asn Thr Asp His Ala Gln
            20                  25                  30 aat agc gtg acg gcg ccc tcg ccc tat gca cag ccc agc tcc acc ttt     144
Asn Ser Val Thr Ala Pro Ser Pro Tyr Ala Gln Pro Ser Ser Thr Phe
        35                  40                  45 gat gcc ctc tct cca tcc cct gcc att ccc tcc aac aca gat tac ccg     192
Asp Ala Leu Ser Pro Ser Pro Ala Ile Pro Ser Asn Thr Asp Tyr Pro
    50                  55                  60 ggc cca cac agc ttc gat gtg tcc ttc cag cag tca agc act gcc aag     240
Gly Pro His Ser Phe Asp Val Ser Phe Gln Gln Ser Ser Thr Ala Lys
65                  70                  75                  80 tca gcc acc tgg acg tat tcc acc gaa ctg aag aag ctg tac tgc cag     288
Ser Ala Thr Trp Thr Tyr Ser Thr Glu Leu Lys Lys Leu Tyr Cys Gln
                85                  90                  95 att gcg aag aca tgc ccc atc cag atc aag gtg atg acc cca ccc cca     336
Ile Ala Lys Thr Cys Pro Ile Gln Ile Lys Val Met Thr Pro Pro Pro
            100                 105                 110 cag ggc gct gtt atc cgt gcc atg cct gtc tac aag aaa gct gag cat     384
Gln Gly Ala Val Ile Arg Ala Met Pro Val Tyr Lys Lys Ala Glu His
        115                 120                 125 gtc acc gag gtt gtg aaa cga tgc cct aac cat gag ctg agc cgt gag     432
```

```
Val Thr Glu Val Val Lys Arg Cys Pro Asn His Glu Leu Ser Arg Glu
    130                 135                 140 ttc aat gag gga cag att gcc cct ccc agt cat ctg att cga gta gaa      480
Phe Asn Glu Gly Gln Ile Ala Pro Pro Ser His Leu Ile Arg Val Glu
145                 150                 155                 160 ggg aac agc cat gcc cag tat gta gaa gat cct atc acg gga agg cag      528
Gly Asn Ser His Ala Gln Tyr Val Glu Asp Pro Ile Thr Gly Arg Gln
                165                 170                 175 agc gtg ctg gtc cct tat gag cca cca cag gtt ggc act gaa ttc aca      576
Ser Val Leu Val Pro Tyr Glu Pro Pro Gln Val Gly Thr Glu Phe Thr
            180                 185                 190 aca gtc ctg tac aat ttc atg tgt aac agc agc tgc gtc gga gga atg      624
Thr Val Leu Tyr Asn Phe Met Cys Asn Ser Ser Cys Val Gly Gly Met
        195                 200                 205 aac aga cgt cca att tta atc atc gtt act ctg gaa acc aga gat ggg      672
Asn Arg Arg Pro Ile Leu Ile Ile Val Thr Leu Glu Thr Arg Asp Gly
210                 215                 220 caa gtc ctg ggc cga cgg tgc ttt gag gcc cgg atc tgt gct tgc cca      720
Gln Val Leu Gly Arg Arg Cys Phe Glu Ala Arg Ile Cys Ala Cys Pro
225                 230                 235                 240 gga aga gac cgg aag gca gat gaa gac agc atc aga aag cag caa gta      768
Gly Arg Asp Arg Lys Ala Asp Glu Asp Ser Ile Arg Lys Gln Gln Val
                245                 250                 255 tcg gac agc gca aag aac ggc gat gct ttc cgt cag aat aca cac gga      816
Ser Asp Ser Ala Lys Asn Gly Asp Ala Phe Arg Gln Asn Thr His Gly
            260                 265                 270 atc cag atg act tcc atc aag aaa cgg aga tcc cca gat gat gag ctg      864
Ile Gln Met Thr Ser Ile Lys Lys Arg Arg Ser Pro Asp Asp Glu Leu
        275                 280                 285 ctg tac cta cca gtg aga ggt cgt gag acg tac gag atg ttg ctg aag      912
Leu Tyr Leu Pro Val Arg Gly Arg Glu Thr Tyr Glu Met Leu Leu Lys
    290                 295                 300 atc aaa gag tca ctg gag ctc atg cag tac ctc cct cag cac acg atc      960
Ile Lys Glu Ser Leu Glu Leu Met Gln Tyr Leu Pro Gln His Thr Ile
305                 310                 315                 320 gaa acg tac agg cag cag cag cag cag cag cac cag cac cta ctt cag     1008
Glu Thr Tyr Arg Gln Gln Gln Gln Gln Gln His Gln His Leu Leu Gln
                325                 330                 335

<210> SEQ ID NO 54
<211> LENGTH: 336
<212> TYPE: PRT
<213> ORGANISM: Mus musculus

<400> SEQUENCE: 54

Pro Gln Tyr Thr Asn Leu Gly Leu Leu Asn Ser Met Asp Gln Gln Ile
1               5                   10                  15

Gln Asn Gly Ser Ser Ser Thr Ser Pro Tyr Asn Thr Asp His Ala Gln
            20                  25                  30

Asn Ser Val Thr Ala Pro Ser Pro Tyr Ala Gln Pro Ser Ser Thr Phe
        35                  40                  45

Asp Ala Leu Ser Pro Ser Pro Ala Ile Pro Ser Asn Thr Asp Tyr Pro
    50                  55                  60

Gly Pro His Ser Phe Asp Val Ser Phe Gln Gln Ser Ser Thr Ala Lys
65                  70                  75                  80

Ser Ala Thr Trp Thr Tyr Ser Thr Glu Leu Lys Lys Leu Tyr Cys Gln
                85                  90                  95

Ile Ala Lys Thr Cys Pro Ile Gln Ile Lys Val Met Thr Pro Pro Pro
            100                 105                 110
```

-continued

```
Gln Gly Ala Val Ile Arg Ala Met Pro Val Tyr Lys Lys Ala Glu His
        115                 120                 125
Val Thr Glu Val Val Lys Arg Cys Pro Asn His Glu Leu Ser Arg Glu
    130                 135                 140
Phe Asn Glu Gly Gln Ile Ala Pro Pro Ser His Leu Ile Arg Val Glu
145                 150                 155                 160
Gly Asn Ser His Ala Gln Tyr Val Glu Asp Pro Ile Thr Gly Arg Gln
                165                 170                 175
Ser Val Leu Val Pro Tyr Glu Pro Pro Gln Val Gly Thr Glu Phe Thr
            180                 185                 190
Thr Val Leu Tyr Asn Phe Met Cys Asn Ser Ser Cys Val Gly Gly Met
        195                 200                 205
Asn Arg Arg Pro Ile Leu Ile Ile Val Thr Leu Glu Thr Arg Asp Gly
    210                 215                 220
Gln Val Leu Gly Arg Arg Cys Phe Glu Ala Arg Ile Cys Ala Cys Pro
225                 230                 235                 240
Gly Arg Asp Arg Lys Ala Asp Glu Asp Ser Ile Arg Lys Gln Gln Val
                245                 250                 255
Ser Asp Ser Ala Lys Asn Gly Asp Ala Phe Arg Gln Asn Thr His Gly
            260                 265                 270
Ile Gln Met Thr Ser Ile Lys Lys Arg Arg Ser Pro Asp Asp Glu Leu
        275                 280                 285
Leu Tyr Leu Pro Val Arg Gly Arg Glu Thr Tyr Glu Met Leu Leu Lys
    290                 295                 300
Ile Lys Glu Ser Leu Glu Leu Met Gln Tyr Leu Pro Gln His Thr Ile
305                 310                 315                 320
Glu Thr Tyr Arg Gln Gln Gln Gln Gln His Gln His Leu Leu Gln
                325                 330                 335
```

```
<210> SEQ ID NO 55
<211> LENGTH: 1020
<212> TYPE: DNA
<213> ORGANISM: Homo sapiens
<220> FEATURE:
<221> NAME/KEY: CDS
<222> LOCATION: (1)..(1020)

<400> SEQUENCE: 55
```

```
cca cag tac acg aac ctg ggg ctc ctg aac agc atg gac cag cag att      48
Pro Gln Tyr Thr Asn Leu Gly Leu Leu Asn Ser Met Asp Gln Gln Ile
1               5                   10                  15 cag aac ggc tcc tcg tcc acc agt ccc tat aac aca gac cac gcg cag      96
Gln Asn Gly Ser Ser Ser Thr Ser Pro Tyr Asn Thr Asp His Ala Gln
            20                  25                  30 aac agc gtc acg gcg ccc tcg ccc tac gca cag ccc agc tcc acc ttc     144
Asn Ser Val Thr Ala Pro Ser Pro Tyr Ala Gln Pro Ser Ser Thr Phe
        35                  40                  45 gat gct ctc tct cca tca ccc gcc atc ccc tcc aac acc gac tac cca     192
Asp Ala Leu Ser Pro Ser Pro Ala Ile Pro Ser Asn Thr Asp Tyr Pro
    50                  55                  60 ggc ccg cac agt ttc gac gtg tcc ttc cag cag tcg agc acc gcc aag     240
Gly Pro His Ser Phe Asp Val Ser Phe Gln Gln Ser Ser Thr Ala Lys
65                  70                  75                  80 tcg gcc acc tgg acg tat tcc act gaa ctg aag aaa ctc tac tgc caa     288
Ser Ala Thr Trp Thr Tyr Ser Thr Glu Leu Lys Lys Leu Tyr Cys Gln
                85                  90                  95 att gca aag aca tgc ccc atc cag atc aag gtg atg acc cca cct cct     336
Ile Ala Lys Thr Cys Pro Ile Gln Ile Lys Val Met Thr Pro Pro Pro
```

```
Ile Ala Lys Thr Cys Pro Ile Gln Ile Lys Val Met Thr Pro Pro
            100                 105                 110 cag gga gct gtt atc cgc gcc atg cct gtc tac aaa aaa gct gag cac      384
Gln Gly Ala Val Ile Arg Ala Met Pro Val Tyr Lys Lys Ala Glu His
        115                 120                 125 gtc acg gag gtg gtg aag cgg tgc ccc aac cat gag ctg agc cgt gaa      432
Val Thr Glu Val Val Lys Arg Cys Pro Asn His Glu Leu Ser Arg Glu
130                 135                 140 ttc aac gag gga cag att gcc cct cct agt cat ttg att cga gta gag      480
Phe Asn Glu Gly Gln Ile Ala Pro Pro Ser His Leu Ile Arg Val Glu
145                 150                 155                 160 ggg aac agc cat gcc cag tat gta gaa gat ccc atc aca gga aga cag      528
Gly Asn Ser His Ala Gln Tyr Val Glu Asp Pro Ile Thr Gly Arg Gln
                165                 170                 175 agt gtg ctg gta cct tat gag cca ccc cag gtt ggc act gaa ttc acg      576
Ser Val Leu Val Pro Tyr Glu Pro Pro Gln Val Gly Thr Glu Phe Thr
            180                 185                 190 aca gtc ttg tac aat ttc atg tgt aac agc agt tgt gtt gga ggg atg      624
Thr Val Leu Tyr Asn Phe Met Cys Asn Ser Ser Cys Val Gly Gly Met
        195                 200                 205 aac cgc cgt cca att tta atc att gtt act ctg gaa acc aga gat ggg      672
Asn Arg Arg Pro Ile Leu Ile Ile Val Thr Leu Glu Thr Arg Asp Gly
210                 215                 220 caa gtc ctg ggc cga cgc tgc ttt gag gcc cgg atc tgt gct tgc cca      720
Gln Val Leu Gly Arg Arg Cys Phe Glu Ala Arg Ile Cys Ala Cys Pro
225                 230                 235                 240 gga aga gac agg aag gcg gat gaa gat agc atc aga aag cag caa gtt      768
Gly Arg Asp Arg Lys Ala Asp Glu Asp Ser Ile Arg Lys Gln Gln Val
                245                 250                 255 tcg gac agt aca aag aac ggt gat ggt acg aag cgc ccg ttt cgt cag      816
Ser Asp Ser Thr Lys Asn Gly Asp Gly Thr Lys Arg Pro Phe Arg Gln
            260                 265                 270 aac aca cat ggt atc cag atg aca tcc atc aag aaa cga aga tcc cca      864
Asn Thr His Gly Ile Gln Met Thr Ser Ile Lys Lys Arg Arg Ser Pro
        275                 280                 285 gat gat gaa ctg tta tac tta cca gtg agg ggc cgt gag act tat gaa      912
Asp Asp Glu Leu Leu Tyr Leu Pro Val Arg Gly Arg Glu Thr Tyr Glu
290                 295                 300 atg ctg ttg aag atc aaa gag tcc ctg gaa ctc atg cag tac ctt cct      960
Met Leu Leu Lys Ile Lys Glu Ser Leu Glu Leu Met Gln Tyr Leu Pro
305                 310                 315                 320 cag cac aca att gaa acg tac agg caa cag caa cag cag cac cag         1008
Gln His Thr Ile Glu Thr Tyr Arg Gln Gln Gln Gln Gln His Gln
                325                 330                 335 cac tta ctt cag                                                     1020
His Leu Leu Gln
        340

<210> SEQ ID NO 56
<211> LENGTH: 340
<212> TYPE: PRT
<213> ORGANISM: Homo sapiens

<400> SEQUENCE: 56

Pro Gln Tyr Thr Asn Leu Gly Leu Leu Asn Ser Met Asp Gln Gln Ile
1               5                   10                  15

Gln Asn Gly Ser Ser Thr Ser Pro Tyr Asn Thr Asp His Ala Gln
            20                  25                  30

Asn Ser Val Thr Ala Pro Ser Pro Tyr Ala Gln Pro Ser Ser Thr Phe
        35                  40                  45
```

```
Asp Ala Leu Ser Pro Ser Pro Ala Ile Pro Ser Asn Thr Asp Tyr Pro
    50              55                  60

Gly Pro His Ser Phe Asp Val Ser Phe Gln Gln Ser Ser Thr Ala Lys
65              70                  75                  80

Ser Ala Thr Trp Thr Tyr Ser Thr Glu Leu Lys Lys Leu Tyr Cys Gln
                85                  90                  95

Ile Ala Lys Thr Cys Pro Ile Gln Ile Lys Val Met Thr Pro Pro Pro
            100                 105                 110

Gln Gly Ala Val Ile Arg Ala Met Pro Val Tyr Lys Lys Ala Glu His
            115                 120                 125

Val Thr Glu Val Val Lys Arg Cys Pro Asn His Glu Leu Ser Arg Glu
    130                 135                 140

Phe Asn Glu Gly Gln Ile Ala Pro Pro Ser His Leu Ile Arg Val Glu
145                 150                 155                 160

Gly Asn Ser His Ala Gln Tyr Val Glu Asp Pro Ile Thr Gly Arg Gln
                165                 170                 175

Ser Val Leu Val Pro Tyr Glu Pro Pro Gln Val Gly Thr Glu Phe Thr
            180                 185                 190

Thr Val Leu Tyr Asn Phe Met Cys Asn Ser Ser Cys Val Gly Gly Met
        195                 200                 205

Asn Arg Arg Pro Ile Leu Ile Ile Val Thr Leu Glu Thr Arg Asp Gly
        210                 215                 220

Gln Val Leu Gly Arg Arg Cys Phe Glu Ala Arg Ile Cys Ala Cys Pro
225                 230                 235                 240

Gly Arg Asp Arg Lys Ala Asp Glu Asp Ser Ile Arg Lys Gln Gln Val
            245                 250                 255

Ser Asp Ser Thr Lys Asn Gly Asp Gly Thr Lys Arg Pro Phe Arg Gln
            260                 265                 270

Asn Thr His Gly Ile Gln Met Thr Ser Ile Lys Lys Arg Arg Ser Pro
        275                 280                 285

Asp Asp Glu Leu Leu Tyr Leu Pro Val Arg Gly Arg Glu Thr Tyr Glu
    290                 295                 300

Met Leu Leu Lys Ile Lys Glu Ser Leu Glu Leu Met Gln Tyr Leu Pro
305                 310                 315                 320

Gln His Thr Ile Glu Thr Tyr Arg Gln Gln Gln Gln Gln His Gln
            325                 330                 335

His Leu Leu Gln
            340
```

CELL REGULATORY GENES, ENCODED PRODUCTS, AND USES RELATED THERETO

This application claims the benefit of United States provisional application Nos: 60/087,216 filed May 29, 1998, and 60/062,076 filed Oct. 15, 1997. These applications are incorporated by reference herein.

FEDERAL FUNDING

This invention was supported by NIH Grant No. GM 52027 and the government has certain rights to this invention.

1. BACKGROUND OF THE INVENTION

Neoplasia is characterized by deregulated cell growth and division. Inevitably, molecular pathways controlling cell growth must interact with those regulating cell division. It was not until very recently, however, that experimental evidence became available to bring such connection to light. Cyclin A was found in association with the adenovirus oncoprotein E1A in virally transformed cells (Giordona et al. *Cell* 58:981 (1989); and Pines et al. *Nature* 346:760 (1990)). The cell-cycle gene implicated most strongly in oncogenesis thus far is the human cyclin D1. It was originally isolated through genetic complementation of yeast G1 cyclin deficient strains (Xiong et al. *Cell* 65:691 (1991); and Lew et al. *Cell* 66:1197 (1991)), as cellular genes whose transcription is stimulated by CSF-1 in murine macrophages (Matsushine et al. *Cell* 65:701 (1991)) and in the putative oncogene PRAD1 rearranged in parathyroid tumors (Montokura et al. *Nature* 350:512 (1991).

However, the creation of a mutant onocogene is only one of the requirements needed for tumor formation; tumorigenesis appears to also require the additional inactivation of a second class of critical genes: the "anti-oncogenes" or "tumor-suppressing genes." Tumor suppressor genes are a family of genes that negatively regulate cell growth and are lost or inactivated in most cancers. In their natural state these genes act to suppress cell proliferation. Damage to such genes leads to a loss of this suppression, and thereby results in tumorigenesis. Thus, the deregulation of cell growth may be mediated by either the activation of oncogenes or the inactivation of tumor-suppressing genes (Weinberg, R. A., (September 1988) *Scientific Amer*. pp 44–51).

Oncogenes and tumor-suppressing genes have a basic distinguishing feature. The oncogenes identified thus far have arisen only in somatic cells, and thus have been incapable of transmitting their effects to the germ line of the host animal. In contrast, mutations in tumor-suppressing genes can be identified in germ line cells, and are thus transmissible to an animal's progeny.

The classic example of a hereditary cancer is retinoblastomas in children. The incidence of the retinoblastomas is determined by a tumor suppressor gene, the retinoblastoma (RB) gene (Weinberg, R. A., (September 1988) *Scientific Amer*. pp 44–51; Hansen et al. (1988) *Trends Genet* 4:125–128). Individuals born with a lesion in one of the RB alleles are predisposed to early childhood development of retinoblastomas. Inactivation or mutation of the second RB allele in one of the somatic cells of these susceptible individuals appears to be the molecular event that leads to tumor formation (Caveneee et al. (1983) *Nature* 305:799–784; Friend et al. (1987) *PNAS* 84:9059–9063).

The RB tumor-suppressing gene has been localized onto human chromosome 13. The mutation may be readily transmitted through the germ line of afflicted individuals (Cavenee, et al. (1986) *New Engl. J. Med* 314:1201–1207). Individuals who have mutations in only one of the two naturally present alleles of this tumor-suppressing gene are predisposed to retinoblastoma. Inactivation of the second of the two alleles is, however, required for tumorigenesis (Knudson (1971) *PNAS* 68:820–823).

A second tumor-suppressing gene is the p53 gene (Green (1989) *Cell* 56:1–3; Mowat et al (1985 *Nature* 314:633–636). The protein encoded by the p53 gene is a nuclear protein that forms a stable complex with both the SV40 large T antigen and the adenovirus E1B 55 kd protein. The p53 gene product may be inactivated by binding to these proteins.

Based on cause and effect analysis of p53 mutants, the functional role of p53 as a "cell-cycle checkpoint", particularly with respect to controlling progression of a cell from G1 phase into S phase, has implicated p53 as able to directly or indirectly affect cycle cyle machinery. The first firm evidence for a specific biochemical link between p53 and the cell-cycle comes a finding that p53 apparently regulates expression of a second protein, p21, which inhibits cyclin-dependent kinases (CDKs) needed to drive cells through the cell-cycle, e.g. from G1 into S phase. For example, it has been demonstrated that non-viral transformation, such as resulting at least in part from a mutation of deletion of of the p53 tumor suppressor, can result in loss of p21 from cyclin/CDK complexes. As described by Xiong et al. (1993) *Nature* 366:701–704, induction of p21 in response to p53 represents a plausible mechanism for effecting cell-cycle arrest in response to DNA damage, and loss of p53 may deregulate growth by loss of the p21 cell-cycle inhibitor.

More recently, researchers discovered yet another tumor suppressing gene, p73, which closely resembles p53. Not only does this protein bear a strong structural identity with p53, it also possess similar functional attributes. For instance, this protein disclosed the growth-inhibiting and apoptosis promoting effects, it triggered p21 production, suggesting thereby that it inhibited cell growth through the same pathway as that used by p53. Here, we describe the discovery of a novel family of cell regulatory genes, the p-63 family, which exhibits considerable sequence identity with p53 and and p73, and appears to possess similar functional attributes.

2. SUMMARY OF THE INVENTION

The p53 tumor suppressor protein is involved in multiple central cellular processes, including transcription, DNA repair, genomic stability, senescence, cell cycle control and apoptosis. p53 is functionally inactivated by structural mutations, interaction with viral products, and endogenous cellular mechanisms in the majority of human cancers. In fact, the p53 protein is one of the most frequently mutated tumor suppressor to be identified in human cancers. More than 50% of primary human tumor cells over-express a variety of mutant p53 forms. p73 which shares considerable structural identity maps to chromosomal region 1p36, a region which is frequently deleted in neuroblastoma and other tumors.

Here we describe a third family of cell regulatory genes, encoding the p63-family of proteins which also demonstrate considerable structural or sequence identity to the DNA-binding, oligomerization, and transactivation domains of p53. p63 differs from p53 in that multiple p63 transcripts yielding six major protein products have been discovered by cDNA cloning. For example, the six major p63 products are listed in FIG. 2 C. It was found that unlike p53, the p63 gene encodes multiple isotypes with remarkably divergent abilities. For instance, p63 variants possessing the N-terminus, i.e., TAp63γ, showed strong transactivation and cell-death inducing abilities. TAp63γ transactivates p53 reporter genes and may induce apoptosis. In addition, it was found that the predominant p63 isotypes in many epithelial tissues lack an acidic N-terminus corresponding to the transactivation domain of p53. p63 variants which lack the transactivation domain, i.e. ΔNp63α, ΔNp63γ, suppressed transactivation by both p53 and p63. Additionally, these variants lacking the N-terminus may possibly regulate growth and may play an essential role in the regenerative processes, particularly regeneration of epithelial tissue. In one aspect, the invention discloses that these truncated p63 variants can act as dominant-negative agents towards transactivation by p53, thereby suggesting the possibility of physiological interactions amongst members of the p53 family. Examples of these variants include the disclosed ΔNp63α and ΔNp63γ. Thus, in one embodiment, the p63 family of cell-regulatory proteins are involved in the modulation of cell growth or regulate the growth phenotype of a cell.

One aspect of the invention features a substantially pure preparation of a cell regulatory protein, or a fragment thereof, the full-length form of the cell regulatory protein having an amino acid sequence at least 70% homologous to the amino acid sequence represented in one of SEQ ID Nos. 13–24; the polypeptide has an amino acid sequence at least 80% homologous to the amino acid sequence represented in one of SEQ ID Nos. 13–24; the polypeptide has an amino acid sequence at least 90% homologous to the amino acid sequence represented in one of SEQ ID Nos. 13–24; the polypeptide has an amino acid sequence at least 95% homologous to the amino acid sequence represented in one of SEQ ID Nos. 13–24; the polypeptide has an amino acid sequence identical to the amino acid sequence represented in one of SEQ ID Nos. 13–24. In a preferred embodiment: the fragment comprises at least 5 contiguous amino acid residues of SEQ ID Nos. 13–24; the fragment comprises at least 20 contiguous amino acid residues of SEQ ID Nos. 13–24; the fragment comprises at least 50 contiguous amino acid residues of SEQ ID Nos. 13–24.

In yet another embodiment, the fragment includes the DNA binding domain of p63 and comprises at least 5 contiguous amino acid residues of SEQ ID Nos. 13–24; the fragment includes the DNA binding domain of p63 and comprises at least 20 contiguous amino acid residues of SEQ ID Nos. 13–24; the fragment includes the DNA binding domain of p63 and comprises at least 50 contiguous amino acid residues of SEQ ID Nos. 13–24.

Figure 25:
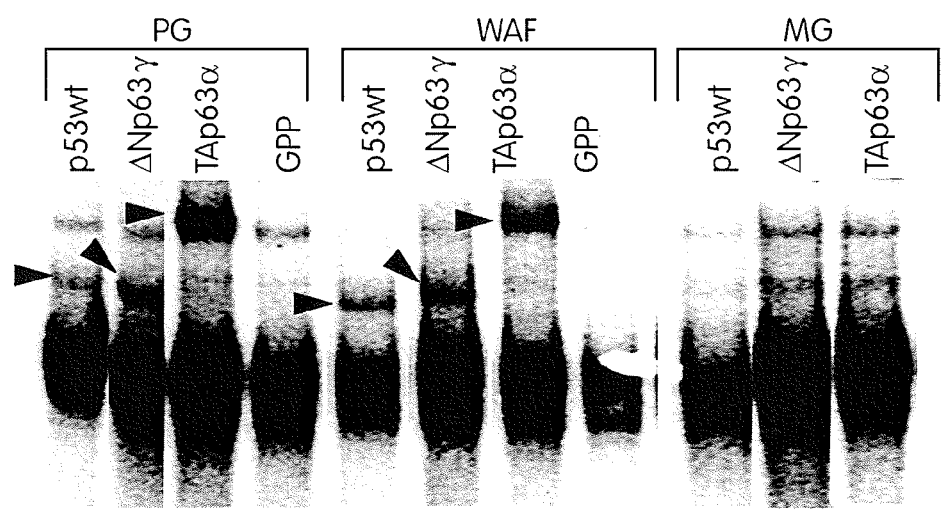

The DNA binding domain of these nucleic acid transcripts are remarkably conserved. The six variants demonstrate 100% identity in this region and this domain also demonstrates considerable identity to the corresponding DNA-binding domains of p53 and p73. It was found that p63 variants bound the target sequences which are bound by p53, for example, ΔNp63γ, p53, and Tap63α all yielded significant mobility shifts with three separate oligonucleotides, specifically, with a minimal p53 binding sequence, a p53 binding site in the p21 promoter WAF, and a mutant p53 binding site. Results of the assay are shown in FIG. 25.

Another aspect of the present invention features a polypeptide, of the cell regulator protein family, which functions in one of either role of an agonist of cell-cycle regulation or an antagonist of cell-cycle regulation. In a preferred embodiment: the subject cell regulator-protein specifically binds a target DNA or protein; e.g. specifically binds a target DNA; e.g. is reasonably expected to transactivate genes involved in cell cycle arrest, such as p21; interacts with the DNA repair and synthetic machinery, such as proliferating cellular nuclear antigen, GADD 45, or proteins modulating apoptosis. In a more preferred embodiment, the cell regulator-protein regulates aand/or modulates growth of an eukaryotic cell-cycle, e.g. a mammalian cell-cycle, e.g., a human cell-cycle; the cell regulator protein inhibits cell growth of a eukaryotic cell, e.g., a human cell; the tumor suppressor-protein inhibits progression of a eukaryotic cell from G1 phase into S phase, e.g., inhibits progression of a mammalian cell from G1 phase into S phase, e.g., inhibits progression of a human cell from G1 phase into S phase; the cell regulator-protein suppresses tumor growth, e.g. in a tumor cell, e.g. in a tumor cell having an unimpaired p53 or p63 or p53-like protein checkpoint. Yet another aspect of the present invention concerns an immunogen comprising a cell regulator-protein of the present invention, or a fragment thereof, in an immunogenic preparation, the immunogen being capable of eliciting an immune response specific for the cell regulator-protein; e.g. a humoral response, e.g., an antibody response; e.g. a cellular response. Thus, in one embodiment, the p-63 family of cell-regulatory proteins are involved in the modulation of cell growth or regulate the growth phenotype of a cell.

Another aspect of the present invention features recombinant cell regulator-protein, or a fragment thereof, cell regulatory protein, or a fragment thereof, the full-length form of the cell regulatory genes protein having an amino acid sequence at least 70% homologous to the amino acid sequence represented in one of SEQ ID Nos. 13–24; the polypeptide has an amino acid sequence at least 80% homologous to the amino acid sequence represented in one of SEQ ID Nos. 13–24; the polypeptide has an amino acid sequence at least 90% homologous to the amino acid sequence represented in one of SEQ ID Nos. 13–24; the polypeptide has an amino acid sequence at least 95% homologous to the amino acid sequence represented in one of SEQ ID Nos. 13–24; the polypeptide has an amino acid sequence identical to the amino acid sequence represented in one of SEQ ID Nos. 13–24. In a preferred embodiment: the fragment comprises at least 5 contiguous amino acid residues of SEQ ID Nos. 13–24; the fragment comprises at least 20 contiguous amino acid residues of SEQ ID Nos. 13–24; the fragment comprises at least 50 contiguous amino acid residues of SEQ ID Nos. 13–24.

In yet another embodiment, the fragment includes the DNA binding domain of p63 and comprises at least 5 contiguous amino acid residues of SEQ ID Nos. 13–24; the fragment includes the DNA binding domain of p63 and comprises at least 20 contiguous amino acid residues of SEQ ID Nos. 13–24; the fragment includes the DNA binding domain of p63 and comprises at least 50 contiguous amino acid residues of SEQ ID Nos. 13–24.

In yet another embodiment, the fragment includes the core domain of p63 and comprises at least 5 contiguous amino acid residues of SEQ ID Nos. 13–24; the fragment includes the core domain of p63 and comprises at least 20 contiguous amino acid residues of SEQ ID Nos. 13–24; the fragment includes the core domain of p63 and comprises at least 50 contiguous amino acid residues of SEQ ID Nos. 13–24. The core domain extends from about amino acids "PQY" through about amino acid "HLLQ", for instance, in TAp63γ, this region extends from about amino acid 70 through about amino acid 409.

In a preferred embodiment, the recombinant cell regulator-protein functions in one of either role of an agonist of cell-cycle regulation or an antagonist of cell-cycle regulation. In a preferred embodiment: the subject p63 protein specifically binds a target DNA or protein; e.g. specifically binds a target DNA; e.g. is reasonably expected to transactivate genes involved in cell cycle arrest, such as p21; interact with the DNA repair and synthetic machinery, such as proliferating cellular nuclear antigen, GADD 45, or proteins modulating apoptosis. In a more preferred embodiment: the p63 protein regulates and/or modulates growth of an eukaryotic cell-cycle, e.g. a mammalian cell-cycle, e.g., a human cell-cycle; the p63 protein inhibits cell growth of a eukaryotic cell, e.g., a human cell; the p63 protein inhibits progression of a eukaryotic cell from G1 phase into S phase, e.g., inhibits progression of a mammalian cell from G1 phase into S phase, e.g., inhibits progression of a human cell from G1 phase into S phase; the tumor suppressor-protein suppresses tumor growth, e.g. in a tumor cell, e.g. in a tumor cell having an unimpaired p53 or p63 or p53-like protein checkpoint. Thus, in one embodiment, the p-63 family of cell-regulatory proteins are involved in the modulation of cell growth or regulate the growth phenotype of a cell.

In yet other preferred embodiments, the recombinant tumor-suppressor-protein is a fusion protein further comprising a second polypeptide portion having an amino acid sequence from a protein unrelated the protein of SEQ ID Nos. 13–24. Such fusion proteins can be functional in a two-hybrid assay.

Another aspect of the present invention provides a substantially pure nucleic acid having a nucleotide sequence which encodes a cell regulator-protein, or a fragment thereof, having an amino acid sequence at least 70% homologous to one of SEQ ID Nos. 13–24. In a more preferred embodiment: the nucleic acid encodes a protein having an amino acid sequence at least 80% homologous to SEQ ID No. 5, more preferably at least 90% homologous to SEQ ID No. 5, and most preferably at least 95% homologous to SEQ ID No. 5; the nucleic acid encodes a protein having an amino acid sequence at least 80% homologous to SEQ ID No. 8, more preferably at least 90% homologous to SEQ ID No. 8, and most preferably at least 95% homologous to SEQ ID No. 8 the nucleic acid encodes a protein having an amino acid sequence at least 80% homologous to SEQ ID No. 7, more preferably at least 90% homologous to SEQ ID No. 7, and most preferably at least 95% homologous to SEQ ID No. 7.

In a preferred embodiment: the subject cell regulator-protein specifically binds a target DNA or protein; for example transactivate genes involved in cell cycle arrest, such as p21; interact with the DNA repair and synthetic machinery, such as proliferating cellular nuclear antigen, GADD 45, or proteins modulating apoptosis. In a more preferred embodiment: the cell regulator-protein regulates and/or modulates growth of an eukaryotic cell-cycle, e.g. a mammalian cell-cycle, e.g., a human cell-cycle; the cell regulator-protein inhibits cell growth of a eukaryotic cell, e.g., a human cell; the cell regulator-protein inhibits progression of a eukaryotic cell from G1 phase into S phase, e.g., inhibits progression of a mammalian cell from G1 phase into S phase, e.g., inhibits progression of a human cell from G1 phase into S phase; the cell regulator-protein suppresses tumor growth, e.g. in a tumor cell, e.g. in a tumor cell having an unimpaired p53 or p63 or p53-like protein checkpoint. Thus, in one embodiment, the p-63 family of cell-regulatory proteins are involved in the modulation of cell growth or regulate the growth phenotype of a cell.

In another embodiment, the nucleic acid hybridizes under stringent conditions to a nucleic acid probe corresponding to at least 12 consecutive nucleotides of SEQ ID No. 1; more preferably at least 20 consecutive nucleotides of SEQ ID No. 1; more preferably to at least 40 consecutive nucleotides of SEQ ID No. 1.

In a further embodiment, the nucleic acid hybridizes under stringent conditions to a nucleic acid probe corresponding to at least 12 consecutive nucleotides of SEQ ID No. 2; more preferably at least 20 consecutive nucleotides of SEQ ID No. 2; more preferably to at least 40 consecutive nucleotides of SEQ ID No. 2.

In yet a further embodiment, the nucleic acid hybridizes under stringent conditions to a nucleic acid probe corresponding to at least 12 consecutive nucleotides of SEQ ID No. 3; more preferably at least 20 consecutive nucleotides of SEQ ID No. 3; more preferably to at least 40 consecutive nucleotides of SEQ ID No. 3.

In yet a further embodiment, the nucleic acid hybridizes under stringent conditions to a nucleic acid probe corresponding to at least 12 consecutive nucleotides of SEQ ID No. 6; more preferably at least 20 consecutive nucleotides of SEQ ID No. 6; more preferably to at least 40 consecutive nucleotides of SEQ ID No. 6.

Furthermore, in certain embodiments, the cell regulator nucleic acid will comprise a transcriptional regulatory sequence, e.g. at least one of a transcriptional promoter or transcriptional enhancer sequence, operably linked to the cell regulator-gene sequence so as to render the recombinant cell regulator gene sequence suitable for use as an expression vector.

The present invention also features transgenic non-human animals, e.g. mice, which either express a heterologous cell regulator-gene, e.g. derived from humans, or which mis-express their own cell regulator-gene, e.g. where p63, p53 or p73 expression is disrupted. Such a transgenic animal can serve as an animal model for studying cellular disorders comprising mutated or mis-expressed cell regulator alleles.

The present invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of one of SEQ ID Nos. 1–12, or naturally occurring mutants thereof. In preferred embodiments, the probe/primer further comprises a label group attached thereto and able to be detected, e.g. the label group is selected from a group consisting of radioisotopes, fluorescent compounds, enzymes, and enzyme co-factors. Such probes can be used as a part of a diagnostic test kit for identifying transformed cells, such as for measuring a level of a p63, p73 or p53 encoding nucleic acid in a sample of cells isolated from a patient; e.g. for measuring the mRNA level in a cell or determining whether the genomic cell regulator gene has been mutated or deleted.

The present invention also provides a method for treating an animal having unwanted cell growth characterized by a loss of wild-type cell regulator-protein function, comprising administering a therapeutically effective amount of an agent able to transactivate genes involved in cell cycle arrest. For instance, a therapeutically effective amount of a p63 variant comprising a transactivating domain, for example Tap63γ. In one embodiment, the method comprises administering a nucleic acid construct encoding a cell regulator protein, e.g. a polypeptide represented in one of SEQ ID Nos. 13–24, under conditions wherein the construct is incorporated by cell regulator-deficient cells and the polypeptide is expressed, e.g. by gene therapy techniques. In another embodiment, the method comprises administering a cell regulator mimetic, e.g. a peptidomimetic, which binds to and transactivates genes involved in cell-cycle arrest.

Another aspect of the present invention provides a method of determining if a subject, e.g. a human patient, is at risk for a disorder characterized by unwanted cell proliferation, comprising detecting, in a tissue of the subject, the presence or absence of a genetic lesion characterized by at least one of (i) a mutation of a gene encoding a protein represented by one of SEQ ID Nos. 13–24, or a homolog thereof; or (ii) the mis-expression of the cell regulator-gene, e.g. the p63, p53 or p73 gene. In preferred embodiments: detecting the genetic lesion comprises ascertaining the existence of at least one of a deletion of one or more nucleotides from said gene, an addition of one or more nucleotides to said gene, an substitution of one or more nucleotides of said gene, a gross chromosomal rearrangement of said gene, a gross alteration in the level of a messenger RNA transcript of said gene, the presence of a non-wild type splicing pattern of a messenger RNA transcript of said gene, or a non-wild type level of said protein. For example, detecting the genetic lesion can comprise (i) providing a probe/primer comprising an oligonucleotide containing a region of nucleotide sequence which hybridizes to a sense or antisense sequence of one of SEQ ID Nos. 1–12, or naturally occurring mutants thereof, or 5' or 3' flanking sequences naturally associated with the cell regulator-gene; (ii) exposing the probe/primer to nucleic acid of the tissue; and (iii) detecting, by hybridization of the probe/primer to the nucleic acid, the presence or absence of the genetic lesion; e.g. wherein detecting the lesion comprises utilizing the probe/primer to determine the nucleotide sequence of the cell regulator-gene and, optionally, of the flanking nucleic acid sequences; e.g. wherein detecting the lesion comprises utilizing the probe/primer in a polymerase chain reaction (PCR); e.g. wherein detecting the lesion comprises utilizing the probe/primer in a ligation chain reaction (LCR). In alternate embodiments, the level of said protein is detected in an immunoassay.

Yet another aspect of the invention pertains to a peptidomimetic which transactivates genes involved in cell-cycle arrest.

Like p53, p63 is believed to be a multifunctional protein that exerts a variety of effects and plays a central role in the regulation of the cell cycle. For instance, overexpression of p63, particularly p63 variants comprising a transactivating domain may induce growth arrest, associated with the $G_0/G_1$ checkpoint, apoptosis occurring either through the $G_0/G_1$ checkpoint, or the S-phase or cell differentiation. In particular, p63 is implicated in the mechanism that senses damaged DNA, and controls its repair and in the

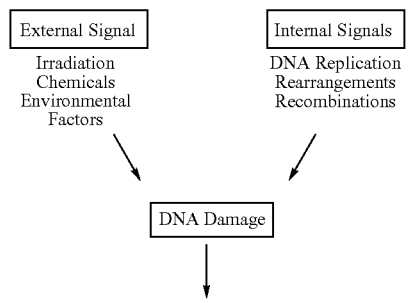

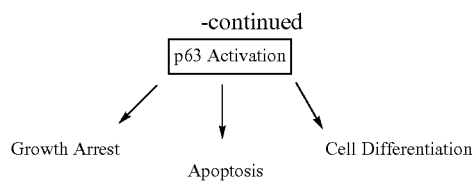

induction of cell death. It is possible that, this may be accomplished by transactivation of the proliferating cell nuclear antigen (PCNA), involved in DNA replication and repair and the GADD-45 gene, whose product interacts with DNA. Furthermore, p63 may also bind several transcription associated proteins, which are involved in DNA damage and repair machinery. The role of p63 in tumorigenesis may be demonstrated by using p63 knocked out mice. Development of a high frequency of tumors in adult life would be indicative that p63, like p53, functions as a cell regulator gene. It is known in the art that p53 transactivates the pro-apoptotic gene, Bax (Miyashita and Reed 1995), in addition to an array of genes responsive to oxidative stress. Based on these observations p53 has been implicated in inducing cell-cycle arrest to allow for repair processes and/or the induction of cell death in the event of unmitigated stress. It was seen that p63 variants comprising a transactivation domain, i.e., TAp63γ, exhibited strong transcriptional activation of the p53 reporter. p63 variants lacking the transactivational domain, e.g., Δp63 are implicated in the regeneration of epithelial cells allowing proliferation of the epithelial cells. It is interesting that the ΔN variants, or dominant negative, versions of p63 seem to be the isotype expressed in many cancers. This may be tied to the observation that many types of cancer, particularly cervical carcinoma, show an overexpression of chromosome 3q, where the p63 gene is located. If this chromosomal amplification results in the overexpression of a ΔNp63 product which opposes p53 or transactivating p63 forms, the experiments that follow show that the dominant negative variants do in fact suppress the transactivating forms p63 and p53. Therefore, these p63 variants may be implicated in cancer biology and possible diagnostic/prognostic applications.

Thus, in one embodiment, the p-63 family of cell-regulatory proteins are involved in the modulation of cell growth or regulate the growth phenotype of a cell. Because of its various roles activation of p63 may result in different outcomes as shown below:

Another aspect of the invention features related DNA and polypeptide sequences which are characterized by a particular percent homology or identity as determined by any of various mathematical algorithms known in the art. A number of mathematical algorithms have been developed to find and measure homology between two DNA or polypeptide sequences. For example the local homology algorithm of Smith and Waterman ((1981) Advances in Applied Mathematics 2:482–89) is used in the alignment software program called "BestFit," which is available from the GCG software package (Genetics Computer Group, 575 Science Drive, Madison, Wis. 53711; www.gcg.com). Other methods for aligning sequences include the homology alignment algorithm of Needleman and Wunsch ((1970) J. Mol. Biol. 48: 443) and the similarity search method of Pearson and Lipman ((1988) Proc. Natl. Acad. Sci. (USA) 85: 2444. These algorithms are available as computerized software such as GAP, FASTA and TFASTA in the Wisconsin Genetic Software Package Release 7.0, Genetics Computer Group, 575 Science Dr., Madison, Wis.). Alternatively, sequences can be aligned manually by inspection, and the best analysis, yielding the greatest degree of homology, is chosen.

These methods to describe the sequence relationships between two or more polynucleotides require the analysis of certain elements of these sequences and the defining of certain parameters with which to analyze them. First, a "reference sequence" is a defined sequence used as a basis for a sequence comparison. A reference sequence may be a subset of a larger sequence, for example, as a segment of a full-length cDNA or gene sequence is given in a sequence listing or may comprise a complete cDNA or gene sequence. Generally, a reference sequence is at least 25 nucleotides in length, frequently at least 25 nucleotides in length and often at least 50 nucleotides in length. Since two polynucleotides may each comprise both a sequence that is similar between the two polynucleotides and a sequence that is divergent between the two polynucleotides, sequence comparisons between two or more polynucleotides typically performed by comparing sequences of the two polynucleotides over a "comparison window" to identify and compare local regions of sequence similarity. A comparison window, as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e. gaps) of 20 percent or less as compared to the reference sequence (which does not comprise additions or deletions) for optimal alignment of the two sequences.

Other features and advantages of the invention will be apparent from the following detailed description, and from the claims. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

3. BRIEF DESCRIPTION OF THE FIGURES

FIG. 1. Primary Structure Alignments of p53, p73, and p63.

Human p53, human p73β, human Tap63 γ are presented, with residues identical to p53 shaded in gray, and remaining consensus residues shaded in black (SEQ ID NOS: 25, 26, 15, and 21).

Figure 2B:
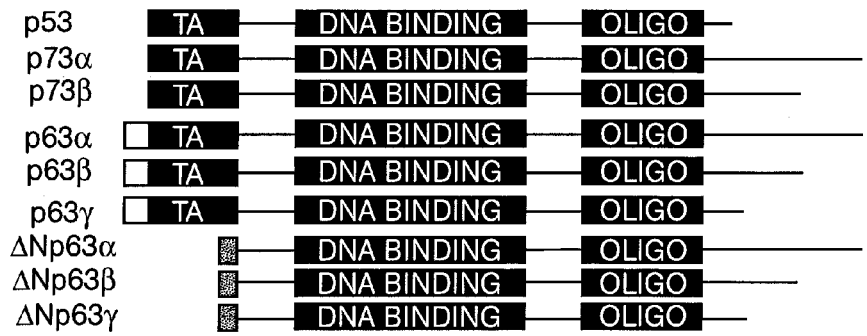
Figures 2C, 2D:
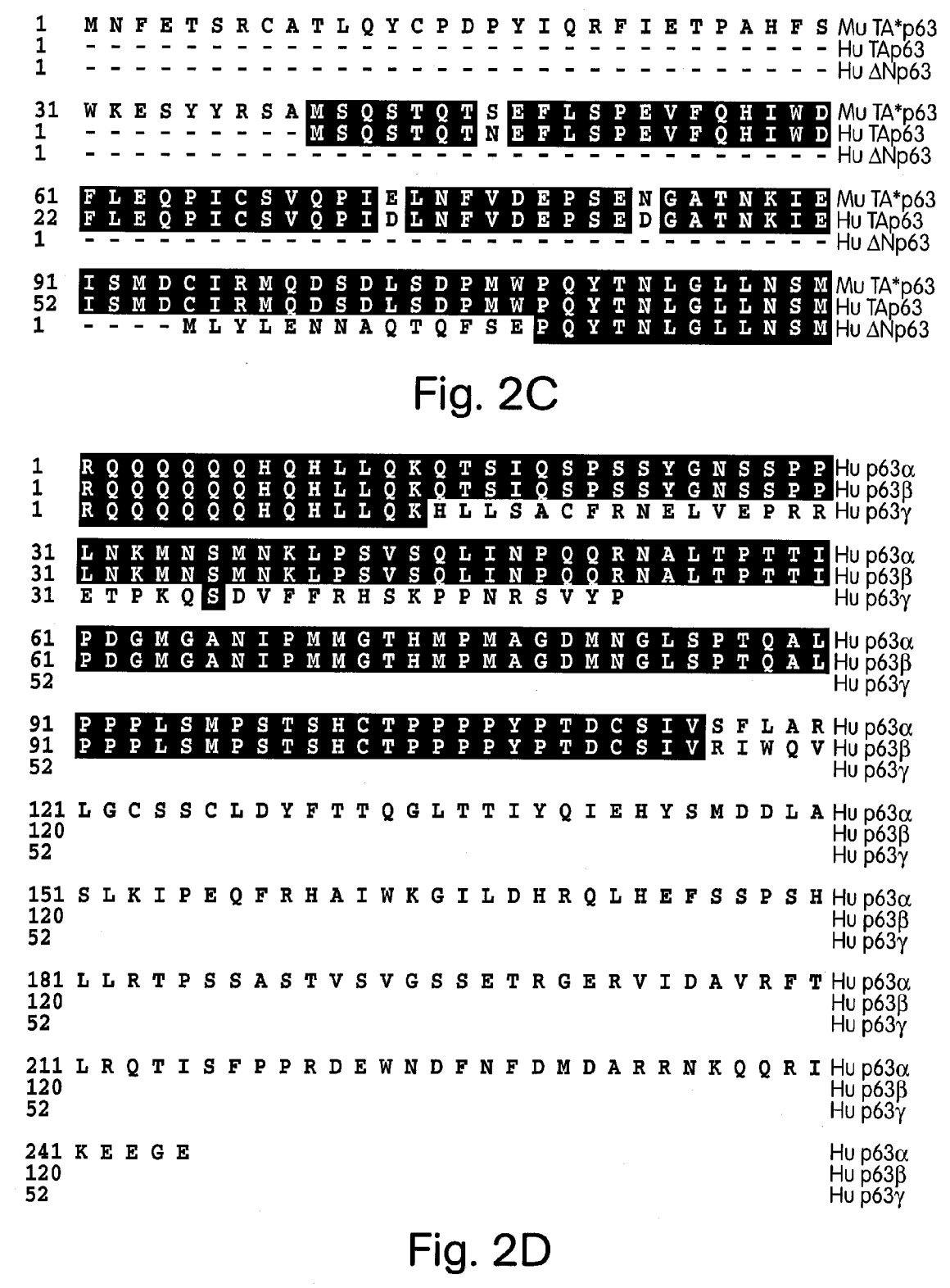

FIG. 2. Genomic Origin and Diversity of p63 Isotypes (A) Schematic of human p63 gene structure highlighting positions of exons (coding sequences in black), the two promoters in exon one (black arrow) and exon 3' (gray arrow), and the major post-transcriptional splicing events which give rise to the major p63 isotypes.

(B) Domain structure of p53, p73α and β, and the major p63 isotypes, Tap63 αβ, and γ, and ΔNp63 a, β, and y, highlighting regions involved in transactivation (TA), DNA binding, and oligomerization (oligo). White box denotes 39aa N-terminal extension unique to TA*p63. Gray box represents 14aa unique to ΔNp63.

(C) Sequence alignment of N-termini of murine human p63 including that found in TA*p63, TAp63, and ΔNp63 (SEQ ID NOS: 45, 46, and 47).

(D) Alignment and comparison of the human p63 a, β, and y C-terminal sequences (SEQ ID NOS: 48, 49, and 50).

FIG. 3. Chromosomal Localization of Human and Mouse p63 Gene.

(A) Schematic of chromosome 3 showing localization of human p63 gene at 3q27-29 based on fluorescence in situ hybridization with a p63 genomic PAC clone.

(B) Schematic of proximal end of mouse chromosome 16 showing location of murine p63 gene, as determined by linkage analysis against Jackson Laboratory interspecific backcross panels BBS and BSB. Loci mapping to similar positions are presented in alphabetical order, and missing typing inferred from surrounding data where assignment was unambiguous.

FIG. 4. Immunolocalization of p63 in Human Epithelial Tissues.

Paraffin sections of normal human epithelial tissues probed with monoclonal antibodies to p63 using an alkaline phosphatase reporter system.

(A) p63 staining in foreskin showing nuclear localization of p63 in basal epithelial cells.

(B) p63 localization to basal cells of ectocervical epithelium.

(C) p63 localization in basal cells of vaginal epithelium.

(D) p63 staining of basal cells of urothelium.

(E) p63 staining of epithelial cell layer below luminal cells in prostate.

FIG. 5. Tissue Distribution of p63 Isotypes (A) RT-PCR analysis of total RNA prepared from various adult mouse tissues using oligonucleotide primers designed to amplify TAp63 isotypes, revealing a ~410 pb product in heart, testis, kidney/adrenal, thymus, brain, and cerebellum.

(B) RT-PCR analysis using template RNA in (A) with oligonucleotide primers designed to yield a ~240 bp product for ΔNp63 isotypes, revealing expected product in kidney/adrenal, spleen, and thymus.

(C) Tel electrophoresis of RNA used as template in RT-PCR analyses to determine template integrity.

(D) Analysis of p63 transcripts in human epithelial tissues. RT-PCR analyses of RNA from primary human foreskin keratinocytes, ectocervical cells, and the human cervical carcinoma cell line ME180 using oligonucleotides designed to amplify TAp63 transcripts (left panel) and ΔNp63 transcripts (right panel). The ME180 cells show products corresponding to both the TAp63 and the ΔNp63 transcripts, while RNA from primary keratinocytes and ectocervical cells yield predominantly products from ΔNp63 transcripts.

(E) Western blot of primary human foreskin keratinocytes (1° HFK), ME180 human cervical carcinoma cells (ME180), and BHK cells expressing epitope-tagged p63 isotypes (TA*p63γ, TAp63γ, ΔNp63γ, TA*p63a, TAp63a, and ΔNp63a) using the 4A4 anti-p63 monoclonal antibody. The major p63 species in primary keratinocytes migrates slightly faster than the epitopetagged ΔNp63a protein.

Figure 6:
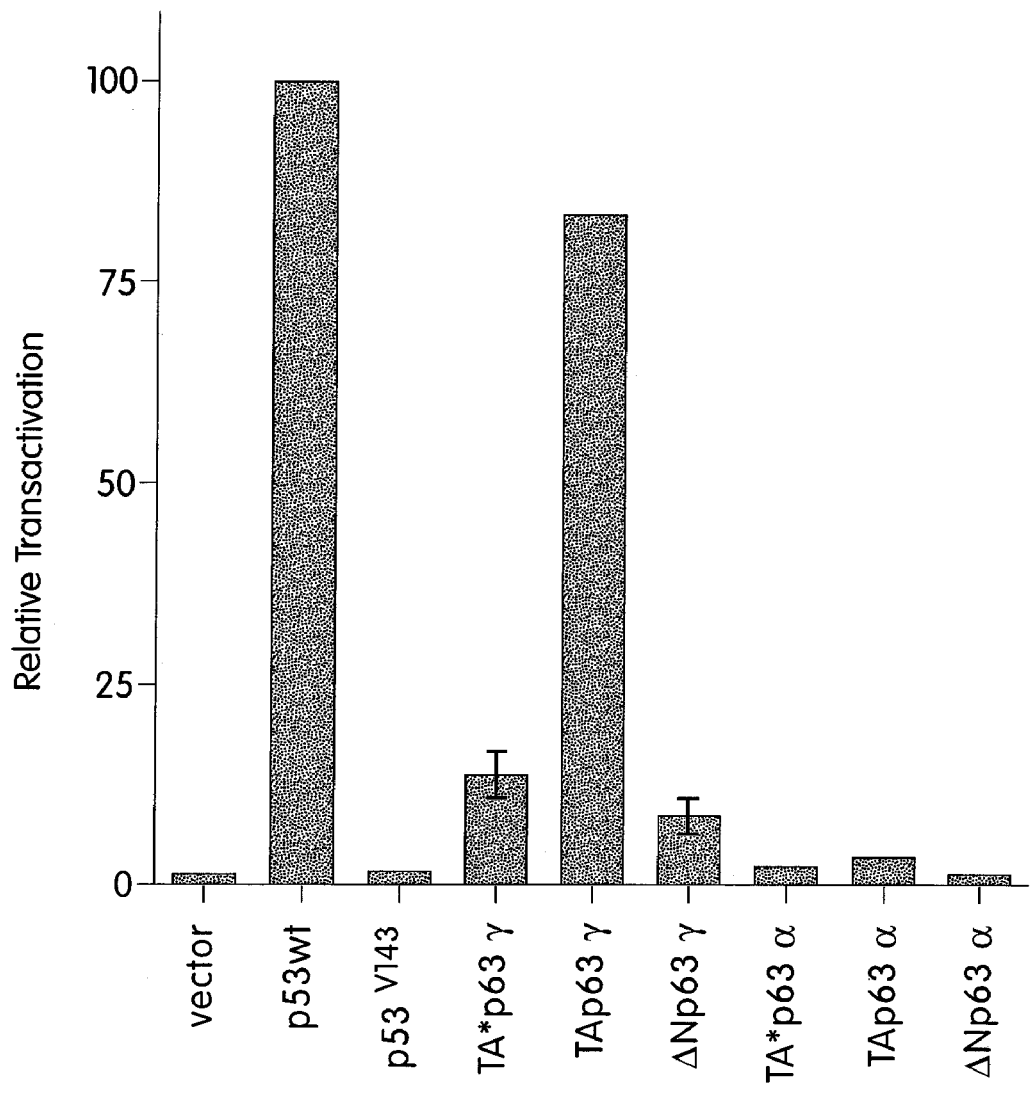

FIG. 6. Transactivation of p53-Reporter Genes by p63 Isotypes

Transcriptional activation of p53-reporter gene in Saos-2 cells transfected with the indicated p53 and p63 expression constructs. Chemiluminescence signal from reporter β-galactosidase assays were performed and normalized for transfection efficiency using assays for co-transfected, constitutively expressed luciferase vectors. Error bars indicate standard deviation in triplicate assays.

FIG. 7. Induction of Apoptosis by p63 Isotypes

BHK cells transfected with idential amounts of wildtype p53 (A) mutant p53 (B), TAp63γ (C), ΔNp63γ(D), and ΔNp63a(E), were processed for immunofluorescence after 16 hours using epitope-tagged antibodies (left panel) and Hoechst dye for DNA staining (right panel). Wildtype p53- and TAp63γ-expressing cells showed high levels of apoptosis (arrows) despite very low protein expression, while ΔNp63γ yielded high protein expression and modest levels of apoptosis. Mutant p53 and ΔNp63a showed high levels of protein expression but control levels of apoptosis.

FIG. 8. Interactions Amongst p63 Isotypes and p53 in Transactivation Assays (A) Transactivation analysis in Saos-2 cells transfected with a constant amount of wildtype p53 expression vector, minimal p53-reporter construct, and either ΔNp63γ or ΔNp63a expression vectors at ratios of 1:5 or 1:1 with respect to p53, as indicated.

(B) Transactivation analysis in Saos-2 cells transfected with a constant amount of TAp63γ expression vector, p53-reporter construct, and either ΔNp63γ or ΔNp63a expression vectors at ratios of 1:5 or 1:1 with respect to TAp63γ, as indicated.

FIGS. 9–9A. Represent nucleic acid and amino acid sequences represented by SEQ ID Nos.: 1 and 13 respectively.

FIGS. 10–10A. Represent nucleic acid and amino acid sequences represented by SEQ ID Nos.: 2 and 14 respectively.

FIGS. 11–11A. Represent nucleic acid and amino acid sequences represented by SEQ ID Nos.: 3 and 15 respectively.

FIGS. 12–12A. Represent nucleic acid and amino acid sequences represented by SEQ ID Nos.: 4 and 16 respectively.

FIGS. 13–13A. Represent nucleic acid and amino acid sequences represented by SEQ ID Nos.: 5 and 17 respectively.

FIG. 14. Represents nucleic acid and amino acid sequences represented by SEQ ID Nos.: 6 and 18 respectively.

FIGS. 15–15A. Represent nucleic acid and amino acid sequences represented by SEQ ID Nos.: 7 and 19 respectively.

FIGS. 16–16A. Represent nucleic acid and amino acid sequences represented by SEQ ID Nos.: 8 and 20 respectively.

FIGS. 17–17A. Represent nucleic acid and amino acid sequences represented by SEQ ID Nos.: 9 and 21 respectively.

FIGS. 18–18A. Represent nucleic acid and amino acid sequences represented by SEQ ID Nos.: 10 and 22 respectively.

FIGS. 19–19A. Represent nucleic acid and amino acid sequences represented by SEQ ID Nos.: 11 and 23 respectively.

FIG. 20. Represents nucleic acid and amino acid sequences represented by SEQ ID Nos.: 12 and 24 respectively.

Figure 21:
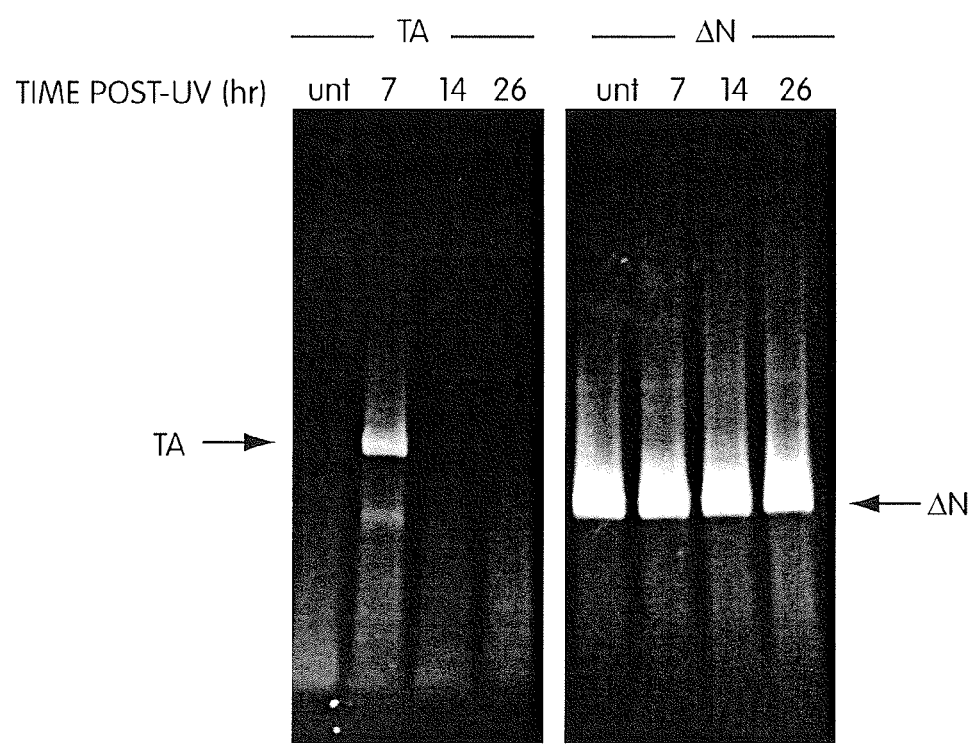

FIG. 21 shows induction of transactivating version of p63 upon UV irradiation. The time course is similar, but not identical, to p53's induction by UV. This is the first demonstration that p63 (and in particular, the transactivating, p53-like, version) can respond to stress signals such as UV/DNA damage. Primary human foreskin keratinocytes were exposed to UV irradiation (300 J/m$^2$), then harvested at times indicated. Total RNA was prepared, and RT-PCR on equal amounts of RNA was performed using primers specific for transactivating (TA) or truncated (ΔN) N-terminal domains of p63 (Yang et al., 1998). TA-p63 is not detectable in untreated (unt) keratinocytes, but expression is induced at 7 hrs after UV treatment. ΔN-p63 appears to remain unchanged from untreated cells at all time points taken.

Figure 22:
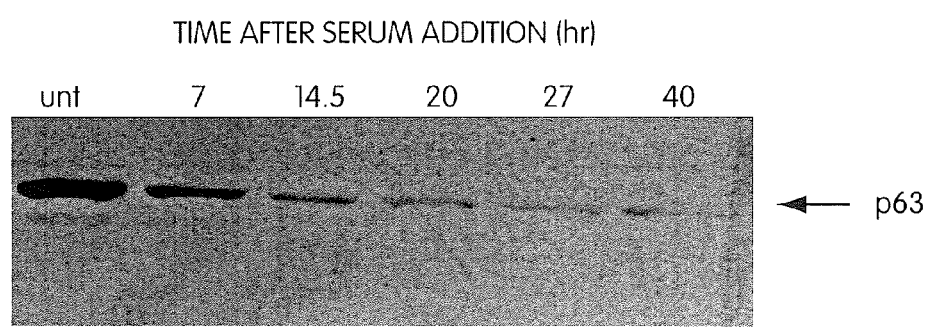

FIG. 22 shows that p63 protein levels, while high in the basal, proliferative/regenerative layer of squamous epithelia, decreases dramatically upon differentiation/maturation of these keratinocytes. This may implicate p63 in differentiation processes that are important for both oncogenesis and normal development. Primary human foreskin keratinocytes were treated with 10% fetal bovine serum to induce differentiation, and harvested at times indicated. Cells were lysed in RIPA buffer, boiled in Lammeli buffer, and proteins fractionated by SDS gel electrophoresis. Immunoblotting was performed using an anti-p63 mouse monoclonal antibody, 4A4, which recognizes all p63 isoforms identified to date. p63 protein levels in keratinocytes are seen to decrease progressively upon differentiation, as compared to untreated (unt) samples.

Figure 23:
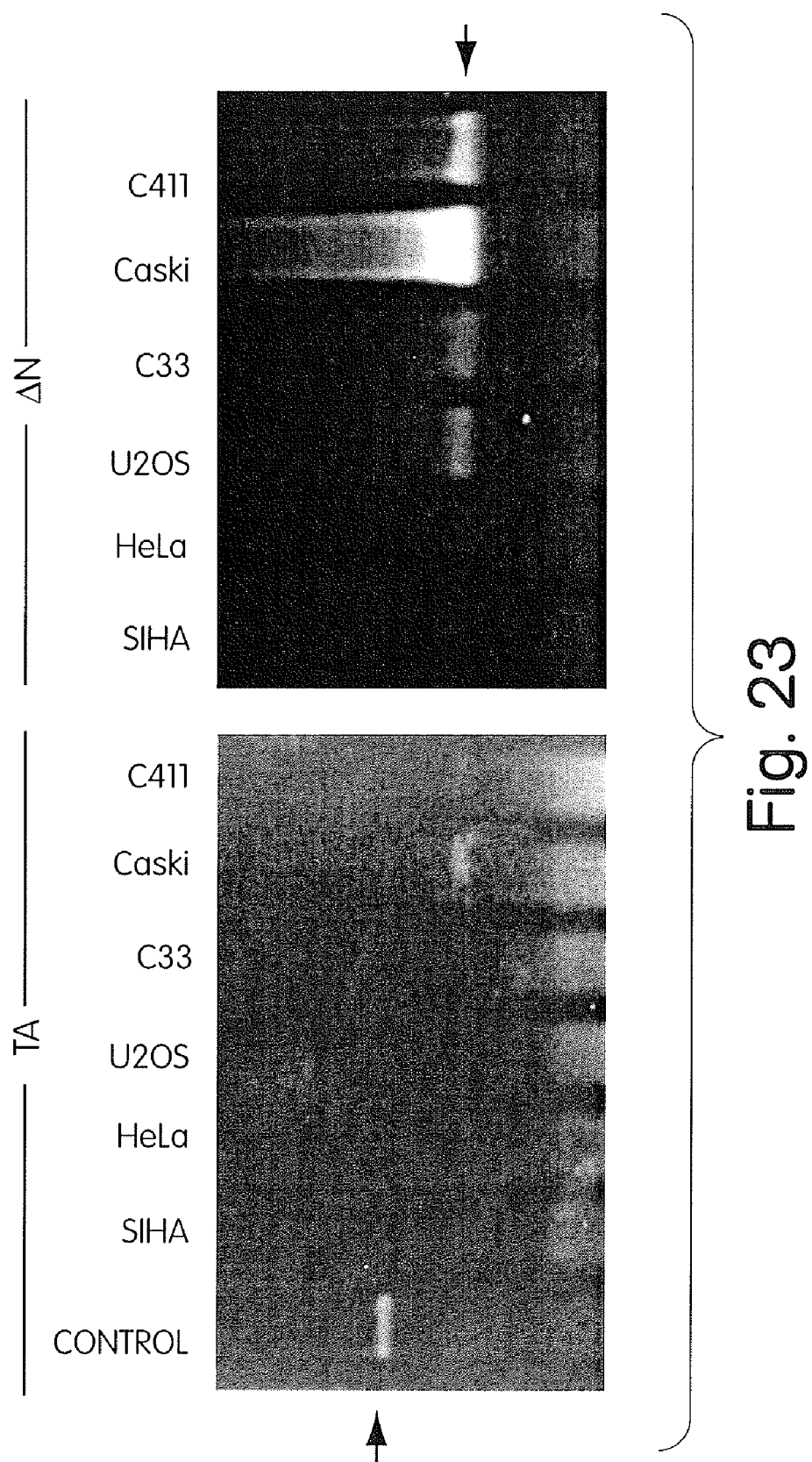

FIG. 23 shows p63 RNA expression in some human cancer cell lines, mostly cervical carcinoma. RT-PCR was performed on total RNA from several human tumor cell lines (all are cervical carcinoma cell lines except U20S, which is a human osteocarcinoma line) using primers specific for transactivating (TA) or truncated (ΔN) N-terminal domains of p63 (see FIG. 1), as indicated. Amongst these cell lines, only the ME180 control cell line showed a TA-p63 transcript. Instead, a majority showed expression of ΔN-p63, which has been demonstrated to act as a dominant negative protein towards both the tumor suppressor p53, as well as transactivating isotypes of p63.

Figure 24:
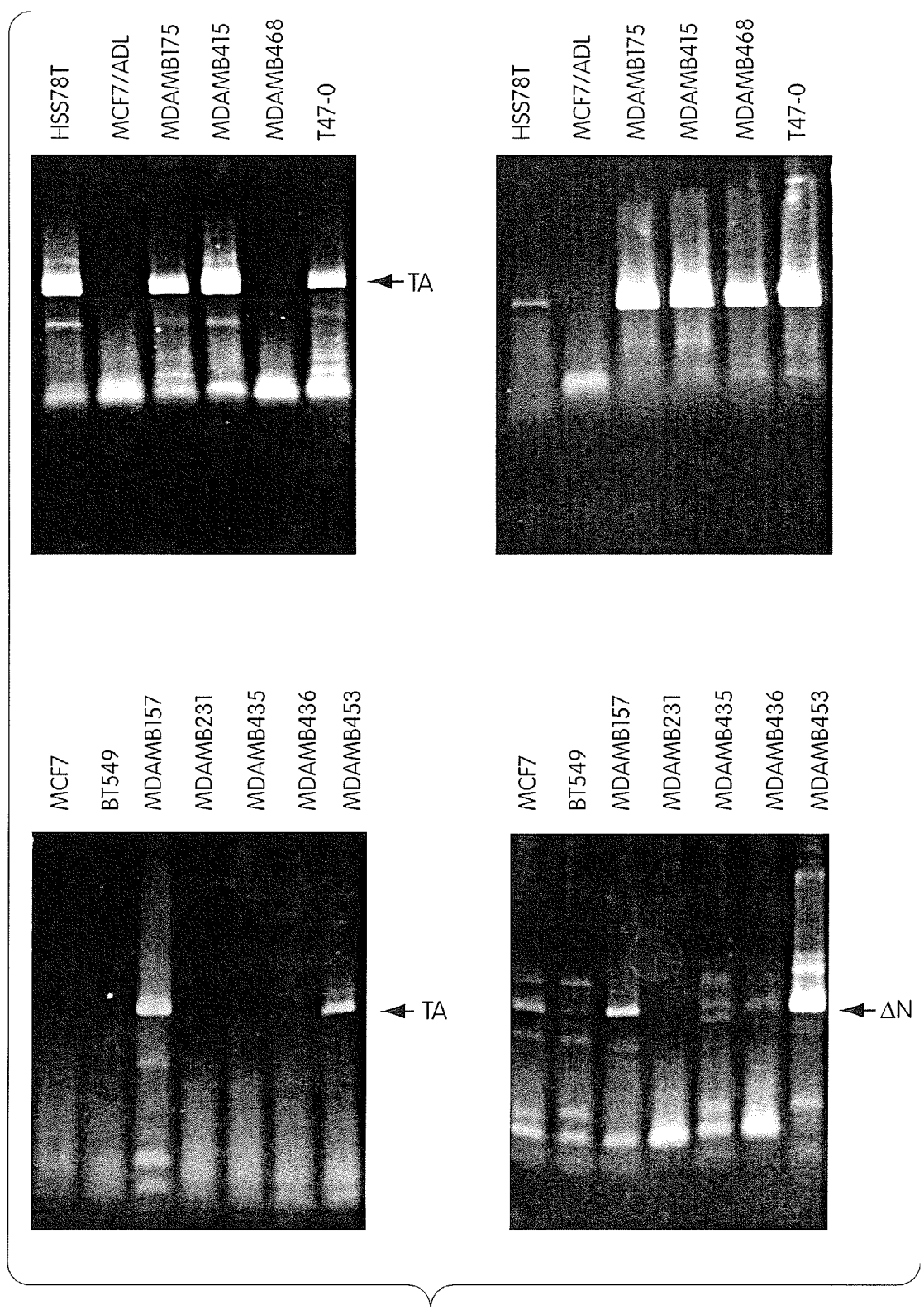

FIG. 24 just shows p63 RNA expression in some human breast cancer cell lines. It is useful to note that p63 is expressed in these cancers. ΔN versions also strongly express in some of these lines. RT-PCR was performed on total RNA from breast cancer cell lines using primers specific for transactivating (TA) or truncated (ΔN) N-terminal domains of p63 (see FIG. 1), as indicated. p63 was detected in a majority of cell lines tested, with some specimens containing both transcript isotypes.

FIG. 25 shows the results of an electrophoretic shift assay. Electrophoretic mobility shift assays (EMSA) were performed using three separate, $^{32}$P radiolabeled oligonucelotides: a minimal p53 binding sequence site (PG), a p53 binding site in the p2 1 promoter (WAF), and a mutant p53 binding site (MG, *Kern et al., 1992) with lysates of 293 human kidney cells transfected with p53, ΔNp63γ, TAp63α, and green fluorescent protein (GFP), p53, ΔNp63γ, and TAp63α lysates all yielded significant mobility shifts of both PG and WAF oligonucleotides (highlighted by arrows), while the GFP protein, included as negative control, failed to display a similar shift. None of the lysates showed a shift of the control, non-p53 binding oligonucleotide, MO, thus demonstrating the specificity of p53, ΔNp63γ, and TAp63α interactions with the p53-binding sites.

4. DETAILED DESCRIPTION OF THE INVENTION

4.1. General

The present invention concerns the discovery of a new family of cell regulatory proteins, referred to herein as the p63 family of proteins, which demonstrate certain sequence identity to known tumor suppressor proteins p53 and p73. The p63 proteins may generally be represented by the general formula: X-Y-Z, wherein X represents the N-termini of the proteins, e.g. a ΔN, a TA•, or TA polypeptide sequence (infra), Y represents the core domain of the protein, and Z represents the C termini, e.g., the α, β, or γ polypeptide sequences (infra). The mouse and human p63 were identified by using a novel PCR based strategy. Specifically, it was observed that the intron-exon organization was conserved between p53 and p73, by using the known exon and intron sizes for these genes it was possible to amplify portions of two adjacent exons and the intervening intron. The rationale being that sequence similarities between the exonic regions would demonstrate a related gene, while differences in size would indicate a novel family member. By this technique we identified at least one new paralog of the p53/p73/p63 related family. Mouse cDNA was isolated using the RACE (5' rapid amplification of cDNA ends) technique and the sequencing of the amplification product indicated that the amplified cDNA possessed a truncated N-terminus, i.e. the transactivation domain was absent in this product. Additional splice variants of the mouse p63 were identified by screening a cDNA library with a probe corresponding to exons 5 through 9 of p63. In general, splice variants differing in the C-terminus have been designated as α, β, and γ forms, whereas p63 members differing in the N-terminus are designated as the ΔN and TA forms, wherein the ΔN form lack the transactivational domain.

The appended sequence listing, provides a list of the nucleic acid and protein sequences that are included within the scope of this invention.

TABLE 1

Guide to p63 sequences in Sequence Listing

| | Nucleotide Sequence | Amino Acid Sequence |
|---|---|---|
| hu-TAp63α | SEQ ID No. 1 | SEQ ID No. 13 |
| hu-TAp63β | SEQ ID No. 2 | SEQ ID No. 14 |
| hu-TAp63γ | SEQ ID NO. 3 | SEQ ID NO. 15 |
| hu-ΔNp63α | SEQ ID No. 4 | SEQ ID No. 16 |
| hu-ΔNp63β | SEQ ID No. 5 | SEQ ID No. 17 |
| hu-ΔNp63γ | SEQ ID No. 6 | SEQ ID No. 18 |
| mu-TA*p63α | SEQ ID No. 7 | SEQ ID No. 19 |
| mu-TA*p63β | SEQ ID No. 8 | SEQ ID No. 20 |
| mu-TA*p63γ | SEQ ID No. 9 | SEQ ID No. 21 |
| mu-ΔNp63α | SEQ ID No. 10 | SEQ ID No. 22 |
| mu-ΔNp63β | SEQ ID No. 11 | SEQ ID No. 23 |
| mu-ΔNp63γ | SEQ ID No. 12 | SEQ ID No. 24 |

By fluorescence in situ hybridization (FISH), the human p63 gene has been localized to chromosomal position 3q27-29. Early expression data suggests that p63 is expressed at steady-state detectable levels in various adult tissues. The p63 proteins can be divided into two classes—one with p53-like properties and the other lacking p53-associated functions such as transcriptional activation and apoptosis. p63 transcripts were detected in a wide range of adult tissues, including heart, testis, kidney/adrenal, spleen, thymus, and brain, typically showing a predominance of either the TA or AN isotypes. Analysis of human epithelial tissues has provided further insights into endogenous p63 expression, as immunohistochemistry with anti-p63 monoclonal antibodies revealed strong and discrete labeling of the nuclei of basal cells within the epidermis, ectocervical epithelium, urothelium, and prostate epithelium, while more differentiated, suprabasal cells showed little or no labeling. The presence of p63 in basal cell layers of epithelial tissues is significant because these cells have an essential role in the regenerative processes of these epithelia. Specifically, the basal cells are thought to be progenitor, or stem, populations for suprabasal layers, and as such are the proliferative components of these tissues. This finding that these epithelial cells predominantly express ΔNp63 isotypes is consistent with growth-permitting requirements of proliferating cells, and may underlie the regenerative abilities of normal epithelial tissues.

It is contemplated by the present invention that the cloned p63-genes set out in the appended sequence listing, in addition to representing a inter-species family of related genes, are also each part of an intra-species family. That is, it is anticipated that other paralogs of the human and mouse p63 proteins exist in those animals, and orthologs of each p63 gene are conserved amongst other animals. For instance, at low to medium stringency conditions, another transcript was observed and this probably represents a new paralogous gene related to the p/53/p73/p63 family of genes, or may a splice variant of p63 as set forth in SEQ ID No. 1.

The p53 protein consists of 393 amino acids with various functional domains, evolutionarily conserved domains and regions which have been designated as mutational hotspots. The functional domains include: a transactivational domain (amino acids 20–50), sequence specific DNA binding domain (amino acids 100–293) nuclear localization sequence (amino acids 316–325), and the oligomerization domain (amino acids 319–360). It was found that the homology between p73 and p53 was considerable within the most conserved p53 domains. The transactivational domain (amino acids 1–45) exhibited 29% identity, the DNA binding region 63% identity (amino acids 113–290) and the oligomerization domain 38% identity with p53 (amino acids 319–363).

Interestingly it was observed that the sequence identity between the mouse and human p63 sequences was considerably high, both at the nucleotide and protein levels, specifically, the mouse and human p63 beta forms exhibit 90.8% identity at the DNA level and 98.6% identity at the protein level, the alpha forms showed 83.4% at the DNA level and 97.8% at the protein level. The sequence identity between p63 and p73 alpha form is about 57.4% identity and the p63 and p73 beta form shows about 69.7% identity at the protein level. p63 alpha form and p53 exhibit 43.8% identity at the protein level.

Accordingly, certain aspects of the present invention relate to nucleic acids encoding p63 polypeptides, the p63 polypeptides themselves (including various fragments), antibodies immunoreactive with p63 proteins, and preparations of such compositions. Moreover, the present invention provides diagnostic and therapeutic assays and reagents for detecting and treating disorders involving, for example, aberrant expression (or loss) of p63.

In addition, drug discovery assays are provided for identifying agents which can modulate the biological function of p63 proteins, such as by altering the binding of p63 molecules to target proteins or DNA sequences, or other extracellular/matrix factors. Furthermore, based on the considerable sequence identity with p53, the skilled artisan could reasonably appreciate that the p63-family of proteins would play a significant role as a cell regulator, a tumor suppressor, function in cell cycle control various developmental processes, apoptosis, gene expression and tumorigenesis. p63 may also be implicated in hematopoiesis, muscle wasting (e.g. cachexia) and neuronal differentiation (and degenerative disorders related thereto). It is known that p53 probably exists as a tetramer and dominant negative mutants of p53, which function by overwhelming the wild-type protein and prevent it from functioning probably forms a heteromeric protein containing both the mutant and wild-type subunits in which the wild type subunits are unable to function. In one aspect, the inventors demonstrate that the p63 protein products lacking the transactivational domains, for example the ΔNp63α and ΔNp63γ have dominant negative effects on the activity of p53. Similarly, these dominant negative forms may exert their function by forming a heteromeric protein with either wild-type p53 or p63 and hence prevent the wild type protein from functioning.

4.2. Definitions

For convenience, the meaning of certain terms and phrases used in the specification, examples, and appended claims, are provided below.

A "p63" cell regulatory protein as referred to herein, refers to proteins that may generally be represented by the formula: X-Y-Z, wherein X represents the N-termini of the proteins, e.g. a TA, TA*, or ΔN polypeptide sequence, Y represents the core domain of the protein, and Z represents the C termini, e.g., the α, β, or γ polypeptide sequences. Illustrative examples include proteins represented by SEQ ID Nos. 13–24, and homologs thereof.

A "p53 protein" refers to the sequence designated by GenBank Accession Number K03199 and orthologs thereto.

"P73" refers to the sequences disclosed by Kaghad et al., Cell 90:809–819 (1997).

The term "agonist", as used herein, is meant to refer to an agent that mimics or upregulates (e.g. potentiates or supplements) p63 bioactivity. Δp63 agonist can be a wild-type p63 protein or derivative thereof having at least one bioactivity of the wild-type p63. A p63 agonist can also be a compound that upregulates expression of a gene or which increases at least one bioactivity of a p63 protein. An agonist can also be a compound which increases the interaction of a p63 polypeptide with another molecule, e.g, a target peptide or nucleic acid.

"Antagonist" as used herein is meant to refer to an agent that downregulates (e.g. suppresses or inhibits) at least one p63 bioactivity. A p63 antagonist can be a compound which inhibits or decreases the interaction between a p63 protein and another molecule, e.g., a target peptide, such as angiotensin I or a kinin. Accordingly, a preferred antagonist is a compound which inhibits or decreases hydrolysis of a target peptide. An antagonist can also be a compound that downregulates expression of a p63 gene or which reduces the amount of p63 protein present.

The term "antibody" as used herein is intended to whole antibodies, e.g., of any isotype (IgG, IgA, IgM, IgE, etc), and includes fragments thereof which are also specifically reactive with an vertebrate, e.g., mammalian, p63 protein. Antibodies can be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a p63 protein. Nonlimiting examples of such proteolytic and/or recombinant fragments include Fab, F(ab')2, Fab', Fv, fragments, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal, or other purified preparations of antibodies and recombinant antibodies.

The term "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for that gene or allele. When a subject has two different alleles of a gene, the subject is said to be heterozygous for the gene. Alleles of a specific gene can differ from each other in a single nucleotide, or several nucleotides, and can include substitutions, deletions, and/or insertions of nucleotides. An allele of a gene can also be a form of a gene containing mutations.

The term "allelic variant of a polymorphic region of an p63 gene" refers to a region of the p63 gene having one of several nucleotide sequences found in that region of the gene in other individuals.

The phenomenon of "apoptosis" is well known, and can be described as a programmed death of cells. As is known, apoptosis is contrasted with "necrosis", a phenomenon when cells die as a result of being killed by a toxic material, or other external effect. Apoptosis involves chromatic condensation, membrane blebbing, and fragmentation of DNA, all of which are generally visible upon microscopic examination.

"Biological activity" or "bioactivity" or "activity" or "biological function", which are used interchangeably, for the purposes herein means an effector or antigenic function that is directly or indirectly performed by a p63 polypeptide (whether in its native or denatured conformation), or by any subsequence thereof. Biological activities include binding to polypeptides, particularly in the formation of homomeric complexes or heteromeric complexes with other p53 or p73 homologs, binding to other proteins or molecules; activity as a DNA binding protein, as a transcription regulator, ability to bind damaged DNA etc. A p63 bioactivity can be modulated by directly affecting the p63 polypeptide. Alternatively, an p63 bioactivity can be altered by modulating the level of the p63 polypeptide, such as by modulating expression of the p63 gene.

As used herein the term "bioactive fragment of a p63 polypeptide" refers to a fragment of a full-length p63 polypeptide, wherein the fragment specifically agonizes (mimics) or antagonizes (inhibits) the activity of a wild-type p63 polypeptide. The bioactive fragment preferably is a fragment capable of interacting with at least one other molecule, protein or DNA, with which a full length p63 protein can bind.

The term "an aberrant activity", as applied to an activity of a polypeptide such as p63, refers to an activity which differs from the activity of the wild-type or native polypeptide or which differs from the activity of the polypeptide present in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in the activity; for example, an aberrant polypeptide can interact with a different target peptide. A cell can have an aberrant p63 activity due to overexpression or underexpression of the gene encoding p63.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric polypeptide" or "fusion polypeptide" is a fusion of a first amino acid sequence encoding one of the subject p63 polypeptides with a second amino acid sequence defining a domain (e.g. polypeptide portion) foreign to and not substantially homologous with any domain of a p63 polypeptide. A chimeric polypeptide may present a foreign domain which is found (albeit in a different polypeptide) in an organism which also expresses the first polypeptide, or it may be an "interspecies", "intergenic", etc. fusion of polypeptide structures expressed by different kinds of organisms. In general, a fusion polypeptide can be represented by the general formula $(X)_n$-$(Y)_m$-$(Z)_n$, wherein Y represents a portion of the p63 polypeptide, and X and Z are each independently absent or represent amino acid sequences which are not related to the native p63 sequence found in an organism, or which are not found as a polypeptide chain contigous with the p63 sequence, where m is an integer greater than or equal to one, and each occurence of n is, indepenedently, 0 or an integer greater than or equal to 1 (n and m are preferably no greater than 5 or 10).

The term "nucleotide sequence complementary to the nucleotide sequence set forth in SEQ ID NO. x" refers to the nucleotide sequence of the complementary strand of a nucleic acid strand having SEQ ID NO. x. The term "complementary strand" is used herein interchangeably with the term "complement". The complement of a nucleic acid strand can be the complement of a coding strand or the complement of a non-coding strand.

A "delivery complex" shall mean a targeting means (e.g. a molecule that results in higher affinity binding of a gene, protein, polypeptide or peptide to a target cell surface and/or increased cellular or nuclear uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes or a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a p63 polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a polypeptide with the same biological activity.

A disease, disorder or condition "associated with" or "characterized by" an aberrant p63 activity refers to a disease, disorder or condition in a subject which is caused by or contributed to by an aberrant p63 activity.

The term "equivalent" is understood to include nucleotide sequences encoding functionally equivalent p63 polypeptides or functionally equivalent peptides having an activity of an p63 protein such as described herein. Equivalent nucleotide sequences will include sequences that differ by one or more nucleotide substitutions, additions or deletions, such as allelic variants; and will, therefore, include sequences that differ from the nucleotide sequence of the p63 gene shown in SEQ ID NOs: 1–12, due to the degeneracy of the genetic code.

As used herein, the terms "gene", "recombinant gene" and "gene construct" refer to a nucleic acid comprising an open reading frame encoding a p63 polypeptide of the present invention, including both exon and (optionally) intron sequences.

A "recombinant gene" refers to nucleic acid encoding a p63 polypeptide and comprising p63-encoding exon sequences, though it may optionally include intron sequences which are derived from, for example, a chromosomal p63 gene or from an unrelated chromosomal gene. Exemplary recombinant genes encoding the subject p63 polypeptide are represented in the appended Sequence Listing. The term "intron" refers to a DNA sequence present in a given p63-gene which is not translated into protein and is generally found between exons.

The term "growth" or "growth state" of a cell refers to the proliferative state of a cell as well as to its differentiative state. Accordingly, the term refers to the phase of the cell cycle in which the cell is, e.g., G0, G1, G2, prophase, metaphase, or telophase, as well as to its state of differentiation, e.g., undifferetiated, partially differentiated, or fully differentiated. Without wanting to be limited, differentiation of a cell is usually accompanied by a decrease in the proliferative rate of a cell.

"Homology" or "identity" or "similarity" refers to sequence similarity between two peptides or between two nucleic acid molecules, with identity being a more strict comparison. Homology and identity can each be determined by comparing a position in each sequence which may be aligned for purposes of comparison. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences. An "unrelated" or "non-homologous" sequence shares less than 40% identity, though preferably less than 25% identity, with one of the p63 sequences of the present invention.

The term "interact" as used herein is meant to include detectable interactions (e.g. biochemical interactions) between molecules, such as interaction between protein—protein, protein-nucleic acid, nucleic acid-nucleic acid, and protein-small molecule or nucleic acid-small molecule in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject p63 polypeptides preferably includes no more than 10 kilobases (kb) of nucleic acid sequence which naturally immediately flanks the p63 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "modulation" as used herein refers to both upregulation (i.e., activation or stimulation (e.g., by agonizing or potentiating)) and downregulation (i.e. inhibition or suppression (e.g., by antagonizing, decreasing or inhibiting)).

The term "mutated gene" refers to an allelic form of a gene, which is capable of altering the phenotype of a subject having the mutated gene relative to a subject which does not have the mutated gene. If a subject must be homozygous for this mutation to have an altered phenotype, the mutation is said to be recessive. If one copy of the mutated gene is sufficient to alter the genotype of the subject, the mutation is said to be dominant. If a subject has one copy of the mutated gene and has a phenotype that is intermediate between ±20 that of a homozygous and that of a heterozygous subject (for that gene), the mutation is said to be co-dominant.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse, though transgenic amphibians, such as members of the *Xenopus* genus, and transgenic chickens can also provide important tools for understanding and identifying agents which can affect, for example, embryogenesis and tissue formation. The term "chimeric animal" is used herein to refer to animals in which the recombinant gene is found, or in which the recombinant gene is expressed in some but not all cells of the animal. The term "tissue-specific chimeric animal" indicates that one of the recombinant p63 gene sis present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long.

A "polymorphic gene" refers to a gene having at least one polymorphic region.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to a gene product.

The term "recombinant protein" refers to a polypeptide of the present invention which is produced by recombinant DNA techniques, wherein generally, DNA encoding a p63 polypeptide is inserted into a suitable expression vector which is in turn used to transform a host cell to produce the heterologous protein. Moreover, the phrase "derived from", with respect to a recombinant p63 gene, is meant to include within the meaning of "recombinant protein" those proteins having an amino acid sequence of a native p63 polypeptide, or an amino acid sequence similar thereto which is generated by mutations including substitutions and deletions (including truncation) of a naturally occurring form of the polypeptide.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention to identify compounds that modulate a p63 bioactivity.

As used herein, the term "specifically hybridizes" or "specifically detects" refers to the ability of a nucleic acid molecule of the invention to hybridize to at least approximately 6, 12, 15, 20, 30, 50, 100, 150, 200, 300, 350, 400 or 425 contiguous nucleotides of a p63 gene, such as designated in any one of SEQ ID Nos: 1–12, or a sequence complementary thereto, or naturally occuring mutants thereof, such that it has less than 15%, preferably less than 10%, and more preferably less than 5% background hybridization to a cellular nucleic acid (e.g. mRNA or genomic DNA) encoding a protein other than a p63 protein, as defined herein. In preferred embodiments, the oligonucleotide probe detects only a p63 gene, e.g., it does not substantially hybridize to transcripts encoding either p53 or p73, or complements thereof.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the p63 genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of p63 polypeptide.

As used herein, the term "transfection" means the introduction of a nucleic acid, e.g., via an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a p63 polypeptide or, in the case of anti-sense expression from the transferred gene, the expression of a naturally-occurring form of the p63 polypeptide is disrupted.

As used herein, the term "transgene" means a nucleic acid sequence (encoding, e.g., one of the p63 polypeptides, or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the p63 polypeptide, e.g. either agonistic or antagonistic forms. However, transgenic animals in which the recombinant p63 gene is silent are also contemplated, as for example, the FLP or CRE recombinase dependent constructs described below. Moreover, "transgenic animal" also includes those recombinant animals in which gene disruption of one or more p63 genes is caused by human intervention, including both recombination and antisense techniques.

The term "treating" as used herein is intended to encompass curing as well as ameliorating at least one symptom of the condition or disease.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucteotide changes.

4.3. Nucleic Acids of the Present Invention

As described below, one aspect of the invention pertains to isolated nucleic acids comprising a nucleotide sequence encoding p63 polypeptides, variants and/or equivalents of such nucleic acids.

Preferred nucleic acids including coding sequences from vertebrate p63 gene, especially a mammalian p63 gene. Regardless of the species, particularly preferred p63 nucleic acids encode polypeptides that are at least 70%, 75%, 80%, 90%, 95%, 97%, or 98% similar to an amino acid sequence of a vertebrate p63 protein. In one embodiment, the nucleic acid is a cDNA encoding a polypeptide having at least one bio-activity of the subject p63 polypeptide. Preferably, the nucleic acid includes all or a portion of the nucleotide sequence corresponding to the nucleic acid of SEQ ID Nos 1–12.

Still other preferred nucleic acids of the present invention encode a p63 polypeptide which is comprised of at least 2, 5, 10, 25, 50, 100, 150 or 200 contiguous amino acid residues. For example, preferred nucleic acid molecules for use as probes/primer or antisense molecules (i.e. noncoding nucleic acid molecules) can comprise at least about 6, 12, 20, 30, 50, 60, 70, 80, 90 or 100 base pairs in length, whereas coding nucleic acid molecules can comprise about 50, 60, 70, 80, 90, or 100 base pairs.

In yet another embodiment, the fragment includes the DNA binding domain of p63 and comprises at least 5 contiguous amino acid residues of SEQ ID Nos. 13–24; the fragment includes the DNA binding domain of p63 and comprises at least 20 contiguous amino acid residues of SEQ ID Nos. 13–24; the fragment includes the DNA binding domain of p63 and comprises at least 50 contiguous amino acid residues of SEQ ID Nos. 13–24.

Another aspect of the invention provides a nucleic acid which hybridizes under low, medium, or high stringency conditions to a nucleic acid sequences represented by SEQ ID NOs: 1, 2, 3, or 4. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–12.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature of salt concentration may be held constant while the other variable is changed. In a preferred embodiment, a p63 nucleic acid of the present invention will bind to one of SEQ ID NOs 1–12 under moderately stringent conditions, for example at about 2.0×SSC and about 40° C. In a particularly preferred embodiment, a p63 nucleic acid of the present invention will bind to one of SEQ ID NOs: 1–12 under high stringency conditions.

Preferred nucleic acids have a sequence at least 70%, and more preferably 80% identical and more preferably 90% and even more preferably at least 95% identical to an amino acid sequence of a p63 gene, e.g., such as a sequence shown in one of SEQ ID NOS: 13–24. Nucleic acids at least 90%, more preferably 95%, and most preferably at least about 98–99% identical with a nucleic sequence represented in one of SEQ ID NOS: 1–12 are of course also within the scope of the invention. In preferred embodiments, the nucleic acid is mammalian and in particularly preferred embodiments, includes all or a portion of the nucleotide sequence corresponding to the coding region of one of SEQ ID NOs: 1–12.

Nucleic acids having a sequence that differs from the nucleotide sequences shown in one of SEQ ID NOs: 1–12 due to degeneracy in the genetic code are also within the scope of the invention. Such nucleic acids encode functionally equivalent peptides (i.e., a peptide having a biological activity of a p63 polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a p63 polypeptide. However, it is expected that DNA sequence polymorphisms that do lead to changes in the amino acid sequences of the subject p63 polypeptides will exist among mammals. One skilled in the art will appreciate that these variations in one or more nucleotides (e.g., up to about 3–5% of the nucleotides) of the nucleic acids encoding polypeptides having an activity of a p63 polypeptide may exist among individuals of a given species due to natural allelic variation.

Also within the scope of the invention are nucleic acids encoding splicing variants of p63 proteins or natural homologs of p63 proteins which consist essentially of one of the two units of p63. Such homologs can be cloned by hybridization or PCR, as further described herein.

The polynucleotide sequence may also encode for a leader sequence, e.g., the natural leader sequence or a heterologous leader sequence. For example, the desired DNA sequence may be fused in the same reading frame to a DNA sequence which aids in expression and secretion of the polypeptide from the host cell, for example, a leader sequence which functions as a secretory sequence for controlling transport of the polypeptide from the cell. The protein having a leader sequence is a preprotein and may have the leader sequence cleaved by the host cell to form the mature form of the protein.

The polynucleotide of the present invention may also be fused in frame to a marker sequence, also referred to herein as "Tag sequence" encoding a "Tag peptide", which allows for marking and/or purification of the polypeptide of the present invention. In a preferred embodiment, the marker sequence is a hexahistidine tag, e.g., supplied by a PQE-9 vector. Numerous other Tag peptides are available commercially. Other frequently used Tags include myc-epitopes (e.g., see Ellison et al. (1991) *J Biol Chem* 266:21150–21157) which includes a 10-residue sequence from c-myc, the pFLAG system (International Biotechnologies, Inc.), the pEZZ-protein A system (Pharmacia, N.J.), and a 16 amino acid portion of the *Haemophilus influenza* hemagglutinin protein. Furthermore, any polypeptide can be used as a Tag so long as a reagent, e.g., an antibody interacting specifically with the Tag polypeptide is available or can be prepared or identified.

As indicated by the examples set out below, p63 protein-encoding nucleic acids can be obtained from mRNA present in any of a number of eukaryotic cells, e.g., and is preferably obtained from metazoan cells, more preferably from vertebrate cells and even more preferably from mammalian cells. It should also be possible to obtain nucleic acids encoding p63 polypeptides of the present invention from genomic DNA from both adults and embryos. For example, a gene encoding a p63 protein can be cloned from either a cDNA or a genomic library in accordance with protocols described herein, as well as those generally known to persons skilled in the art. cDNA encoding a p63 protein can be obtained by isolating total mRNA from a cell, e.g., a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a p63 protein can also be cloned using established polymerase chain reaction techniques in accordance with the nucleotide sequence information provided by the invention. A preferred nucleic acid is a cDNA represented by a sequence selected from the group consisting of SEQ ID NOs: 1–12.

Preferred nucleic acids encode a vertebrate p63 polypeptide comprising an amino acid sequence at least 80% identical, more preferably 90% identical and most preferably 95% identical with an amino acid sequence contained in any of SEQ ID Nos: 13–24. Nucleic acids which encode polypeptides at least about 90%, more preferably at least about 95%, and most preferably at least about 98–99% homology with an amino acid sequence represented in SEQ ID No: 13–24 are also within the scope of the invention. In one embodiment, the nucleic acid is a cDNA encoding a peptide having at least one activity of the subject vertebrate p63 polypeptide. Preferably, the nucleic acid includes all or a portion of the nucleotide sequence corresponding to the coding region of SEQ ID Nos: 1–12.

Preferred nucleic acids encode a bioactive fragment of a vertebrate p63 polypeptide comprising an amino acid sequence at least 80% identical or identical, more preferably 90% identical or identical and most preferably 95% identical or identical with an amino acid sequence selected from the group consisting of SEQ ID No: 13–24. For instance, these bioactive fragments may include the DNA binding domains, transactivation domains, oligomerization domain, etc. Nucleic acids which encode polypeptides which are at least about 90%, more preferably at least about 95%, and most preferably these at least about 98–99% homologous or identical, with an amino acid sequence represented in SEQ ID No: 13–24 are also within the scope of the invention.

Preferred bioactive fragments of p63 polypeptides include polypeptides having one or more of the following biological activities: activity as a tumor suppressor, functions in cell cycle control of various developmental processes, apoptosis, gene expression, modulation of proliferation and differentiation, and tumorigenesis. Assays for determining whether given homolog of a p63 exhibits these or other biological activities are known in the art and are further described herein.

In yet another embodiment, the fragment includes the DNA binding domain of p63 and comprises at least 5 contiguous amino acid residues of SEQ ID Nos. 13–24; the fragment includes the DNA binding domain of p63 and comprises at least 20 contiguous amino acid residues of SEQ ID Nos. 13–24; the fragment includes the DNA binding domain of p63 and comprises at least 50 contiguous amino acid residues of SEQ ID Nos. 13–24.

In yet another embodiment, the fragment includes the core domain of p63 and comprises at least 5 contiguous amino acid residues of SEQ ID Nos. 13–24; the fragment includes the core domain of p63 and comprises at least 20 contiguous amino acid residues of SEQ ID Nos. 13–24; the fragment includes the core domain of p63 and comprises at least 50 contiguous amino acid residues of SEQ ID Nos. 13–24.

4.3.1 Probes and Primers

The nucleotide sequences determined from the cloning of p63 genes from mammalian organisms will further allow for the generation of probes and primers designed for identifying and/or cloning p63 homologs in other cell types, e.g., from other tissues, as well as p63 homologs from other mammalian organisms. For instance, the present invention also provides a probe/primer comprising a substantially purified oligonucleotide, which oligonucleotide comprising a nucleotide sequence that hybridizes under stringent conditions to at least approximately 12, preferably 25, more preferably 40, 50 or 75 consecutive nucleotides of sense or anti-sense sequence selected from the group consisting of SEQ ID No: 1–12 or naturally occurring mutants thereof. For instance, primers based on the nucleic acid represented in SEQ ID NOs:1–12 can be used in PCR reactions to clone p63 homologs.

In yet another embodiment, the invention provides probes/primers comprising a substantially purified oligonucleotide comprising a nucleotide sequence that hybridizes under moderately stringent conditions to at least approximately 12, 16, 25, 40, 50 or 75 consecutive nucleotides sense or antisense sequence selected from the group consisting of SEQ ID NOS. 1–12, or naturally occurring mutants thereof.

In particular, these probes are useful because they provide a method for detecting mutations in tumor suppressor genes such as p63, p73, p53 or Rb etc. Nucleic acid probes which are complementary to the wild-type p63 and can form mismatches with mutant p63 genes are provided, which allow for detection by enzymatic or chemical cleavage or by shifts in electrophonetic mobility.

Likewise, probes based on the subject p63 sequences can be used to detect transcripts or genomic sequences encoding the same or homologous proteins, for use, e.g, in prognostic or diagnostic assays. In preferred embodiments, the probe further comprises a label group attached thereto and able to be detected, e.g., the label group is selected from amongst radioisotopes, fluorescent compounds, enzymes, and enzyme co-factors.

4.3.2 Antisense, Ribozyme and Triplex Techniques

Another aspect of the invention relates to the use of the isolated nucleic acid in "antisense" therapy. As used herein, "antisense" therapy refers to administration or in situ generation of oligonucleotide molecules or their derivatives which specifically hybridize (e.g., bind) under cellular conditions, with the cellular mRNA and/or genomic DNA encoding one or more of the subject p63 proteins so as to inhibit expression of that protein, e.g., by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a p63 protein. Alternatively, the antisense construct is an oligonucleotide probe which is generated ex vivo and which, when introduced into the cell causes inhibition of expression by hybridizing with the mRNA and/or genomic sequences of a p63 gene. Such oligonucleotide probes are preferably modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958–976; and Stein et al. (1988) Cancer Res 48:2659–2668. With respect to antisense DNA, oligodeoxyribonucleotides derived from the translation initiation site, e.g., between the −10 and +10 regions of the p63 nucleotide sequence of interest, are preferred.

Antisense approaches involve the design of oligonucleotides (either DNA or RNA) that are complementary to p63 mRNA. The antisense oligonucleotides will bind to the p63 mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. Nature 372:333). Therefore, oligonucleotides complementary to either the 5' or 3' untranslated, non-coding regions of a p63 gene could be used in an antisense approach to inhibit translation of endogenous p63 mRNA. Oligonucleotides complementary to the 5' untranslated region of the mRNA should include the complement of the AUG start codon. Antisense oligonucleotides complementary to mRNA coding regions are less efficient inhibitors of translation but could also be used in accordance with the invention. Whether designed to hybridize to the 5', 3' or coding region of p63 mRNA, antisense nucleic acids should be at least six nucleotides in length, and are preferably less that about 100 and more preferably less than about 50, 25, 17 or 10 nucleotides in length.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. the oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–12148), or a chimeric RNA-DNA analogue (Inoue et al., 1987, FEBS Lett. 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate olgonucleotides can be prepared by use of controlled pore glass polymer supports (Sarin et al., 1988, Proc. Natl. Acad. Sci. U.S.A. 85:7448–7451), etc.

While antisense nucleotides complementary to the p63 coding region sequence can be used, those complementary to the transcribed untranslated region and to the region comprising the initiating methionine are most preferred.

The antisense molecules can be delivered to cells which express p63 in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it is often difficult to achieve intracellular concentrations of the antisense sufficient to suppress translation on endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous p63 transcripts and thereby prevent translation of the p63 mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al, 1982, Nature 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue; (e.g., for brain, herpesvirus vectors may be used), in which case administration may be accomplished by another route (e.g., systematically).

Ribozyme molecules designed to catalytically cleave p63 mRNA transcripts can also be used to prevent translation of p63 mRNA and expression of p63 (See, e.g., PCT International Publication WO90/11364, published Oct. 4, 1990; Sarver et al., 1990, Science 247:1222–1225 and U.S. Pat. No. 5,093,246). While ribozymes that cleave mRNA at site specific recognition sequences can be used to destroy p63 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. There are a number of potential hammerhead ribozyme cleavage sites within the nucleotide sequence of human p63 cDNA (FIG. 1). Preferably the ribozyme is engineered so that the cleavage recognition site is located near the 5' end of the p63 mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a p63 gene.

As in the antisense approach, the ribozymes can be composed of modified oligonucleotides (e.g., for improved stability, targeting, etc.) and should be delivered to cells which express the p63 gene in vivo. A preferred method of delivery involves using a DNA construct "encoding" the robozyme under the control of a strong constitutive pol III or pol II promoter, so that transfected cells will produce sufficient quantities of the ribozyme to destroy endogenous p63 messages and inhibit translation. Because ribozymes unlike antisense molecules, are catalytic, a lower intracellular concentration is required for efficiency.

Endogenous p63 gene expression can also be reduced by inactivating or "knocking out" the p63 gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional p63 (or a completely unrelated DNA sequence) flanked by DNA homologous to the endogenous p63 gene (either the coding regions or regulatory regions of the p63 gene) can be used, with or without a selectable marker and/or a negative selectable marker, to transfect cells that express p63 in vivo. Insertion of the DNA construct, via targeted homologous recombination, results in inactivation of the p63 gene. Such approaches are particularly suited in the agricultural field where modifications to ES (embryonic stem) cells can be used to generate animal offspring with an inactive p63 (e.g., see Thomas & Capecchi 1987 and Thompson 1989, supra). However this approach can be adapted for use in humans provided the recombinant DNA constructs are directly administered or targeted to the required site in vivo using appropriate viral vectors, e.g., herpes virus vectors for delivery to brain tissue; e.g., the hypothalamus and/or choroid plexus.

Alternatively, endogenous p63 gene expression can be reduced by targeting deoxyribonucleotide sequences complementary to the regulatory region of the p63 gene (i.e., the p63 promoter and/or enhancers) to form triple helical structures that prevent transcription of the p63 gene in target cells in the body. (See generally, Helene, C. 1991, Anticancer Drug Des., 6(6):569–84; Helene, C., et al., 1992, Ann, N.Y. Accad. Sci., 660:27–36; and Maher, L. J., 1992, Bioassays 14(12):807–15).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

4.3.3. Vectors Encoding p63 Proteins and 163 Expressing Cells

The invention further provides plasmids and vectors encoding an p63 protein, which can be used to express an p63 protein in a host cell. The host cell may be any prokaryotic or eukaryotic cell. Thus, a nucleotide sequence derived from the cloning of mammalian p63 proteins, encoding all or a selected portion of the full-length protein, can be used to produce a recombinant form of an p63 polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures well known in the art.

Vectors that allow expression of a nucleic acid in a cell are referred to as expression vectors. Typically, expression vectors used for expressing an p63 protein contain a nucleic acid encoding an p63 polypeptide, operably linked to at least one transcriptional regulatory sequence. Regulatory sequences are art-recognized and are selected to direct expression of the subject p63 proteins. Transcriptional regulatory sequences are described in Goeddel; Gene Expression Technology: Methods in Enzymology 185, Academic Press, San Diego, Calif. (1990). In one embodiment, the expression vector includes a recombinant gene encoding a peptide having an agonistic activity of a subject p63 polypeptide, or alternatively, encoding a peptide which is an antagonistic form of an p63 protein.

Suitable vectors for the expression of a p63 polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used. In an illustrative embodiment, a p63 polypeptide is produced recombinantly utilizing an expression vector generated by sub-cloning the coding sequence of one of the p63 genes represented in SEQ ID NOs: 1 or 3.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, $2^{nd}$ Ed., ed. by Sambrook, Fritsch and Maniatis (Cold Spring Harbor Laboratory Press: 1989) Chapters 16 and 17.

In some instances, it may be desirable to express the recombinant p63 polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III)

When it is desirable to express only a portion of a p63 protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from E. coli (Ben-Bassat et al. (1987) J. Bacteriol. 169:751–757) and Salmonella typhimurium and its in vitro activity has been demonstrated on recombinant proteins (Miller et al. (1987) PNAS 84:2718–1722). Therefore, removal of an N-terminal methionine, if desired, can be achieved either in vivo by expressing p63 derived polypeptides in a host which produces MAP (e.g., E. coli or CM89 or S. cerevisiae), or in vitro by use of purified MAP (e.g., procedure of Miller et al., supra).

Moreover, the gene constructs of the present invention can also be used as part of a gene therapy protocol to deliver nucleic acids encoding either an agonistic or antagonistic form of one of the subject p63 proteins. Thus, another aspect of the invention features expression vectors for in vivo or in vitro transfection and expression of a p63 polypeptide in particular cell types so as to reconstitute the function of, or alternatively, abrogate the function of p63 in a tissue. This could be desirable, for example, when the naturally-occurring form of the protein is misexpressed or the natural protein is mutated and less active.

In addition to viral transfer methods, non-viral methods can also be employed to cause expression of a subject p63 polypeptide in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject p63 polypeptide gene by the targeted cell. Exemplary targeting means of this type include liposomal derived systems, poly-lysine conjugates, and artificial viral envelopes.

In other embodiments transgenic animals, described in more detail below could be used to produce recombinant proteins.

4.4. Polypeptides of the Present Invention

The present invention makes available isolated p63 polypeptides which are isolated from, or otherwise substantially free of other cellular proteins, especially other signal transduction factors and/or transcription factors which may normally be associated with the p63 polypeptide. The term "substantially free of other cellular proteins" (also referred to herein as "contaminating proteins") or "substantially pure or purified preparations" are defined as encompassing preparations of p63 polypeptides having less than about 20% (by dry weight) contaminating protein, and preferably having less than about 5% contaminating protein. Functional forms of the subject polypeptides can be prepared, for the first time, as purified preparations by using a cloned gene as described herein. Full length proteins or fragments corresponding to one or more particular motifs and/or domains or to arbitrary sizes, for example, at least 5, 10, 25, 50, 75 and 100, amino acids in length are within the scope of the present invention.

In yet another embodiment, the fragment includes the core domain of p63 and comprises at least 5 contiguous amino acid residues of SEQ ID Nos. 13–24; the fragment includes the core domain of p63 and comprises at least 20 contiguous amino acid residues of SEQ ID Nos. 13–24; the fragment includes the core domain of p63 and comprises at least 50 contiguous amino acid residues of SEQ ID Nos. 13–24.

In yet another embodiment, the fragment includes the DNA binding domain of p63 and comprises at least 5 contiguous amino acid residues of SEQ ID Nos. 13–24; the fragment includes the DNA binding of p63 and comprises at least 20 contiguous amino acid residues of SEQ ID Nos. 13–24; the fragment includes the DNA binding of p63 and comprises at least 50 contiguous amino acid residues of SEQ ID Nos. 13–24.

For example, isolated p63 polypeptides can be encoded by all or a portion of a nucleic acid sequence shown in any of SEQ ID NOS. 1–12. Isolated peptidyl portions of p63 proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a p63 polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") p63 protein.

Another aspect of the present invention concerns recombinant forms of the p63 proteins. Recombinant polypeptides preferred by the present invention, in addition to native p63 proteins (e.g., as set forth in SEQ ID NO: 6), are encoded by a nucleic acid, which is at least 60%, more preferably at least 80%, and more preferably 85%, and more preferably 90%, and more preferably 95% identical to an amino acid sequence represented by SEQ ID Nos: 13–24 or encoded by SEQ ID NOs. 13–24. Polypeptides which are encoded by a nucleic acid that is at least about 98–99% identical with the sequence of SEQ ID NOS: 1 or 3 or which are 98–99% identical with the amino acid sequence set forth in SEQ ID NO: 2 are also within the scope of the invention.

In a preferred embodiment, a p63 protein of the present invention is a mammalian p63 protein and even more preferably a human p63 protein. In a particularly preferred embodiment the p63 protein has an amino acid sequence as set forth in SEQ ID Nos: 13–24. In particularly preferred embodiment, the p63 protein retains p63 bioactivity. It will be understood that certain post-translational modifications, e.g., phosphorylation and the like, can increase the apparent molecular weight of the p63 protein relative to the unmodified polypeptide chain.

The present invention further pertains to recombinant forms of one of the subject p63 polypeptides. Such recombinant p63 polypeptides preferably are capable of functioning in one of either role of an agonist or antagonist of at least one biological activity of a wild-type ("authentic") p63 protein of the appended sequence listing. The term "evolutionarily related to", with respect to amino acid sequences of p63 proteins, refers to both polypeptides having amino acid sequences which have arisen naturally, and also to mutational variants of human p63 polypeptides which are derived, for example, by combinatorial mutagenesis.

In general, polypeptides referred to herein as having an activity (e.g., are "bioactive") of a p63 protein are defined as polypeptides which include an amino acid sequence encoded by all or a portion of the nucleic acid sequences shown in one of SEQ ID NOS: 1–12 and which mimic or antagonize all or a portion of the biological/biochemical activities of a naturally occurring p63 protein. Preferred bioactive fragments of p63 polypeptides include polypeptides having one or more of the following biological activities: activity as a tumor suppressor, functions in cell cycle control various developmental processes, apoptosis, gene expression and tumorigenesis. Other biological activities of the subject p63 proteins are described herein or will be reasonably apparent to those skilled in the art. According to the present invention, a polypeptide has biological activity if it is a specific agonist or antagonist of a naturally-occurring form of a p63 protein.

Assays for determining whether a compound, e.g, a protein, such as an p63 protein or variant thereof, has one or more of the above biological activities are well known in the art.

In another embodiment, the coding sequences for the polypeptide can be incorporated as a part of a fusion gene including a nucleotide sequence encoding a different polypeptide. This type of expression system can be useful under conditions where it is desirable to produce an immunogenic fragment of a p63 protein. For example, the VP6 capsid protein of rotavirus can be used as an immunologic carrier protein for portions of the p63 polypeptide, either in the monomeric form or in the form of a viral particle. The nucleic acid sequences corresponding to the portion of a subject p63 protein to which antibodies are to be raised can be incorporated into a fusion gene construct which includes coding sequences for a late vaccinia virus structural protein to produce a set of recombinant viruses expressing fusion proteins comprising p63 epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a p63protein and the poliovirus capsid protein can be created to enhance immunogenicity of the set of polypeptide antigens (see, for example, EP Publication No: 0259149; and Evans et al (1989) Nature 339:385; Huang et al. (1988) J. Virol. 62:3855; and Schlienger et al. (1992) J. Virol. 66:2).

The Multiple antigen peptide system for peptide-based immunization can also be utilized to generate an immunogen, wherein a desired portion of a p63 polypeptide is obtained directly from organo-chemical synthesis of the peptide onto an oligomeric branching lysine core (see, for example, Posnett et al. (1988) JBC 263:1719 and Nardelli et al. (1992) J. Immunol. 148:914). Antigenic determinants of p63 proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the p63 polypeptides of the present invention. For example, p63 polypeptides can be generated as glutathione-S-transferase (GST-fusion) proteins. Such GST-fusion proteins can enable easy purification of the p63 polypeptide, as for example by the use of glutathione-derivatized matrices (see, for example, Current Protocols in Molecular Biology, eds. Ausubel et al. (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a $Ni^{2+}$ metal resin. The purification leader sequence can then be subsequently removed by treatment with enterokinase to provide the purified protein (e.g., see Hochuli et al. (1987) J. Chromatography 411:177; and Janknecht et al. PNAS 88:8972). Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al. John Wiley & Sons: 1992).

The present invention further pertains to methods of producing the subject p63 polypeptides. For example, a host cell transfected with a nucleic acid vector directing expression of a nucleotide sequence encoding the subject polypeptides can be cultured under appropriate conditions to allow expression of the peptide to occur. Suitable media for cell culture are well known in the art. The recombinant p63 polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant p63 polypeptide is a fusion protein containing a domain which facilitates its purification, such as GST fusion protein.

Moreover, it will be generally appreciated that, under certain circumstances, it may be advantageous to provide homologs of one of the subject p63 polypeptides which function in a limited capacity as one of either a p63 agonist (mimetic) or a p63 antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of p63 proteins.

Homologs of each of the subject p63 proteins can be generated by mutagenesis, such as by discrete point mutation(s), or by truncation. For instance, mutation can give rise to homologs which retain substantially the same, or merely a subset, of the biological activity of the p63 polypeptide from which it was derived. Alternatively, antagonistic forms of the protein can be generated which are able to inhibit the function of the naturally occurring form of the protein, such as by competitively binding to an p63 receptor.

The recombinant p63 polypeptides of the present invention also include homologs of the wildtype p63 proteins, such as versions of those protein which are resistant to proteolytic cleavage, as for example, due to mutations which alter ubiquitination or other enzymatic targeting associated with the protein.

p63 polypeptides may also be chemically modified to create p63 derivatives by forming covalent or aggregate conjugates with other chemical moieties, such as glycosyl groups, lipids, phosphate, acetyl groups and the like. Covalent derivatives of p63 proteins can be prepared by linking the chemical moieties to functional groups on amino acid sidechains of the protein or at the N-terminus or at the C-terminus of the polypeptide.

Modification of the structure of the subject p63 polypeptides can be for such purposes as enhancing therapeutic or prophylactic efficacy, stability (e.g., ex vivo shelf life and resistance to proteolytic degradation), or post-translational modifications (e.g., to alter phosphorylation pattern of protein). Such modified peptides, when designed to retain at least one activity of the naturally-occurring form of the protein, or to produce specific antagonists thereof, are considered functional equivalents of the p63 polypeptides described in more detail herein. Such modified peptides can be produced, for instance, by amino acid substitution, deletion, or addition. The substitutional variant may be a substituted conserved amino acid or a substituted non-conserved amino acid.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, $2^{nd}$ ed., Ed. by L. Stryer, WH Freeman and Co.: 1981). Whether a change in the amino acid sequence of a peptide results in a functional p63 homolog (e.g., functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject p63 proteins as well as truncation mutants, and is especially useful for identifying potential variant sequences (e.g., homologs). The purpose of screening such combinatorial libraries is to generate, for example, novel p63 homologs which can act as either agonists or antagonist, or alternatively, possess novel activities all together. Thus, combinatorially-derived homologs can be generated to have an increased potency relative to a naturally occurring form of the protein.

In one embodiment, the variegated library of p63 variants is generated by combinatorial mutagenesis at the nucleic acid level, and is encoded by a variegated gene library. For instance, a mixture of synthetic oligonucleotides can be enzymatically ligated into gene sequences such that the degenerate set of potential p63 sequences are expressible as individual polypeptides, or alternatively, as a set of larger fusion proteins (e.g., for phage display) containing the set of p63 sequences therein. There are many ways by which such libraries of potential p63 homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential p63 sequences. The synthesis of degenerate oligonucleotides is well known in the art (see for example, Narang, S A (1983) Tetrahedron 39:3; Itakura et al. (1981) Recombinant DNA, Proc $3^{rd}$ Cleveland Sympos. Macromolecules. ed. A G Walton, Amsterdam: Elsevier pp 273–289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386–390; Roberts et al. (1992) PNAS 89:2429–2433; Devlin et al. (1990) Science 249: 404–406; Cwirla et al. (1990) PNAS 87: 6378–6382; as well as U.S. Pat. Nos. 5,223,409, 5,198,346, and 5,096,815).

Likewise, a library of coding sequence fragments can be provided for a p63clone in order to generate a variegated population of p63 fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a p63coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of p63 homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate p63 sequences created by combinatorial mutagenesis techniques. Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, PNAS USA 89:7811–7815; Yourvan et al., 1992, Parallel Problem Solving from Nature, 2. In Maenner and Manderick, eds., Elsevir Publishing Co., Amsterdam, pp. 401–410; Delgrave et al., 1993, Protein Engineering 6(3):327–331).

The invention also provides for reduction of the p63 proteins to generate mimetics, e.g., peptide or non-pepide agents, such as small molecules, which are able to disrupt binding of a p63 polypeptide of the present invention with a nucleotide, such as proteins, e.g. receptors. Thus, such mutagenic techniques as described above are also useful to map the determinants of the p63 proteins which participate in protein—protein interactions involved in, for example, binding of the subject p63 polypeptide to a target peptide. To illustrate, the critical residues of a subject p63 polypeptide which are involved in molecular recognition of its receptor can be determined and used to generate p63 derived peptidomimetics or small molecules which competitively inhibit binding of the authentic p63 protein with that moiety. By employing, for example, scanning mutagenesis to map the amino acid residues of the subject p63 proteins which are involved in binding other proteins, peptidomimetic compounds can be generated which mimic those residues of the p63 protein which facilitate the interaction. Such mimetics may then be used to interfere with the normal function of a p63 protein. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the $9^{th}$ American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), and β-aminoalcohols (Gordon et al. (1985) Biochem Biophys Res Commun 126:419; and Dann et al. (1986) Biochem Biophys Res Commun 134:71).

4.5. Anti-63 Antibodies and Uses Therefor

Another aspect of the invention pertains to an antibody specifically reactive with a mammalian p63 protein, e.g., a wild-type or mutated p63 protein. For example antibodies may be made as described in teh appended rxamples or by using other standard protocols (See, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a mammalian p63 polypeptide or an antigenic fragment which is capable of eliciting an antibody response, or a fusion protein as described above).

In one aspect, this invention includes monoclonal antibodies to p63 that show p63 is highly expressed in the basal cells of various epithelial tissues, including epidermis, ectocervical epithelium, vaginal epithelium, urothelium, and prostate epthelium, all of which represent common sites of human carcinomas (basal cell carcinoma of skin, cervical carcinoma with and without human papilloma virus association, bladder and urothelial carcinoma, and prostate carcinoma). Therefore, in one embodiment this invention provides a diagnostic tool for the analysis of p63 expression in general, and in particular, as a diagnostic for analysis of carcinomas.

Techniques for conferring immunogenicity on a protein or peptide include conjugation to carriers or other techniques well known in the art. An immunogenic portion of a p63 protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a p63 protein of a mammal, e.g., antigenic determinants of a protein set forth in SEQ ID No: 2 or closely related homologs (e.g., at least 90% identical, and more preferably at least 95% identical).

Following immunization of an animal with an antigenic preparation of a p63 polypeptide, anti-p63 antisera can be obtained and, if desired, polyclonal anti-p63 antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495–497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77–96). Hybridoma cells can be screened immunochemically for production of antibodies specifically reactive with a mammalian p63 polypeptide of the present invention and monoclonal antibodies isolated from a culture comprising such hybridoma cells. In one embodiment anti-human p63 antibodies specifically react with the protein encoded by the DNA of Hup63geno (PAC). The Hup63geno (PAC) clone was deposited with the American Type Culture Collectuion (ATCC), 1081 University Blvd., Manassas, Va. 20110, under the terms fo the Budapest Treaty. The deposit was made on Oct. 13, 1997 and received ATCC accession number 209359.

The term antibody as used herein is intended to include fragments thereof which are also specifically reactive with one of the subject mammalian p63 polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for a p63 protein conferred by at least one CDR region of the antibody. In preferred embodiments, the antibodies, the antibody further comprises a label attached thereto and able to be detected, (e.g., the label can be a radioisotope, fluorescent compound, enzyme or enzyme co-factor).

Anti-p63 antibodies can be used, e.g., to monitor p63 protein levels in an individual for determining, e.g., whether a subject has a disease or condition associated with an aberrant p63 protein level, or allowing determination of the efficacy of a given treatment regimen for an individual afflicted with such a disorder. The level of p63 polypeptides may be measured from cells in bodily fluid, such as in blood samples.

Another application of anti-p63 antibodies of the present invention is in the immunological screening of cDNA libraries constructed in expression vectors such as λgt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a p63 protein, e.g., other orthologs of a particular p63 protein or other paralogs from the same species, can then be detected with antibodies, as, for example, reacting nitrocellulose filters lifted from infected plates with anti-p63 antibodies. Positive phage detected by this assay can then be isolated from the infected plate. Thus, the presence of p63 homologs can be detected and cloned from other animals, as can alternate isoforms (including splicing variants) from humans.

In another embodiment, a panel of monoclonal antibodies may be used, wherein each of the epitopes involved p63 functions are represented by a monoclonal antibody. Loss or perturbation of binding of a monoclonal antibody in the panel would be indicative of a mutational attention of the p63 protein and thus of the p63 gene.

4.6. Transgenic Animals

One aspect of the present invention relates to transgenic non-human animals having germline and/or somatic cells in which the biological activity of one or more tumor supressor genes, e.g., p63, p53, p73 proteins, combinations thereof, are altered by a chromosomally incorporated transgene.

In one preferred embodiment, the transgene disrupts at least a portion of a genomic p63 gene. For instance, the transgene may delete all or a portion of the genomic p63 gene by replacement recombination, or may functionally interrupt one or more of a regulatory sequence or coding sequence of the genomic p63 gene by insertion recombination.

In another preferred embodiment, the transgene encodes a p63 protein, and expression of the transgene in cells of the transgenic animal results in altered regulation of the level of the p63 protein relative to normal expression of the wild-type p63 protein.

In still other preferred embodiments, the transgene encodes a mutant p63 protein, such as dominant negative p63 protein which antagonizes at least a portion of the biological function of a wild-type p63 protein.

Yet another preferred transgenic animal includes a transgene encoding an antisense transcript which, when transcribed from the transgene, hybridizes with a genomic p63 gene or a mRNA transcript thereof, and inhibits expression of the genomic p63 gene.

In one embodiment, the present invention provides a desired non-human animal or an animal (including human)

cell which contains a predefined, specific and desired alteration rendering the non-human animal or animal cell predisposed to cancer. Specifically, the invention pertains to a genetically altered non-human animal (most preferably, a mouse), or a cell (either non-human animal or human) in culture, that is defective in at least one of two alleles of a tumor-suppressor gene such as the p63 gene. The inactivation of at least one of these tumor suppressor alleles results in an animal with a higher susceptibility to tumor inductionor other proliferative or differentiative disorders, or disorders marked by abberrant signal transduction, e/g/, from a cytokine or growth factor. A genetically altered mouse of this type is able to serve as a useful model for hereditary cancers and as a test animal for carcinogen studies. The invention additionally pertains to the use of such non-human animals or animal cells, and their progeny in research and medicine.

Furthermore, it is contemplated that cells of the transgenic animals of the present invention can include other transgenes, e.g., which alter the biological activity of a second tumor suppressor gene or an oncogene. For instance, the second transgene can functionally disrupt the biological activity of a second tumor suppressor gene, such as p53, p73, DCC, $p21^{cip\ 1}$, $p27^{kip\ 1}$, Rb, Mad or E2F. Alternatively, the second transgene can cause overexpression or loss of regulation of an oncogene, such as ras, myc, a cdc25 phosphatase, Bcl-2, Bcl-6, a transforming growth factor, neu, int-3, polyoma virus middle T antigen, SV40 large T antigen, a papillomaviral E6 protein, a papillomaviral E7 protein, CDK4, or cyclin D1.

A preferred transgenic non-human animal of the present invention has germline and/or somatic cells in which one or more alleles of a genomic p63 gene, a p73 gene, a p53 gene, and combinations thereof, are disrupted by a chromosomally incorporated transgene, wherein the transgene includes a marker sequence providing a detectable signal for identifying the presence of the transgene in cells of the transgenic animal, and replaces at least a portion of the genomic p63 gene or is inserted into the genomic p63 gene or disrupt expression of a wild type p63 protein.

Another aspect of the present invention relates to cells and tissues isolated from the subject transgenic animals. For instance, the present invention provides composition of cells, isolated ex vivo, which include a diploid genome having a chromosomally incorporated transgene, which transgene functionally modifies the biological activity of one or more p63 proteins. In preferred embodiments, the transgene deletes all or a portion of a genomic p63 gene by replacement recombination, or functionally interrupts one or more of a regulatory sequence or coding sequence of the genomic p63 gene by insertion recombination. For instance, one class of such cells contemplated by the present invention include transgenes which have (i) at least a portion of the genomic p63 gene which directs recombination of the transgene with the genomic p63 gene, and (ii) a marker sequence which provides a detectable signal for identifying the presence of the transgene in a cell.

The animals of this invention can be used as a source of cells, differentiated or precursor, which can be immortalized in cell culture. In a preferred embodiment, the cells are stem cells or pluripotent progenitor cells. For instance, such cells can be precursors of hematopoietic cells, neuronal cells, pancreatic cells, hepatic cells, chondrocytes, osteocytes, myocytes, or combinations thereof.

Still another aspect of the present invention relates to methods for generating non-human animals and stem cells having a functionally disrupted endogenous p63 gene. In a preferred embodiment, the method comprises the steps of:
 (i) constructing a transgene construct including (a) a recombination region having at least a portion of the p63 gene, which recombination region directs recombination of the transgene with the p63 gene, and (b) a marker sequence which provides a detectable signal for identifying the presence of the transgene in a cell;
 (ii) transfering the transgene into stem cells of a non-human animal;
 (iii) selecting stem cells having a correctly targeted homologous recombination between the transgene and the p63 gene;
 (iv) transfering cells identified in step (iii) into a non-human blastocyst and implanting the resulting chimeric blastocyst into a non-human female; and
 (v) collecting offspring harboring an endogenous p63 gene allele having the correctly targeted recombinantion.

Yet another aspect of the invention provides a method for evaluating the carcinogenic potential of an agent by (i) contacting a transgenic animal of the present invention with a test agent, and (ii) comparing the number of transformed cells in a sample from the treated animal with the number of transformed cells in a sample from an untreated transgenic animal or transgenic animal treated with a control agent. The difference in the number of transformed cells in the treated animal, relative to the number of transformed cells in the absence of treatment with a control agent, indicates the carcinogenic potential of the test compound.

Another aspect of the invention provides a method of evaluating an anti-proliferative activity of a test compound. In preferred embodiments, the method includes contacting a transgenic animal of the present invention, or a sample of cells from such animal, with a test agent, and determining the number of transformed cells in a specimen from the transgenic animal or in the sample of cells. A statistically significant decrease in the number of transformed cells, relative to the number of transformed cells in the absence of the test agent, indicates the test compound is a potential anti-proliferative agent.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

4.7 Screening Assays for p63 Therapeutics

The invention provides for p63 therapeutic compounds for treating diseases or conditions caused by, or contributed to by an abnormal p63 activity, e.g., a predisposition to form tumors. The compounds that can be used for this purpose can be any type of compound, including a protein, a peptide, peptidomimetic, small molecule, and nucleic acid. A nucleic acid can be, e.g., a gene, an antisense nucleic acid, a ribozyme, or a triplex molecule. A compound of the invention can be an agonist or an antagonist. Preferred p63 agonists include p63 proteins or derivatives thereof which mimic at least one p63 activity, e.g., the ability to activate transcription, act as a tumor suppressor, inhibit tumorigenesis by eliminating potentially tumorigeale cells hydrolysis of a target peptide or nucleic acids encoding such. Other preferred agonists include compounds which are capable of increasing the production of p63 protein in cells, e.g., compounds capable of upregulating the expression of a p63 gene. Preferred p63 antagonists include compounds which decrease or inhibit interaction of a p63 protein with a target gene. In a preferred embodiment, a p63 antagonist is a modified form of a target peptide, which is capable of interacting with the target gene, but which does not have biological activity, e.g., will not act as a transcription factor.

It is possible that when p63 functions as a transcription factor, it uses its central domain to bind to its target sequence. This region of p63 may also b a target for other proteins that interact with it. These proteins, could increase or decrease transactivation. Accordingly, compounds modulating the interaction of such proteins with p63 could be agonists or antagonists.

Thus, the invention provides methods for identifying p63 agonist and antagonist compounds, comprising selecting compounds which are capable of modulating the interaction of an p63 protein with another molecule referred to herein as "p63 binding partner". A p63 binding partner can be a target gene or a target oncoprotein etc. A p63 binding partner can also be a polypeptide which is not a target peptide and which may, e.g., interact with a p63 protein at sites other than its major binding domain. In yet other embodiments of the invention, an p63 therapeutic is a compound which is capable of binding to a p63 protein, e.g., a wild-type p63 protein or a mutated form of a p63 protein, and thereby modulate the catalytic activity of the p63-protein or degrade or cause the p63 protein to be degraded. For example, such an p63 therapeutic can be an antibody or derivative thereof which interacts specifically with an p63 protein (either wild-type or mutated).

In a further embodiment, the p63 therapeutic of the invention is capable of acting on an p63 gene, e.g., to modulate its expression.

The compounds of the invention can be identified using various assays depending on the type of compound and activity of the compound that is desired. Set forth below are at least some assays that can be used for identifying p63 therapeutics. It is within the skill of the art to design additional assays for identifying p63 therapeutics.

4.7.1 Cell-Free Assays

Cell-free assays can be used to identify compounds which modulate the interaction between an p63 protein and a p63 binding partner, such as a target gene or peptide. In a preferred embodiment, cell-free assays for identifying such compounds consist essentially in combining together in a reaction mixture a p63 protein, a p63 binding partner and a test compound or a library of test compounds. A test compound can be a derivative of a p63 binding partner, e.g., an biologically inactive target peptide, or the test compound can be a small molecule.

Accordingly, an exemplary screening assay of the present invention includes the steps of (a) forming a reaction mixture including: (i) a p63 polypeptide, (ii) a p63 binding partner (e.g., p21 such as a target gene, examples include activation of p21, which exhibits the cell cycle and/or GADD45 a repair protein activated by pathways that respond to irradiation damage), and (iii) a test compound; and (b) detecting interaction of the p63 and the p63 binding protein. The p63 polypeptide and p63 binding partner can be produced recombinantly, purified from a source, e.g., plasma, or chemically synthesized, as described herein. A statistically significant change (potentiation or inhibition) in the interaction of the p63 and p63 binding protein in the presence of the test compound, relative to the interaction in the absence of the test compound, indicates a potential agonist (mimetic or potentiator) or antagonist (inhibitor) of p63 bioactivity for the test compound. The compounds of this assay can be contacted simultaneously. Alternatively, a p63 protein can first be contacted with a test compound for an appropriate amount of time, following which the p63 binding partner is added to the reaction mixture. The efficacy of the compound can be assessed by generating dose response curves from data obtained using various concentrations of the test compound. Moreover, a control assay can also be performed to provide a baseline for comparison. In the control assay, isolated and purified p63 polypeptide or binding partner is added to a composition containing the p63 binding partner or p63 polypeptide, and the formation of a complex is quantitated in the absence of the test compound.

Complex formation between a p63 protein and a p63 binding partner may be detected by a variety of techniques. Modulation of the formation of complexes can be quantitated using, for example, detectably labeled proteins such as radiolabeled, fluorescently labeled, or enzymatically labeled p63 proteins or p63 binding partners, by immunoassay, or by chromatographic detection.

Typically, it will be desirable to immobilize either p63 or its binding partner to facilitate separation of complexes from uncomplexed forms of one or both of the proteins, as well as to accommodate automation of the assay. Binding of p63 to a p63 binding partner, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/p63 (GST/p63) fusion proteins can be adsorbed onto glutathione sepharose beads (Sigma Chemical, St. Louis, Mo.) or glutathione derivatized microtitre plates, which are then combined with the p63 binding partner, e.g. an $^{35}$S-labeled p63 binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of p63 protein or p63 binding partner found in the bead fraction quantitated from the gel using standard electrophoretic techniques such as described in the appended examples.

Other techniques for immobilizing proteins on matrices are also available for use in the subject assay. For instance, either p63 or its cognate binding partner can be immobilized utilizing conjugation of biotin and streptavidin. For instance, biotinylated p63 molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with p63 can be derivatized to the wells of the plate, and p63 trapped in the wells by antibody conjugation. As above, preparations of a p63 binding protein and a test compound are incubated in the p63 presenting wells of the plate, and the amount of complex trapped in the well can be quantitated. Exemplary methods for detecting such complexes, in addition to those described above for the GST-immobilized complexes, include immunodetection of complexes using antibodies reactive with the p63 binding partner, or which are reactive with p63 protein and compete with the binding partner; as well as enzyme-linked assays which rely on detecting an enzymatic activity associated with the binding partner, either intrinsic or extrinsic activity. In the instance of the latter, the enzyme can be chemically conjugated or provided as a fusion protein with the p63 binding partner. To illustrate, the p63 binding partner can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as anti-p63 antibodies, can be used. Alternatively, the protein to be detected in the complex can be "epitope tagged" in the form of a fusion protein which includes, in addition to the p63 sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, N.J.).

Cell-free assays can also be used to identify compounds which interact with a p63 protein and modulate an activity of a p63 protein. Accordingly, in one embodiment, a p63 protein is contacted with a test compound and the actual transcription of a target gene activity of p63 is monitored. In one embodiment, the abililty of p63 to bind to and/or to hydrolyze a target peptide, e.g, angiotensin I or a kinin, such as bradykinin is determined. The binding affinity of p63 to a target peptide can be determined according to methods known in the art. Determination of the enzymatic activity of p63 can be performed with the aid of the substrate furana-cryloyl-L-phenylalanyl-glycyl-glycine (FAPGG) under conditions described in Holmquist et al. (1979) Anal. Biochem. 95:540 and in U.S. Pat. No. 5,259,045. The subject screening assays can be accomplished in any vessel suitable for containing the reactants. Examples include microtitre plates, test tubes, and micro-centrifuge tubes.

4.7.2. Cell Based Assays

In addition to cell-free assays, such as described above, the readily available source of p63 proteins provided by the present invention also facilitates the generation of cell-based assays for identifying small molecule agonists/antagonists and the like. Such assays can be used, e.g., to identify compounds which modulate expression of a p63 gene, modulate translation of a p63 mRNA, or which modulate the stability of a p63 mRNA or protein. Accordingly, in one embodiment, a cell which is capable of producing p63, [include e.g. of cells], is incubated with a test compound and the amount of p63 produced in the cell medium is measured and compared to that produced from a cell which has not been contacted with the test compound. The specificity of the compound vis a vis p63 can be confirmed by various control analysis, e.g., measuring the expression of one or more control gene.

Compounds which can be tested include small molecules, proteins, and nucleic acids. In particular, this assay can be used to determine the efficacity of p63 antisense molecules or ribozymes.

In another embodiment, the effect of a test compound on transcription of an p63 gene is determined by transfection experiments using a reporter gene operatively linked to at least a portion of the promoter of an p63 gene. A promoter region of a gene can be isolated, e.g., from a genomic library according to methods known in the art. The reporter gene can be any gene encoding a protein which is readily quantifiable, e.g, the luciferase or CAT gene, well known in the art.

In another embodiment, the invention provides a method for detecting functional p63 protein in cells, preferably mammalian cells. 'functional p63' means a p63 protein which is able to activate gene transcription. The invention relates to a method of determining the presence of functional p63 based on the dependence of transactivation of certain target genes by p63. Examples include the p21 gene or repair proteins for instance those activated by irradiation damage. The method comprises (a) stimulating mammalian cells to increase expression of the target MRNA; and (b) coparing the level of the MRNA in stimulated cells to the level of MRNA in unstimulated cells.

For instance, primary cultures of mammalian cells can also be used. Such cells can be biopsies taken from mammalian tumors. Mammalian cell cultures can be initiated from biopsies by surgical incisional or escisional methods. In one embodiment, the cells may be stimulated in step (a) by irradiating the cells in order to induce or stimulate expression of the repair proetins.

The RNA can be isolated from irradiated mammalian cells by methods known to those skilled in the art.

4.7.3 Ubiguitin-Mediated Proteolysis

Furthermore, the present invention, by making available purified and recombinant forms of the subject p63 proteins, facilitates the development of assays that can be used to screen for drugs which inhibit the proteolysis of p63, such as by inhibiting ubiquitination of p63, or ubiquitin-mediated proteolysis of p63. For instance, in addition to agents which disrupt binding of p63 to other cellular (or viral) proteins, inhibitors of ubiquitin conjugating enzymes ("E2" enzymes) or ubiquitin ligases ("E3" enzymes) may prevent transfer of ubiquitin to p63.

Assays for the measurement of ubiquitination can be generated in many different forms, and include assays based on cell-free systems, e.g. purified proteins or cell lysates, as well as cell-based assays which utilize intact cells. Assays as described herein can be used in conjunction with the subject p63 proteins to generate a ubiquitin-conjugating system for detecting agents able to inhibit particular E2- or E3-mediated ubiquitination of p63 proteins. Such inhibitors can be used, for example, in the treatment of proliferative and/or differentiative disorders, to modulate apoptosis, and in the treatment of viral infections, such by adenoviruses or papillomaviruses.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target. Accordingly, potential inhibitors of p63 ubiquitination can be detected in a cell-free assay generated by consitution of a functional ubiquitin-protein ligase system in a cell lysate, such as generated by charging a reticulocyte lysate (Hersko et al. (1983) *J Biol Chem* 258: 8206–6214) with a p63 polypeptide and, as needed, a specific E1, E2 or E3 enzyme (cellular or viral in origin), and ubiquitin. In an alternative format, the assay can be derived as a reconstituted protein mixture.

In yet other embodiments, the present assay comprises an in vivo ubiquitin-conjugating system, such as a cell able to conduct the p63 protein through at least a portion of a ubiquitin-mediated proteolytic pathway.

The level of ubiquitination of the substrate p63 protein brought about by the system is measured in the presence and absence of a candidate agent, and a decrease in the level ubiquitin conjugation is indicative of an inhibitory activity for the candidate agent. As described below, the level of ubiquitination of the p63 protein can be measured by determining the actual concentration of protein:ubiquitin conjugates formed; or inferred by detecting some other quality of the subject protein affected by ubiquitination, including the proteolytic degradation of the protein. A statistically significant decrease in ubiquitination of the p63 protein in the presence of the test compound is indicative of the test compund being, as appropriately inferred from the assay format, an inhibitor of ubiquitin conjugation to p63 and/or ubiquitin-mediated degradation of p63.

In preferred in vitro embodiments of the present assay, the ubiquitin-conjugating system comprises a reconstituted protein mixture of at least semi-purified proteins. With respect to measuring ubiquitination, the purified protein mixture can substantially lack any proteolytic activity which would degrade the p63 substrate protein and/or components of the ubiquitin conjugating system. For instance, the reconstituted system can be generated to have less than 10% of the proteolytic activity associated with a typical reticulocyte lysate, and preferably no more than 5%, and most preferably less than 2%. Alternatively, the mixture can be generated to include, either from the onset of ubiquitination or from some point after ubiquitin conjugation of the p63 protein, a ubiquitin-dependent proteolytic activity, such as a purified proteosome complex, that is present in the mixture at measured amounts.

In the subject method, ubiquitin conjugating systems derived from purified proteins hold a number of significant advantages over cell lysate or wheat germ extract based assays (collectively referred to hereinafter as "lysates"). Unlike the reconstituted protein system, without knowledge of particular kinetic parameters for Ub-independant and Ub-dependent degradation of the p63 protein in the lysate, discerning between the two pathways can be extremely difficult. Measuring these parameters, if at all possible, is further made tedious by the fact that cell lysates tend to be inconsistent from batch to batch, with potentially significant variation between preparations. Evaluation of a potential inhibitor using a lysate system is also complicated in those circumstances where the lysate is charged with mRNA encoding the p63 protein, as such lysates may continue to synthesize the protein during the assay, and will do so at unpredictable rates.

Using similar considerations, knowledge of the concentration of each component of the ubiquitin conjugation pathway can be required for each lysate batch, along with the degradative kinetic data, in order to determine the necessary time course and calculate the sensitivity of experiments performed from one lysate preparation to the next.

Furthermore, the lysate system can be unsatisfactory where the p63 protein itself has a relatively short half-life, especially if due to degradative processes other than the ubiquitin-mediated pathway to which an inhibitor is sought. For example, in assays for an inhibitor of HPV-induced ubiquitination of p53, lysate based systems can be difficult to use, in addition to the reasons set forth above, due to the short half-life of p53 even in extracts which lack HPV proteins. In such systems, the ability to measure HPV-mediated ubiquitination of p53 is made difficult by the already rapid, ongoing degradation of p53 presumably occurring by proteolytic processes which are not mediated by any HPV proteins.

The use of reconstituted protein mixtures allows more careful control of the reaction conditions in the ubiquitin-conjugating system. Moreover, the system can be derived to favor discovery of inhibitors of particular steps of the ubiquitination process. For instance, a reconstituted protein assay can be generated which does not facilitate degradation of the ubiquitinated p63 protein. The level of ubiquitin conjugated p63 can easily be measured directly in such a system, both in the presence and absence of a candidate agent, thereby enhancing the ability to detect a inhibitor of p63 ubiquitination. Alternatively, the Ub-conjugating system can be allowed to develop a steady state level of p63:Ub conjugates in the absence of a proteolytic activity, but then shifted to a degradative system by addition of purified Ub-dependent proteases. Such degradative systems would be amenable to identifying direct inhibitors of ubiquitin-mediated proteolysis of p63.

The purified protein mixture includes a purified preparation of the p63 protein and ubiquitin under conditions which drive the conjugation of the two molecules. For instance, the mixture can include a ubiquitin-activating enzyme (E1), a ubiquitin-conjugating enzyme (E2), and a nucleotide triphosphate (e.g. ATP). Alternatively, the E1 enzyme, the ubiquitin, and the nucleotide triphosphate can be substituted in the system with a pre-activated ubiquitin in the form of an E1::Ub conjugate. Likewise, a pre-activated ubiquitin can instead comprise an E2::Ub conjugate which can directly transfer the pre-activated ubiquitin to the p63 protein substrate. Furthermore, the reconstituted mixture can also be generated to include at least one auxiliary substrate recognition protein (E3) which may be, for example, of cellular or viral origin. In illustrative embodiments described below, in order to generate an assay which approximates the ubiquitination of p63 in HPV-16 or HPV-18 infected cells, the reconstitutated ubiquitin conjugating system may further include an E6 protein of HPV origin, as well as an E6-associated protein (E6-AP) of cellular origin.

In one embodiment of the present assay, the products of a non-degradative ubiquitin-conjugating system are separated by gel electrophoresis, and the level of ubiquitinated p63 protein assessed, using standard electrophesis protocols, by measuring an increase in molecular weight of the p63 protein that corresponds to the addition of one or more ubiquitin chains. For example, one or both of the p63 protein and ubiquitin can be labeled with a radioisotope such as $^{35}$S, $^{14}$C, or $^3$H, and the isotopically labeled protein bands quantified by autoradiographic techniques. Standardization of the assay samples can be accomplished, for instance, by adding known quantities of labeled proteins which are not themselves subject to ubiquitination or degradation under the conditions which the assay is performed. Similarly, other means of detecting electrophoretically separated proteins can be employed to quantify the level of ubiquitination of the p63 protein, including immunoblot analysis using antibodies specific for either the p63 protein or ubiquitin, or derivatives thereof. As described below, the antibody can be replaced with another molecule able to bind one of either the p63 protein or ubiquitin. By way of illustration, one embodiment of the present assay comprises the use of biotinylated ubiquitin in the conjugating system. The biotin label is detected in a gel during a subsequent detection step by contacting the electrophoretic products (or a blot thereof) with a streptavidin-conjugated label, such as a streptavidin linked fluorochrome or enzyme, which can be readily detected by conventional techniques. Moreover, where a reconstituted protein mixture is used (rather than a lysate) as the conjugating system, it may be possible to simply detect the p63 protein and ubiquitin conjugates in the gel by standard staining protocols, including coomassie blue and silver staining.

In another embodiment, an immunoassay or similar binding assay, is used to detect and quantify the level of ubiquitinated p63 protein produced in the ubiquitin-conjugating system. Many different immunoassay techniques are amenable for such use and can be employed to detect and quantitate the p63 protein:Ub conjugates. For example, the wells of a microtitre plate (or other suitable solid phase) can be coated with an antibody which specifically binds one of either the p63 protein or ubiquitin. After incubation of the ubiquitin-conjugated system with and without the candidate agent, the products are contacted with the matrix bound antibody, unbound material removed by washing, and ubiquitin conjugates of the p63 protein specifically detected. To illustrate, if an antibody which binds the p63 protein is used to sequester the protein on the matrix, then a detectable anti-ubiquitin antibody can be used to score for the presence of ubiquitinated p63 protein on the matrix.

In similar fashion, epitope-tagged ubiquitin, such as myc-ub (see Ellison et al. (1991) *J. Biol. Chem.* 266:21150–21157; ubiquitin which includes a 10-residue sequence encoding a protein of c-myc) can be used in conjunction with antibodies to the epitope tag. A major advantage of using such an epitope-tagged ubiquitin approach for detecting Ub:protein conjugates is the ability of an N-terminal tag sequences to inhibit ubiquitin-mediated proteolysis of the conjugated p63 protein.

Other ubiquitin derivatives include detectable labels which do not interfere greatly with the conjugation of ubiquitin to the p63 protein. Such detectable lables can include fluorescently-labeled (e.g. FITC) or enzymatically-labeled ubiquitin fusion proteins. These derivatives can be produced by chemical cross-linking, or, where the label is a protein, by generation of a fusion protein. Several labeled ubiquitin derivatives are commercially available.

Moreover, the p63 protein can be generated as a glutathione-S-transferase (GST) fusion protein. As a practical matter, such GST fusion protein can enable easy purification of the p63 protein in the preparation of components of the ubiquitin-conjugating system (see, for example, *Current Protocols in Molecular Biology*, eds. Ausubel et al. (NY: John Wiley & Sons, 1991); Smith et al. (1988) *Gene* 67:31; and Kaelin et al. (1992) *Cell* 70:351) Moreover, glutathione derivatized matrices (e.g. glutathione-sepharose or glutathione-coated microtitre plates) can be used to sequester free and ubiquitinated forms of the p63 protein from the ubiguitin-conjugating system, and the level of ubiquitin immobilized can be measured as described. Likewise, where the matrix is generated to bind ubiquitin, the level of sequestered GST-p63 protein can be detected using agents which bind to the GST moiety (such as anti-GST antibodies), or, alternatively, using agents which are enzymatically acted upon by GST to produce detectable products (e.g. 1-chloro-2,4-dinitrobenzene; Habig et al. (1974) *J Biol Chem* 249:7130). Similarly, other fusion proteins involving the p63 protein and an enzymatic activity are contemplated by the present method. For example, fusion proteins containing β-galactosidase or luciferase, to name but a few, can be employed as labels to determine the amount of p63 protein sequestered on a matrix by virtue of a conjugated ubiquitin chain.

Moreover, such enzymatic fusion proteins can be used to detect and quantitate ubiquitinated p63 protein in a heterogeneous assay, that is one which does not require separation of the components of the conjugating system. For example, ubiquitin conjugating systems can be generated to have a ubiquitin-dependent protease which degrades the p63 protein. The enzymatic activity of the fusion protein provides a detectable signal, in the presence of substrate, for measuring the level of the p63 protein ubiquitination. Similarly, in a non-degradative conjugating system, ubiquitination of the p63 protein portion of the fusion protein can allosterically influence the enzymatic activity associated with the fusion the protein and thereby provides a means for monitoring the level of ubiquitin conjugation.

In binding assay-type detection steps set out above, the choice of which of either the p63 protein or ubiquitin should be specifically sequestered on the matrix will depend on a number of factors, including the relative abundance of both components in the conjugating system. For instance, where the reaction conditions of the ubiquitin conjugating system provide ubiquitin at a concentration far in excess of the level of the p63 protein, (e.g., one order of magnitude or greater) sequestering the ubiquitin and detecting the amount of p63 protein bound with the ubiquitin can provide less dynamic range to the detection step of the present method than the converse embodiment of sequestering the p63 protein and detecting ubiquitin conjugates from the total p63 protein bound to the matrix. That is, where ubiquitin is provided in great excess relative to the p63 protein, the percentage of ubiquitin conjugated p63 protein in the total ubiquitin bound to the matrix can be small enough that any diminishment in ubiquitination caused by an inhibitor can be made difficult to detect by the fact that, for example, the statistical error of the system (e.g. the noise) can be a significant portion of the measured change in concentration of bound p63 protein.

Furthermore, it is clear that manipulating the reaction conditions and reactant concentrations in the ubiquitin-conjugating system can be carried out to provide, at the detection step, greater sensitivity by ensuring that a strong ubiquitinated protein signal exists in the absence of any inhibitor.

Furthermore, drug screening assays can be generated which do not measure ubiquitination per se, but rather detect inhibitory agents on the basis of their ability to interfere with binding of p63 with any immediate upstream or downstream component of the ubiquitin conjugation or proteolysis pathways. Such assays, which are based on disrupting protein—protein interactions, can be carried out as described above for other p63 interactors.

In still further embodiments of the present assay, the ubiquitin-conjugating system is generated in whole cells, taking advantage of cell culture techniques to support the subject assay. For example, as described below, the ubiquitin-conjugating system (including the p63 protein and detection means) can be constituted in a eukaryotic cell culture system, including mammalian and yeast cells. Advantages to generating the subject assay in an intact cell include the ability to detect inhibitors which are functional in an environment more closely approximating that which therapeutic use of the inhibitor would require, including the ability of the agent to gain entry into the cell. Furthermore, certain of the in vivo embodiments of the assay, such as examples given below, are amenable to high through-put analysis of candidate agents.

The components of the ubiquitin-conjugating system, including the p63 protein, can be endogenous to the cell selected to support the assay. Alternatively, some or all of the components can be derived from exogenous sources. In any case, the cell is ultimately manipulated after incubation with a candidate inhibitor in order to facilitate detection of ubiquitination or ubiquitin-mediated degradation of the p63 protein. As described above for assays performed in reconstituted protein mixtures or lysate, the effectiveness of a candidate inhibitor can be assessed by measuring direct characteristics of the p63 protein, such as shifts in molecular weight by electrophoretic means or detection in a binding assay. For these embodiments, the cell will typically be lysed at the end of incubation with the candidate agent, and the lysate manipulated in a detection step in much the same manner as might be the reconstituted protein mixture or lysate.

Indirect measurement of ubiquitination of the p63 protein can also be accomplished by detecting a biological activity associated with the p63 protein that is either attenuated by ubiquitin-conjugation or destroyed along with the p63 protein by ubiquitin-dependent proteolytic processes. As set out above, the use of fusion proteins comprising the p63 protein and an enzymatic activity are representative embodiments of the subject assay in which the detection means relies on indirect measurement of ubiquitination of the p63 protein by quantitating an associated enzymatic activity.

Where the p63 protein has a relatively short half-life due to ubiquitin-dependent or independent degradation in the cell, preferred embodiments of the assay either do not require cell lysis, or, alternatively, generate a longer lived detection signal that is independent of the p63 protein's fate after lysis of the cell. With respect to the latter embodiment, the detection means can comprise, for example, a reporter gene construct which includes a positive transcriptional regulatory element that binds and is responsive to the p63 protein. For instance, p63 responsive elements can be used to construct the reporter gene. These can include a creatine kinase enhancer, an interleukin-6 promoter, a c-fos promoter, a β-actin promoter, an hsc70 promoter, a c-jun promoter, a p53 promoter, and a CYC1 hybrid promoter containing a p53/p63-binding sequence. The gene product is a detectable label, such as luciferase or β-galactosidase, or a selectable marker, such as an enzyme which confers resistance to antibiotic or other drug, and is produced in the intact cell. The label can be measured in a subsequent lysate of the cell. However, the lysis step is preferably avoided, and providing a step of lysing the cell to measure the label will typically only be employed where detection of the label cannot be accomplished in whole cells. Such embodiments of the subject assay are particularly amenable to high through-put analysis in that proliferation of the cell can provide a simple measure of inhibition of the ubiquitin-mediated degradation of the p63 protein.

To illustrate, the plasmid pTKluc described in PCT Publication WO95/18974 comprises a luciferase gene whose expression is driven by the core Herpes simplex virus thymidine kinase (TK) promoter which has been modified with either p53 (p53RE/TK), myc (mycRE/TK), or Sp1 (Sp1RE/TK) binding sites. This reporter gene construct is expected to be sensitive to the level of p63 in the cell. For instance, When the construct lacking any of the modifications to the TK promoter is transfected into mammalian cells, the detectable luciferase activity should be low because this core TK promoter fragment does not contain the upstream activating sequences necessary for efficient transcriptional activation of the luciferase gene by p53, and accordingly, should not be transactivated by p63. However transfection with the constructs in which TK is further modified to contain either 3 or 6 response-elements (RE) for one of p53, myc or Sp1, the detectable luciferase activity should increases in cells which express appropriate forms of p63. For example, the level of luciferase expression is significantly higher in p53-producing cells (e.g. ML1 cells) transfected with the p53RETK-containing construct than with the TK construct. Likewise, endogenous myc and Sp1 proteins can drive expression of the mycRE/TK and Sp1RE/TK constructs. As set out above, it is expected that p63 will be degraded by the ubiquitin pathway. However, Sp1 is not known to be degraded by any ubiquitin-mediated pathway, and the SP1RE/TK construct can therefore be used as a control in the present assays. Thus, in the presence of an agent which inhibits ubiquitin-mediated degradation of p63 in a cell harboring a p53RE/TK construct, the level of luciferase activity would increase relative to that in the cell not treated with the candidate agent.

4.8 Diagnostic and Prognostic Assays

The present methods provide means for determining if a subject is at risk for developing a disease or condition associated with disorder marked by an aberrant p63 activity, e.g., an aberrant level of p63 protein or particular isoform thereof. As set forth below, diseases or conditions that can be caused by an abnormal p63 level or catalytic activity include diseases or conditions caused by or contributed to by an abnormal amount of a target peptide of p63.

According to a diagnostic method of the present invention, loss of the wild-type p63 is detected. This loss may be due to either deletional and/or point mutational events. If only a single p63 allele is mutated, an early neoplastic state is indicated. However, if both alleles are mutated then a late neoplastic state is indicated. The p63 allele which is not deleted (i.e., that on the sister chromosome to the chromosome carrying the deletion) can be screened for point mutations, such as missense, and frameshift mutations. These mutations could lead to non-functional p63 gene products. In addition, the point mutational events may occur in the regulatory regions, such as in the promoter of the p63 gene, could lead to a loss or diminution of expression of the p63 mRNA.

In order to detect the loss of the p63 wild-type gene in tissue, it is helpful to isolate the tissue from the surrounding normal tissues. Means for enriching tumor preparations are known in the art, e.g., cytometry. Detection of point mutations may be accomplished by molecular cloning of the p63 allele (or alleles) present in tumor tissue. Alternatively, the polymerase chain reaction can be used to amplify p63 gene sequences directly from a genomic DNA preparation. The DNA sequence of the amplified sequences can be determined.

Specific deletions of the p63 gene can also be detected. For example, restriction fragment length polymorphism (RFLP) probes for the p63 genes may also be used to score the loss of a p63 allele. Loss of the wild-type p63 genes may also be detected on the basis of the loss of the wild type expression products of p63. Such expression products include the mRNA as well as the p63 protein product itself.

In one embodiment, the diagnostic method comprises determining whether a subject has an abnormal mRNA and/or protein level of p63, such as by Northern blot analysis, reverse transcription—polymerase chain reaction (RT-PCR), in situ hybridization, immunoprecipitation, Western blot hybridization, or immunohistochemistry. According to the method, cells are obtained from a subject and the p63 protein or mRNA level is determined and compared to the level of p63 protein or mRNA level in a healthy subject. An abnormal level of p63 polypeptide or mRNA level is likely to be indicative of an aberrant p63 activity.

In another embodiment, the diagnostic method comprises measuring at least one activity of p63. For example, the ability to induce transactivation of target genes, e.g. genes involved in cell cycle arrest. Comparison of the results obtained with results from similar analysis performed on p63 proteins from healthy subjects will be indicative of whether a subject has an abnormal p63 activity.

In preferred embodiments, the methods for determining whether a subject is at risk for developing a disease, such as a predisposition to develop tumors, associated with an aberrant p63 activity is characterized as comprising detecting, in a sample of cells from the subject, the presence or absence of a genetic lesion characterized by at least one of (i) an alteration affecting the integrity of a gene encoding a p63 polypeptide, or (ii) the mis-expression of the p63 gene. To illustrate, such genetic lesions can be detected by ascertaining the existence of at least one of (i) a deletion of one or more nucleotides from a p63 gene, (ii) an addition of one or more nucleotides to a p63 gene, (iii) a substitution of one or more nucleotides of a p63 gene, (iv) a gross chromosomal rearrangement of a p63 gene, (v) a gross alteration in the level of a messenger RNA transcript of a p63 gene, (vii) aberrant modification of an p63 gene, such as of the methylation pattern of the genomic DNA, (vii) the presence of a non-wild type splicing pattern of a messenger RNA transcript of a p63 gene, (viii) a non-wild type level of a p63 polypeptide, (ix) allelic loss of a p63 gene, and/or (x) inappropriate post-translational modification of a p63 polypeptide. As set out below, the present invention provides a large number of assay techniques for detecting lesions in a p63 gene. These methods include, but are not limited to, methods involving sequence analysis, Southern blot hybridization, restriction enzyme site mapping, and methods involving detection of absence of nucleotide pairing between the nucleic acid to be analyzed and a probe. These and other methods are further described infra.

Specific diseases or disorders, e.g., genetic diseases or disorders, are associated with specific allelic variants of polymorphic regions of certain genes, which do not necessarily encode a mutated protein. Thus, the presence of a specific allelic variant of a polymorphic region of a gene in a subject can render the subject susceptible to developing a specific disease or disorder. Polymorphic regions in genes, e.g, p63 genes, can be identified, by determining the nucleotide sequence of genes in populations of individuals. If a polymorphic region is identified, then the link with a specific disease can be determined by studying specific populations of individuals, e.g, individuals which developed a specific disease, such as hypertension. A polymorphic region can be located in any region of a gene, e.g., exons, in coding or non coding regions of exons, introns, and promoter region.

In an exemplary embodiment, there is provided a nucleic acid composition comprising a nucleic acid probe including a region of nucleotide sequence which is capable of hybridizing to a sense or antisense sequence of a p63 gene or naturally occurring mutants thereof, or 5' or 3' flanking sequences or intronic sequences naturally associated with the subject p63 genes or naturally occurring mutants thereof. The nucleic acid of a cell is rendered accessible for hybridization, the probe is contacted with the nucleic acid of the sample, and the hybridization of the probe to the sample nucleic acid is detected. Such techniques can be used to detect lesions or allelic variants at either the genomic or mRNA level, including deletions, substitutions, etc., as well as to determine mRNA transcript levels.

A preferred detection method is allele specific hybridization using probes overlapping the mutation or polymorphic site and having about 5, 10, 20, 25, or 30 nucleotides around the mutation or polymorphic region. In a preferred embodiment of the invention, several probes capable of hybridizing specifically to allelic variants are attached to a solid phase support, e.g., a "chip". Oligonucleotides can be bound to a solid support by a variety of processes, including lithography. For example a chip can hold up to 250,000 oligonucleotides (GeneChip, Affymetrix). Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligase chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the p63 gene (see Abravaya et al. (1995) *Nuc Acid Res* 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a p63 gene under conditions such that hybridization and amplification of the p63 gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In a preferred embodiment of the subject assay, mutations in, or allelic variants, of a p63 gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the p63 gene and detect mutations by comparing the sequence of the sample p63 with the corresponding wild-type (control) sequence. Exemplary sequencing reactions include those based on techniques developed by Maxim and Gilbert (*Proc. Natl. Acad Sci USA* (1977) 74:560) or Sanger (Sanger et al (1977) *Proc. Nat. Acad. Sci* 74:5463). It is also contemplated that any of a variety of automated sequencing procedures may be utilized when performing the subject assays (*Biotechniques* (1995) 19:448), including sequencing by mass spectrometry (see, for example PCT publication WO 94/16101; Cohen et al. (1996) *Adv Chromatogr* 36:127–162; and Griffin et al. (1993) *Appl Biochem Biotechnol* 38:147–159). It will be evident to one skilled in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers, et al. (1985) *Science* 230:1242). In general, the art technique of "mismatch cleavage" starts by providing heteroduplexes formed by hybridizing (labelled) RNA or DNA containing the wild-type p63 sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl. Acad Sci USA* 85:4397; Saleeba et al. (1992) Methods Enzymod. 217: 286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in p63 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a p63 sequence, e.g., a wild-type p63 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations or the identity of the allelic variant of a polymorphic region in p63 genes. For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) *Mutat Res* 285:125–144; and Hayashi (1992) *Genet Anal Tech Appl* 9:73–79). Single-stranded DNA fragments of sample and control p63 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting point mutations or the identity of the allelic variant of a polymorphic region include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al. (1986) *Nature* 324:163); Saiki et al (1989) *Proc. Natl. Acad Sci USA* 86:6230). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238. In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren, U. et al., Science 241:1077–1080 (1988). The OLA protocol uses two oligonucleotides which are designed to be capable of hybridizing to abutting sequences of a single strand of a target. One of the oligonucleotides is linked to a separation marker, e.g,. biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., Proc. Natl. Acad. Sci. (U.S.A.) 87:8923–8927 (1990). In this method, PCR is used to achieve the exponential amplification of target DNA, which is then detected using OLA.

Several techniques based on this OLA method have been developed and can be used to detect specific allelic variants of a polymorphic region of an SR-BI gene. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) Nucleic Acids Res 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting single nucleotide polymorphisms in an p63 gene. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Several primer-guided nucleotide incorporation procedures for assaying polymorphic sites in DNA have been described (Komher, J. S. et al., Nucl. Acids. Res. 17:7779–7784 (1989); Sokolov, B. P., Nucl. Acids Res. 18:3671 (1990); Syvanen, A.-C., et al., Genomics 8:684–692 (1990); Kuppuswamy, M. N. et al., Proc. Natl. Acad. Sci. (U.S.A.) 88:1143–1147 (1991); Prezant, T. R. et al., Hum. Mutat. 1:159–164 (1992); Ugozzoli, L. et al., GATA 9:107–112 (1992); Nyren, P. et al., Anal. Biochem. 208:171–175 (1993)). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., Amer. J. Hum. Genet. 52:46–59 (1993)).

For mutations that produce premature termination of protein translation, the protein truncation test (PTT) offers an efficient diagnostic approach (Roest, et. al., (1993) *Hum. Mol. Genet.* 2:1719–21; van der Luijt, et. al., (1994) *Genomics* 20:1–12). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

The methods described herein may be performed, for example, by utilizing pre-packaged diagnostic kits comprising at least one probe nucleic acid, primer set; and/or antibody reagent described herein, which may be conveniently used, e.g., in clinical settings to diagnose patients exhibiting symptoms or family history of a disease or illness involving a p63 polypeptide.

Any cell type or tissue may be utilized in the diagnostics described below. In a preferred embodiment a bodily fluid, e.g., blood, is obtained from the subject to determine the presence of a mutation or the identity of the allelic variant of a polymorphic region of an p63 gene. A bodily fluid, e.g, blood, can be obtained by known techniques (e.g. venipuncture). Alternatively, nucleic acid tests can be performed on dry samples (e.g. hair or skin). For prenatal diagnosis, fetal nucleic acid samples can be obtained from maternal blood as described in International Patent Application No. WO91/07660 to Bianchi. Alternatively, amniocytes or chorionic villi may be obtained for performing prenatal testing.

When using RNA or protein to determine the presence of a mutation or of a specific allelic variant of a polymorphic region of a p63 gene, the cells or tissues that may be utilized must express the p63 gene. Preferred cells for use in these methods include megakaryocytes, which have been shown to express the 3 zinc finger proteins of the invention (see Examples). Alternative cells or tissues that can be used, can be identified by determining the expression pattern of the specific p63 gene in a subject, such as by Northern blot analysis.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Antibodies directed against wild type or mutant p63 polypeptides or allelic variant thereof, which are discussed above, may also be used in disease diagnostics and prognostics. Such diagnostic methods, may be used to detect abnormalities in the level of p63 polypeptide expression, or abnormalities in the structure and/or tissue, cellular, or subcellular location of a p63 polypeptide. Structural differences may include, for example, differences in the size, electronegativity, or antigenicity of the mutant p63 polypeptide relative to the normal p63 polypeptide. Protein from the tissue or cell type to be analyzed may easily be detected or isolated using techniques which are well known to one of skill in the art, including but not limited to western blot analysis. For a detailed explanation of methods for carrying out Western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of p63 polypeptides. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the p63 polypeptide, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an anti-p63 polypeptide specific antibody is via linkage to an enzyme and use in an enzyme immunoassay (EIA) (Voller, "The Enzyme Linked Immunosorbent Assay (ELISA)", *Diagnostic Horizons* 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) *Enzyme Immunoassay*, CRC Press, Boca Raton, Fla., 1980; Ishikawa, et al., (eds.) *Enzyme Immunoassay*, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Moreover, it will be understood that any of the above methods for detecting alterations in a gene or gene product or polymorphic variants can be used to monitor the course of treatment or therapy.

4.9 Methods of Treating Diseases

In general, the invention provides methods for treating or preventing a disease caused by or contributed to by aberrant expression or activity of a p63 gene product, comprising administering to the subject an effective amount of a pharmaceutical composition comprising a compound which is capable of modulating a p63 activity, such that the disease is treated or prevented in the subject. Among the approaches which may be used to ameliorate disease symptoms involving an aberrant p63 activity are, for example, gene therapy, antisense, ribozyme, and triple helix molecules described above. Other suitable compounds include the compounds identified in the drug screening assays above, as well as the various antagonists and agonist forms of the protein.

In a preferred embodiment, the compounds of the present invention are useful for regulating tumorigensis. In fact, based on the significant nucleotide and amino acid sequence homology with p53, p63 is a logical target for cancer therapy. The mutation spectrum of p53 provide clues to the critical functional regions of the gene, that, when mutated, contribute to the carcinogenic process. Since about 80% of the missense mutations are in the sequence-specific DNA binding midregion of the protein, investigators have focused on the transcription transactivator function of p53. However, these missense mutations and the resultant amino acid substitutions can cause aberrant protein conformations that also may alter other functional domains, including those in the carboxyl-terminus of the p53 protein. This positively charged region contains the putative major nuclear localization signal (amino acids 316–325), the oligomerization domain (amino acids 319–360), and a DNA damage-binding domain (amino acids 318–393). p53 sequence-specific DNA binding and transcriptional transactivation can also be modulated by post-translational mechanisms, including serine phosphorylation and the redox regulation of the cysteine residues responsible for binding zinc to p53. The structure-function relationship revealed by the analysis of the p53 mutation spectrum, provides us with strategies for the development of rational cancer therapy; particularly because of the considerable sequence identity between p53 and p63. As discussed above, it has been observed that the sequence identity between p63 and p73 alpha form is about 57.4% identity and the p63 and p73 beta form shows about 69.7% identity at the protein level. p63 alpha form and p53 exhibit 43.8% identity at the protein level.

In one embodiment, this invention is directed to the development of drugs to mimic the cell regulator function of p63. Strategies to screen potential drugs are suggested by the development of assays reflecting the biologic functions of the p63 protein: its binding to specific DNA sequences, its function as a transcription factor, its function as an inducer of apoptosis, and its ability to form complexes with cellular or viral oncoproteins. For instance, in one embodiment, apoptosis, the cell death pathway may be enhanced by anticancer therapies. Cells exposed to agents that produce DNA damage, such as double-strand breaks, may use the p53/p63-mediated pathway to induce apoptosis. It is known in the art that certain cell growth factors act as survival factors of cancer cells, therefore, reduction of these factors would produce apoptosis, e.g., the use of anti-EGF-recptor monoclonal antibodies, which block the EGF mediated growth signal cascade, have been shown to act synergistically with anti-cancer drugs. Thus, modulating the survival factors, survival factor pathways, their cellular receptors and inhibitors provide novel methods of inhibiting tumorigeneisis. It is possible that p63 may mediate apoptosis by both transcriptional transactivation of genes that enhance apoptosis and transcription transrepression of genes that inhibit apoptosis. These genes their encoded proteins may also be targets for therapeutic strategies.

It is known in the art that certain DNA viruses have oncoproteins that that bind to p53 and inactivate its functions, it is likely that these would also inactivate the functions of the closely analogous p63. The E6 protein of the oncogenic strains of the human papillomavirus binds to p53 via E6-AP, a specific ubiquitin protein ligase and enhances the digestion of p53, and possible th edigestion of p63. Drugs that inhibit either the formation of this protein complex or the digestion of either p53 or p63, might have a therapeutic benefit in tumors associated with human papillomavirus infections, such as cervical, penile, and rectal carcinomas.

p63 has been mapped to chromosome 3, i.e., 3q27. Deletions of regions of chromosome 3 have been implicated in lung, uterine, breast, testicular, and ovarian cancers, von Hippel-Lindau and 3p deletion syndrome, renal cell and nasopharyngeal carcinomas, mesotheliomas, and various haematological malignancies. In particular, chromosomal breaks at 3q27 have been implicated in intermediate grade non-Hodgkin's lymphomas (NHL). The pathologic heterogeneity of NHL is reflected at the cellular level by the various pathways underlying NHL pathogenesis. In particular, two main categories of genetic lesions, activation of dominantly acting oncogenes and deletion of tumor-suppression genes are known in the art as contributing to lymphonogenesis. In particular, oncogene activation in NHL most commonly occurs through non-random chromosomal translocations.

In many instances, these translocations involve reciprocal exchanges between an antigen receptor locus (the immunoglobulin loci or the TCR in B- and T-cell malignancies, respectively) and various protoooncogene loci. Once the protooncogne is juxtaposed to an antigen receptor locus, its expression becomes regulated by immunoglulin TCR promoters and enhancers. The resulting transcriptional deregulation may be one factor causing activation of the translocated protooncogene. Accordingly, in one embodiment it is contemplated that overexpression of the p63-B forms may be implicated in NHL.

In yet another embodiment, the invention contemplates the use of a combination of strategies, for example, a low dose of a DNA damaging agent to arrest normal cells in $G_1$ of the cell cycle and a delayed dose of an antimitotic agent to target the mutant p63 tumor cells that continue to progress into the S phase, $G_2$, and mitosis.

As observed in the case of p53, it is likely that tumor derived p63 mutations will target amino acid residues that are important for the structural integrity of the core domain of p63. Failure of muatnt proteins to bind to DNA has been attributed to the structural defects in the proteins such as structural rearrangements, local unfolding of the structure, or denaturation of the core domain. Therefore, mutant p63 can have altered sequence specific DNA-binding and function as a transcription factor either by inhibiting its transactivator activity or by changing its specificity of DNA binding and the repertoire of genes that are transcriptionally transactivated. Although, it would seem difficult to reverse mutant conformations to the wild type, numerous strategies have been considered. First, certain like p53, certain p63 mutant proteins are believed to have temperature sensitive phenotypes, including increased transcription-transcativator and growth inhibition activities at the lower permissive temperature when compared to the non-permissive higher temperature. Second, certain peptide drugs can later the conformation of mutant p63 in cells. Third, certain p63 mutants can still form tetramers and cooperate with transfected wild-type p63 in the transcriptional tranactivation of reporter gene constructs. It would appear that p63 missense mutants most likely to assume a wild-type protein conformation apear to be those with a substituted amino acid in the sequence specific DNA binding site. Mutations resulting in amino acid substitutions in the interior of the p63 protein may be a thermodynamically less stable folded structure and require other strategies. Tumors having these interior p63 mutations also bind to cellular proteins which could lead to either dominant negative or gain of oncogenic activities. Therefore, strategies such as targeting the mutant gene by triple Dna helox and antisense approaches could result in diminishing these activities and have a therapeutic benefit.

The efficacy of p53 gene therapy in human cancer cells has been demonstrated in vitro by Lee et al., Cancer Metastasis Rev., 14:149–61 (1995), the efficacy as xenografts in athymic nude mice has been demonstrated by Lesoon-Wood et al., Hum. Gene Ther. 6:395–405 (1995); Clayman et al., Cancer Res. 55:1–12 (1995); and Liu et al., Cancer Res. 55:3117–22 (1995). The p53 gene, i.e., at p53 complementary DNA expression vector was successfully transferred any transfection or infection using either a replication defective retroviral or an adenoviral vector and tumor cell growth was inhibited. In fact, the succes of these expression vectors has led to the approval of phase I protocols in humans. In yet another embodiment, the use of the p53 complementary DNA expression vectors in gene therapy protocols is contemplated.

4.9.1. Tumor Vaccines

The treatment of cancer with tumor vaccines has been a goal of physicians and scientists ever since effective immunization against infectious disease with vaccines was developed. In the past, major tumor antigens had not been molecularly characterized. Recent advances are, however, beginning to define potential molecular targets and strategies and this had evolved with the principle that T-cell mediated responses are a key target for approaches to cancer immunization. In addition, these antigens are not truly foreign and tumor antigens fit more with a self/altered self paradigm, compared to a non-self paradigm for antigens recognized in infectious diseases. Antigens that have been used in the art include the glycolipids and glycoproteins e.g. gangliosides, the developmental antigens, e.g., MAGE, tyrosinase, melan-A and gp75, and mutant oncogene products, e.g., p53, ras, and HER-2/neu. Vaccine possibilities include purified proteins and glycolipids, peptides, cDNA expressed in various vectors, and a range of immune adjuvants.

Yet another aspect of the present invention relates to the modification of tumor cells, and/or the immune response to tumor cells in a patient by administering a vaccine to enhance the anti-tumor immune response in a host. The present invention provides, for examples, tumor vaccines based on administration of expression vectors encoding a mutant tumor suppressor gene, e.g., p53, p73, or p63, or portions thereof, or immunogenic preparations of polypeptides.

In general, it is noted that malignant transformation of cells is commonly associated with phenotypic changes. Such changes can include loss, gain, or alteration in the level of expression of certain proteins. It has been observed that in some situations the immune system may be capable of recognizing a tumor as foreign and, as such, mounting an immune response against the tumor (Kripke, M., *Adv. Cancer Res.* 34, 69–75 (1981)). This hypothesis is based in part on the existence of phenotypic differences between tumor cells and normal cells, which is supported by the identification of tumor associated antigens (TAAs) (Schreiber, H., et al. *Ann. Rev. Immunol.* 6, 465–483 (1988)). TAAs are thought to distinguish a transformed cell from its normal counterpart. For example, three genes encoding TAAs expressed in melanoma cells, MAGE-1, MAGE-2 and MAGE-3, have recently been cloned (van der Bruggen, P., et al. *Science* 254, 1643–1647 (1991)). That tumor cells under certain circumstances can be recognized as foreign is also supported by the existence of T cells which can recognize and respond to tumor associated antigens presented by MHC molecules. Such TAA-specific T lymphocytes have been demonstrated to be present in the immune repertoire and are capable of recognizing and stimulating an immune response against tumor cells when properly stimulated in vitro (Rosenberg, S. A., et al. *Science* 233, 1318–1321 (1986); Rosenberg, S. A. and Lotze, M. T. *Ann. Rev. Immunol.* 4, 681–709 (1986)). In the case of melanoma cells both the tyrosinase gene (Brichard, V., et al. *J. Exp. Med.* 178:489 (1993)) and the Melan-A gene (Coulie et al. *J. Exp. Med.* 180:35)) have been identified as genes coding for antigens recognized by autologous CTL on melanoma cells.

Induction of T lymphocytes is a critical initial step in a host's immune response. Activation of T cells results in cytokine production, T cell proliferation, and generation of T cell-mediated effector functions. T cell activation requires an antigen-specific signal, often called a primary activation signal, which results from stimulation of a clonally-distributed T cell receptor (TcR) present on the surface of the T cell. This antigen-specific signal is usually in the form of an antigenic peptide bound either to a major histocompatibility complex (MHC) class I protein or an MHC class II protein present on the surface of an antigen presenting cell (APC). CD4+, helper T cells recognize peptides associated with class II molecules which are found on a limited number of cell types, primarily B cells, monocytes/macrophages and dendritic cells. In most cases class II molecules present peptides derived from proteins taken up from the extracellular environment. In contrast, CD8+, cytotoxic T cells (CTL) recognize peptides associated with class I molecules. Class I molecules are found on almost all cell types and, in most cases, present peptides derived from endogenously synthesized proteins. For a review see Germain, R., *Nature* 322, 687–691 (1986).

The importance of T cells in tumor immunity has several implications which are important in the development of anti-tumor vaccines. Since antigens are processed and presented before they are recognized by T cells, they may be derived from any protein of the tumor cell, whether extracellular or intracellular. In addition, the primary amino acid sequence of the antigen is more important than the three-dimensional structure of the antigen. Tumor vaccine strategies may use the tumor cell itself as a source of antigen, or may be designed to enhance responses against specific gene products. (Pardoll, D. 1993. *Annals of the New York Academy of Sciences* 690:301).

The present invention provides for various tumor vaccination methods and reagents which can be used to elicit an anti-tumor response against transformed cells which express/display a mutant p63, p53, or p73, or which have been engineered to present an antigen of a mutant p63, p53, or p73. In general, the tumor vaccine strategies of the present invention fall into two categorie: (1) strategies that use the tumor cell itself as a source of tumor antigen, and (2) antigen-specific vaccine strategies that are designed to generate immune responses against specific antigens of mutant p63, p53, or p73s.

In general, a p63, p53, or p73 vaccine polypeptide will include at least a portion of the p63, p53, or p73 polypeptide including a site of mutation which, when occurring in the full-length protein, results in loss of its biological activity. Where the p63, p53, or p73 tumor vaccine comprises a sufficient portion of a mutant p63, p53, or p73 protein, the p63, p53, or p73 protein can be further mutated to render the vaccine polypeptide biologically inactive.

In one embodiment, a tumor cell which otherwise does not express a mutant p63, p53, or p73 can be rendered immunogenic as a target for CTL recognition by association of a p63, p53, or p73 vaccine polypeptide. For example, this can be accomplished by the use of gene transfer vectors. Such gene transfer vectors may be administered in any biologically effective carrier, e.g. any formulation or composition capable of effectively delivering the p63, p53, or p73 vaccine gene to cells in vivo. Alternatively, cells from the patient or other host organism can be transfected with the tumor vaccine construct ex vivo, allowed to express the p63, p53, or p73 protein, and, preferably after inactivation by radiation or the like, administered to an individual. In particular, viral vectors represent an attractive method for delivery of tumor vaccine antigens because viral proteins are expressed de novo in infected cells, are degraded within the cytosol, and are transported to the endoplasmic reticulum where the degraded peptide products associate with MHC class I molecules before display on the cell surface (Spooner et al. (1995) *Gene Therapy* 2:173).

Approaches include insertion of the subject gene into viral vectors including recombinant retroviruses, adenovirus, adeno-associated virus, vaccinia virus, and herpes simplex virus-1, or plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene transfer, choice of the particular gene delivery system will depend on such factors as the phenotype of the intended target and the route of administration, e.g. locally or systemically.

In addition to viral transfer methods, such as those illustrated above, non-viral methods can also be employed to cause expression of a subject p63, p53, or p73 polypeptide in the tissue of an animal in order to ellicit a cellular immune response. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the vaccine gene by the targeted cell. Exemplary gene delivery systems of this type include liposomal derived systems, poly-lysine conjugates, and artificial viral envelopes.

In another embodiment the mutant p63, p53, or p73 peptides of the present invention may be directly delivered to the patient. Although such expression constructs as exemplified above have been shown to be an efficient means by which to obtain expression of peptides in the context of class I molecules, vaccination with isolated peptides has also been shown to result in class I expression of the peptides in some cases. For example, the use of synthetic peptide fragments containing CTL epitopes which are presented by class I molecules has been shown to be an effective vaccine against infection with lymphocytic choriomeningitis virus (Schultz et al. 1991. *Proc. Natl. Acad. Sci. USA* 88:2283) or sendai virus (Kast et al. 1991. *Proc Natl Acad. Sci.* 88:2283). Subcutaneous administration of a CTL epitope has also been found to render mice resistant to challenge with human papillomavirus 16-transformed tumor cells (Feltkamp et al. (1993) *Eur. J. Immunol.* 23:2242–2249). It is contemplated that such peptides may be presented in the context of tumor cell class I antigens or by other, host-derived class I bearing cells (Huang et al. 1994. *Science* 264:961).

The mutant p63, p53, or p73 proteins, and portions thereof, may be used in the preparation of vaccines prepared by known techniques (c.f., U.S. Pat. Nos. 4,565,697; 4,528, 217 and 4,575,495). p63, p53, or p73 polypeptides displaying antigenic regions capable of eliciting protective immune response are selected and incorporated in an appropriate carrier. Alternatively, an antitumor antigenic portion of a p63, p53, or p73 protein may be incorporated into a larger protein by expression of fused proteins.

The p63, p53, or p73 antitumor vaccines above may be administered in any conventional manner, including oranasally, subcutaneously, intraperitoneally or intramuscularly. The vaccine may further comprise, as discussed infra, an adjuvant in order to increase the immunogenicity of the vaccine preparation.

In some cases it may be advantageous to couple the p63, p53, or p73 polypeptide vaccine to a carrier, in particular a macromolecular carrier. The carrier can be a polymer to which the p63, p53, or p73 polypeptide is bound by hydrophobic non-covalent inneraction, such as a plastic, e.g., polystyrene, or a polymer to which the polypeptide is covalently bound, such as a polysaccharide, or a polypeptide, e.g., bovine serum albumin, ovalbumin or keyhole limpet hemocyanin. The carrier should preferably be non-toxic and non-allergenic. The p63, p53, or p73 polypeptide may be multivalently coupled to the macromolecular carrier as this provides an increased immunogenicity of the vaccine preparation. It is also contemplated that the p63, p53, or p73 polypeptide may be presented in multivalent form by polymerizing the polypeptide with itself.

In addition, the vaccine formulations may also contain one or more stabilizer, exemplary being carbohydrates such as sorbitol, mannitol, starch, sucrose, dextrin, and glucose, proteins such as albumin or casein, and buffers such as alkaline metal phosphate and the like.

The inclusion of CD4+ epitopes in the tumor vaccine in order to further enhance an anti-tumor response is also within the scope of the invention.

In other embodiments, the tumor cell itself can be used as the source of antitumor p63, p53, or p73 antigens. See, for review, Pardoll, D. 1993. *Annals of the New York Academy of Sciences* 690:301. For example, cells which have been identified through phenotyping as expressing a mutant p63, p53, or p73 can be used to generate a CTL response against a tumor. For example, tumor-infiltrating lymphocytes (TILs) may be derived from tumor biopsies which have such a phenotype. Following such protocols as described by Hom et al. (1991) *J Immunotherap* 10:153, TILs can be isolated from tumor specimens and grown in the presence of interleukin-2 in order to generate oligoclonal populations of activated T-lymphocytes that are cytolytic to the tumor cells expressing the mutant p63, p53, or p73.

In other embodiments, whole cell vaccines can be used to treat cancer patients. Such vaccines can include, for example, irradiated autologous or allogenic tumor cells which express (endogenously or recombaintly) a mutant p63, p53, or p73 polypeptide (or fragment thereof), or lysates of such cells.

In clinical settings, the therapeutic compound of the present invention can be introduced into a patient by any of a number of methods, each of which is familiar in the art. For instance, a pharmaceutical preparation of the gene delivery system or peptide can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle or peptide can be introduced by catheter (see U.S. Pat. No. 5,328,470) or by stereotactic injection (e.g. Chen et al. (1994) *PNAS* 91: 3054–3057). A vaccine gene can be delivered in a gene therapy construct by electroporation using techniques described, for example, by Dev et al. ((1994) *Cancer Treat Rev* 20:105–115).

The pharmaceutical preparation of the vaccine therapy construct or peptide can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral or adenoviral vectors, the pharmaceutical preparation can comprise one or more cells which produce the gene delivery system.

Suitable pharmaceutical vehicles for administration to a patient are known to those skilled in the art. For parenteral administration, the p63, p53, or p73 immunogen will usually be dissolved or suspended in sterile water or saline. For enteral administration, the immunogen will be incorporated into an inert carrier in tablet, liquid, or capsular form. The preparation may also be emulsified or the active ingredient encapsulated in liposome vehicles. The composition or formulation to be administered will, in any event, contain a quantity of the p63, p53, or p73 polypeptide adequate to achieve the desired immunized state in the subject being treated. The immunogen preparations according to the invention may also contain other peptides or other immunogens.

Suitable carriers may be starches or sugars and include lubricants, flavorings, binders, and other materials of the same nature. For instance, the immunogen can be formulated as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The immunogen, which may be coupled to a carrier, is preferably administered after being mixed with immunization adjuvants. Conventional adjuvants include, for example, complete or incomplete Freund's adjuvant, aluminum hydroxide, Quil A, EMA, DDA, TDM-Squalene, lecithin, alum, saponin, and such other adjuvants as are well known to those in the art, and also mixtures thereof. For example, the p63, p53, or p73 immunogen may be mixed with the N-butyl ester (murabutide) of the muramyl dipeptide (MDP; N-acetyl-glucosamine-3-yl-acetyl-L-alanyl-D-isoglutamine) diluted in a saline solution. The mixture may then be emulsified by means of an equal volume of squalene in the presence of arlacel (excipients). It is also possible to use other adjuvants such as analogues of MDP, bacterial fractions such as streptococcal preparations (OK 432), Biostim (01K2) or modified lipopolysaccharide preparations (LPS), peptidoglycans (N-Opaca) or proteoglycans (K-Pneumonia). In the case of these excipients, water-in-oil emulsions are preferable to oil-in-water emulsions.

The use of the instant invention is predicted to be of benefit in the treatment of any type of tumor which harbors a mutant p63, p53, or p734 gene. For example, treatment of tumors of the lung, breast, brain, bone, skin, bladder, kidney, ovary, or lymphocytes is contemplated. In a preferred embodiment the tumor vaccine of the present invention is used to treat melanoma.

In addition to enhancing the immune response against a tumor at its original site, the tumor cell vaccine of the current invention may also be used in a method for preventing or treating metastatic spread of a tumor or preventing or treating recurrence of a tumor. Thus, administration of modified tumor cells or modification of tumor cells in vivo as described herein can provide tumor immunity against cells of the original, unmodified tumor as well as metastases of the original tumor or possible regrowth of the original tumor.

Subjects develop an anti-tumor specific T cell response which is specific for mutant forms of p63, p53, or p73 proteins and is effective in keeping the patients disease free. Thus, the subject develops anti-tumor specific immunity. It is also contemplated that the invention may be useful in inducing immunity to tumors in susceptible individuals before they arise, for example in the case of familial malignancies. A strong hereditary component has been identified for certain types of malignancies, for example certain breast and colon cancers and in susceptability to melanoma. In families with a known susceptibility to a particular malignancy and in which one individual presently has a tumor bearing a mutant p63, p53, or p73 protein, peptides presented by class I molecules of these patients could be administered to susceptible, histocompatible family members to induce an anti-tumor response in the recipient against the type of tumor to which the family is susceptible. This anti-tumor response could provide protective immunity to subsequent development of a tumor in the immunized recipient.

4.9.1. Effective Dose

Toxicity and therapeutic efficacy of such compounds can be determined by standard pharmaceutical procedures in cell cultures or experimental animals, e.g., for determining The $Ld_{50}$ (The Dose Lethal To 50% Of The Population) And The $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.9.2 Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

In clinical settings, a gene delivery system for the therapeutic p63 gene can be introduced into a patient by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) PNAS 91: 3054–3057). A p63 gene, such as any one of the sequences represented in the group consisting of SEQ ID NOS 1 and 3 or a sequence homologous thereto can be delivered in a gene therapy construct by electroporation using techniques described, for example, by Dev et al. ((1994) Cancer Treat Rev 20:105–115).

The pharmaceutical preparation of the gene therapy construct or compound of the invention can consist essentially of the gene delivery system in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4.9.3. Kits

The invention further provides kits for use in diagnostics or prognostic methods or for treating a disease or condition associated with an aberrant p63 protein. In one embodiment, the kit comprises a pharmaceutical composition containing an effective amount of an p63 antagonist therapeutic and instructions for use in treating or preventing tumorigenesis. In yet another embodiment, the kit comprises a pharmaceutical composition comprising an effective amount of an p63 agonist therapeutic.

Yet other kits can be used to determine whether a subject has or is likely to develop a disease or condition associated with an aberrant p63 activity. Such a kit can comprise, e.g., one or more nucleic acid probes capable of hybridizing specifically to at least a portion of an p63 gene or allelic variant thereof, or mutated form thereof.

4.10. Additional Uses for p63 Proteins and Nucleic Acids

The p63 nucleic acids of the invention can further be used in the following assays. The p63 gene can also be used as a chromosomal marker in genetic linkage studies involving genes other than p63.

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986). All references cited herein are inorporated by reference in their entirety.

Exemplification

The invention now being generally described, it will be more readily understood by reference to the following examples which are included merely for purposes of illustration of certain aspects and embodiments of the present invention, and are not intended to limit the invention.

EXAMPLES

I. Identification of Human and Murine p63

It has been obsreved that the intron-exon organization was conserved between p73 and p53 (Kaghad et al., 1997), and from known exon and intron sizes for these two genes, it was possible to identify new members of this gene family using a PCR-based strategy of amplifying two exons in a conserved domain and their intervening intron. Sequence similarity in exonic regions would demonstrate a related gene, while differences in size and/or sequence or introns from p53 and p73 would indicate a novel family member. Non-degenerate and degenerate primers were designed based in sequence homology among p53 and p73 cDNAs from various species. Primers (5'-GGCCTCGAGTACAAITW-CATGTGTAAYAG (SEQ ID NOS: 27) and 5'GGCATC-GATTCTCTTCCAGGGCAAGCACA) (SEQ ID NOS: 28) designed to anneal to regions in exon 7 and exon 8, respectively, of p73 and p53, were used to amplify products from human and mouse total genomic DNA with the following conditions:

pre-PCR: 80° C. 2 min, add TAQ polymerase, 94° C. 5 min.

'Touchdown PCR': 94° C. 1 min, 65° C. 1 min, 72° C. 2 min for 3 cycles:

94° 1 min, 64° C. 1 min, 72° C. 2 min for 3 cycles; 94° C. 1 min, 63° C. 1 min, 72° C. 2 min for 3 cycles; 94° C. 1 min, 62° C. 1 min, 72° C. 2 min for 2 cycles; 94° C. 1 min, 61° C. 1 min, 72° C. 2 min for 2 cycles; 94° C. 1 min, 60° C. 1 min, 72° C. 2 min for 2 cycles; 94° C. 1 min, 59° C. 1 min, 72° C. 2 min for 2 cycles; 94° C. 1 min, 58° C. 1 min, 72° C. 2 min for 20 cycles; 72° C. 7 min The above generated amplicons of approximately 800 bp and 900 bp from human and mouse genomic DNA, respectively. Comparison with known sizes of the corresponding intron (7) in p73 and p53 indicated that these amplicons were derived from a novel gene that shared homology in exonic regions, as demonstrated by their ability to be generated with the above primers. The amplicons were then subcloned into a pCDNA3 or pCDNA3 or pCDNA3-GFP vector and sequenced using T7, SP6, and GFP primers. Sequence analysis confirmed homology with regions in exon 7 and exon 8 of the p73 and p53 genes, showing strong nucleotide similarity and near identity at the amino acid level, particularly to p73.

II. Cloning of p63 Via Exon-Bridging

The recent discovery of the p53-related gene, p73, suggested that other members of the p53 gene family exist in mammalian genomes. Given the absence of p53-related sequences in available expressed sequence tag (EST) libraries, it was possible that p53-related genes were expressed at relatively low levels or in a tissue-restricted manner, and that standard hybridization or polymerase chain reaction (PCR) approaches would be difficult. However, examination of the central portions of p53 and p73 showed a remarkable conservation of intron positions, while the size and sequences of these introns remained distinct between these genes (Kaghad et al., 1997; Yang et al., submitted). We therefore designed PCR primers that would anneal to regions in contiguous exons conserved between p53 and p73 such that the amplification product would include the intervening intron. As products from the p53 and p73 genes were predictable on the basis of known intron sizes and sequence, we analyzed novel products for ones possessing terminal sequence homolocy with p53 and p73 bordering non-conserved intronic sequences. One primer pair designed to span intron 7 yielded an 800 basepair (bp) and 900 bp PCR product from human and mouse, respectively, genomic DNA (not shown). The ends of these products displayed sequence homology with the 3' end of exon 7 and the 5'-end of exon 8 of p53 and p73, while the intervening sequence showed no homology with introns of either gene. The 800 bp amplicon derived from human genomic DNA was used as a hybridization probe to screen a human PAC library, which yielded a single clone of 120 Kb. Similarly, the 900 bp amplicon from the mouse genomic DNA was used to isolate a single, 16.5 Kb clone from a lambda DASH II murine genomic DNA phage library. Partial sequencing of exon 7 of the human and mouse genomic clones confirmed the presence of exonic sequences with similarity to those of p53 and p73, and yet the presence of third base codon differences and of conserved substitutions, demonstrating that this gene was a novel member of the p53 family.

To deduce the amino acid sequence of the protein, or proteins, encoded by this gene, we constructed a CDNA library from E15 murine embryos lacking p73 and p53 genes (p73-/-, p53-/-; Yang et al., unpublished results) and screened pools of the fractionated library by PCR and subsequent hybridization. Three full-length cDNAs were obtained, all of which shared a central domain with approximately 60 and 85% amino acid identity with the DNA binding domains of p53 and p73, respectively (FIG. 1). Human cDNAs were deduced from sequencing reverse transcriptase-polymerase chain reaction (RT-PCR) products from the SK-N-MC neuroepithelioma cell line, and these revealed a remarkably high level of primary amino acid sequence conservation, bordering on 99%, with the mouse cDNAs (FIG. 1). Of the three murine cDNAs initially isolated, one encoded an acidic N-terminus similar to that required for transcriptional activation by p53 and p73. Interestingly, the murine CDNA clone with the acidic N-terminus contains an additional 39 amino acids upstream of the methionine start site seen in human sequences to date (FIGS. 1, 2). These N-termini have been denoted TA* for the longer N-terminus and TA for the sequence starting with the amino acid sequence MSQ (FIGS. 1, 2). The other two murine cDNAs clones encoded proteins with a truncated N-terminus (AN) lacking the acidic, putative transactivation domain. Further transcript and cDNA analysis from both murine and human sources revealed the expression of additional variants. In total, at least six different transcripts, derived from alternative splicing events and encoding proteins with two different N-termini (TA*/TA and ΔN) and three different C-termini (α, β, and Y), are described (FIG. 2). Partial analysis of the murine and human genes indicated that the transcripts that give rise to the truncated N-terminal proteins were derived from an alternative promoter and initiation codon in intron 3 (exon 3'; FIG. 2A). Additionally, a splicing variant in exon 9 of both species alternatively deleting four amino acids was detected in both species (not shown). To reflect the high degree of homology of the human and murine sequences to p53 and p73, as well as the immense complexity of these gene products with predicted molecular weights ranging from 44,000 to 72,000 daltons, we propose that this gene be called p63.

Figure 3A:
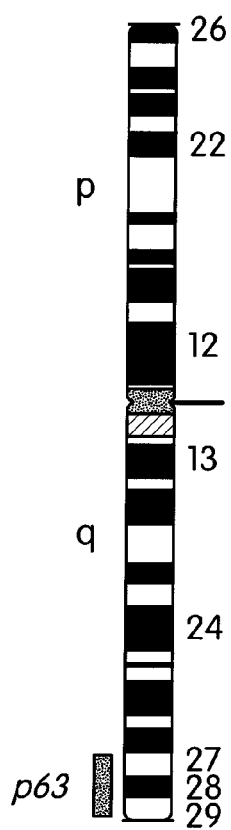
Figure 3B:
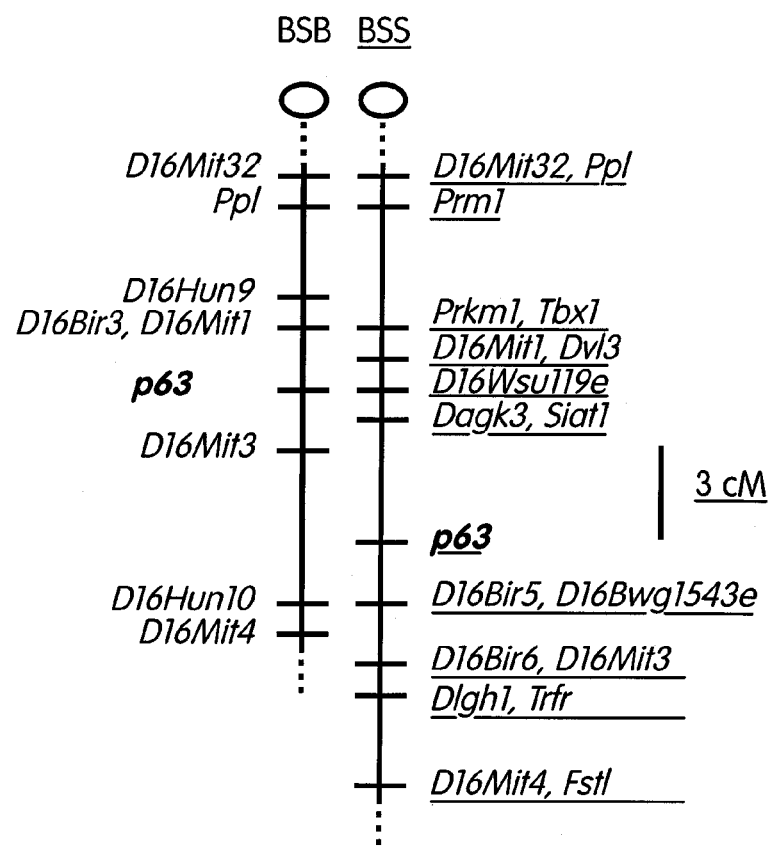
Figure 4A:
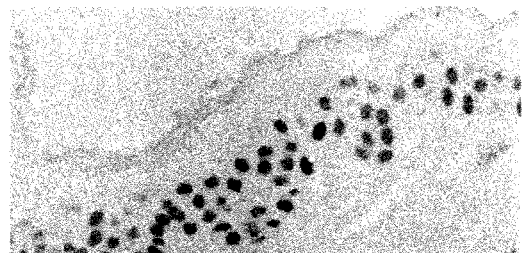
Figure 4B:
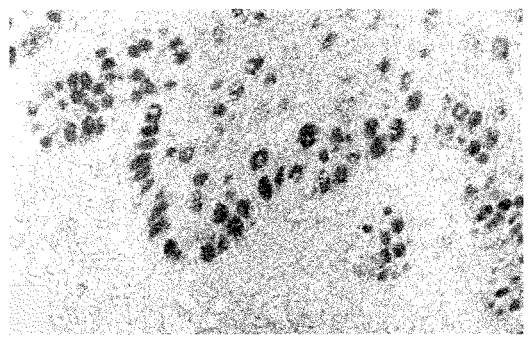
Figure 4C:
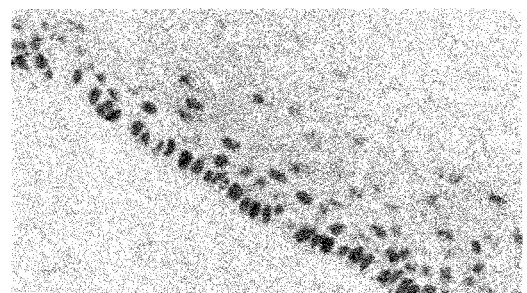
Figure 4D:
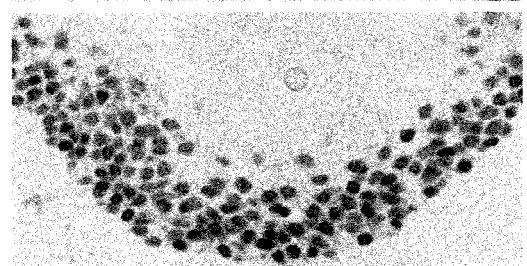
Figure 4E:
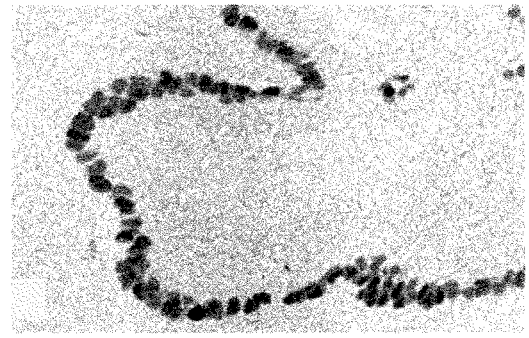

To map the human p63 gene, we employed fluorescence in situ hybridization (FISH) techniques on human metaphase chromosome spreads using the human p63 PAC clone as a probe. The p63 PAC clone hybridized to the long arm of chromosome 3, at approximately 3q27-29 (FIG. 3A). We also mapped the murine p63 gene using linkage analysis, which showed that p63 is located on the proximal portion of chromosome 16 between anonymous DNA markers D 16Mit 1 and D16Mit3 (FIG. 3B). This region is known to be syntenic with human chromosome 3q27-29, in agreement with the in situ analysis of the human p63 gene.

Hup63geno (PAC) has since been deposited at the ATCC (10801 University Blvd., Masassas, Va. 20110) under the terms of the Budapest Treaty. The deposit was made on Oct. 13, 1997 and received ATCC accession number 209359.

III. Mapping of Human p63 Gene

To map the human p63 gene, we used fluorescense in situ hybridization (FISH) on human metaphase chromosome spreads using the human p63 PAC clone as a probe. The p63 PAC clone hybridized to the long arm of chromosome 3 at approximately 3q27-28 (FIG. 2A). Fluorescence in situ hybridization (FISH) was performed on human metaphase spreads using Hupo63geno (PAC) as a probe. The methods used protocols that are well known in the art. By this method, p63 was mapped to human chromosome 3q27-29, a region implicated in various human syndromes including B-cell lymphoma and large diffuse cell lymphoma.

IV. Cloning of Human p63 cDNAs

Sequence information for human p63 transcripts were obtained by RT-PCR on total RNA isolated from the SK-B-MC cell line.

V. Cloning of Murine p63 Gene

The 900 bp amplicon derived from mouse genomic DNA, described above, was used as a probe in hybridization screens for the murine homolog of the p63 gene. Screening of a 129 mouse genomic phage library (in lambda DASH II) yielded a clone with a 16.5 kb insert containing the murine p63 gene. Hybridization screens were done as per standard protocols, under the following conditions: prehybridization incubation (without probe) for 4 hrs at 50–55° C., in hybridization solution (50% formamide, 5×SSC, 2.5× Denhardts, 150 ug/ml salmon sperm DNA, 0.1% SDS); hybridization with $^{32}$P-labeled probe (in hybridization solution) for 16 hrs at 40° C.; washes done in 0.5×Ssc, 0.1% SDS at 50° C. The 16.5 kb insert was released by a NotI digestion, subcloned into the pZero vector, and sequenced in its entirety. Sequence analysis showed the clone to contain a portion of the murine p63 gene, extending from intron 4 through intron 10.

VI. Cloning of Murine p63 cDNAs

5' Rapid Amplification of cDNA Ends (RACE) was used to obtain further sequence information on p63 not contained within the murine genomic clone. Total RNA was isolated from c15 embryos lacking both p53 and p73, generated from mice bearing targeted mutations in both genes, and used as the template in a first stand cDNA synthesis reaction with a murine p63-specific primer (5'-GGCATCGATGAACT-CACGGCTCAGCTC) (SEQ ID NOS: 28) An 'adapter' primer (5'-TTTAGTGAGGGTTAATAAGCGGC-CGCGTCGTGACTGGGAGCGC) (SEQ ID NOS: 30) was then ligated to the cDNA product using T4 RNA ligase. PCR was subsequently performed on the ligation product using primers (5'-GCCCTGGAGGCGGCCGCTTATTAACCCT-CAC (SEQ ID NOS: 31) and 5'-GGCATCGATGTAGA-CAGGCATGGCACG) (SEQ ID NOS: 32) with the conditions described in I. An approximately 610 bp amplicon was generated, subcloned into pCDNA3 vector, and sequenced in its entirety. The 5'RACE product yielded a sequence corresponding to a N-terminal truncated form of murine p63.

A bacterial plasmid cDNA library was constructed from mRNA isolated from e15 embryos lacking both p53 and p73, described above, and screened for p63 cDNAs. Hybridization screens were done essentially as described in V., using a probe, corresponding to exons 5 to 9 of p63, generated by RT-PCR on total p73-/-; 53-/- mouse RNA with primers (5'-GGGCTCGAGCTGAAGAAGCTGTACTGC (SEQ ID NOS: 35) and 5'-GGGATCGATCTCCGTTTCTTGATG-GAA) (SEQ ID NOS: 34). Three clones were identified and sequenced in their entirety. These corresponded to three different, full-length splice variants of murine p63.

VII. Murine p63 Gene Targeting Vector

The 16.5 kb genomic fragment described in V. was used to construct a vector for targeted disruption of the p63 gene by homologous recombination in murine embryonic stem (ES) cells. Briefly, the p63 gene fragment was subcloned into the pBluescript SK (-) vector via a NotI/NarI digestion followed by ligation to compatible cohesive ends generated by a NotI/ClaI digestion of the vector plasmid. This construct, pSK-murp63geno, was then digested with SpeI and ClaI to remove a 2900 bp region corresponding to portions of intron 5, all of exon 6, intron 6, exon 7, intron 7, exon 8, and portions of intron 9 (note: exon and intron designations based on exon sequence homology with p73 and p53). This region was then replaced with the neomycin resistance gene under control of the PGK promotor (PGK-NeoR), yielding pSK-murp63genoNeo. This plasmid was then digested with SacII/NheI, removing a 2200 bp fragment corresponding to a portion of intron 4 that was then replaced with the herpes simplex virus thymidine kinase gene (HSV-TK), yielding the final p63 gene targeting vector, pSK-murp63ko. This vector will be linearized and introduced into murine ES cells via electroporation. Double selection with G418 and gancyclovir, followed by DNA hybridization with external probes will identify ES clones which have under gone homologous recombination. These will then be used in blastocyst reconstitutions to generate chimeric mice bearing the targeted disruption in p63. Breeding of these chimeric mice with wildtype mice and intercrosses from subsequent F1 and F2 generations will yield mice deficient in one or both copies of the p63 gene.

VIII. Cloning of Human p63 and Possible Novel, Related Genes Using Murine p63 cDNA We obtained a human genomic library enriched for chromosome 22 from the ATCC and probed with a murine p63 cDNA fragment corresponding to exons 5 to 9, described in VI. Hybridizations were done as described in V, but lower stringency washes were used (5×SSC/0.1% SDS). These screens yielded one clone containing a 4 kb insert that was then subcloned into pZero vector and sequenced in its entirety. Sequence analysis showed that this clone was identical to previously obtained human p63 cDNAs in the corresponding exonic regions. This result demonstrated the ability to clone the human p63 gene using a cross-species (mouse) cDNA probe. Additional clones which yielded positive signals in our hybridization screens have been identified and will be purified and sequenced to determine if they are novel members of the p73, p63, p53 family.

IX. Immunofluorescence

Transfection of baby hamster kidney (BHK) cells with myc-epitope tagged p63 cDNAs in pCDNAA3 vector and subsequent immunofluorescence detection of protein was done essentially as described in Heald et al., 1993.

X. Expression of p63 in Human and Murine Tissues

As the p63 cDNAs were derived from murine embryos and human cell lines, it was important to determine their expression in normal adult tissues. To address this issue, we immunized mice with bacterially-expressed glutathione-S-transferase-p63 fusion proteins, and produced an array of monoclonal antibodies which recognize an epitope common to murine and human p63 and ΔN-p63 proteins (Experimental Procedures). Using one of these antibodies, the 4A4 clone, we probed paraffin sections of archival normal human tissues including foreskin, cervix, vaginal epithelium, urothelium, and prostate (FIGS. 4A–D). In all of these tissues, the 4A4 monoclonal antibody showed strong nuclear staining concentrated in the basal cells of the epithelium. The predominant localization of p63 to the basal layer of these stratified squamous and transitional epithelia is interesting in that these cells act as the progenitors of the suprabasal cells, which undergo differentiation and cell death in regenerative epithelia (Jetten and Harvat, 1997). In the prostate, the relationship between these p63-positive basal cells and the luminal cells is less well established, but it is thought that the basal cells are likewise the progenitors of the suprabasal, secretory cells (Myers and Grizzle, 1997).

Figure 5A:
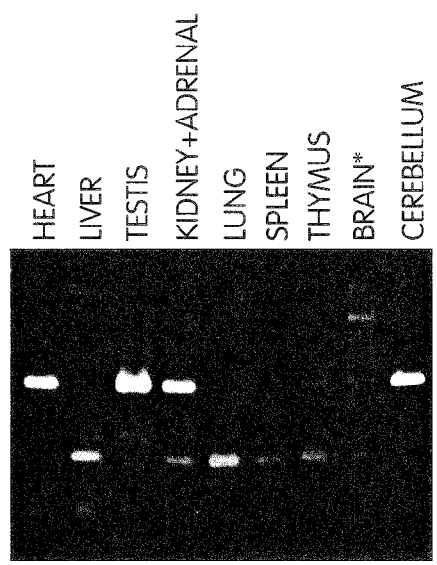
Figure 5B:
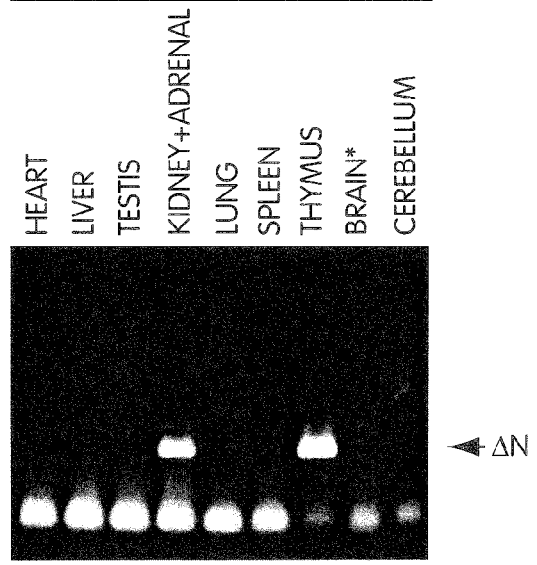
Figure 5C:
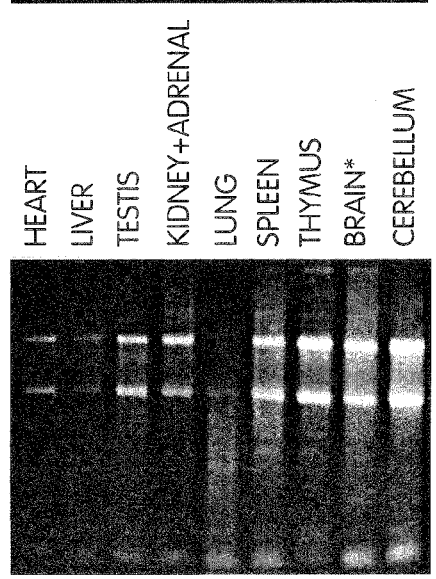

To obtain a more extensive survey of p63 expression in adult tissues, we prepared total RNA from various murine tissues and performed RT-PCR reactions specific for the two different p63 N-termini, TA and ΔN. This analysis revealed the presence of transcripts encoding TAp63 variants in heart, testis, kidney/adrenal, thymus, brain (minus cerebellum), and cerebellum (FIG. 5a). The ΔNp63 transcript was detected in the kidney/adrenal, spleen, and thymus, but absent from the heart, liver, testis, and brain, despite the normalization of template RNA concentration in each reaction (FIGS. 5B,C). This RT-PCR analysis indicated that TAp63 and ΔNp63 transcripts are widely expressed in adult tissues.

Figure 5D:
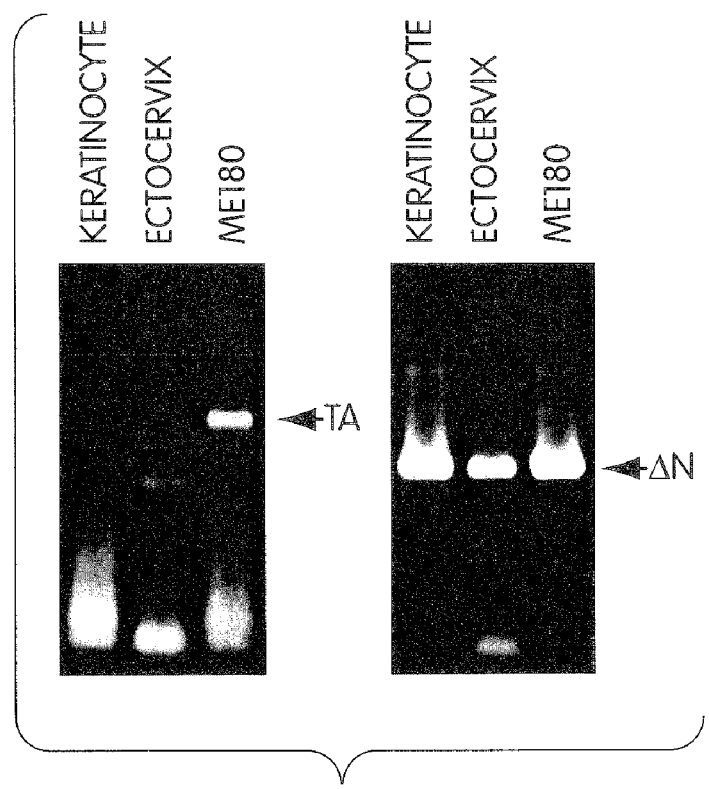

The immunohistochemistry on human epithelial tissues revealed high levels of p63 expression in basal cells (FIG. 3). To determine which p63 isotypes were expressed in these cells, RT-PCR reactions were performed on RNA prepared from primary human foreskin keratinocytes, human ectocervix, and ME 180 cervical carcinoma cells. While RNA derived from the ME 180 cells yielded a positive signal in the RT-PCR reaction designed to amplify transcripts encoding the acidic N-terminus, the primary keratinocytes and the ectocervical cells showed little or no product (FIG. 5D, TA). In contrast, RNA from all three sources showed robust signals in the RT-PCR reaction designed to amplify the ΔNp63 transcript (FIG. 5D, ΔN).

Figure 5E:
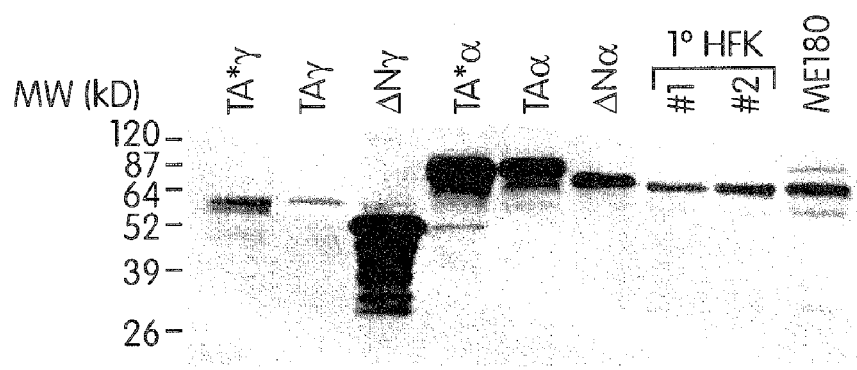

The analysis of RNA from primary keratinocytes indicated that the major p63 transcripts in these cells encoded ΔNp63 isotypes. To address this possibility at the protein level, we performed immunoblotting on protein lysates derived from human primary foreskin keratinocytes (HFK) and ME180 cervical carcinoma cells with the 4A4 monoclonal antibody. Lysates of baby hamster kidney (BHK) cells transfected with mammalian expression vectors encoding epitope-tagged p63 isotypes were included as controls for molecular weight comparison (FIG. 5E). Significantly, the major product detected in primary keratinocytes and ME180 migrates at approximately 8okDa, slightly faster than the Myc epitope-tagged ΔNp63α. (FIG. 5E). The ME180 cells also express a less abundant, though detectable, product migrating at approximately 90–95 kDa, similar to that of TAp63α (FIG. 5E). These data, taken together with the abundant ΔNp63 RT-PCR product from the ME180 cell line and primary keratinocyte RNA, are consistent with notion that these epithelial cells predominantly express the ΔNp63α isotype.

XI. Transactivation Functions of p63 Isotypes

The central domain of all p63 variants is highly homologous with the DNA binding domains of p53 and p73, suggesting that at least some p63 isotypes function as transcriptional activators. The ΔNp63 variants, however, lack the N-terminal acidic residues thought to participate in transactivation functions of p53 and p73 (Ko and Prives, 1996; Levine, 1997; Kaghad et al., 1997). To determine whether any of the p63 isotypes can act as transactivators, we tested their ability to induce expression from a reporter gene under the control of a p53-responsive element. Six p63 constructs, specifically TAp63α, TAp63Y, ΔNp63α, ΔNp63Y, TA*p63α, and TA*p63Y, as well as wildtype and mutant p53 expression vectors, were separately expressed in Saos-2 human osteosarcoma cells, which lack endogenous p53, along with a β-galactosidase reporter construct containing multiple copies of a minimal p53 binding sequence (PG-13, Kem et al., 1992). Lysates from cells expressing wildtype p53 yielded a strong β-galactosidase signal, while those expressing the p53 mutant showed only a background signal (FIG. 6). Of the p63 isotypes tested in Saos-2 cells, only TAp63y exhibited strong transcriptional activation of the p53 reporter, with levels approaching 80% of that seen with p53. Interestingly, the TA*p63Y isotype, which has a 39 amino acid N-terminal extension not found in TAp63Y, proved to be a weak transactivator in Saos-2 cells, suggesting possible regulatory elements within this additional domain. As expected, neither the ΔNp63Y nor the ΔNp63α variant, both of which lack the putative transctivation domain, showed strong reporter activity (FIG. 6), although the ΔNp63Y gave a low but detectable signal. Surprisingly, however, the ΔNp63α isotype also failed to yield a significant level of reporter gene expression, despite having the same transactivation domain as TAp63Y. A similar lack of transactivation was seen with TA*p63α, pointing to additional regulatory facets of p63 involving its C-terminal domain.

XII. Induction of Apoptosis by p63 Isotypes

Figures 7A, 7B, 7C, 7D, 7E:
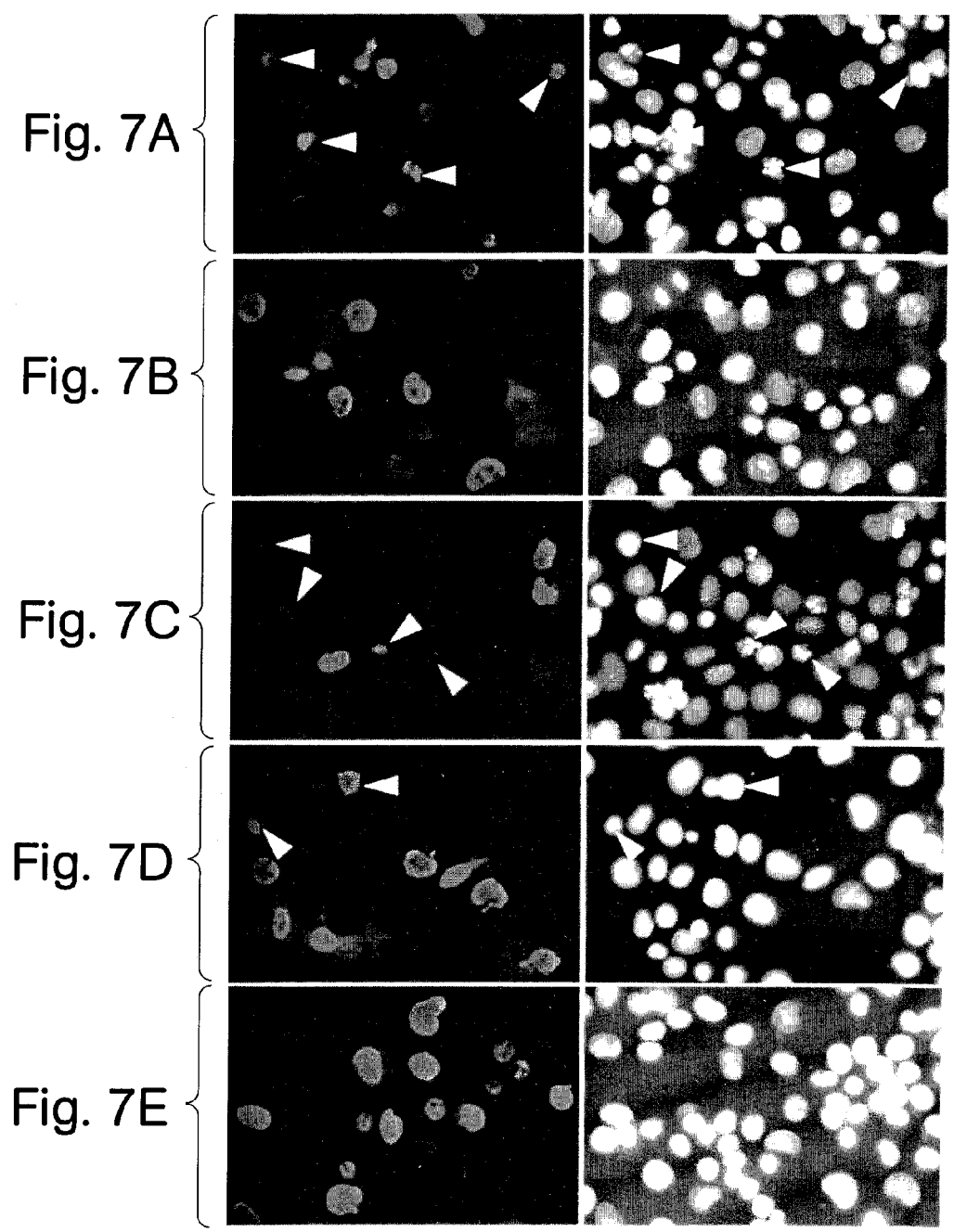

Expression of wildtype p53 induces apoptosis in a wide variety of cells, whereas many p53 mutants have lost this ability (Oren, 1994). To determine whether any of the p63 isotypes possess similar death-inducing activities, we compared the fates of baby hamster kidney (BHK) cells transfected with p53 or p73 vectors with those expressing p63 isotypes. BHK cells were transfected with the p53, p73, and p63 expression vectors and fixed 16 hours later. Cells were labeled using anti-Myc and anti-HA epitope tag antibodies to detect expressed proteins and with the DNA fluorochrome Hoechst 33278. Approximately 90% of the wildtype p53-expressing cells appeared raised from the substrate and showed highly condensed, lobated nuclei characteristic of apoptotic cells (FIG. 7A). In contrast, those expressing the p53(V143A) mutant showed a very low percentage of apoptotic cells, despite high levels of exogenous protein expression (FIG. 7B). Cells transfected with TAp637 proved highly vulnerable to cell death, as evidenced by nuclear morphology, despite the generally low protein levels generated from exogenous expression in these cells. However, an overexposure of the epitope-tag immunofluorescence image showed a good correspondence between apoptotic cells and TAp63Y expression (FIG. 7C). Curiously, cells expressing the ΔNp63Y isotype, which yielded low but measurable activity in the β-galactosidase assays (FIG. 6), also exhibited a slight but noticeable level of apoptosis. The percentage of cell death induced by ΔNp63Y however, was considerably less than those seen in cells expressing p53 or TAp63Y, despite the fact that ΔNp63Y accumulates to very high levels in BHK cells (FIG. 7D). Apoptosis was virtually absent in cells expressing high levels of either ΔNp63α (FIG. 7E), TAp63α, or TA*p63α, consistent with the lack of transactivation seen with these variants. Finally, p73α and p73β exhibited little or no apoptotic activity in these cells at 16 hours, despite high levels of accumulation.

XIII. ΔN-p63γ Suppresses Transactivation by p53, and Enhances that of TA-p63γ

Figure 8B:
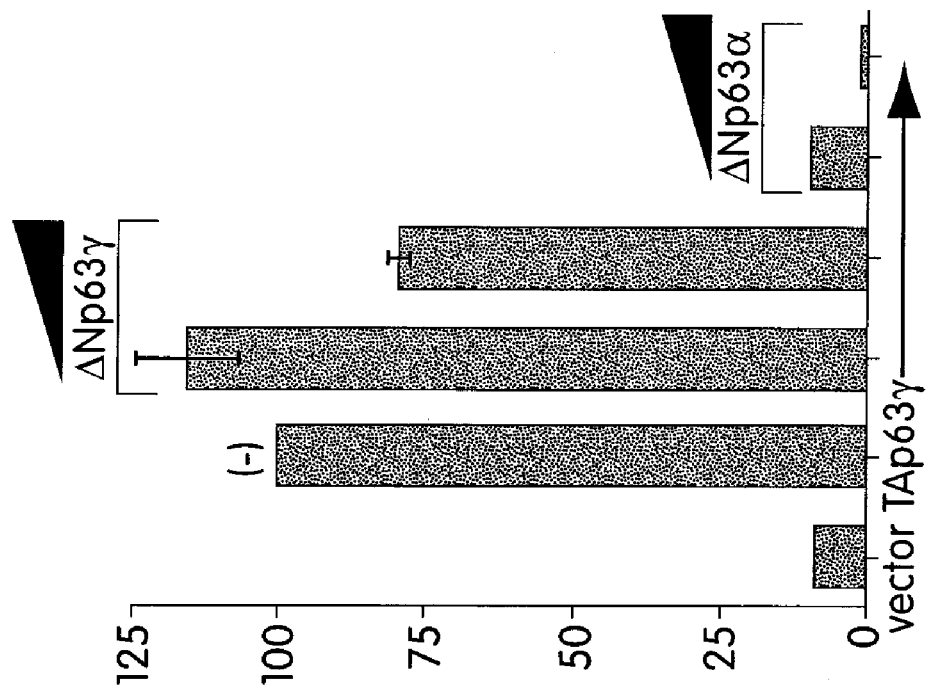
Figure 8A:
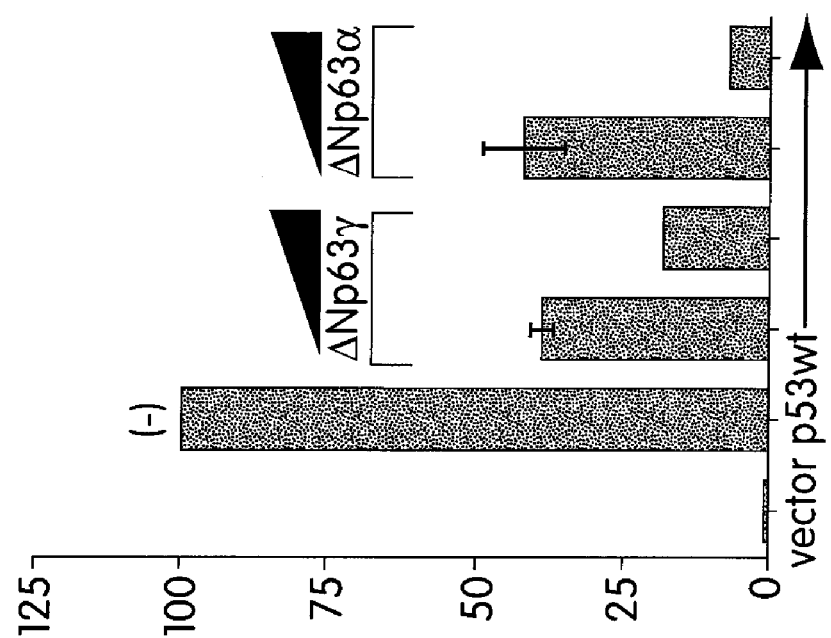

The ability of the TAp63γ isotype to transactivate reporter genes bearing p53-responsive elements suggested that, in general, p63 isotypes can interact with p53 DNA binding sites. As the ΔNp63Y isotypes lack the acidic N-terminus similar to that required for transcriptional activation by p53, it seemed feasible that such isotypes could act in a dominant-negative manner towards both p53 and transactivating versions of p63, such as TAp63Y. To test whether ΔNp63Y isotypes could in fact suppress the transactivation ability of p53, we transfected Saos-2 cells with a constant amount wildtype p53 and varying concentrations of either ΔNp63Y or ΔNp63α and assayed for transactivation of the PG-13 β-gal reporter gene. At a 5:1 DNA ratio of p53 and ΔNp63Y transfected into Saos-2 cells, reporter activity was reduced to 37% that of p53 alone, while a 1:1 ratio yielded less than 20% the transactivation of p53 (FIG. 8A). ΔN-p63a also showed a similar, dose-dependent inhibition of p53 transactivation, with the higher suppressor concentration (1:1) giving near background (vector alone) levels of reporter signal (FIG. 8A).

We next asked if ΔN-p63 isotypes could likewise affect transactivation by TAp63y. Paradoxically, cells co-transfected with TAp63Y and ΔNp63Y (5:1) yielded reporter expression slightly above that seen with TAp63Y alone (FIG. 8B). Higher levels of ΔNp63Y in the cotransfection (1:1 ratio) suppressed transactivation by TA-p63Y by a modest 20% (FIG. 8B). In contrast, ΔN-p63α proved to be a strong suppressor of transactivation by TAp63Y, yielding only background levels of reporter signal, even when co-transfected at one-fifth the DNA concentration of TAp63Y (FIG. 8B).

Several mechanisms could underlie the ability of ΔNp63 isotypes to suppress p53 and p63 in these assays. For example, given the high degree of sequence homology within the DNA binding domains of the p53 and p63 proteins, it is likely that p63 can bind p53 DNA target sites in a competitive manner. To address this possibility, we asked whether p63 isotypes, particularly those lacking detectable transactivation capabilities, could nonetheless interact with p53 DNA binding sites. Electrophoretic mobility shift assays (EMSA) were performed using three separate oligonucelotides: a minimal p53 binding sequence site (PG), a p53 binding site in the p21 promoter (WAF), and a mutant p53 binding site (MG; Kern et al., 1992) with lysates of 293 human kidney cells transfected with p53, ΔNp63Y, TAp63α and green fluorescent protein. p53, ΔNp63Y and TAp63α lysates all yielded significant shifts of both PG and WAF oligonucleotides, while GFP, included as a negative control, failed to display a similar shift (not shown). None of the lysates showed a shift of the control, non-p53 binding oligonucleotide, MG, thus demonstrating the specificity of p53, ΔNp63Y and TAp63a. interactions with the p53-binding sites.

Another mechanism by which p63 isotypes could affect transactivation by p53 and p63 is via direct protein—protein interactions, presumably through their oligomerization domains, We tested the potential for such interactions using a glutathione S-transferase (GST), TA*p63Y fusion construct (GST-TA*p63Y). Co-expression in BHK cells and subsequent binding assays showed strong associations between GST-TA*p63Y and p63Y isotypes, including and ΔNp63α but failed to reveal an interaction with p53.

XIV. Electrophoretic Mobility Shift Assays (EMSA)

This invention provides nucleic acids encoding a DNA binding domain of a p63 cell regulator protein. Assays for determining the location of a DNA binding domain in proteins include gel retardation assays, well known in the art. Briefly, recombinant proteins comprising various portions of a p63 cell regulator protein can be produced and their interaction with DNA can be measured by incubation with a DNA target sequence and separation of the complexes by gel electrophoresis. The DNA target sequence of a p63 cell regulator protein can be determined, e.g., by binding site selection experiments, well known in the art. Binding site selection experiments are performed by incubation of a DNA binding protein, e.g., a p63 cell regulator protein with a degenerate pool of labeled double stranded oligonucleotides and isolation of the oligonucleotides which interact specifically with the DNA binding protein. Individual oligonucleotides are then sequenced.

EMSAs were performed essentially as described in Yang, A. et al., (1998), Mol Cell 2, 305–316. Briefly, human 293 kidney cells were transfected with p53, p63, and GFP expression vectors, as indicated in FIG. 25, using the calcium phosphate transfection method previously described (Heald et al., 1993, Cell 74, 463–474; Yang et al., 1998). Cells were lysed in 150 μl detergent lysis buffer (50 mM Tris pH 8, 150 mM NaCl, 0.1% Triton X-100) ~24 hrs after transfection. Lysates were then incubated for 1 hr at room temperature with 100 pM $^{32}$P radiolabeled, double-stranded oligonucleotides in binding buffer (16 mM Hepes-KOH pH 7.5, 60 mM Kcl, 30 mM NaCl, 10% glycerol, 1 mM dithiothreitol, 10 μg/ml BSA). The following oligonucleotides were used, with annealing of oligonucleotide pairs performed prior to incubation with lysate extracts above. PG: 5'-CCTGCCTGGACTTGCCTGG (SEQ ID NOS: 35)+ 5'-CCAGGCAAGTCCAGGCAGG (SEQ ID NOS: 36) WAF: 5'-GAACATGTCCCAACATGTTG (SEQ ID NOS: 37)+5Õ-CAACATGTTGGGACATGTTC (SEQ ID NOS: 35) MG: 5'-CCTTAATGGACTTTAATGGA (SEQ ID NOS: 39)+5Õ-CCATTAAAGTCCATTAAGG (SEQ ID NOS: 40).

XV. Induction of p63 in Response to UV/DNA Damage

These experiments show that like p53 p63 is induced in response to stress signals such as UV-DNA damage.

RT-PCR Analysis

Total RNA was isolated from tissues and cell lines using RNAzol, dissolved in 10 mM Tris pH8, 1 mMEDTA (TE), and quantified using ultraviolet absorption at 260 nm. RT-PCR reactions were performed with the One-Step RT-PCR kit (Gibco-BRL), using 0.25 ug total RNA in 25 ul reactions under the following conditions: 50° C. 30 min; 94° C. 2 min; 94° C. 30 sec, 52° C. 30 sec, 72° C. 1 min for 40 cycles; 72° C. 5 min. The following primers were used: human p63 TA-specific reaction: 5'-ATGTCCCAGAGCCACACAG (SEQ ID NOS: 41) and 5'-AGCTCATGGTTGGGGCAC (SEQ ID NOS: 42); human p63 ▲N-specific reaction: 5'-CAGACTCAATTTAGTGAG (SEQ ID NOS: 43) and 5'-AGCTCATGGTTGGGGCAC (SEQ ID NOS: 44).

UV-Irradiation of Human Keratinocytes

Human foreskin primary keratinocytes were cultured in Keratinocyte-SFM media (Gibco-BRL) and maintained in 5% $CO_2$. The keratinocytes were treated with 300 J/m$^2$ UV irradiation, and harvested at times indicated for total RNA using RNAzol, as described above. RNA from untreated keratinocytes obtained from the same culture was used as a control.

Differentiation of Human Keratinocytes

Human foreskin primary keratinocytes were cultured in Keratinocyte-SFM media (Gibco-BRL) and maintained in 5% $CO_2$. To induce differentiation, Keratinocyte-SFM media was replaced with DMEM media (Gibco-BRL) containing 10% fetal bovine serum (FBS). Cells were harvested for RNA after addition of DMEM/10% FBS at times indicated. RNA from untreated keratinocytes obtained from the same culture was used as a control.

XVI. Screening for Mutations of the p63 Gene in Human Tumors and Diseases.

Direct sequencing, using standard techniques, of the p63 gene will yield information on the genomic organization (i.e. intron/exon boundaries) and nucleotide sequence for exons, introns and promoter regions of p63. An important biological and diagnostic application for these data will be to screen for sequence mutations and/or polymorphisms (including nucleotide substitutions, insertions, or deletions) that may result in a loss or gain of function of the p63 gene. These screens will employ the use of techniques standard in the field, including, but not restricted to, single strand conformation polymorphism (SSCP) analysis, and direct sequencing of DNA or RNA samples obtained from patients.

As one means of enabling this application, we have isolated a PAC clone of an approximately 120 kilobase genomic segment containing the p63 gene. Briefly, an 800 bp amplicon, derived from PCR on human genomic DNA and corresponding to portions of exon 7 and 8 and intervening intron, was used as a probe in hybridization screens for the human p63 gene. Screening (done by Genome Systems) of a human genomic PAC library (made from white blood cells, male) yielded one clone containing the p63 gene. We have confirmed the identity of this PAC clone using by PCR. Hup63geno (PAC) has been deposited at the ATCC (10801 University Blvd., Masassas, VA 20110) under the terms of the Budapest Treaty. The deposit was made on Oct. 13, 1997 and received ATCC accession number 209359. The Hup63geno (PAC) clone likely contains a majority of the p63 gene, as the DNA probe used hybridizes to a core, central domain of the gene. Regardless, the sequence information, as well as the use of DNA probes derived from this PAC clone render the isolation of any portion of the p63 gene missing from this clone a standard and obvious application.

XVII. Lineage-Specific Expression of p63 in Genital Tract Neoplasia

Vulvar, cervical, endometrial, and ovarian epithelial neoplasms, mixed mullerian tumors (MMMT), stromal sarcomas and adjacent normal epithelia were studied. Serial sections were stained with monoclonal antibodies to p63 and p53. Percentages of cells staining were estimated for each neoplastic phenotype. It was found that in the vulva or cervix, p63 expression was limited to squamous epithelium and reserve cell populations. Staining was uniformly negative in benign and neoplastic endocervical glandular epithelium. Staining was weak (less than 10%) or absent in all but 2 endometrial adenocarcinomas, in all MMMTs, and in all ovarian neoplasms except one low grade transitional carcinoma. When present in adenocarcinomas, p63 staining predominated in basal/reserve type cells and foci of squamous metaplasia. P53 expression was conspicuous ($\geq 10\%$) only in endometrial serous carcinomas (12/16), one stromal sarcoma, and one MMMT, and did not co-localize with p63.

Therefore, it appears that p63 is a unique homologue of p53 which, in the cervix, is expressed exclusively in squamous epithelium or reserve cells. In glandular lesions of other sites, p63 predominates in reserve cells, areas of squamous differentiation and basal cell populations. The sharp differences in expression of p63 between glandular and squamous epithelium, particularly in the cervix, may provide insights into the mechanisms determining phenotype in both benign and neoplastic epithelial proliferations.

XVIII. P63 is a Differentiation Specific Marker in Cervical Squamous Epithelium

The distribution of p63 expression in a range of cervical squamous epithelia was examined and contrasted it with markers for cell proliferation (Ki-67) because p63 is homologous to p53 and p53 regulation has been implicated in the pathogenesis of HPV-related squamous neoplasia.

31 biopsies classified as reactive, atrophic, intraepithelial and invasive cervical squamous epithelial alterations, as well as normal mucosa, were analyzed by immunohistochemistry for p53 and Ki-67 for distribution and correlation with morphologic phenotype. It was found that distribution of p63 closely paralleled squamous cell differentiation, staining all nuclei in the lower one third to one half of normal squamous epithelium only. Diffuse staining of all epithelial cells occurred in immature epithelia, including atrophy, immature metaplasia, immature LSILs (papillary immature metaplasia) and the immature cells of conventional low and high grade SIL and invasive cancer. In contrast, Ki-67 staining was more diffuse in neoplastic lesions, being expressed in both differentiated and undifferentiated cell nuclei, and less frequently expressed in benign processes.

Therefore, it appears that p63 is a unique homologue of p53 which, in the cervix, is expressed almost exclusively in immature squamous epithelium irrespective of the pathologic process. The morphological and immunohistochemical evidence are consistent with a role of p63 in cell differentiation, uncoupled from both cell proliferation and HPV expression. Cessation or down-regulation of p63 expression may play a critical role in the process of squamous differentiation, both benign and neoplastic.

We claim:

1. An isolated nucleic acid, which encodes a protein comprising an amino acid sequence that is at least about 99% identical to the amino acid sequence set forth in SEQ ID NOs: 13, 14, 15, 16, 17 or 18, wherein said protein: (a) binds a p53-responsive element; (b) transactivates a target gene from a p53-responsive element; or (c) induces apoptosis.

2. The isolated nucleic acid of claim 1, which encodes a protein comprising the amino acid sequence set forth in SEQ ID NO: 13.

3. The isolated nucleic acid of claim 1, which encodes a protein comprising the amino acid sequence set forth in SEQ ID NO: 14.

4. The isolated nucleic acid of claim 1, which encodes a protein comprising the amino acid sequence set forth in SEQ ID NO: 15.

5. The isolated nucleic acid of claim 1, which encodes a protein comprising the amino acid sequence set forth in SEQ ID NO: 16.

6. The isolated nucleic acid of claim 1, which encodes a protein comprising the amino acid sequence set forth in SEQ ID NO: 17.

7. The isolated nucleic acid of claim 1, which encodes a protein comprising the amino acid sequence set forth in SEQ ID NO: 18.

8. The isolated nucleic acid of claim 1, which encodes a protein that binds to a p53-responsive element.

9. The isolated nucleic acid of claim 8, which encodes a protein that binds to a p53-responsive element selected from the group consisting of a minimal p53 target DNA binding sequence; and a p53 target DNA binding sequence in a p21 promoter.

10. The isolated nucleic acid molecule of claim 1, further comprising a transcriptional regulatory sequence operably linked to said nucleic acid sequence so as to render said nucleotide sequence suitable for use as an expression vector.

11. An expression vector comprising a nucleic acid of claim 10.

12. The nucleic acid of claim 1, which encodes a protein that oligomerizes.

13. An isolated nucleic acid, which comprises a nucleotide sequence that is at least about 99% identical to the nucleotide sequence set forth in SEQ ID NOs: 1, 2, 3, 4, 5 or 6, which nucleic acid encodes a protein that: (a) binds a p53-responsive element; (b) transactivates a target gene from a p53-responsive element; or (c) induces apoptosis.

14. The isolated nucleic acid of claim 13, which comprises the nucleotide sequence set forth in SEQ ID NO: 1.

15. The isolated nucleic acid of claim 13, which comprises the nucleotide sequence set forth in SEQ ID NO: 2.

16. The isolated nucleic acid of claim 13, which comprises the nucleotide sequence set forth in SEQ ID NO: 3.

17. The isolated nucleic acid of claim 13, which comprises the nucleotide sequence set forth in SEQ ID NO: 4.

18. The isolated nucleic acid of claim 13, which comprises the nucleotide sequence set forth in SEQ ID NO: 5.

19. The isolated nucleic acid of claim 13, which comprises the nucleotide sequence set forth in SEQ ID NO: 6.

20. A method for detecting the presence of a p63 nucleic acid in a sample comprising contacting a biological sample with a nucleic acid of claim 1, and detecting a hybridization product, wherein the p63 nucleic acid of the sample encodes a protein which (a) binds to a p53 responsive element, (b) transactivates a target gene from a p53 responsive element or (c) induces apoptosis, and wherein the p63 nucleic acid of the sample can bind to a nucleic acid of claim 1 under conditions of 2.0 SSC at 40° C.

* * * * *

UNITED STATES PATENT AND TRADEMARK OFFICE
CERTIFICATE OF CORRECTION

| | | |
|---|---|---|
| PATENT NO. | : 7,294,459 B1 | Page 1 of 1 |
| APPLICATION NO. | : 09/174493 | |
| DATED | : November 13, 2007 | |
| INVENTOR(S) | : Yang et al. | |

It is certified that error appears in the above-identified patent and that said Letters Patent is hereby corrected as shown below:

In the Specification

Column 1, Lines 12-14, should read:
--This invention was made with government support under GM052027 awarded by the National Institutes of Health. The government has certain rights in the invention.--

Signed and Sealed this
Fourteenth Day of January, 2025

Derrick Brent
*Acting Director of the United States Patent and Trademark Office*